US008409836B2

(12) United States Patent
Vehmaanperä et al.

(10) Patent No.: US 8,409,836 B2
(45) Date of Patent: Apr. 2, 2013

(54) TREATMENT OF CELLULOSIC MATERIAL AND ENZYMES USEFUL THEREIN

(75) Inventors: Jari Vehmaanperä, Klaukkala (FI); Marika Alapuranen, Rajamäki (FI); Terhi Puranen, Nurmijärvi (FI); Matti Siika-Aho, Helsinki (FI); Jarno Kallio, Järvenpää (FI); Satu Hooman, Espoo (FI); Sanni Voutilainen, Lohja (FI); Teemu Halonen, Espoo (FI); Liisa Viikari, Helsinki (FI)

(73) Assignee: Roal Oy, Rajamaki (FI)

( * ) Notice: Subject to any disclaimer, the term of this patent is extended or adjusted under 35 U.S.C. 154(b) by 0 days.

(21) Appl. No.: 12/917,603

(22) Filed: Nov. 2, 2010

(65) Prior Publication Data

US 2011/0045544 A1    Feb. 24, 2011

Related U.S. Application Data

(60) Division of application No. 12/141,976, filed on Jun. 19, 2008, now abandoned, which is a continuation of application No. PCT/FI2006/050558, filed on Dec. 15, 2006.

(60) Provisional application No. 60/753,258, filed on Dec. 22, 2005.

(30) Foreign Application Priority Data

Dec. 22, 2005  (FI) ..................... 20051318

(51) Int. Cl.
*C12N 9/00* (2006.01)
*C07H 21/02* (2006.01)
*C07H 21/04* (2006.01)
*C07K 1/00* (2006.01)
*C07K 14/00* (2006.01)
*C07K 17/00* (2006.01)
*C12P 21/06* (2006.01)

(52) U.S. Cl. ...... 435/183; 536/23.1; 536/23.2; 530/350; 435/69.1

(58) Field of Classification Search ............... 435/183, 435/69.1; 536/23.1, 23.2; 530/350
See application file for complete search history.

(56) References Cited

U.S. PATENT DOCUMENTS

| | | | |
|---|---|---|---|
| 4,966,850 A | 10/1990 | Yu et al. | |
| 5,763,254 A | 6/1998 | Woldike et al. | |
| 5,912,157 A | 6/1999 | von der Osten et al. | |
| 5,948,672 A | 9/1999 | Rasmussen et al. | |
| 5,958,082 A | 9/1999 | Lund et al. | |
| 6,001,639 A | 12/1999 | Schulein et al. | |
| 6,022,725 A | 2/2000 | Fowler et al. | |
| 6,071,735 A | 6/2000 | Schulein et al. | |
| 6,103,464 A | 8/2000 | Fowler et al. | |
| 6,197,564 B1 | 3/2001 | Kofod et al. | |
| 6,723,549 B2 | 4/2004 | Miettinen-Oinonen et al. | |
| 6,982,159 B2 | 1/2006 | Dunn-Coleman et al. | |
| 7,785,853 B2 * | 8/2010 | Lange et al. | 435/195 |
| 2002/0168751 A1 | 11/2002 | Miettenen-Oinonen et al. | |
| 2002/0192774 A1 | 12/2002 | Ahring et al. | |
| 2004/0005674 A1 | 1/2004 | Duck et al. | |
| 2004/0053373 A1 | 3/2004 | Foody et al. | |
| 2004/0197890 A1 * | 10/2004 | Lange et al. | 435/209 |
| 2005/0164355 A1 | 7/2005 | Vlasenko et al. | |
| 2005/0214920 A1 | 9/2005 | Harris et al. | |
| 2006/0246566 A1 | 11/2006 | Vehmaanpera et al. | |

FOREIGN PATENT DOCUMENTS

| | | |
|---|---|---|
| EP | 0495258 | 7/1992 |
| FI | 20055205 | 11/2006 |
| FR | 2786784 | 6/2007 |
| JP | 08-056663 | 3/1996 |
| WO | 9629397 | 9/1996 |
| WO | 9713853 | 4/1997 |
| WO | 9806858 | 2/1998 |
| WO | 9812307 | 3/1998 |
| WO | 0142433 | 6/2001 |
| WO | 0170998 | 9/2001 |
| WO | 0224926 | 3/2002 |
| WO | 0226979 | 4/2002 |
| WO | 02095014 | 11/2002 |
| WO | 03000941 | 1/2003 |
| WO | 03062409 | 7/2003 |
| WO | 03078644 | 9/2003 |
| WO | 2004053039 | 6/2004 |
| WO | 2004056981 | 6/2004 |
| WO | 2005001065 | 1/2005 |
| WO | 2005047499 | 5/2005 |
| WO | 2005067531 | 7/2005 |
| WO | 2005074656 | 8/2005 |
| WO | 2005118828 | 12/2005 |
| WO | 2006117432 | 11/2006 |

OTHER PUBLICATIONS

*Chaetomidium* pingtungium, accession No. AX657623, 2003.*
Tomme et al., Studies of the cellulolytic system of *Trichoderma reesei* QM 9414, Analysis of domain function in two cellobiohydrolases by limited proteolysis, Eur J Biochem. 170(3):575-81, 1988.
English Translation of Office Action relating to corresponding RU Application No. 2008123954/10(029060).
Marchler-Bauer, et al., "CD-Search: Protein Domain Annotations on the Fly," Nucleic Acids Research, 2004, vol. 32.
Marchler-Bauer, et al., "CDD: Specific Functional Annotation with the Conserved Domain Database," Nucleic Acids Research, 2009, vol. 37.
Marchler-Bauer, et al,. "CDD: A Conserved Domain Database for the Functional Annotation of Proteins," Nucleic Acids Research, 2011, vol. 39.
Marri, R. "Human Biochemistry," 1993, publishing house "World" Moscow, 1993.
Supplementary European Search Report relating to corresponding EP Application No. 06830936.8.

(Continued)

*Primary Examiner* — Wu-Cheng Winston Shen
(74) *Attorney, Agent, or Firm* — Banner & Witcoff, Ltd.

(57) ABSTRACT

The present invention relates to the production of sugar hydrolysates from cellulosic material. The method may be used e.g. for producing fermentable sugars for the production of bioethanol from lignocellulosic material. Cellulolytic enzymes and their production by recombinant technology is described, as well as uses of the enzymes and enzyme preparations.

29 Claims, 16 Drawing Sheets

OTHER PUBLICATIONS

De Palma-Fernandez, E., et al., "Purification and Characterization of Two β-Glucosidases From the Thermophilic fungus *Thermoascus aurantiacus*," Folia Microbiol. 47 (6), 685-690 (2002).
English Abstract of "Selection of a *Chaetomium* Thermophile Strain Producing Thermostable Cellulases" by Kvachadze, L., et al.
Bernfeld, "Amylases, α and β," Methods in Enzymology, Eds. Colowick and Kaplan, Academic Press, New York, 1:149-158 (1955).
*Acremonium* cellulolyticus, accession No. BD168028.
*Acremonium* thermophilum, accession No. AX657569.
*Aspergillus aculeatus* xylanase, accession No. AR137844.
*Aspergillus aculeatus* xylanase, accession No. AR149839.
*Aspergillus aculeatus* EGV, accession No. AF054512.
*Aspergillus aculeatus* β-glocosidase, accession No. D64088.
*Aspergillus niger* EG, accession No. A62441.
*Aspergillus niger*, accession No. A62445.
*Aspergillus niger* EG, accession No. A69663.
*Aspergillus niger* EG, accession No. AF331518.
*Aspergillus oryzae*, accession No. AX616738.
*Aspergillus sojae* XynXI, accession No. AB040414.
*Aspergillus terreus* fam 10 xyn, DQ087436.
Office Action relating to corresponding RU Application No. 2008123954/10(029060).
*Chaetomium* thermophilum, accession No. AY861347.
*Emericella nidulans*, accession No. AF420020.
*Exidia glandulosa*, accession No. AX657613.
*Exidia glandulosa*, accession No. AX657615.
*Fusarium oxysporum* EGI, accession No. AR012243.
*Gibberella zeae* xylanase, accession No. AY575962.
*Humicola grisea* var thermoidea, EGI, accession No. D63516.
*Humicola grisea* XYNI, accession No. AB001030.
*Humicola grisea* var thermoidea, EGL3, accession No. AB003107.
*Humicola insolens* EG5, accession No. A23635.
*Humicola insolens* endoglucanase, accession No. A35275.
*Humicola insolens* EGI, accession No. AR012244.
*Magnaporthe grisea* XYL5, accession No. AY144348.
*Magnaporthe grisea*, accession No. AY849670.
*Magnaporthe grisea* hypothetical, accession No. XP_364573.
*Magnaporthe grisea* 70-15 hypothetical, accession No. XP_363402.
*Magnaporthe grisea* 70-15 hypothetical, accession No. XM_364947.
*Melanocarpus alboyces* Cel45A, accession No. AJ515703.
*Melanocarpus alboyces* cellulose sequence Cel7A, accession No. AJ515704.
*Myceliophthora thermophila* EGI, accession No. AR071934.
*Myceliophthora thermophila*, accession No. AR094305.
*Neurospora crassa* hypothetical, accession No. XM_330871.
*Neurospora crassa* hypothetical, accession No. XM_324477.
*Oryza sativa*, accession No. AK108948.
*Penicillium chrysogenum* xylanase, accession No. AY583585.
*Scytalidum thermophilum*, accession No. AX657627.
*Talaromyces emersonii* EG, accession No. AF440003.
*Talaromyces emersonii*, accession No. AX172287.
*Talaromyces emersonii*, accession No. AX254752.
*Talaromyces emersonii* xylanase, accession No. AX403831.
*Talaromyces emersonii*, accession No. AY072918.
*Talaromyces emersonii*, accession No. AY081766.
*Thermoascus aurantiacus* XynA, accession No. AF127529.
*Thermoascus aurantiacus*, accession No. AF421954.
*Thermoascus aurantiacus*, accession No. AF478686.
*Thermoascus aurantiacus* EG1 endoglucanase sequence, accession No. AF487830.
*Thermoascus aurantiacus* XYNA sequence, accession No. AJ132635.
*Thermoascus aurantiacus*, accession No. AX657575.
*Chaetomium* thermophilum, accession No. AX657571.
*Thermoascus aurantiacus* EGI, accession No. AY055121.
*Thermoascus aurantiacus*, accession No. AY840982.
*Thermoascus aurantiacus* XynA, accession No. P23360.
*Thielavia australiensis*, accession No. AX657577.
*Thielavia terrestris* EG45, accession No. CQ827970.
*Trichoderma reesei* CBHI/Cel7A, accession No. AR088330.
*Trichoderma reesei* Cel3B, accession No. AY281374.
*Trichoderma viride*, accession No. AY368687.
*Trichophaea saccata*, accession No. AX657607.
*Chatomidiom* pingtunggium, accession No. AX657623.
*Neurospora crassa*, accession No. XM_324308.
Supplementary European Search Report relating to corresponding EP Application No. 06830936.8, (2009).
Gomes, I., et al., "Simultaneous Production of High Activities of Thermostable Endoglucanase and β-glucosidase by the Wild Thermophilic Fungus *Thermoascus aurantiacus*," Appl Microbiol Biotechnol (2000) 53: 461-468.
Voutilainen, S., et al., "Cloning, Expression and Characterization of Novel Thermostable Family 7 Cellobiohydrolases," Biotechnology and Bioengineering, vol. 101, No. 3, Oct. 15, 2008.
De Palma-Fernandez, E., et al., "Purification and Characterization of Two β-Glucosidases From the Thermophilic fungus *Thermoascus aurantiacus*," Folia Microbial. 47 (6), 685-690 (2002).
Uozumi, N., et al., "Secretion of Thermophilic Bacterial Cellobiohydrolase in *Saccharomyces cerevisiae*," Journal of Fermentation and Bioengineering vol. 75, No. 6, 399-404. 1993.
Damaso, M., et al., "Application of Xylanase From *Thermomyces lanuginosus* IOC-4145 for Enzymatic Hydrolysis of Corncob and Sugarcane Bagasse," Applied Biochemistry and Biotechnology, vol. 113-116, 2004.
English Abstract of "Selection of a *Chaetomium* Thermophile Strain Producing Thermostable Cellulases" by Kvachadze, L., et al., (1997).
Badger, "Ethanol from cellulose: a general review," In: Trends in New Crops and New Uses, Janick and Whipkey (eds.), ASHS Press, Alexandria, VA, USA, pp. 17-21 (2002).
Bailey and Nevalainen, "Induction, isolation and testing of stable *Trichoderma reesei* mutants with improved production of solubilizing cellulose," Enz. Microbiol. Technol., 3:153-157 (1981).
Bailey and Poutanen, "Production of xylanases by strains of *Aspergillus*," Application. Microbiol. Biotechnol., 30:5-10 (1989).
Bailey and Linko, "Production of b-galactosidase by *Aspergillus oryzae* in submerged bioreactor cultivation," J. Biotechnol., 16:57-66 (1990).
Bailey et al., "Interlaboratory testing for assay of xylanase activity," J. Biotechnol., 23:257-270 (1992).
Bailey et al., "Hydrolytic properties of two cellulases of *Trichoderma reesei* expressed in yeast," Biotehnol. Application. Biochem., 17:65-76 (1993).
Bernfeld, "Amylases, alpha and beta," Methods in Enzymology, Eds. Colowick and Kaplan, Academic Press, New York, 1:149-158 (1955).
Coen, "The polymerase chain reaction," Curr. Prot. Mol. Biol., Ausubel et al. (eds.), John Wiley & Sons. Inc., Hoboken, USA, Chapter 15, 3 pages, Supplement 73 (2001).
Haakana et al., "Cloning of ellulose genes from Melanocarpus albomyces and their efficient expression in *Trichoderma reesei*," Enz. Microbiol. Technol., 34:159-167 (2004).
Henrissat, "A classification of glycosyl hydrolases based on amino acid sequence similarities," Biochem. J., 280:309-316 (1991).
Henrissat and Bairoch, "New families in the classification of glycosyl hydrolases based on amino acid sequence similarities," Biochem. J., 293:781-788 (1993).
Henrissat et al., "A scheme for designating enzymes that hydrolyse the polysaccharides in the cell wall of plants," FEBS Letters, 425:352-354 (1998).
Hong J. et al., "Cloning of a gene encoding a thermo-stabile endo-β 1,4-glucanase from *Thermoascus aurantiacus* and its expression in yeast," Biotech. Letters, 25:657-661 (2003a).
Hong J. et al., "Cloning of a gene encoding thermostable cellobiohydrolase from *Thermoascus aurantiacus* and its expression in yeast," Application. Microbiol. Biotechnol., 63:42-50 (2003b).
Joutsjoki et al., "Transformation of *Trichoderma reesei* with the Hormoconis resinae glucoamylase P (gamP) gene: production of a heterologous glucoamylase by *Trichoderma reesei*," Curr. Genet., 24:223-228 (1993).
Karhunen T., Mäntylä A., Nevalainen K. M. H. and Suominen P. L. "High frequency one-step gene replacement in *Trichoderma reesei*. I. Endoglucanase I overproduction," Mol. Gen. Genet., 241:515-522 (1993).

Kurabi et al., "Enzymatic hydrolysis of steam-exploded and ethanol organosolv-pretreated Douglas-Fir by novel and commercial fungal cellulases," Appl. Biochem and Biotechn., vol. 121-124:219-229 (2005).
Lever, "A new reaction for colorimetric determination of carbohydrates," Anal. Biochem., 47:276-279 (1972).
Lowry et al., "Protein measuremen with the Folin phenol reagent," J. Biol. Chem., 193:265-275 (1951).
Parry et al., "Biochemical characterization and mode of action of a thermostable endoglucanase purified from *Thermoascus aurantiacus*," Arch. of Biochem. and Biophys., 404:243-253 (2002).
Srisodsuk et al., "Role of the interdomain linker peptide of *Trichoderma reesei* cellobiohydrolase I in its interaction with crystalline cellulose," J. Biol. Chem., Oct. 5, 268(28):20756-20761 (1993).
Sundberg and Poutanen, "Purification and properties of two acetylxylan esterases of *Trichoderma reesei*," Biotechnol. Application. Biochem., 13:1-11 (1991).
Suumäkki et al., "*Trichoderma reesei* cellulases and their core domains in the hydrolysis and modification of chemical pulp," Cellulose, 7:189-209 (2000).
Tenkanen et al., "Two major xylanases of *Trichoderma reesei*," Enzyme Microbiol. Technol., 14:566-574 (1992).
Tomme et al., "Chromatographic separation of cellulolytic enzymes," Methods in Enzymol., 160:187-192 (1988).
Tuohy et al., "Kinetic parameters and mode of action of cellobiohydrolases produced by Talaromyces emersonii," Biochem. Biophys. Acta, 1596:366-380 (2002).
van Petegem et al ., "Atomic resolution structure of major endoglucanase from *Thermoascus aurantiacus*," Biochem. and Biophys. Res. Comm., 296:161-166 (2002).
van Tilbeurgh et al., "Fluorogenic and chromogenic glycosides as substrates and ligands of carbohydrases," Methods Enzymol., 160:45-59 (1988).
Wyman, "Twenty years of trials, tribulations, and research progress in bioethanol technology," Applied Biochemistry and Biotechnology, 91-93:5-21 (2001).
*Acremonium cellulolyticus*, accession No. BD168028, (2003).
*Acremonium thermophilum*, accession No. AX657569, (2003).
*Aspergillus aculeatus* xylanase, accession No. AR137844, (2001).
*Aspergillus aculeatus* xylanase, accession No. AR149839, (2001).
*Aspergillus aculeatus* EGV, accession No. AF054512, (1998).
*Aspergillus aculeatus* β-glucosidase, accession No. D64088, (2000).
*Aspergillus niger* EG, accession No. A62441, (1998).
*Aspergillus niger*, accession No. A62445, (1998).
*Aspergillus niger* EG, accession No. A69663, (1999).
*Aspergillus niger* EG, accession No. AF331518, (2007).
*Aspergillus oryzae*, accession No. AX616738, (2003).
*Aspergillus sojae* XynXl, accession No. AB040414, (2009).
*Aspergillus terreus* fam 10 xyn, DQ087436, (2006).
Office Action relating to corresponding RU Application No. 2008123954/10(029060), (2010).
Office Action relating to corresponding EP Application No. 06830936.8 issued Oct. 14, 2011.
Carrard, et al., "Cellulose-binding Domains Promote Hydrolysis of Different Sites on Crystalline Cellulose," PNAS, Sep. 12, 2000, vol. 97, No. 19.
Gundllapalli Moses, et al., "Domain Engineering of *Saccharomyces cerevisiae* Exoglucanases," Biotechnology Letters (2005) 27: 355-362.
Ito, et al., "Improvement of Cellulose-Degrading Ability of a Yeast Strain Displaying *Trichoderma Reesei* Endoglucanase II by Recombination of Cellulose-Binding Domains," Biotechnol. Prog. 2004, 20, 688-691.
*Chaetomium thermophilum*, accession No. AY861347, (2005).
*Emericella nidulans*, accession No. AF420020, (2003).
*Exidia glandulosa*, accession No. AX657613, (2003).
*Exidia glandulosa*, accession No. AX657615, (2003).
*Fusarium oxysporum* EGI, accession No. AR012243, (1998).
*Gibberella zeae* xylanase, accession No. AY575962, (2005).
*Humicola grisea var thermoidea*, EGI, accession No. D63516, (2005).
*Humicola grisea* XYNI, accession No. AB001030, (2005).
*Humicola grisea var thermoidea*, EGL3, accession No. AB003107, (2002).
*Humicola insolens* EG5, accession No. A23635, (1995).
*Humicola insolens* endoglucanase, accession No. A35275, (2002).
*Humicola insolens* EGI, accession No. AR012244, (1998).
*Magnaporthe grisea* XYL5, accession No. AY144348, (2002).
*Magnaporthe grisea*, accession No. AY849670, (2005).
*Magnaporthe grisea* hypothetical, accession No. XP_364573, (2008).
*Magnaporthe grisea* 70-15 hypothetical, accession No. XP_363402, (2008).
*Magnaporthe grisea* 70-15 hypothetical, accession No. XM_364947, (2006).
Melanocarpus alboyces Cel45A, accession No. AJ515703, (2005).
Melanocarpus alboyces cellulose sequence Cel7A, accession No. AJ515704, (2005).
Myceliophthora thermophila EGI, accession No. AR071934, (2000).
Myceliophthora thermophila, accession No. AR094305, (2000).
*Neurospora crassa* hypothetical, accession No. XM_330871, (2006).
*Neurospora crassa* hypothetical, accession No. XM_324477, (2006).
*Oryza sativa*, accession No. AK108948, (2008).
*Penicillium chrysogenum* xylanase, accession No. AY583585, (2006).
Scytalidum thermophilum, accession No. AX657627, (2003).
Talaromyces emersonii EG, accession No. AF440003, (2002).
Talaromyces emersonii, accession No. AX172287, (2001).
Talaromyces emersonii, accession No. AX254752, (2001).
Talaromyces emersonii xylanase, accession No. AX403831, (2002).
Talaromyces emersonii, accession No. AY072918, (2005).
Talaromyces emersonii, accession No. AY081766, (2002).
*Thermoascus aurantiacus* XynA, accession No. AF127529, (2000).
*Thermoascus aurantiacus*, accession No. AF421954, (2007).
*Thermoascus aurantiacus*, accession No. AF478686, (2003).
*Thermoascus aurantiacus* EG1 endoglucanase sequence, accession No. AF487830, (2003).
*Thermoascus aurantiacus* XYNA sequence, accession No. AJ132635, (2006).
*Thermoascus aurantiacus*, accession No. AX657575, (2003).
*Chaetomium thermophilum*, accession No. AX657571, (2003).
*Thermoascus aurantiacus* EGI, accession No. AY055121, (2004).
*Thermoascus aurantiacus*, accession No. AY840982, (2004).
*Thermoascus aurantiacus* XynA, accession No. P23360, (2005).
*Thielavia australiensis*, accession No. AX657577, (2003).
*Thielavia terrestris* EG45, accession No. CQ827970, (2004).
*Trichoderma reesei* CBHI/Cel7A, accession No. AR088330, (2000).
*Trichoderma reesei* Cel3B, accession No. AY281374, (2007).
*Trichoderma viride*, accession No. AY368687, (2003).
*Trichophaea saccata*, accession No. AX657607, (2003).
*Chaetomidium pingtungium*, accession No. AX657623, (2003).
*Neurospora crassa*, accession No. XM_324308, (2006).
Extended European Search Report relating to corresponding EP Application No. 12151850.0, issued Apr. 16, 2012.
Extended European Search Report relating to corresponding EP Application No. 12151852.6, issued Apr. 16, 2012.
BIOSIS, Database Accession No. PREV199800478288, Jun. 1996.
UNIPROT, Database Accession No. Q8TGI8, Jun. 1, 2002.
EM_EST, Database Accession No. CK917207, Mar. 12, 2004.
EM_HGT, Database Accession No. Ay849670, Feb. 20, 2005.
EM_EST, Database Accession No. DV547597, Oct. 28, 2005.
Hong, et al., "Unusual Hydrophobic Linker Region of β-Glucosidase (BGLII) from *Thermoascus aurantiacus* is Required for Hyper-Activation by Organic Solvents," Appl. Microbiol. Biotechnol. (2006) 73: 80-88.
Hong, et al., "Cloning and Functional Expression of Thermostable β-Glucosidase Gene from *Thermoascus aurantiacus*," Appl. Microbiol. Biotechnol. (2007) 73: 1331-1339.
Khandke, et al., "Purification of Xylanase, β-Glucosidase, Endocellulase, and Exocellulase from a Thermophilic Fungus, *Thermoascus aurantiacus*," Archives of Biochemistry and Biophysics, vol. 74, No. 2, Nov. 1, 1989, 491-500.

Leite, et al., "Characterization and Comparison of Thermostability of Purified β-Glucosidases from a Mesophilic *Aureobasidium pullulans* and a Thermophilic *Thermoascus aurantiacus*," Process Biochemistry, 42 (2007) 1101-1106.

Leite, et al., "Production and Characteristics Comparison of Crude β-Glucosidases Produced by Microorganisms *Thermoascus aurantiacus* e *Aureobasidium pullulans* in Agriculture Wastes," Enzyme and Microbiol. Technology, 43 (2008) 391-395.

Murray, et al., "Expression in *Trichoderma reesei* and Characterisation of a Thermostable Family 3 β-Glucosidase from the Moderately Thermophilic Fungus Talaromyces Emersonii," Protein Expression and Purification, 28 (2004) 248-257.

Perry, et al., "Biochemical Characterization and Mechanism of Action of a Thermostable β-Glucosidase Purified from *Thermoascus aurantiacus*," Biochem. J. (2001) 353, 117-127.

Tong, et al., "Purification and Properties of the Cellulases from the Thermophilic Fungus *Thermoascus aurantiacus*," Biochem. Jnl. (1980) 191, 83-94.

Office Action relating to corresponding AU Application No. 2006326963 issued Dec. 9, 2011.

English Abstract of JP 08-056663.

* cited by examiner

US 8,409,836 B2

TREATMENT OF CELLULOSIC MATERIAL AND ENZYMES USEFUL THEREIN

RELATED APPLICATIONS

This application is a divisional of U.S. application Ser. No. 12/141,976, filed Jun. 19, 2008, which is a continuation of PCT application no. PCT/FI2006/050558, designating the United States and filed Dec. 15, 2006; which claims the benefit of the filing date of Finnish application no. 20051318, filed Dec. 22, 2005; and U.S. application No. 60/753,258, filed Dec. 22, 2005; each of which is hereby incorporated herein by reference in its entirety for all purposes.

FIELD

The present invention relates to the production of sugar hydrolysates from cellulosic material. More precisely the invention relates to production of fermentable sugars from lignocellulosic material by enzymatic conversion. The fermentable sugars are useful e.g. in the production of bioethanol, or for other purposes. In particular the invention is directed to a method for treating cellulosic material with cellobiohydrolase, endoglucanase, beta-glucosidase, and optionally xylanase, and to enzyme preparations and the uses thereof. The invention is further directed to novel cellulolytic polypeptides, polynucleotides encoding them, and to vectors and host cells containing the polynucleotides. Still further the invention is directed to uses of the polypeptides and to a method of preparing them.

BACKGROUND

Sugar hydrolysates can be used for microbial production of a variety of fine chemicals or biopolymers, such as organic acids e.g. lactic acid, or ethanol or other alcohols e.g. n-butanol, 1,3-propanediol, or polyhydroxyalkanoates (PHAs). The sugar hydrolysates may also serve as raw material for other non-microbial processes, e.g., for enrichment, isolation and purification of high value sugars or various polymerization processes. One of the major uses of the sugar hydrolysates is in the production of biofuels. The production of bioethanol and/or other chemicals may take place in an integrated process in a biorefinery (Wyman 2001).

Limited resources of fossil fuels, and increasing amounts of $CO_2$ released from them and causing the greenhouse phenomenon have raised a need for using biomass as a renewable and clean source of energy. One promising, alternative technology is the production of biofuels i.e. ethanol from cellulosic materials. In the transportation sector biofuels are for the time being the only option, which could reduce the $CO_2$ emissions by an order of magnitude. The ethanol can be used in existing vehicles and distribution systems and thus it does not require expensive infrastructure investments. Sugars derived from lignocellulosic renewable raw materials can also be used as raw materials for a variety of chemical products that can replace oil-based chemicals.

Most of the carbohydrates in plants are in the form of lignocellulose, which essentially consists of cellulose, hemicellulose, pectin and lignin. In a lignocellulose-to-ethanol process the lignocellulosic material is first pretreated either chemically or physically to make the cellulose fraction more accessible to hydrolysis. The cellulose fraction is then hydrolysed to obtain sugars that can be fermented by yeast into ethanol. Lignin is obtained as a main co-product that may be used as a solid fuel.

Bioethanol production costs are high and the energy output is low, and there is continuous research for making the process more economical. Enzymatic hydrolysis is considered the most promising technology for converting cellulosic biomass into fermentable sugars. However, enzymatic hydrolysis is used only to a limited amount at industrial scale, and especially when using strongly lignified material such as wood or agricultural waste the technology is not satisfactory. The cost of the enzymatic step is one of the major economical factors of the process. Efforts have been made to improve the efficiency of the enzymatic hydrolysis of the cellulosic material (Badger 2002).

US 2002/019 2774 A1 describes a continuous process for converting solid lignocellulosic biomass into combustible fuel products. After pretreatment by wet oxidation or steam explosion the biomass is partially separated into cellulose, hemicellulose and lignin, and is then subjected to partial hydrolysis using one or more carbohydrase enzymes (EC 3.2). Celluclast™, a commercial product by Novo Nordisk A/S containing cellulase and xylanase activities is given as an example.

US 2004/000 5674 A1 describes novel enzyme mixtures that can be used directly on lignocellulose substrate, whereby toxic waste products formed during pretreatment processes may be avoided, and energy may be saved. The synergistic enzyme mixture contains a cellulase and an auxiliary enzyme such as cellulase, xylanase, ligninase, amylase, protease, lipidase or glucuronidase, or any combination thereof. Cellulase in considered to include endoglucanase (EG), beta-glucosidase (BG) and cellobiohydrolase (CBH). The examples illustrate the use of a mixture of *Trichoderma* xylanase and cellulase preparations.

Kurabi et al. (2005) have investigated enzymatic hydrolysis of steam-exploded and ethanol organosolv-pretreated Douglas-fir by novel and commercial fungal cellulases. They tested two commercial *Trichoderma reesei* cellulase preparations, and two novel preparations produced by mutant strains of *Trichoderma* sp. and *Penicillium* sp. The *Trichoderma* sp. preparation showed significantly better performance than the other preparations. The better performance was believed to be at least partly due to a significantly higher beta-glucosidase activity, which relieves product inhibition of cellobiohydrolase and endoglucanase.

US 2004/005 3373 A1 pertains a method of converting cellulose to glucose by treating a pretreated lignocellulosic substrate with an enzyme mixture comprising cellulase and a modified cellobiohydrolase I (CBHI). The CBHI has been modified by inactivating its cellulose binding domain (CBD). Advantages of CBHI modification are e.g. better recovery and higher hydrolysis rate with high substrate concentration. The cellulase is selected from the group consisting of EG, CBH and BG. The CBHI is preferably obtained from *Trichoderma*.

US 2005/016 4355 A1 describes a method for degrading lignocellulosic material with one or more cellulolytic enzymes in the presence of at least one surfactant. Additional enzymes such as hemicellulases, esterase, peroxidase, protease, laccase or mixture thereof may also be used. The presence of surfactant increases the degradation of lignocellulosic material compared to the absence of surfactant. The cellulolytic enzymes may be any enzyme involved in the degradation of lignocellulose including CBH, EG, and BG.

There is a huge number of publications disclosing various cellulases and hemicellulases.

Cellobiohydrolases (CBHs) are disclosed e.g. in WO 03/000 941, which relates to CBHI enzymes obtained from various fungi. No physiological properties of the enzymes are provided, nor any examples of their uses. Hong et al. (2003b) characterizes CBHI of *Thermoascus aurantiacus* produced in yeast. Applications of the enzyme are not described. Tuohy et al. (2002) describe three forms of cellobiohydrolases from *Talaromyces emersonii*.

Endoglucanases of the cel5 family (EGs fam 5) are described e.g. in WO 03/062 409, which relates to compositions comprising at least two thermostable enzymes for use in feed applications. Hong et al. (2003a) describe production of thermostable endo-β-1,4-glucanase from *T. aurantiacus* in yeast. No applications are explained. WO 01/70998 relates to β-glucanases from *Talaromyces*. They also describe β-glucanases from *Talaromyces emersonii*. Food, feed, beverage, brewing, and detergent applications are discussed. Lignocellulose hydrolysis is not mentioned. WO 98/06 858 describes beta-1,4-endoglucanase from *Aspergillus niger* and discusses feed and food applications of the enzyme. WO 97/13853 describes methods for screening DNA fragments encoding enzymes in cDNA libraries. The cDNA library is of yeast or fungal origin, preferably from *Aspergillus*. The enzyme is preferably a cellulase. Van Petegem et al. (2002) describe the 3D-structure of an endoglucanase of the cel5 family from *Thermoascus aurantiacus*. Parry et al. (2002) describe the mode of action of an endoglucanase of the cel5 family from *Thermoascus aurantiacus*.

Endoglucanases of the cel7 family (EGs fam 7) are disclosed e.g. in U.S. Pat. No. 5,912,157, which pertains *Myceliphthora* endoglucanase and its homologues and applications thereof in detergent, textile, and pulp. U.S. Pat. No. 6,071,735 describes cellulases exhibiting high endoglucanase activity in alkaline conditions. Uses as detergent, in pulp and paper, and textile applications are discussed. Bioethanol is not mentioned. U.S. Pat. No. 5,763,254 discloses enzymes degrading cellulose/hemicellulose and having conserved amino acid residues in CBD.

Endoglucanases of the cel45 family (EGs fam 45) are described e.g. in U.S. Pat. No. 6,001,639, which relates to enzymes having endoglucanase activity and having two conserved amino acid sequences. Uses in textile, detergent, and pulp and paper applications are generally discussed and treating of lignocellulosic material is mentioned but no examples are given. WO 2004/053039 is directed to detergent applications of endoglucanases. U.S. Pat. No. 5,958,082 discloses the use of endoglucanase, especially from *Thielavia terrestris* in textile application. EP 0495258 relates to detergent compositions containing *Humicola* cellulase. U.S. Pat. No. 5,948,672 describes a cellulase preparation containing endoglucanase, especially from *Humicola* and its use in textile and pulp applications. Lignocellulose hydrolysis is not mentioned.

A small amount of beta-glucosidase (BG) enhances hydrolysis of biomass to glucose by hydrolyzing cellobiose produced by cellobiohydrolases. Cellobiose conversion to glucose is usually the major rate-limiting step. Beta-glucosidases are disclosed e.g. in US 2005/021 4920, which relates to BG from *Aspergillus fumigatus*. The enzyme has been produced in *Aspergillus oryzae* and *Trichoderma reesei*. Use of the enzyme in degradation of biomass or detergent applications is generally discussed but not exemplified. WO02/095 014 describes an *Aspergillus oryzae* enzyme having cellobiase activity. Use in the production of ethanol from biomass is generally discussed but not exemplified. WO2005/074656 discloses polypeptides having cellulolytic enhancing activity derived e.g. from *T. aurantiacus; A. fumigatus; T. terrestris* and *T. aurantiacus*. WO02/26979 discloses enzymatic processing of plant material. U.S. Pat. No. 6,022,725 describes cloning and amplification of the beta-glucosidase gene of *Trichoderma reesei*, and U.S. Pat. No. 6,103,464 describes a method for detecting DNA encoding a beta-glucosidase from a filamentous fungus. No application examples are given.

Xylanases are described e.g. in FR2786784, which relates to a heat-stable xylanase, useful e.g. in treating animal feed and in bread making The enzyme is derived from a thermophilic fungus, particularly of the genus *Thermoascus*.

U.S. Pat. No. 6,197,564 describes enzymes having xylanase activity, and obtained from *Aspergillus aculeatus*. Their application in baking is exemplified. WO 02/24926 relates to *Talaromyces* xylanases. Feed and baking examples are given. WO01/42433 discloses thermostable xylanase from *Talaromyces emersonii* for use in food and feed applications.

The best-investigated and most widely applied cellulolytic enzymes of fungal origin have been derived from *Trichoderma reesei* (the anamorph of *Hypocrea jecorina*). Consequently also most of the commercially available fungal cellulases are derived from *Trichoderma reesei*. However, the majority of cellulases from less known fungi have not been applied in processes of practical importance such as in degrading cellulosic material, including lignocellulose.

There is a continuous need for new methods of degrading cellulosic substrates, in particular lignocellulosic substrates, and for new enzymes and enzyme mixtures, which enhance the efficiency of the degradation. There is also a need for processes and enzymes, which work at high temperatures, thus enabling the use of high biomass consistency and leading to high sugar and ethanol concentrations. This approach may lead to significant saving in energy and investments costs. The high temperature also decreases the risk of contamination during hydrolysis. The present invention aims to meet at least part of these needs.

BRIEF DESCRIPTION

It has now surprisingly been found that cellulolytic enzymes, and especially cellobiohydrolases obtainable from *Thermoascus aurantiacus, Acremonium thermophilum*, or *Chaetomium thermophilum* are particularly useful in hydrolyzing cellulosic material. In addition to cellobiohydrolases these fungi also have endoglucanases, betaglucosidases and xylanases that are very suitable for degrading cellulosic material. The enzymes are kinetically very effective over a broad range of temperatures, and although they have high activity at high temperatures, they are also very efficient at standard hydrolysis temperatures. This makes them extremely well suited for varying cellulosic substrate hydrolysis processes carried out both at conventional temperatures and at elevated temperatures.

The present invention provides a method for treating cellulosic material with cellobiohydrolase, endoglucanase and beta-glucosidase, whereby said cellobiohydrolase comprises an amino acid sequence having at least 80% identity to SEQ ID NO: 2, 4, 6 or 8, or to an enzymatically active fragment thereof.

The invention further provides an enzyme preparation comprising cellobiohydrolase, endoglucanase and beta-glucosidase, wherein said cellobiohydrolase comprises an amino acid sequence having at least 80% identity to SEQ ID NO: 2, 4, 6 or 8, or to an enzymatically active fragment thereof.

The use of said enzyme preparation for degrading cellulosic material is also provided, as well as the use of said method in a process for preparing ethanol from cellulosic material.

The invention is also directed to a polypeptide comprising a fragment having cellulolytic activity and being selected from the group consisting of:
  a) a polypeptide comprising an amino acid sequence having at least 66% identity to SEQ ID NO:4, 79% identity to SEQ ID NO:6, 78% identity to SEQ ID NO:12, 68% identity to SEQ ID NO:14, 72% identity to SEQ ID NO:16, 68% identity to SEQ ID NO:20, 74% identity to SEQ ID NO:22 or 24, or 78% identity to SEQ ID NO:26;

b) a variant of a) comprising a fragment having cellulolytic activity; and c) a fragment of a) or b) having cellulolytic activity.

One further object of the invention is an isolated polynucleotide selected from the group consisting of:

a) a nucleotide sequence of SEQ ID NO: 3, 5, 11, 13, 15, 19, 21, 23 or 25, or a sequence encoding a polypeptide of claim 35;

b) a complementary strand of a)

c) a fragment of a) or b) comprising at least 20 nucleotides; and d) a sequence that is degenerate as a result of the genetic code to any one of the sequences as defined in a), b) or c).

The invention still further provides a vector, which comprises said polynucleotide as a heterologous sequence, and a host cell comprising said vector. *Escherichia coli* strains having accession number DSM 16728, DSM 16729, DSM 17324, DSM 17323, DSM 17729, DSM 16726, DSM 16725, DSM 17325 or DSM 17667 are also included in the invention.

Other objects of the invention are enzyme preparations comprising at least one of the novel polypeptides, and the use of said polypeptide or enzyme preparation in fuel, textile, detergent, pulp and paper, food, feed or beverage industry.

Further provided is a method for preparing a polypeptide comprising a fragment having cellulolytic activity and being selected from the group consisting of:

a) a polypeptide comprising an amino acid sequence having at least 66% identity to SEQ ID NO:4, 79% identity to SEQ ID NO:6, 78% identity to SEQ ID NO:12, 68% identity to SEQ ID NO:14, 72% identity to SEQ ID NO:16, 68% identity to SEQ ID NO:20, 74% identity to SEQ ID NO:22 or 24, or 78% identity to SEQ ID NO:26;

b) a variant of a) comprising a fragment having cellulolytic activity; and c) a fragment of a) or b) having cellulolytic activity, said method comprising transforming a host cell with a vector encoding said polypeptide, and culturing said host cell under conditions enabling expression of said polypeptide, and optionally recovering and purifying the polypeptide produced.

Still further provided is a method of treating cellulosic material with a spent culture medium of at least one microorganism capable of producing a polypeptide as defined above, wherein the method comprises reacting the cellulosic material with the spent culture medium to obtain hydrolysed cellulosic material.

Specific embodiments of the invention are set forth in the dependent claims.

Other objects, details and advantages of the present invention will become apparent from the following drawings, detailed description and examples.

DETAILED DESCRIPTION

Figure 1A:
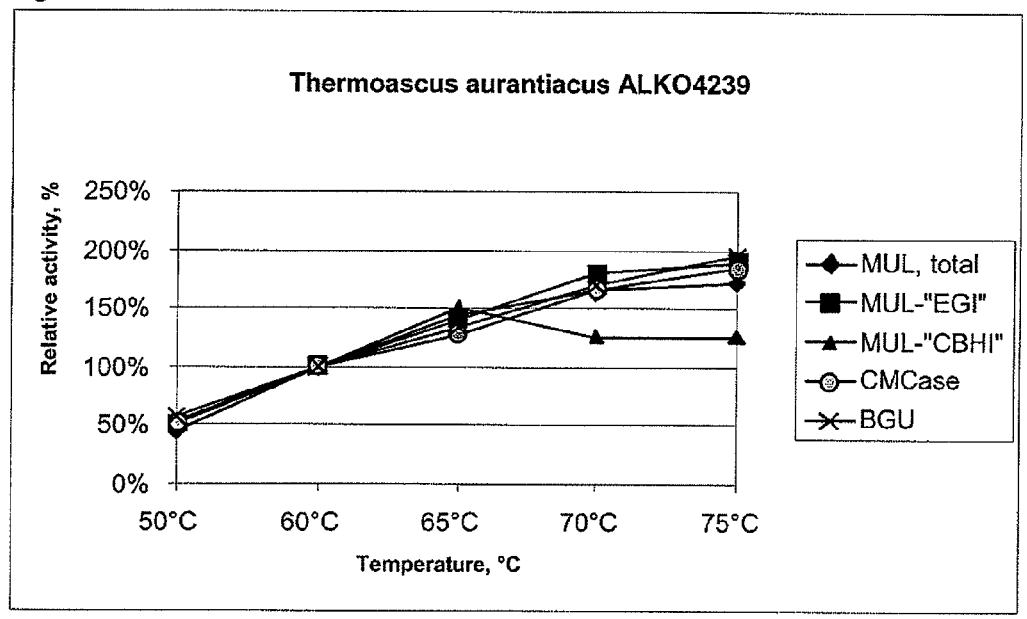
FIG. 1. Temperature dependencies of the cellulase and beta-glucosidase activities in the supernatants of the tested six fungal strains. The incubation time in the assay was 60 min at the given temperature, the assay pH was 5.0 (MUL-activity) or 4.8 (CMCase or BGU). Activity obtained at 60° C. is set as the relative activity of 100%. A) *Thermoascus aurantiacus* ALKO4239, B) *Thermoascus aurantiacus* ALKO4242, C) *Acremonium thermophilum* ALKO4245, D) *Talaromyces thermophilus* ALKO4246, E) *Chaetomium thermophilum* ALKO4261, F) *Chaetomium thermophilum* ALKO4265.
Figure 1B:
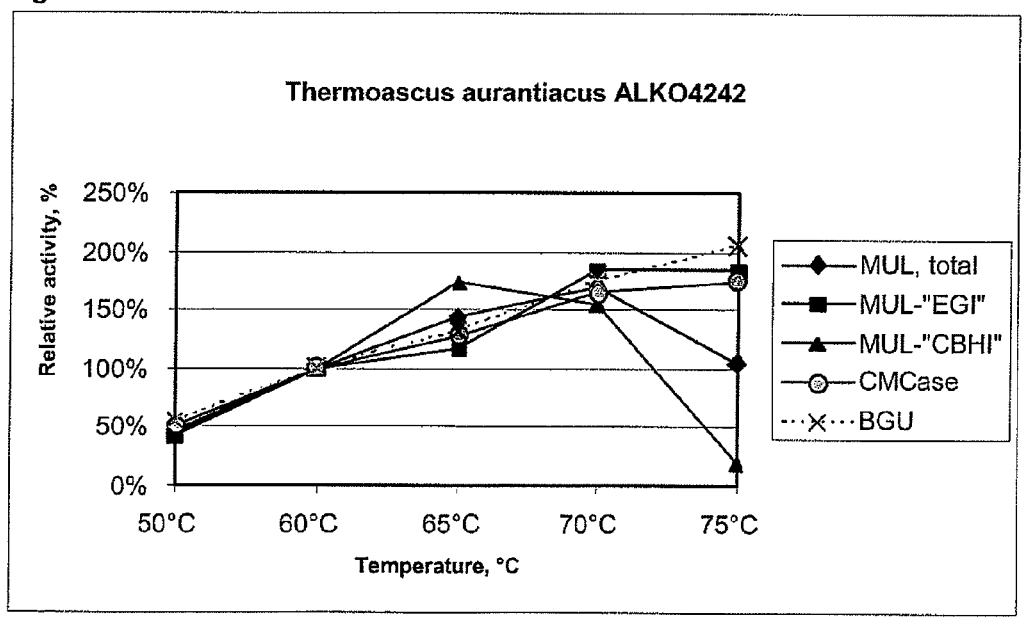
Figure 1C:
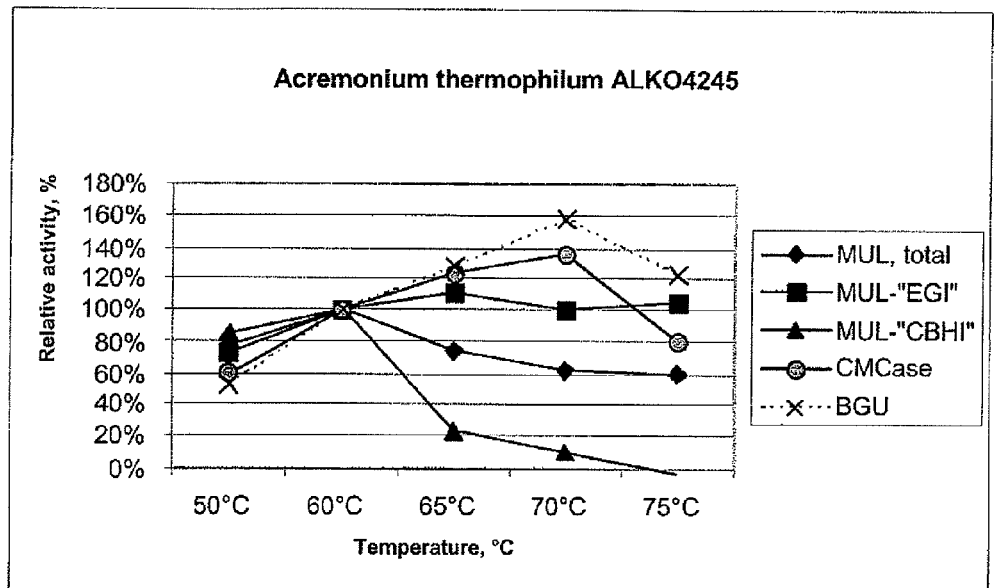
Figure 1D:
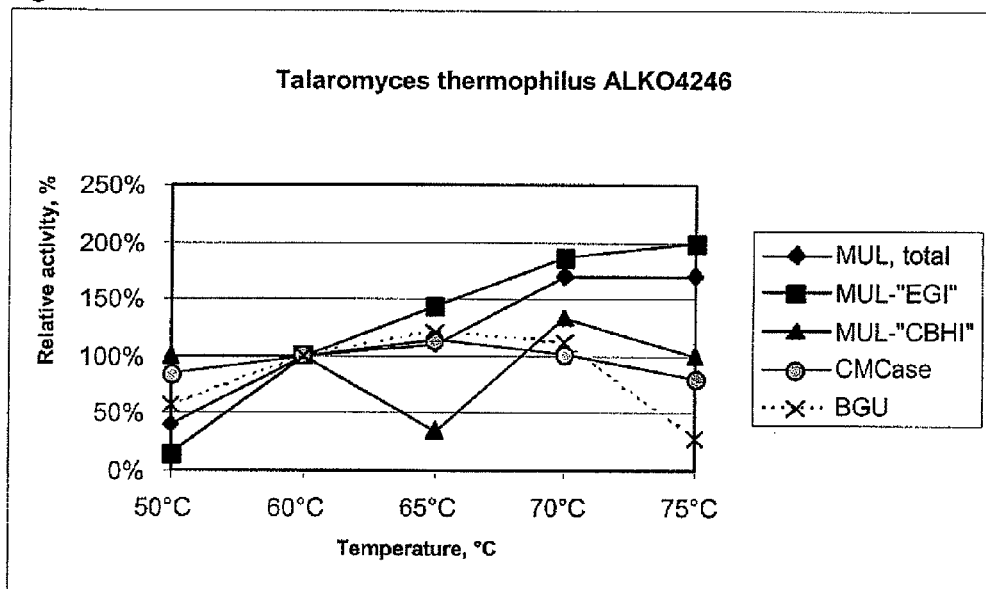
Figure 1E:
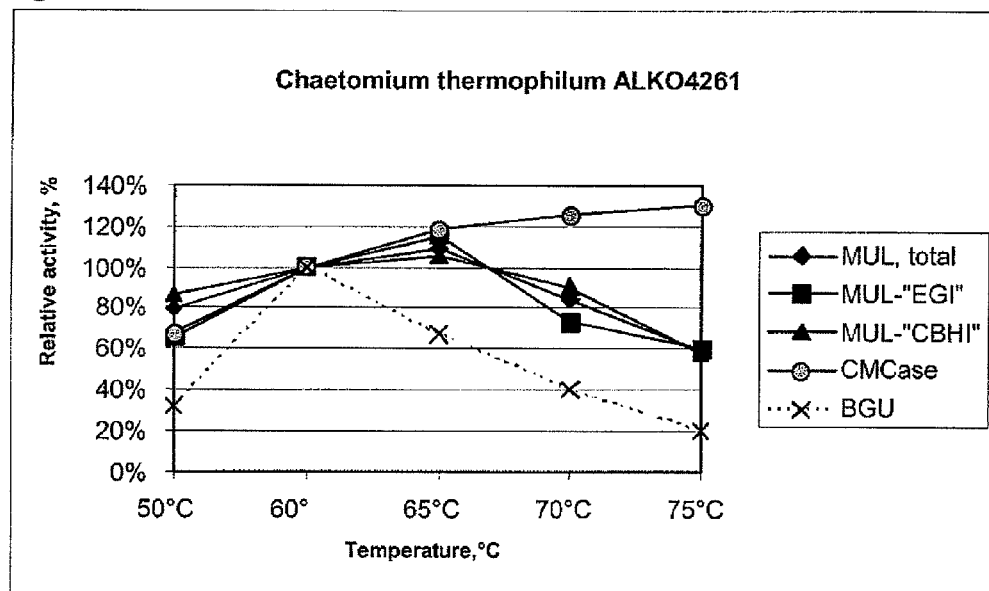
Figure 1F:
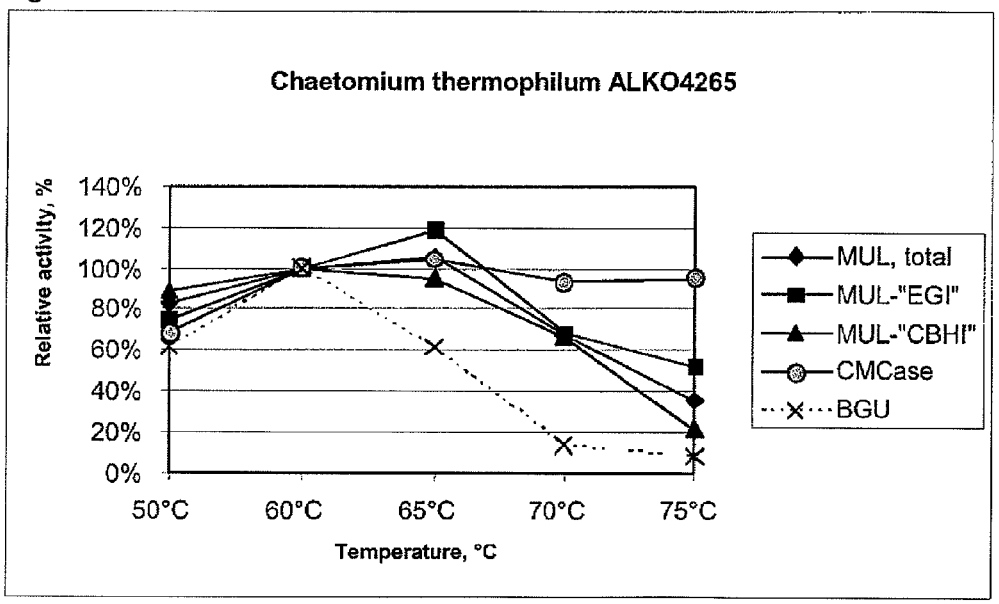

Cellulose is the major structural component of higher plants. It provides plant cells with high tensile strength helping them to resist mechanical stress and osmotic pressure. Cellulose is a β-1,4-glucan composed of linear chains of glucose residues joined by β-1,4-glycosidic linkages. Cellobiose is the smallest repeating unit of cellulose. In cell walls cellulose is packed in variously oriented sheets, which are embedded in a matrix of hemicellulose and lignin. Hemicellulose is a heterogeneous group of carbohydrate polymers containing mainly different glucans, xylans and mannans. Hemicellulose consists of a linear backbone with β-1,4-linked residues substituted with short side chains usually containing acetyl, glucuronyl, arabinosyl and galactosyl. Hemicellulose can be chemically cross-linked to lignin. Lignin is a complex cross-linked polymer of variously substituted p-hydroxyphenylpropane units that provides strength to the cell wall to withstand mechanical stress, and it also protects cellulose from enzymatic hydrolysis.

Lignocellulose is a combination of cellulose and hemicellulose and polymers of phenol propanol units and lignin. It is physically hard, dense, and inaccessible and the most abundant biochemical material in the biosphere. Lignocellulose containing materials are for example: hardwood and softwood chips, wood pulp, sawdust and forestry and wood industrial waste; agricultural biomass as cereal straws, sugar beet pulp, corn stover and cobs, sugar cane bagasse, stems, leaves, hulls, husks, and the like; waste products as municipal solid waste, newspaper and waste office paper, milling waste of e.g. grains; dedicated energy crops (e.g., willow, poplar, switchgrass or reed canarygrass, and the like). Preferred examples are corn stover, switchgrass, cereal straw, sugarcane bagasse and wood derived materials.

"Cellulosic material" as used herein, relates to any material comprising cellulose, hemicellulose and/or lignocellulose as a significant component. "Lignocellulosic material" means any material comprising lignocellulose. Such materials are e.g. plant materials such as wood including softwood and hardwood, herbaceous crops, agricultural residues, pulp and paper residues, waste paper, wastes of food and feed industry etc. Textile fibres such as cotton, fibres derived from cotton, linen, hemp, jute and man made cellulosic fibres as modal, viscose, lyocel are specific examples of cellulosic materials.

Cellulosic material is degraded in nature by a number of various organisms including bacteria and fungi. Cellulose is typically degraded by different cellulases acting sequentially or simultaneously. The biological conversion of cellulose to glucose generally requires three types of hydrolytic enzymes: (1) Endoglucanases which cut internal beta-1,4-glucosidic bonds; (2) Exocellobiohydrolases that cut the dissaccharide cellobiose from the end of the cellulose polymer chain; (3) Beta-1,4-glucosidases which hydrolyze the cellobiose and other short cello-oligosaccharides to glucose. In other words the three major groups of cellulases are cellobiohydrolases (CBH), endoglucanases (EG) and beta-glucosidases (BG).

Degradation of more complex cellulose containing substrates requires a broad range of various enzymes. For example lignocellulose is degraded by hemicellulases, like xylanases and mannanases. Hemicellulase is an enzyme hydrolysing hemicellulose.

"Cellulolytic enzymes" are enzymes having "cellulolytic activity," which means that they are capable of hydrolysing cellulosic substrates or derivatives thereof into smaller saccharides. Cellulolytic enzymes thus include both cellulases and hemicellulases. Cellulases as used herein include cellobiohydrolase, endoglucanase and beta-glucosidase.

*T. reesei* has a well known and effective cellulase system containing two CBHs, two major and several minor EGs and BGs. *T. reesei* CBHI (Cel7A) cuts sugar from the reducing end of the cellulose chain, has a C-terminal cellulose binding domain (CBD) and may constitute up to 60% of the total secreted protein. *T. reesei* CBHII (Cel6A) cuts sugar from the non-reducing end of the cellulose chain, has an N-terminal cellulose binding domain and may constitute up to 20% of the total secreted protein. Endoglucanases EGI (Cel7B), and EGV (Cel45A) have a CBD in their C-terminus, EGII (Cel5A) has an N-terminal CBD and EGIII (Cel12A) does not have a cellulose binding domain at all. CBHI, CBHII, EGI and EGII are so called "major cellulases" of *Trichoderma* comprising together 80-90% of total secreted proteins. It is known to a man skilled in the art that an enzyme may be active on several substrates and enzymatic activities can be measured using different substrates, methods and conditions. Identifying different cellulolytic activities is discussed for example in van Tilbeurgh et al. 1988.

In addition to a catalytic domain/core expressing cellulolytic activity cellulolytic enzymes may comprise one or more cellulose binding domains (CBDs), also named as carbohydrate binding domains/modules (CBD/CBM), which can be located either at the N- or C-terminus of the catalytic domain. CBDs have carbohydrate-binding activity and they mediate the binding of the cellulase to crystalline cellulose but have little or no effect on cellulase hydrolytic activity of the enzyme on soluble substrates. These two domains are typically connected via a flexible and highly glycosylated linker region.

"Cellobiohydrolase" or "CBH" as used herein refers to enzymes that cleave cellulose from the end of the glucose chain and produce mainly cellobiose. They are also called 1,4-beta-D-glucan cellobiohydrolases or cellulose 1,4-beta-cellobiosidases. They hydrolyze the 1,4-beta-D-glucosidic linkages from the reducing or non-reducing ends of a polymer containing said linkages, such as cellulose, whereby cellobiose is released. Two different CBHs have been isolated from *Trichoderma reesei*, CBHI and CBHII. They have a modular structure consisting of a catalytic domain linked to a cellulose-binding domain (CBD). There are also cellobiohydrolases in nature that lack CBD.

"Endoglucanase" or "EG" refers to enzymes that cut internal glycosidic bonds of the cellulose chain. They are classified as EC 3.2.1.4. They are 1,4-beta-D-glucan 4-glucanohydrolases and catalyze endohydrolysis of 1,4-beta-D-glycosidic linkages in polymers of glucose such as cellulose and derivatives thereof. Some naturally occurring endoglucanases have a cellulose binding domain, while others do not. Some endoglucanases have also xylanase activity (Bailey et al., 1993).

"Beta-glucosidase" or "BG" or "βG" refers to enzymes that degrade small soluble oligosaccharides including cellobiose to glucose. They are classified as EC 3.2.1.21. They are beta-D-glucoside glucohydrolases, which typically catalyze the hydrolysis of terminal non-reducing beta-D-glucose residues. These enzymes recognize oligosaccharides of glucose. Typical substrates are cellobiose and cellotriose. Cellobiose is an inhibitor of cellobiohydrolases, wherefore the degradation of cellobiose is important to overcome end-product inhibition of cellobiohydrolases.

Xylanases are enzymes that are capable of recognizing and hydrolyzing hemicellulose. They include both exohydrolytic and endohydrolytic enzymes. Typically they have endo-1,4-beta-xylanase (EC 3.2.1.8) or beta-D-xylosidase (EC 3.2.1.37) activity that breaks down hemicellulose to xylose. "Xylanase" or "Xyn" in connection with the present invention refers especially to an enzyme classified as EC 3.2.1.8 hydrolyzing xylose polymers of lignocellulosic substrate or purified xylan.

In addition to this cellulases can be classified to various glycosyl hydrolase families according their primary sequence, supported by analysis of the three dimensional structure of some members of the family (Henrissat 1991, Henrissat and Bairoch 1993, 1996). Some glycosyl hydrolases are multifunctional enzymes that contain catalytic domains that belong to different glycosylhydrolase families. Family 3 consists of beta-glucosidases (EC 3.2.1.21) such as Ta BG_81, At BG_101 and Ct BG_76 described herein. Family 5 (formerly known as celA) consists mainly of endoglucanases (EC 3.2.1.4) such as Ta EG_28 described herein. Family 7 (formerly cellulase family celC) contains endoglucanases (EC 3.2.1.4) and cellobiohydrolases (EC 3.2.1.91) such as Ct EG_54, Ta CBH, At CBH_A, At CBH_C and Ct CBH described herein. Family 10 (formerly celF) consists mainly of xylanases (EC 3.2.1.8) such as Ta XYN_30 and At XYN_60 described herein. Family 45 (formerly celK) contains endoglucanases (EC 3.2.1.4) such as At EG_40 and At EG_40_like described herein.

Cellulolytic enzymes useful for hydrolyzing cellulosic material are obtainable from *Thermoascus aurantiacus*, *Acremonium thermophilum*, or *Chaetomium thermophilum*. "Obtainable from" means that they can be obtained from said species, but it does not exclude the possibility of obtaining them from other sources. In other words they may originate from any organism including plants. Preferably they originate from microorganisms e.g. bacteria or fungi. The bacteria may be for example from a genus selected from *Bacillus*, *Azospirillum* and *Streptomyces*. More preferably the enzyme originates from fungi (including filamentous fungi and yeasts), for example from a genus selected from the group consisting of *Thermoascus*, *Acremonium*, *Chaetomium*, *Achaetomium*, *Thielavia*, *Aspergillus*, *Botrytis*, *Chrysosporium*, *Collybia*, *Fomes*, *Fusarium*, *Humicola*, *Hypocrea*, *Lentinus*, *Melanocarpus*, *Myceliophthora*, *Myriococcum*, *Neurospora*, *Penicillium*, *Phanerochaete*, *Phlebia*, *Pleurotus*, *Podospora*, *Polyporus*, *Rhizoctonia*, *Scytalidium*, *Pycnoporus*, *Trametes* and *Trichoderma*.

According to a preferred embodiment of the invention the enzymes are obtainable from *Thermoascus aurantiacus* strain ALKO4242 deposited as CBS 116239, strain ALKO4245 deposited as CBS 116240 presently classified as *Acremonium thermophilium*, or *Chaetomium thermophilum* strain ALKO4265 deposited as CBS 730.95.

The cellobiohydrolase preferably comprises an amino acid sequence having at least 80% identity to SEQ ID NO: 2, 4, 6 or 8, or an enzymatically active fragment thereof.

| Cellobio-hydrolase | Gene | Obtainable from | CBD | nucleic acid SEQ ID NO: | amino acid SEQ ID NO: |
|---|---|---|---|---|---|
| Ta CBH | Ta cel7A | *T. aurantiacus* | − | 1 | 2 |
| At CBH_A | At cel7B | *A. thermophilum* | − | 3 | 4 |
| At CBH_C | At cel7A | *A. thermophilum* | + | 5 | 6 |
| Ct CBH | Ct cel7A | *C. thermophilum* | + | 7 | 8 |

These CBHs have an advantageous cellulose inhibition constant compared to that of *Trichoderma reesei* CBH, and they show improved hydrolysis results when testing various cellulosic substrates. SEQ ID NO: 2 and 4 do not comprise a CBD. Particularly enhanced hydrolysis results may be obtained when a cellulose binding domain (CBD) is attached to a CBH that has no CBD of its own. The CBD may be obtained e.g. from a *Trichoderma* or *Chaetomium* species, and it is preferably attached to the CBH via a linker. The resulting fusion protein containing a CBH core region attached to a CBD via a linker may comprise an amino acid sequence having at least 80% identity to SEQ ID NO: 28 or 30. Polynucleotides comprising a sequence of SEQ ID NO: 27 or 29 encode such fusion proteins.

The endoglucanase may comprise an amino acid sequence having at least 80% identity to SEQ ID NO: 10, 12, 14 or 16, or an enzymatically active fragment thereof. These endoglucanases have good thermostability.

| Endo-glucanase | Gene | Obtainable from | CBD | nucl. acid SEQ ID NO: | amino acid SEQ ID NO: |
|---|---|---|---|---|---|
| Ta EG_28 | Ta cel5A | T. aurantiacus | − | 9 | 10 |
| At EG_40 | At cel45A | A. thermophilum | + | 11 | 12 |
| At EG40_like | At cel45B | A. thermophilum | − | 13 | 14 |
| Ct EG_54 | Ct cel7B | C. thermophilum | + | 15 | 16 |

The beta-glucosidase may comprise an amino acid sequence having at least 80% identity to SEQ ID NO: 22, 24 or 26, or an enzymatically active fragment thereof. These beta-glucosidases have good resistance to glucose inhibition, which is advantageous to avoid end product inhibition during enzymatic hydrolysis of cellulosic material. The beta-glucosidases may also be used in preparing sophorose, a cellulase inducer used in cultivation of T. reesei.

| Beta-glucosidase | Gene | Obtainable from | nucleic acid SEQ ID NO: | amino acid SEQ ID NO: |
|---|---|---|---|---|
| Ta BG_81 | Ta cel3A | T. aurantiacus | 21 | 22 |
| At BG_101 | At cel3A | A. thermophilum | 23 | 24 |
| Ct BG_76 | Ct cel3A | C. thermophilum | 25 | 26 |

The xylanase may comprise an amino acid sequence having at least 80% identity to SEQ ID NO: 18 or 20, or an enzymatically active fragment thereof.

| Xylanase | Gene | Obtainable from | CBD | nucleic acid SEQ ID NO: | amino acid SEQ ID NO: |
|---|---|---|---|---|---|
| Xyn_30 | Ta xyn10A | T. aurantiacus | + | 17 | 18 |
| Xyn_60 | At xyn10A | A. thermophilum | − | 19 | 20 |

By the term "identity" is here meant the global identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 3.0.0, with the following parameters: EMBLO-SUM62, Gap penalty 10.0, Extend penalty 0.5. The algorithm is described in Needleman and Wunsch (1970). The man skilled in the art is aware of the fact that results using Needleman-Wunsch algorithm are comparable only when aligning corresponding domains of the sequence. Consequently comparison of e.g. cellulase sequences including CBD or signal sequences with sequences lacking those elements cannot be done.

According to one embodiment of the invention, a cellulolytic polypeptide is used that has at least 80, 85, 90, 95 or 99% identity to SEQ ID NO: 2, 4, 6, 8, 10, 12, 14, 16, 18, 20, 22, 24 or 26 or at least to its enzymatically active fragment.

By the term "enzymatically active fragment" is meant any fragment of a defined sequence that has cellulolytic activity. In other words an enzymatically active fragment may be the mature protein part of the defined sequence, or it may be only an fragment of the mature protein part, provided that it still has cellobiohydrolase, endoglucanase, beta-glucosidase or xylanase activity.

The cellulolytic enzymes are preferably recombinant enzymes, which may be produced in a generally known manner. A polynucleotide fragment comprising the enzyme gene is isolated, the gene is inserted under a strong promoter in an expression vector, the vector is transferred into suitable host cells and the host cells are cultivated under conditions provoking production of the enzyme. Methods for protein production by recombinant technology in different host systems are well known in the art (Sambrook et al., 1989; Coen, 2001; Gellissen, 2005). Preferably the enzymes are produced as extracellular enzymes that are secreted into the culture medium, from which they can easily be recovered and isolated. The spent culture medium of the production host can be used as such, or the host cells may be removed therefrom, and/or it may be concentrated, filtrated or fractionated. It may also be dried.

Isolated polypeptide in the present context may simply mean that the cells and cell debris have been removed from the culture medium containing the polypeptide. Conveniently the polypeptides are isolated e.g. by adding anionic and/or cationic polymers to the spent culture medium to enhance precipitation of cells, cell debris and some enzymes that have unwanted side activities. The medium is then filtrated using an inorganic filtering agent and a filter to remove the precipitants formed. After this the filtrate is further processed using a semi-permeable membrane to remove excess of salts, sugars and metabolic products.

According to one embodiment of the invention, the heterologous polynucleotide comprises a gene similar to that included in a microorganism having accession number DSM 16723, DSM 16728, DSM 16729, DSM 16727, DSM 17326, DSM 17324, DSM 17323, DSM 17729, DSM 16724, DSM 16726, DSM 16725, DSM 17325 or DSM 17667.

The production host can be any organism capable of expressing the cellulolytic enzyme. Preferably the host is a microbial cell, more preferably a fungus. Most preferably the host is a filamentous fungus. Preferably the recombinant host is modified to express and secrete cellulolytic enzymes as its main activity or one of its main activities. This can be done by deleting major homologous secreted genes e.g. the four major cellulases of Trichoderma and by targeting heterologous genes to a locus that has been modified to ensure high expression and production levels. Preferred hosts for producing the cellulolytic enzymes are in particular strains from the genus *Trichoderma* or *Aspergillus*.

The enzymes needed for the hydrolysis of the cellulosic material according to the invention may be added in an enzymatically effective amount either simultaneously e.g. in the form of an enzyme mixture, or sequentially, or as a part of the simultaneous saccharification and fermentation (SSF). Any combination of the cellobiohydrolases comprising an amino acid sequence having at least 80% identity to SEQ ID NO: 2, 4, 6 or 8 or to an enzymatically active fragment thereof may be used together with any combination of endoglucanases and beta-glucosidases. If the cellulosic material comprises hemicellulose, hemicellulases, preferably xylanases are additionally used for the degradation. The endoglucanases, beta-glucosidases and xylanases may be selected from those described herein, but are not limited to them. They can for example also be commercially available enzyme preparations. In addition to cellulases and optional hemicellulases one or more other enzymes may be used, for example proteases, amylases, laccases, lipases, pectinases, esterases and/or peroxidases. Another enzyme treatment may be carried out before, during or after the cellulase treatment.

The term "enzyme preparation" denotes to a composition comprising at least one of the desired enzymes. The preparation may contain the enzymes in at least partially purified and isolated form. It may even essentially consist of the desired enzyme or enzymes. Alternatively the preparation may be a spent culture medium or filtrate containing one or more cellulolytic enzymes. In addition to the cellulolytic activity, the preparation may contain additives, such as mediators, stabilizers, buffers, preservatives, surfactants and/or culture medium components. Preferred additives are such, which are commonly used in enzyme preparations intended for a particular application. The enzyme preparation may be in the form of liquid, powder or granulate. Preferably the enzyme preparation is spent culture medium. "Spent culture medium" refers to the culture medium of the host comprising the produced enzymes. Preferably the host cells are separated from the said medium after the production.

According to one embodiment of the invention the enzyme preparation comprises a mixture of CBH, EG and BG, optionally together with xylanase and/or other enzymes. The CBH comprises an amino acid sequence having at least 80% identity to SEQ ID NO: 2, 4, 6 or 8 or to an enzymatically active fragment thereof, and it may be obtained from *Thermoascus aurantiacus, Acremonium thermophilum*, or *Chaetomium thermophilum*, whereas EG, BG and xylanase may be of any origin including from said organisms. Other enzymes that might be present in the preparation are e.g. proteases, amylases, laccases, lipases, pectinases, esterases and/or peroxidases.

Different enzyme mixtures and combinations may be used to suit different process conditions. For example if the degradation process is to be carried out at a high temperature, thermostable enzymes are chosen. A combination of a CBH of family 7 with an endoglucanase of family 45, optionally in combination with a BG of family 3 and/or a xylanase of family 10 had excellent hydrolysis performance both at 45° C., and at elevated temperatures.

Cellulolytic enzymes of *Trichoderma reesei* are conventionally used at temperatures in the range of about 40-50° C. in the hydrolysis, and at 30-40° C. in SSF. CBH, EG, BG and Xyn obtainable from *Thermoascus aurantiacus, Acremonium thermophilum*, or *Chaetomium thermophilum* are efficient at these temperatures too, but in addition most of them also function extremely well at temperatures between 50° C. and 75° C., or even up to 80° C. and 85° C., such as between 55° C. and 70° C., e.g. between 60° C. and 65° C. For short incubation times enzyme mixtures are functional up to even 85° C., for complete hydrolysis lower temperatures are normally used.

The method for treating cellulosic material with CBH, EG, BG and Xyn is especially suitable for producing fermentable sugars from lignocellulosic material. The fermentable sugars may then be fermented by yeast into ethanol, and used as fuel. They can also be used as intermediates or raw materials for the production of various chemicals or building blocks for the processes of chemical industry, e.g. in so called biorefinery. The lignocellulosic material may be pretreated before the enzymatic hydrolysis to disrupt the fiber structure of cellulosic substrates and make the cellulose fraction more accessible to the cellulolytic enzymes. Current pretreatments include mechanical, chemical or thermal processes and combinations thereof. The material may for example be pretreated by steam explosion or acid hydrolysis.

A number of novel cellulolytic polypeptides were found in *Thermoascus aurantiacus, Acremonium thermophilum*, and *Chaetomium thermophilum*. The novel polypeptides may comprise a fragment having cellulolytic activity and be selected from the group consisting of a polypeptide comprising an amino acid sequence having at least 66%, preferably 70% or 75%, identity to SEQ ID NO: 4, 79% identity to SEQ ID NO: 6, 78% identity to SEQ ID NO: 12, 68%, preferably 70% or 75%, identity to SEQ ID NO: 14, 72%, preferably 75%, identity to SEQ ID NO: 16, 68%, preferably 70% or 75%, identity to SEQ ID NO: 20, 74% identity to SEQ ID NO: 22 or 24, or 78% identity to SEQ ID NO: 26.

The novel polypeptides may also be variants of said polypeptides. A "variant" may be a polypeptide that occurs naturally e.g. as an allelic variant within the same strain, species or genus, or it may have been generated by mutagenesis. It may comprise amino acid substitutions, deletions or insertions, but it still functions in a substantially similar manner to the enzymes defined above i.e. it comprises a fragment having cellulolytic activity.

The cellulolytic polypeptides are usually produced in the cell as immature polypeptides comprising a signal sequence that is cleaved off during secretion of the protein. They may also be further processed during secretion both at the N-terminal and/or C-terminal end to give a mature, enzymatically active protein. A polypeptide "comprising a fragment having cellulolytic activity" thus means that the polypeptide may be either in immature or mature form, preferably it is in mature form, i.e. the processing has taken place.

The novel polypeptides may further be a "fragment of the polypeptides or variants" mentioned above. The fragment may be the mature form of the proteins mentioned above, or it may be only an enzymatically active part of the mature protein. According to one embodiment of the invention, the polypeptide has an amino acid sequence having at least 80, 85, 90, 95, or 99% identity to SEQ ID NO: 4, 6, 12, 14, 16, 20, 22, 24 or 26, or to a cellulolytically active fragment thereof. It may also be a variant thereof, or a fragment thereof having cellobiohydrolase, endoglucanase, xylanase, or beta-glucosidase activity. According to another embodiment of the invention, the polypeptide consists essentially of a cellulolytically active fragment of a sequence of SEQ ID NO: 4, 6, 12, 14, 16, 20, 22, 24 or 26.

The novel polynucleotides may comprise a nucleotide sequence of SEQ ID NO: 3, 5, 11, 13, 15, 19, 21, 23 or 25, or a sequence encoding a novel polypeptide as defined above, including complementary strands thereof. Polynucleotide as used herein refers to both RNA and DNA, and it may be single stranded or double stranded. The polynucleotide may also be a fragment of said polynucleotides comprising at least 20 nucleotides, e.g. at least 25, 30 or 40 nucleotides. According to one embodiment of the invention it is at least 100, 200 or 300 nucleotides in length. Further the polynucleotide may be degenerate as a result of the genetic code to any one of the sequences as defined above. This means that different codons may code for the same amino acid.

According to one embodiment of the invention the polynucleotide is "comprised in" SEQ ID NO: 3, 5, 11, 13, 15, 19, 21, 23 or 25, which means that the sequence has at least part of the sequence mentioned. According to another embodiment of the invention, the polynucleotide comprises a gene similar to that included in a microorganism having accession number DSM 16728, DSM 16729, DSM 17324, DSM 17323, DSM 17729, DSM 16726, DSM 16725, DSM 17325 or DSM 17667.

The novel proteins/polypeptides may be prepared as described above. The novel polynucleotides may be inserted into a vector, which is capable of expressing the polypeptide encoded by the heterologous sequence, and the vector may be inserted into a host cell capable of expressing said polypeptide. The host cell is preferably of the genus *Trichoderma* or *Aspergillus*.

A heterologous gene encoding the novel polypeptides has been introduced on a plasmid into an *Escherichia coli* strain having accession number DSM 16728, DSM 16729, DSM 17324, DSM 17323, DSM 17729, DSM 16726, DSM 16725, DSM 17325 or DSM 17667.

The novel enzymes may be components of an enzyme preparation. The enzyme preparation may comprise one or more of the novel polypeptides, and it may be e.g. in the form of spent culture medium, powder, granules or liquid. According to one embodiment of the invention it comprises cellobiohydrolase, endoglucanase, beta-glucosidase, and optionally xylanase activity and/or other enzyme activities. It may further comprise any conventional additives.

The novel enzymes may be applied in any process involving cellulolytic enzymes, such as in fuel, textile, detergent, pulp and paper, food, feed or beverage industry, and especially in hydrolysing cellulosic material for the production of biofuel comprising ethanol. In the pulp and paper industry they may be used to modify cellulosic fibre for example in treating kraft pulp, mechanical pulp, or recycled paper.

The invention is illustrated by the following non-limiting examples. It should be understood, however, that the embodiments given in the description above and in the examples are for illustrative purposes only, and that various changes and modifications are possible within the scope of the invention.

EXAMPLES

Example 1

Screening for Strains Expressing Cellulolytic Activity and their Cultivation for Purification About 25 fungal strains from the Roal Oy culture collection were tested for cellulolytic activity including beta-glucosidases. After preliminary screening six strains were chosen for further studies. These were *Thermoascus aurantiacus* ALKO4239 and ALKO4242, *Acremonium thermophilum* ALKO4245, *Talaromyces thermophilus* ALKO4246 and *Chaetomium thermophilum* ALKO4261 and ALKO4265.

The strains ALKO4239, ALKO4242 and ALKO4246 were cultivated in shake flasks at 42° C. for 7 d in the medium 3×B, which contains g/liter: Solka Floc cellulose 18, distiller's spent grain 18, oats spelt xylan 9, $CaCO_3$ 2, soybean meal 4.5, $(NH_4)HPO_4$ 4.5, wheat bran 3.0, $KH_2PO_4$ 1.5, $MgSO_4.H_2O$ 1.5, NaCl 0.5, $KNO_3$ 0.9, locust bean gum 9.0, trace element solution #1 0.5, trace element solution #2 0.5 and Struktol (Stow, Ohio, USA) antifoam 0.5 ml; the pH was adjusted to 6.5. Trace element solution #1 has g/liter: $MnSO_4$ 1.6, $ZnSO_4.7H_2O$ 3.45 and $CoCl_2.6H_2O$ 2.0; trace element solution #2 has g/liter: $FeSO_4.7H_2O$ 5.0 with two drops of concentrated $H_2SO_4$.

The strain ALKO4261 was cultivated in shake flasks in the medium 1×B, which has one third of each of the constituents of the 3×B medium (above) except it has same concentrations for $CaCO_3$, NaCl and the trace elements. The strain was cultivated at 45° C. for 7 d.

The strain ALKO4265 was cultivated in shake flasks in the following medium, g/l: Solka Floc cellulose 40, Pharmamedia™ (Traders Protein, Memphis, Tenn., USA) 10, corn steep powder 5, $(NH_4)_2SO_4$ 5 and $KH_2PO_4$ 15; the pH was adjusted to 6.5. The strain was cultivated at 45° C. for 7 d.

After the cultivation the cells and other solids were collected by centrifugation down and the supernatant was recovered. For the shake flask cultivations, protease inhibitors PMSF (phenylmethyl-sulphonylfluoride) and pepstatin A were added to 1 mM and 10 μg/ml, respectively. If not used immediately, the preparations were stored in aliquots at −20° C.

For the estimation of the thermoactivity of the enzymes, assays were performed of the shake flask cultivation preparations at 50° C., 60° C., 65° C., 70° C. and 75° C. for 1 h, in the presence of 100 μg bovine serum albumin (BSA)/ml as a stabilizer. Preliminary assays were performed at 50° C. and 65° C. at two different pH values (4.8/5.0 or 6.0) in order to clarify, which pH was more appropriate for the thermoactivity assay.

All shake flask supernatants were assayed for the following activities:

Cellobiohydrolase I-like activity ('CBHI') and the endoglucanase I-like activity ('EGI'):

These were measured in 50 mM Na-acetate buffer with 0.5 mM MUL (4-methylumbelliferyl-beta-D-lactoside) as the substrate. Glucose (100 mM) was added to inhibit any interfering beta-glucosidase activity. The liberated 4-methylumbelliferyl was measured at 370 nm. The 'CBHI' and the 'EGI' activities were distinguished by measuring the activity in the presence and absence of cellobiose (5 mM). The activity that is not inhibited by cellobiose represents the 'EGI' activity and the remaining MUL activity represents the 'CBHI' activity (van Tilbeurgh et al, 1988). The assay was performed at pH 5.0 or 6.0 (see below).

The endoglucanase (CMCase) activity:

This was assayed with 2% (w/v) carboxymethylcellulose (CMC) as the substrate in 50 mM citrate buffer essentially as described by Bailey and Nevalainen 1981; Haakana et al. 2004. Reducing sugars were measured with the DNS reagent. The assay was performed at pH 4.8 or 6.0 (see below).

Beta-glucosidase (BGU) activity:

This was assayed with 4-nitrophenyl-β-D-glucopyranoside (1 mM) in 50 mM citrate buffer as described by Bailey and Nevalainen 1981. The liberated 4-nitrophenol was measured at 400 nm. The assay was performed at pH 4.8 or 6.0 (see below).

The relative activities of the enzymes are presented in FIG. 1. The relative activities were presented by setting the activity at 60° C. as 100% (FIG. 1). All strains produced enzymes, which had high activity at high temperatures (65° C.-75° C.).

For protein purifications. ALKO4242 was also grown in a 2 liter bioreactor (Braun Biostat® B, Braun, Melsungen, Germany) in the following medium, g/liter: Solka Floc cellulose 40, soybean meal 10, $NH_4NO_3$ 5, $KH_2PO_4$ 5, $MgSO_4.7H_2O$ 0.5, $CaCl_2.2H_2O$ 0.05, trace element solution #1 0.5, trace element solution #2 0.5. The aeration was 1 vvm, antifoam control with Struktol, stirring 200-800 rpm and temperature at 47° C. Two batches were run, one at pH 4.7±0.2 ($NH_3$/$H_2SO_4$) and the other with initial pH of pH 4.5. The cultivation time was 7 d. After the cultivation the cells and other solids were removed by centrifugation.

The strain ALKO4245 was grown in 2 liter bioreactor (Braun Biostat® B, Braun, Melsungen, Germany) in the following medium, g/liter: Solka Floc cellulose 40, corn steep powder 15, distiller's spent grain 5, oats spelt xylan 3, locust bean gum 3, $(NH_4)_2SO_4$ 5 and $KH_2PO_4$ 5. The pH range was 5.2±0.2 ($NH_3/H_2SO_4$), aeration 1 vvm, stirring 300-600 rpm, antifoam control with Struktol and the temperature 42° C. The cultivation time was 4 d. After the cultivation the cells and other solids were removed by centrifugation.

For enzyme purification, ALKO4261 was grown in a 10 liter bioreactor (Braun Biostat® ED, Braun, Melsungen, Germany) in the following medium, g/liter: Solka Floc cellulose 30, distiller's spent grain 10, oats spelt xylan 5, $CaCO_3$ 2, soybean meal 10, wheat bran 3.0, $(NH_4)_2SO_4$ 5, $KH_2PO_4$ 5, $MgSO_4.7H_2O$ 0.5, NaCl 0.5, $KNO_3$ 0.3, trace element solution #1 0.5 and trace element solution #2 0.5. The pH range was 5.2±0.2 ($NH_3/H_2SO_4$), aeration 1 vvm, stirring 200-600 rpm, antifoam control with Struktol and the temperature 42° C. The cultivation time was 5 d. A second batch was grown under similar conditions except that Solka Floc was added to 40 g/l and spent grain to 15 g/l. The supernatants were recovered by centrifugation and filtering through Seitz-K 150 and EK filters (Pall SeitzSchenk Filtersystems GmbH, Bad Kreuznach, Germany). The latter supernatant was concentrated about ten fold using the Pellicon mini ultrafiltration system (filter NMWL 10 kDa; Millipore, Billerica, Mass., USA).

For enzyme purification, ALKO4265 was also grown in a 10 liter bioreactor (Braun Biostat® ED, Braun, Melsungen, Germany) in the same medium as above, except $KH_2PO_4$ was added to 2.5 g/l. The pH range was 5.3±0.3 ($NH_3/H_3PO_4$), aeration 0.6 vvm, stirring 500 rpm, antifoam control with Struktol and the temperature 43° C. The cultivation time was 7 d. The supernatants were recovered by centrifugation and filtering through Seitz-K 150 and EK filters (Pall SeitzSchenk Filtersystems GmbH, Bad Kreuznach, Germany). The latter supernatant was concentrated about 20 fold using the Pellicon mini ultrafiltration system (filter NMWL 10 kDa; Millipore, Billerica, Mass., USA).

Example 2

Purification and Characterization of Cellobiohydrolases from *Acremonium thermophilum* ALKO4245 and *Chaetomium thermophilum* ALKO4265

*Acremonium thermophilum* ALKO4245 and *Chaetomium thermophilum* ALKO4265 were grown as described in Example 1. The main cellobiohydrolases were purified using p-aminobenzyl 1-thio-β-cellobioside-based affinity column, prepared as described by Tomme et al., 1988.

The culture supernatants were first buffered into 50 mM sodium acetate buffer pH 5.0, containing 1 mM δ-gluconolactone and 0.1 M glucose in order to retard ligand hydrolysis in the presence of β-glucosidases. Cellobiohydrolases were eluted with 0.1 M lactose and finally purified by gel filtration chromatography using Superdex 200 HR 10/30 columns in the ÄKTA system (Amersham Pharmacia Biotech). The buffer used in gel filtration was 50 mM sodium phosphate pH 7.0, containing 0.15 M sodium chloride.

Purified cellobiohydrolases were analysed by SDS-polyacrylamide gel electrophoresis and the molecular mass of both proteins was determined to be approximately 70 kDa evaluated on the basis of the molecular mass standards (Low molecular weight calibration kit, Amersham Biosciences). Purified *Acremonium* and *Chaetomium* cellobiohydrolases were designated as At Cel7A and Ct Cel7A, respectively, following the scheme in Henrissat et al. (1998) (Henrissat, 1991; Henrissat and Bairoch, 1993).

The specific activity of the preparations was determined using 4-methylumbelliferyl-β-D-lactoside (MUL), 4-methylumbelliferyl-β-D-cellobioside (MUG2) or 4-methylumbelliferyl-β-D-cellotrioside (MUG3) as substrate (van Tilbeurgh et al., 1988) in 0.05 M sodium citrate buffer pH 5 at 50° C. for 10 min. Endoglucanase and xylanase activities were determined by standard procedures (according to IUPAC, 1987) using carboxymethyl cellulose (CMC) and birch glucuronoxylan (Bailey et al., 1992) as substrates. Specific activity against Avicel was calculated on the basis of reducing sugars formed in a 24 h reaction at 50° C., pH 5.0, with 1% substrate and 0.25 μM enzyme dosage. The protein content of the purified enzyme preparations was measured according to Lowry et al., 1951. To characterize the end products of hydrolysis, soluble sugars liberated in 24 h hydrolysis experiment, as described above, were analysed by HPLC (Dionex). Purified cellobiohydrolase I (CBHI/Cel7A) of *Trichoderma reesei* was used as a reference.

The specific activities of the purified enzymes and that of *T. reesei* CBHI/Cel7A are presented in Table 1. The purified At Cel7A and Ct Cel7A cellobiohydrolases possess higher specific activities against small synthetic substrates as compared to *T. reesei* CBHI/Cel7A. The specific activity against Avicel was clearly higher with the herein disclosed enzymes. Low activities of the purified enzyme preparations against xylan and CMC may either be due to the properties of the proteins themselves, or at least partially to the remaining minor amounts of contaminating enzymes. The major end product of cellulose hydrolysis by all purified enzymes was cellobiose which is typical to cellobiohydrolases.

TABLE 1

Specific activities (nkat/mg) of the purified cellobiohydrolases and the reference enzyme of *T. reesei* (50° C., pH 5.0, 24 h).

| Substrate | A. thermophilum ALKO4245 Cel7A | C. thermophilum ALKO4265 Cel7A | T. reesei Cel7A |
|---|---|---|---|
| Xylan | 11.3 | 6.7 | 1.3 |
| CMC | 26.2 | 5.5 | 1.0 |
| MUG2 | 9.2 | 18.9 | 4.3 |
| MUG3 | 1.3 | 1.5 | 0.9 |
| MUL | 21.5 | 54.0 | 21.9 |
| Avicel | 1.8 | 1.4 | 0.6 |

Thermal stability of the purified cellobiohydrolases was determined at different temperatures. The reaction was performed in the presence of 0.1% BSA at pH 5.0 for 60 min using 4-methylumbelliferyl-β-D-lactoside as substrate. *C. thermophilum* ALKO4265 CBH/Cel7A and *A. thermophilum* ALKO4245 CBH/Cel7A were stable up to 65° and 60° C., respectively. The *T. reesei* reference enzyme (CBHI/Cel7A) retained 100% of activity up to 55° C.

Example 3

Purification and Characterization of an Endoglucanase from *Acremonium thermophilum* ALKO4245

*Acremonium thermophilum* ALKO4245 was grown as described in Example 1. The culture supernatant was incubated at 70° C. for 24 hours after which it was concentrated by ultrafiltration. The pure endoglucanase was obtained by sequential purification with hydrophobic interaction and cation exchange chromatography followed by gel filtration. The endoglucanase activity of the fractions collected during purification was determined using carboxymethyl cellulose (CMC) as substrate (procedure of IUPAC 1987). Protein content was measured by BioRad Assay Kit (Bio-Rad Laboratories) using bovine serum albumine as standard.

The concentrated culture supernatant was applied to a HiPrep 16/10 Butyl FF hydrophobic interaction column equilibrated with 20 mM potassium phosphate buffer pH 6.0, containing 1 M $(NH_4)_2SO_4$. Bound proteins were eluted with the linear gradient from the above buffer to 5 mM potassium phosphate, pH 6.0. Fractions were collected and the endoglucanase activity was determined as described above. The endoglucanase activity was eluted in a broad conductivity area of 120 to 15 mS/cm.

Combined fractions were applied to a HiTrap SP XL cation exchange column equilibrated with 8 mM sodium acetate, pH 4.5. Bound proteins were eluted with a linear gradient from 0 to 0.25 M NaCl in the equilibration buffer. The protein containing endoglucanase activity was eluted at the conductivity area of 3-7 mS/cm. Cation exchange chromatography was repeated and the protein eluate was concentrated by freeze drying.

The dissolved sample was loaded onto a Superdex 75 HR10/30 gel filtration column equilibrated with 20 mM sodium phosphate buffer pH 7.0, containing 0.15 M NaCl. The main protein fraction was eluted from the column with the retention volume of 13.3 ml. The protein eluate was judged to be pure by SDS-polyacryl amide gel electrophoresis and the molecular weight was evaluated to be 40 kDa. The specific activity of the purified protein, designated as At EG_40, at 50° C. was determined to be 450 nkat/mg (procedure of IUPAC 1987, using CMC as substrate).

Thermal stability of the purified endoglucanase was determined at different temperatures. The reaction was performed in the presence of 0.1 mg/ml BSA at pH 5.0 for 60 min using carboxymethyl cellulose as substrate. *A. thermophilum* EG_40/Cel45A was stable up to 80° C. The *T. reesei* reference enzymes EGI (Cel7B) and EGII (Cel5A) retained 100% of activity up to 60° C. and 65° C., respectively.

Example 4

Purification of an Endoglucanase from *Chaetomium Thermophilum* ALKO4261

*Chaetomium thermophilum* ALKO4261 was grown as described in Example 1. The pure endoglucanase was obtained by sequential purification with hydrophobic interaction and cation exchange chromatography followed by gel filtration. The endoglucanase activity of the fractions collected during purification was determined using carboxymethyl cellulose (CMC) as substrate (procedure of IUPAC 1987).

Ammonium sulfate was added to the culture supernatant to reach the same conductivity as 20 mM potassium phosphate pH 6.0, containing 1 M $(NH_4)_2SO_4$. The sample was applied to a HiPrep 16/10 Phenyl FF hydrophobic interaction column equilibrated with 20 mM potassium phosphate pH 6.0, containing 1 M $(NH_4)_2SO_4$. Elution was carried out with a linear gradient of 20 to 0 mM potassium phosphate, pH 6.0, followed by 5 mM potassium phosphate, pH 6.0 and water. Bound proteins were eluted with a linear gradient of 0 to 6 M Urea. Fractions were collected and the endoglucanase activity was analysed as described above. The protein containing endoglucanase activity was eluted in the beginning of the urea gradient.

The fractions were combined, equilibriated to 16 mM Tris-HCl pH 7.5 (I=1.4 mS/cm) by 10 DG column (Bio-Rad) and applied to a HiTrap DEAE FF anion exchange column equilibrated with 20 mM Tris-HCl, pH 7.5. Bound proteins were eluted with a linear gradient from 0 to 1 M NaCl in the equilibration buffer. Fractions were collected and analyzed for endoglucanase activity as described above. The protein was eluted in the range of 10-20 mS/cm.

The sample was equilibrated to 15 mM sodium acetate, pH 4.5 by 10 DG column (Bio-Rad) and applied to a HiTrap SP XL cation exchange column equilibrated with 20 mM sodium acetate pH 4.5. Proteins were eluted with a linear gradient from 0 to 0.4 M sodium acetate, pH 4.5. Endoglucanase activity was eluted in the range of 1-10 mS/cm. The collected sample was lyophilized.

The sample was dissolved in water and applied to a Superdex 75 HR 10/30 gel filtration column equilibrated with 20 mM sodium phosphate pH 6.0, containing 0.15 M NaCl. Fractions were collected and those containing endoglucanase activity were combined. The protein eluate was judged to be pure by SDS-polyacrylamide gel electrophoresis and the molecular mass was evaluated on the basis of molecular mass standards (prestained SDS-PAGE standards, Broad Range, Bio-Rad) to be 54 kDa. The pI of the purified protein, designated as Ct EG_54 was determined with PhastSystem (Pharmacia) to be ca 5.5.

Example 5

Purification of an Endoglucanase from *Thermoascus Aurantiacus* ALKO4242

*Thermoascus aurantiacus* ALKO4242 was grown as described in Example 1. The pure endoglucanase was obtained by sequential purification with hydrophobic interaction and anion exchange chromatography followed by gel filtration. The endoglucanase activity of the fractions collected during purification was determined using carboxymethyl cellulose (CMC) as substrate (procedure of IUPAC 1987). Protein content was measured by BioRad Assay Kit (Bio-Rad Laboratories) using bovine serum albumine as standard.

The culture supernatant was applied to a HiPrep 16/10 Butyl hydrophobic interaction column equilibrated with 20 mM potassium phosphate buffer pH 6.0, containing 0.7 M $(NH_4)_2SO_4$. Bound proteins were eluted with 0.2 M $(NH_4)_2SO_4$ (I=39 mS/cm). Fractions containing endoglucanase activity were combined and concentrated by ultrafiltration.

The sample was desalted in 10 DG columns (Bio-Rad) and applied to a HiTrap DEAE FF anion exchange column equilibrated with 15 mM Tris-HCL, pH 7.0. Bound proteins were eluted with a linear gradient from 0 to 0.4 M NaCl in the equilibration buffer. The protein containing endoglucanase activity was eluted at the conductivity area of 15-21 mS/cm. Collected fractions were combined and concentrated as above.

The sample was applied to a Sephacryl S-100 HR 26/60 gel filtration column equilibrated with 50 mM sodium acetate buffer pH 5.0, containing 0.05 M NaCl. The protein fraction containing endoglucanase activity was eluted from the column with a retention volume corresponding to a molecular weight of 16 kDa. Collected fractions were combined, concentrated and gel filtration was repeated. The protein eluate was judged to be pure by SDS-polyacryl amide gel electrophoresis and the molecular weight was evaluated to be 28 kDa. The pI of the purified protein, designated as Ta EG_28, was determined in an IEF gel (PhastSystem, Pharmacia) to be about 3.5. The specific activity of Ta EG_28 at 50° C. was determined to be 4290 nkat/mg (procedure of IUPAC 1987, using CMC as substrate).

Example 6

Purification and Characterization of a β-Glucosidase from *Acremonium Thermophilum* ALKO4245

*Acremonium Thermophilum* ALKO4245 was grown as described in Example 1. The pure β-glucosidase was obtained by sequential purification with hydrophobic interaction and anion exchange chromatography followed by gel filtration. The β-glucosidase activity of the fractions collected during purification was determined using 4-nitrophenyl-β-D-glucopyranoside as substrate (Bailey and Linko, 1990). Protein content was measured by BioRad Assay Kit (Bio-Rad Laboratories) using bovine serum albumine as standard.

The culture supernatant was applied to a HiPrep 16/10 Phenyl Sepharose FF hydrophobic interaction column equilibrated with 20 mM potassium phosphate pH 6.0, containing 1 M $(NH_4)_2SO_4$. Bound proteins were eluted with a linear gradient from the equilibration buffer to 5 mM potassium phosphate in the conductivity area 137-16 mS/cm. Collected fractions were combined and concentrated by ultrafiltration.

The sample was desalted in 10 DG columns (Bio-Rad) and applied to a HiTrap DEAE FF anion exchange column equilibrated with 10 mM potassium phosphate pH 7.0. Bound proteins were eluted with a linear gradient from the equilibration buffer to the same buffer containing 0.25 M NaCl in the conductivity area 1.5-12 mS/cm. Anion exchange chromatography was repeated as above, except that 4 mM potassium phosphate buffer pH 7.2 was used. Proteins were eluted at the conductivity area of 6-9 mS/cm. Fractions containing β-glucosidase activity were collected, combined, and concentrated.

The active material from the anion exchange chromatography was applied to a Sephacryl S-300 HR 26/60 column equilibrated with 20 mM sodium phosphate pH 6.5, containing 0.15 M NaCl. The protein with β-glucosidase activity was eluted with a retention volume corresponding to a molecular weight of 243 kDa. The protein was judged to be pure by SDS-polyacrylamide gel electrophoresis and the molecular weight was evaluated to be 101 kDa. The pI of the purified protein, designated as At βG_101, was determined in an IEF gel (PhastSystem, Pharmacia) to be in the area of 5.6-4.9. The specific activity of At βG_101 at 50° C. was determined to be 1100 nkat/mg (using 4-nitrophenyl-β-D-glucopyranoside as substrate, Bailey and Linko, 1990).

Thermal stability of the purified β-glucosidase was determined at different temperatures. The reaction was performed in the presence of 0.1 mg/ml BSA at pH 5.0 for 60 min using 4-nitrophenyl-β-D-glucopyranoside as substrate. *A. thermophilum* βG_101 was stable up to 70° C. The *Aspergillus* reference enzyme (Novozym 188) retained 100% of activity up to 60°.

Example 7

Purification of a β-Glucosidase from *Chaetomium Thermophilum* ALKO4261

*Chaetomium thermophilum* ALKO4261 was grown as described in Example 1. The pure β-glucosidase was obtained by sequential purification with hydrophobic interaction, anion and cation exchange chromatography followed by gel filtration. The β-glucosidase activity of the fractions collected during purification was determined using 4-nitrophenyl-β-D-glucopyranoside as substrate (Bailey and Linko, 1990).

The culture supernatant was applied to a HiPrep 16/10 Phenyl Sepharose FF hydrophobic interaction column equilibrated with 20 mM potassium phosphate pH 6.0, containing 0.8 M $(NH_4)_2SO_4$. The elution was carried out with a linear gradient from the equilibration buffer to 3 mM potassium phosphate, pH 6.0, followed by elution with water and 6 M urea. The first fractions with β-glucosidase activity were eluted in the conductivity area of 80-30 mS/cm. The second β-glucosidase activity was eluted with 6 M urea. The active fractions eluted by urea were pooled and desalted in 10 DG columns (Bio-Rad) equilibrated with 10 mM Tris-HCl pH 7.0.

After desalting, the sample was applied to a HiTrap DEAE FF anion exchange column equilibrated with 15 mM Tris-HCl pH 7.0. The protein did not bind to the column but was eluted during the sample feed. This flow-through fraction was desalted in 10 DG columns (Bio-Rad) equilibrated with 7 mM Na acetate, pH 4.5.

The sample from the anion exchange chromatography was applied to a HiTrap SP FF cation exchange column equilibrated with 10 mM sodium acetate pH 4.5. Bound proteins were eluted with a linear gradient from 10 mM to 400 mM sodium acetate, pH 4.5. The fractions with β-glucosidase activity eluting in conductivity area of 6.5-12 mS/cm were collected, desalted in 10 DG columns (Bio-Rad) equilibrated with 7 mM sodium acetate, pH 4.5 and lyophilized.

The lyophilized sample was diluted to 100 μl of water and applied to a Superdex 75 HF10/30 gel filtration column equilibrated with 20 mM sodium phosphate pH 4.5, containing 0.15 M NaCl. The β-glucosidase activity was eluted at a retention volume of 13.64 ml. Collected fractions were combined, lyophilized and dissolved in water. The protein was judged to be pure by SDS-polyacryl amide gel electrophoresis and the molecular weight was evaluated to be 76 kDa. The protein was designated as Ct βG_76.

Example 8

Purification and Characterization of a β-Glucosidase from *Thermoascus Aurantiacus* ALKO4242

*Thermoascus aurantiacus* ALKO4242 was grown as described in Example 1. The pure β-glucosidase was obtained by sequential purification with hydrophobic interaction, anion and cation exchange chromatography followed by gel filtration. The β-glucosidase activity of the fractions collected during purification was determined using 4-nitrophenyl-β-D-glucopyranoside as substrate (Bailey and Linko, 1990). Protein content was measured by BioRad Assay Kit (Bio-Rad Laboratories) using bovine serum albumine as standard.

The culture supernatant was applied to a HiPrep 16/10 Phenyl Sepharose FF hydrophobic interaction column equilibrated with 20 mM potassium phosphate pH 6.0, containing 0.7 M $(NH_4)_2SO_4$. Bound proteins were eluted with a linear gradient from 0.2 M $(NH_4)_2SO_4$ to 5 mM potassium phosphate, pH 6.0. The β-glucosidase activity was eluted during the gradient in the conductivity area of 28.0-1.1 mS/cm. Fractions were combined and concentrated by ultrafiltration.

The sample was desalted in 10 DG columns (Bio-Rad) and applied to a HiTrap DEAE FF anion exchange column equilibrated with 20 mM Tris-HCl pH 7.0. The enzyme was eluted with a linear gradient from 0 to 0.2 M NaCl in the equilibration buffer and with delayed elution by 20 mM Tris-HCl, containing 0.4 M NaCl. The sample eluting in the conductivity area of ca. 10-30 mS/cm was concentrated by ultrafiltration and desalted by 10 DG column (Bio-Rad).

The sample was applied to a HiTrap SP XL cation exchange column equilibrated with 9 mM sodium acetate pH 4.5. The enzyme was eluted with a linear gradient from 10 mM to 400 mM NaAc and by delayed elution using 400 mM NaAc pH 4.5 Proteins with β-glucosidase activity were eluted broadly during the linear gradient in the conductivity area of 5.0-11.3 mS/cm.

The active material from the cation exchange chromatography was applied to a Sephacryl S-300 HR 26/60 column equilibrated with 20 mM sodium phosphate pH 7.0, containing 0.15 M NaCl. The protein with β-glucosidase activity was eluted with a retention volume corresponding to a molecular weight of 294 kDa. Collected fractions were combined, lyophilized and dissolved in water. The protein was judged to be pure by SDS-polyacrylamide gel electrophoresis and the molecular weight was evaluated to be 81 kDa, representing most likely the monomeric form of the protein. Isoelectric focusing (IEF) was carried out using a 3-9 pI gel. After silver staining, a broad area above pI 5.85 was stained in addition to a narrow band corresponding to pI 4.55. The specific activity of the purified protein, designated as Ta βG_81, at 50° C. was determined to be 600 nkat/mg using 4-nitrophenyl-β-D-glucopyranoside as substrate (Bailey and Linko, 1990).

Thermal stability of the purified β-glucosidase was determined at different temperatures. The reaction was performed in the presence of 0.1 mg/ml BSA at pH 5.0 for 60 min using 4-nitrophenyl-β-D-glucopyranoside as substrate. T. aurantiacus βG_81 was stable up to 75° C. The Aspergillus reference enzyme (Novozym 188) retained 100% of activity up to 60° C.

Example 9

Purification of a Xylanase from Acremonium Thermophilum ALKO4245

Acremonium thermophilum ALKO4245 was grown as described in Example 1. The culture supernatant was incubated at 70° C. for 24 hours after which, it was concentrated by ultrafiltration. The pure xylanase was obtained by sequential purification with hydrophobic interaction and cation exchange chromatography followed by gel filtration. The xylanase activity was determined using birch xylan as substrate (procedure of IUPAC 1987). Protein was assayed by BioRad Protein Assay Kit (Bio-Rad Laboratories) using bovine serum albumin as standard.

The concentrated culture supernatant was applied to a HiPrep 16/10 Butyl FF hydrophobic interaction column equilibrated with 20 mM potassium phosphate buffer pH 6.0, containing 1 M $(NH_4)_2SO_4$. Bound proteins were eluted with the linear gradient from the above buffer to 5 mM potassium phosphate, pH 6.0. The protein fraction was eluted in a broad conductivity area of 120 to 15 mS/cm.

The sample from the hydrophobic interaction column was applied to a HiTrap SP XL cation exchange column equilibrated with 8 mM sodium acetate, pH 4.5. The protein did not bind to this column but was eluted in the flow-through during sample feed. This eluate was concentrated by ultrafiltration. The hydrophobic chromatography was repeated as described above. The unbound proteins were collected and freeze dried.

The dissolved sample was loaded onto the Superdex 75 HR10/30 gel filtration column equilibrated with 20 mM sodium phosphate buffer pH 7.0, containing 0.15 M NaCl. The protein eluted from the column with the retention volume of 11.2 ml was judged to be pure by SDS-polyacrylamide gel electrophoresis. The molecular mass of the purified protein was evaluated on the basis of molecular mass standards (prestained SDS-PAGE standards, Broad Range, Bio-Rad) to be 60 kDa. The specific activity of the protein, designated as At XYN_60, at 50° C. was determined to be 1800 nkat/mg (procedure of IUPAC 1987, using birch xylan as substrate). The relative activity was increased about 1.2 fold at 60° C. and 1.65 fold at 70° C. (10 min, pH 5.0) as compared to 50° C. The specific activity against MUG2 (4-methylumbelliferyl-β-D-cellobioside), MUL (4-methylumbelliferyl-beta-D-lactoside) and MUG3 (4-methylumbelliferyl-β-D-cellotrioside) were 54, 33 and 78 nkat/mg (50° C. pH 5.0 10 min), respectively. This is in agreement with the fact that the family 10 xylanases also show activity against the aryl glucopyranosides (Biely et al. 1997).

Example 10

Purification of a Xylanase from Thermoascus Aurantiacus ALKO4242

Thermoascus aurantiacus ALKO4242 was grown as described in Example 1. The pure xylanase was obtained by sequential purification with hydrophobic interaction, anion, and cation exchange chromatography followed by gel filtration. The xylanase activity was determined using birch xylan as substrate (procedure of IUPAC 1987). Protein was assayed by BioRad Protein Assay Kit (Bio-Rad Laboratories) using bovine serum albumin as standard.

The culture supernatant was applied to a HiPrep 16/10 Phenyl Sepharose FF hydrophobic interaction column equilibrated with 20 mM potassium phosphate buffer pH 6.0, containing 0.7 M $(NH_4)_2SO_4$. Bound proteins were eluted with a two-step elution protocol. The elution was carried out by dropping the salt concentration first to 0.2 M $(NH_4)_2SO_4$ and after that a linear gradient from 20 mM potassium phosphate pH 6.0, containing 0.2 M $(NH_4)_2SO_4$ to 5 mM potassium phosphate pH 6.0 was applied. The protein was eluted with 0.2 M $(NH_4)_2SO_4$ (I=39 mS/cm).

The sample was desalted in 10 DG columns (Bio-Rad) and applied to a HiTrap DEAE FF anion exchange column equilibrated with 15 mM Tris-HCL, pH 7.0. The protein did not bind to the anion exchange column but was eluted in the flow-through. The conductivity of the sample was adjusted to correspond that of 20 mM sodium acetate, pH 4.5 by adding water and pH was adjusted to 4.5 during concentration by ultrafiltration.

The sample was applied to a HiTrap SP XL cation exchange column equilibrated with 20 mM sodium acetate, pH 4.5. Bound proteins were eluted with a linear gradient from the equilibration buffer to the same buffer containing 1

M NaCl. The enzyme was eluted at the conductivity area of 1-7 mS/cm. The sample was lyophilized and thereafter dissolved in water.

The lyophilised sample was dissolved in water and applied to a Superdex 75 HR 10/30 gel filtration column equilibrated with 20 mM sodium phosphate pH 7.0, containing 0.15 M NaCl. The protein was eluted from the column with a retention volume corresponding to a molecular weight of 26 kDa. The protein was judged to be pure by SDS-polyacrylamide gel electrophoresis. The molecular mass of the pure protein was 30 kDa as evaluated on the basis of molecular mass standards (prestained SDS-PAGE standards, Broad Range, Bio-Rad). The pI of the purified protein, designated as Ta XYN_30 was determined with PhastSystem (Pharmacia) to be ca. 6.8. The specific activity of Ta XYN_30 at 50° C. was determined to be 4800 nkat/mg (procedure of IUPAC 1987, using birch xylan as substrate).

Example 11

Internal Amino Acid Sequencing

The internal peptides were sequenced by electrospray ionization combined to tandem mass spectrometry (ESI-MS/MS) using the Q-TOF1 (Micromass) instrument. The protein was first alkylated and digested into tryptic peptides. Generated peptides were desalted and partially separated by nano liquid chromatography (reverse-phase) before applying to the Q-TOF1 instrument. The internal peptide sequences for *Chaetomium thermophilum* and *Acremonium thermophilum* cellobiohydrolases are shown in Table 2. The peptides from *Chaetomium* CBH were obtained after the corresponding cbh gene had been cloned. The peptides determined from *Acremonium* CBH were not utilized in the cloning of the corresponding gene.

TABLE 2

Internal peptide sequences determined from
Chaetomium thermophilum ALKO4265 CBH (1_C-4_C)
and Acremonium thermophilum ALKO4245
CBH (1_A-4_A).

| Peptide | Sequence |
|---|---|
| Peptide 1_C | T P S T N D A N A G F G R |
| Peptide 2_C | V A F S N T D D F N R |
| Peptide 3_C | F S N T D D F N R K |
| Peptide 4_C | P G N S L/I T Q E Y C D A Q/K K |
| Peptide 1_A | V T Q F I/L T G |
| Peptide 2_A | M G D T S F Y G P G |
| Peptide 3_A | C D P D G C D F N |
| Peptide 4_A | S G N S L/I T T D F |

I/L = leucine and isoleucine have the same molecular mass and cannot be distinguished in ESI-MS/MS analysis
Q/K = the molecular mass of glutamine and lysine differs only 0.036 Da and cannot be distinguished in ESI-MS/MS analysis The internal peptide sequences of purified endoglucanases, β-glucosidases, and xylanases of *Acremonium thermophilum* ALKO4245, *Chaetomium thermophilum* ALKO4261 and *Thermoascus aurantiacus* ALKO4242 are listed in Table 3, Table 4 and Table 5.

TABLE 3

Internal peptide sequences determined from
Acremonium thermophilum ALKO4245 EG_40,
Chaetomium thermophilum ALKO4261 EG_54 and
Thermoascus aurantiacus ALKO4242 EG_28
endoglucanases.

| Protein | Peptide | Sequence[a] |
|---|---|---|
| At EG_40 | Peptide 1 | Q S C S S F P A P L K P G C Q W R |
| | Peptide 2 | Y A L T F N S G P V A G K |
| | Peptide 3 | V Q C P S E L T S R |
| | Peptide 4 | N Q P V F S C S A D W Q R |
| | Peptide 5 | Y W D C C K P S C G W P G K |
| | Peptide 6 | P T F T |
| Ct EG_54 | Peptide 1 | E P E P E V T Y Y V |
| | Peptide 2 | Y Y L L D Q T E Q Y |
| | Peptide 3 | R Y C A C M D L W E A N S R |
| | Peptide 4 | P G N T P E V H P Q/K |
| | Peptide 5 | S I/L A P H P C N Q/K |
| | Peptide 6 | Q Q Y E M F R |
| | Peptide 7 | A L N D D F C R |
| | Peptide 8 | W G N P P P R |
| Ta EG_28 | Peptide 1 | I/L T S A T Q W L R |
| | Peptide 2 | G C A I/L S A T C V S S T I/L G Q E R |
| | Peptide 3 | P F M M E R |
| | Peptide 4 | Q Y A V V D P H N Y G R |

[a]I/L = leucine and isoleucine have the same molecular mass and cannot be distinguished in ESI-MS/MS analysis, Q/K = the molecular mass of glutamine and lysine differs only 0.036 Da and cannot be distinguished in ESI-MS/MS analysis.

TABLE 4

Internal peptide sequences determined from
Acremonium thermophilum ALKO4245 βG_101,
Chaetomium thermophilum ALKO4261 βG_76 and
Thermoascus aurantiacus ALKO4242 βG_81
beta-glucosidases.

| Protein | Peptide | Sequence[a] |
|---|---|---|
| At βG_101 | Peptide 1 | S P F T W G P T R |
| | Peptide 2 | V V V G D D A G N P C |
| | Peptide 3 | A F V S Q L T L L E K |
| | Peptide 4 | G T D V L/I Y T P N N K |
| | Peptide 5 | Q P N P A G P N A C V L/I R |
| Ct βG_76 | Peptide 1 | E G L F I D Y R |
| | Peptide 2 | P G Q S G T A T F R |
| | Peptide 3 | E T M S S N V D D R |
| | Peptide 4 | I A L V G S A A V V |
| | Peptide 5 | M W L C E N D R |
| | Peptide 6 | Y P Q L C L Q D G P L G I R |
| | Peptide 7 | E L N G Q N S G Y P S I |
| Ta βG_81 | Peptide 1 | T P F T W G K |
| | Peptide 2 | L C L Q D S L P G V R |
| | Peptide 3 | G V D V Q L G P V A G V A P R |
| | Peptide 4 | V N L T L E |
| | Peptide 5 | F T G V F G E D V V G |
| | Peptide 6 | N D L P L T G Y E K |

[a]I/L = leucine and isoleucine have the same molecular mass and cannot be distinguished in ESI-MS/MS analysis

TABLE 5

Internal peptide sequences determined from
Acremonium thermophilum ALKO4245 XYN_60
and Thermoascus aurantiacus ALKO4242 XYN_30
xylanases.

| Protein | Peptide | Sequence |
|---------|---------|----------|
| At XYN_60 | Peptide 1 | Y N D Y N L E Y N Q K |
|  | Peptide 2 | F G Q V T P E N |
|  | Peptide 3 | V D G D A T Y M S Y V N N K |
|  | Peptide 4 | K P A W T S V S S V L A A K |
|  | Peptide 5 | S Q G D I V P R A K |
| Ta XYN_30 | Peptide 1 | V Y F G V A T D Q N R |
|  | Peptide 2 | N A A I I Q A D F G Q V T P E N S M K |
|  | Peptide 3 | G H T L V W H S Q L P S W V S S I T D K |
|  | Peptide 4 | N H I T T L M T R |
|  | Peptide 5 | A W D V V N E A F N E D G S L R |
|  | Peptide 6 | L Y I N D Y N L D S A S Y P K |
|  | Peptide 7 | A S T T P L L F D G N F N P K P A Y N A I V Q D L Q Q |
|  | Peptide 8 | Q T V F L N V I G E D Y I P I A F Q T A R |

Example 12

Construction of Genomic Libraries for *Thermoascus Aurantiacus*, *Chaetomium Thermophilum* and *Acremonium Thermophilum*

The genomic library of *Chaetomium thermophilum* ALKO4265 and *Acremonium thermophilum* ALKO4245 were made to Lambda DASH®II vector (Stratagene, USA) according to the instructions from the supplier. The chromosomal DNAs, isolated by the method of Raeder and Broda (1985), were partially digested with Sau3A. The digested DNAs were size-fractionated and the fragments of the chosen size (≈5-23 kb) were dephosphorylated and ligated to the BamHI digested lambda vector arms. The ligation mixtures were packaged using Gigapack III Gold packaging extracts according to the manufacturer's instructions (Stratagene, USA). The titers of the *Chaetomium thermophilum* and *Acremonium thermophilum* genomic libraries were $3.6 \times 10^6$ pfu/ml and $3.7 \times 10^5$ pfu/ml and those of the amplified libraries were $6.5 \times 10^{10}$ pfu/ml and $4.2 \times 10^8$ pfu/ml, respectively.

Lambda FIX® II/Xho I Partial Fill-In Vector Kit (Stratagene, USA) was used in the construction of the genomic libraries for *Thermoascus aurantiacus* ALKO4242 and *Chaetomium thermophilum* ALKO4261 according to the instructions from the supplier. The chromosomal DNAs, isolated by the method of Raeder and Broda (1985), were partially digested with Sau3A. The digested DNAs were size-fractionated and the fragments of the chosen size (≈6-23 kb) were filled-in and ligated to the XhoI digested Lambda FIX II vector arms. The ligation mixtures were packaged using Gigapack III Gold packaging extracts according to the manufacturer's instructions (Stratagene, USA). The titers of the *Thermoascus aurantiacus* ALKO4242 and *Chaetomium thermophilum* ALKO4261 genomic libraries were $0.2 \times 10^6$ and $0.3 \times 10^6$ pfu/ml and those of the amplified libraries were $1.8 \times 10^9$ and $3.8 \times 10^9$ pfu/ml, respectively.

Example 13

Cloning of the Cellobiohydrolase (cbh/cel7) Genes from *Thermoascus Aurantiacus*, *Chaetomium Thermophilum* and *Acremonium Thermophilum*

Standard molecular biology methods were used in the isolation and enzyme treatments of DNA (plasmids, DNA fragments), in *E. coli* transformations, etc. The basic methods used are described in the standard molecular biology handbooks, e.g., Sambrook et al. (1989) and Sambrook and Russell (2001).

The probes for screening the genomic libraries which were constructed as described in Example 12 were amplified by PCR using the *Thermoascus aurantiacus* ALKO4242, *Chaetomium thermophilum* ALKO4265 and *Acremonium thermophilum* ALKO4245 genomic DNAs as templates in the reactions. Several primers tested in PCR reactions were designed according to the published nucleotide sequence (WO 03/000941, Hong et al., 2003b). The PCR reaction mixtures contained 50 mM Tris-HCl, pH 9.0, 15 mM $(NH_4)_2SO_4$, 0.1% Triton X-100, 1.5 mM $MgCl_2$, 0.2 mM dNTPs, 5 µM each primer and 1 units of Dynazyme EXT DNA polymerase (Finnzymes, Finland) and ≈0.5-1 µg of the genomic DNA. The conditions for the PCR reactions were the following: 5 min initial denaturation at 95° C., followed by 30 cycles of 1 min at 95° C., either 1 min annealing at 62° C. (±8° C. gradient) for *Thermoascus aurantiacus* ALKO4242 and *Chaetomium* ALKO4265 templates or 1 min annealing at 58° C. (±6° C. gradient) for *Acremonium* ALKO4245 template, 2 min extension at 72° C. and a final extension at 72° C. for 10 min.

DNA products of the expected sizes (calculated from published cbh sequences) were obtained from all genomic templates used. The DNA fragments of the expected sizes were isolated from the most specific PCR reactions and they were cloned to pCR® Blunt-TOPO® vector (Invitrogen, USA). The inserts were characterized by sequencing and by performing Southern blot hybridizations to the genomic DNAs digested with several restriction enzymes. The PCR fragments, which were chosen to be used as probes for screening of the *Thermoascus aurantiacus*, *Chaetomium thermophilum* and *Acremonium thermophilum* genomic libraries are presented in Table 6.

TABLE 6

The primers used in the PCR reactions and probes chosen for screening of the cbh/cel7 genes from *Thermoascus aurantiacus*, *Chaetomium thermophilum* and *Acremonium thermophilum* genomic libraries. The genomic template DNA and the name of the plasmid containing the probe fragment are shown.

| Gene | Forward primer | Reverse primer | Template DNA | Fragment (kb) | Plasmid |
|------|----------------|----------------|--------------|---------------|---------|
| Ta cbh | TCEL11 atgcgaactggcgttgggtcc | TCEL12 gaatttggagctagtgtcgacg | *Thermoascus* ALKO4242 | 0.8 kb | pALK1633 |
| Ct cbh | TCEL7 cgatgccaactggcgctggac | TCEL8 ttcttggtggtgtcgacggtc | *Chaetomium* ALKO4265 | 0.8 kb | pALK1632 |

TABLE 6-continued

The primers used in the PCR reactions and probes chosen for screening of the cbh/cel7 genes from Thermoascus aurantiacus, Chaetomium thermophilum and Acremonium thermophilum genomic libraries. The genomic template DNA and the name of the plasmid containing the probe fragment are shown.

| Gene | Forward primer | Reverse primer | Template DNA | Fragment (kb) | Plasmid |
|---|---|---|---|---|---|
| At cbh | TCEL13 agctcgaccaactgctacacg | TCEL4 accgtgaacttcttgctggtg | Acremonium ALKO4245 | 0.7 kb | pALK1634 |

The deduced amino acid sequences from all these probes had homology to several published CBH sequences (BLAST program, version 2.2.9 at NCBI, National Center for Biotechnology Information; Altschul et al., 1990) of glycoside hydrolase family 7 (Henrissat, 1991; Henrissat and Bairoch, 1993).

The inserts from the plasmids listed in Table 6 were labeled with digoxigenin according to the supplier's instructions (Roche, Germany), and the amplified genomic libraries ($2 \times 10^5$-$3 \times 10^5$ plaques) were screened with the labeled probe fragments. The hybridization temperature for the filters was 68° C. and the filters were washed 2×min at RT using 2×SSC–0.1% SDS followed by 2×15 min at 68° C. using 0.1×SSC–0.1% SDS with the homologous probes used. Several positive plaques were obtained from each of the hybridizations. In screening of the Acremonium ALKO4245 genomic libraries, some of the positive plaques were strongly hybridizing to the probe in question but, in addition, there was an amount of plaques hybridizing more weakly to the probes. This suggested that other cellobiohydrolase gene(s) might be present in the genome, causing cross-reaction. From four to five strongly hybridizing plaques were purified from Thermoascus ALKO4242 and Chaetomium ALKO4265 genomic library screenings. In the case of the Acremonium thermophilum ALKO4245, four out of six purified plaques hybridized weakly by the probe used. The phage DNAs were isolated and characterized by Southern blot hybridizations. The chosen restriction fragments hybridizing to the probe were subcloned to pBluescript II KS+vector and the relevant regions of the clones were sequenced.

In total four cbh/cel7 genes were cloned; one from Thermoascus aurantiacus ALKO4242, one from Chaetomium thermophilum ALKO4265 and two from Acremonium thermophilum ALKO4245 (at the early phase of the work, these had the codes At_cbh_C and At_cbh_A, and were then designated as At cel7A and At cel7B, respectively). Table 7 summarizes the information on the probes used for screening the genes, the phage clones from which the genes were isolated, the chosen restriction fragments containing the full-length genes with their promoter and terminator regions, the plasmid names, and the DSM deposit numbers for the E. coli strains carrying these plasmids.

TABLE 7

The probes used for cloning of cbh/cel7 genes, the phage clone and the subclones chosen, the plasmid number and the number of the deposit of the corresponding E. coli strain.

| Gene | Probe used in screening | Phage clone | The fragment subcloned to pBluescript II | Plasmid no | E. coli deposit no |
|---|---|---|---|---|---|
| Ta cel7A | pALK1633 | F12 | 3.2 kb XbaI | pALK1635 | DSM 16723 |
| Ct cel7A | pALK1632 | F36 | 2.3 kb PvuI-HindIII | pALK1642 | DSM 16727 |
| At cel7B | pALK1634 | F6 | 3.1 kb EcoRI | pALK1646 | DSM 16728 |
| At cel7A | pALK1634 | F2 | 3.4 kb XhoI | pALK1861 | DSM 16729 |

The relevant information on the genes and the deduced protein sequences (SEQ ID NO: 1-8) are summarized in Table 8 and Table 9, respectively.

The peptide sequences of the purified CBH proteins from Chaetomium thermophilum ALKO4265 and Acremonium thermophilum ALKO4245 (Table 2) were found from the deduced amino acid sequences of the clones containing the Ct cel7A and At cel7A genes. Thus, it could be concluded that the genes encoding the purified CBH/Cel7 proteins from Chaetomium thermophilum and Acremonium thermophilum were cloned.

TABLE 8

Summary on the cbh/cel7 genes isolated from Thermoascus aurantiacus ALKO4242, Chaetomium thermophilum ALK04265 and Acremonium thermophilum ALKO4245.

| Cbh gene | Length with introns (bp) [a] | Coding region (bp) [b] | No of introns | Lengths of introns (bp) | SEQ ID NO: |
|---|---|---|---|---|---|
| Ta cel7A | 1439 | 1371 | 1 | 65 | 1 |
| Ct cel7A | 1663 | 1596 | 1 | 64 | 7 |
| At cel7B | 1722 | 1377 | 3 | 134, 122, 87 | 3 |

TABLE 8-continued

Summary on the cbh/cel7 genes isolated from
Thermoascus aurantiacus ALKO4242,
Chaetomium thermophilum ALKO4265 and
Acremonium thermophilum ALKO4245.

| Cbh gene | Length with introns (bp) [a] | Coding region (bp) [b] | No of introns | Lengths of introns (bp) | SEQ ID NO: |
|---|---|---|---|---|---|
| At cel7A | 1853 | 1569 | 4 | 88, 53, 54, 86 | 5 |

[a] The STOP codon is included.
[b] The STOP codon is not included.

TABLE 9

Summary of amino acid sequences deduced from the cbh/cel7 gene sequences from Thermoascus aurantiacus ALKO4242, Chaetomium thermophilum ALK4265 and Acremonium thermophilum ALKO4245. ss, signal sequence.

| CBH protein | No of aas | Length of ss NN/HMM [a] | C-terminal CBD [b] | Predicted MW (Da, ss not incl) [c] | Predicted pI (ss not incl) | Putative N-glycosylation sites [d] | SEQ ID NO: |
|---|---|---|---|---|---|---|---|
| Ta Cel7A | 457 | 17/17 | NO | 46 873 | 4.44 | 2 | 2 |
| Ct Cel7A | 532 | 18/18 | YES, T497 to L532 | 54 564 | 5.05 | 3 | 8 |
| At Cel7B | 459 | 21/21 | NO | 47 073 | 4.83 | 2 | 4 |
| At Cel7A | 523 | 17/17 | YES, Q488 to L523 | 53 696 | 4.67 | 4 | 6 |

[a] The prediction on the signal sequence was made using the program SignalP V3.0 (Nielsen et al., 1997; Bendtsen et al., 2004); the NN value was obtained using neural networks and HMM value using hidden Markov models.
[b] The cellulose-binding domain (CBD), the amino acids of the C-terminal CBD region are indicated (M1 (Met #1) included in numbering)
[c] The predicted signal sequence was not included. The prediction was made using the Compute pI/MW tool at ExPASy server (Gasteiger et al., 2003).
[d] The number of sequences N-X-S/T.

The deduced amino acid sequences of *Thermoascus aurantiacus* Cel7A and *Acremonium thermophilum* Cel7A (core, without the CBD) were most homologous to each other (analyzed by Needleman-Wunsch global alignment, EMBOSS 3.0.0 Needle, with Matrix EBLOSUM62, Gap Penalty 10.0 and Extend Penalty 0.5; Needleman and Wunsch, 1970). In addition, the deduced *Acremonium thermophilum* Cel7A had a lower identity to the deduced *Chaetomium thermophilum* Cel7A. The *Acremonium thermophilum* Cel7B was most distinct from the CBH/Cel7 sequences of the invention.

The deduced *Chaetomium* Cel7A sequence possessed the highest identities (analyzed by Needleman-Wunsch global alignment, EMBOSS Needle, see above) to polypeptides of *Chaetomium thermophilum*, *Scytalidium thermophilum* and *Thielavia australiensis* CBHI described in WO 03/000941. Similarly, the deduced *Thermoascus aurantiacus* Cel7A sequence was highly identical to the published CBHI of the *Thermoascus aurantiacus* (WO 03/000941, Hong et al., 2003b). *Acremonium thermophilum* Cel7B had significantly lower identities to the previously published sequences, being more closely related to the CBHI polypeptide from *Oryza sativa*. The highest homologies of the deduced *Acremonium thermophilum* Cel7A sequence were to *Exidia gladulosa* and *Acremonium thermophilum* CBHI polynucleotides (WO 03/000941). The alignment indicates that the cloned *Thermoascus aurantiacus* ALKO4242, *Chaetomium thermophilum* ALKO4265 and *Acremonium thermophilum* ALKO4245 sequences encode the CBH proteins having high homology to the polypeptides of the glycoside hydrolase family 7, therefore these were designated as Cel7A or Cel7B (Henrissat et al. 1998).

The comparison of the deduced amino acid sequences of the cbh/cel7 genes from *Thermoascus aurantiacus* ALKO4242, *Chaetomium thermophilum* ALKO4265 and *Acremonium thermophilum* ALKO4245 *Thielavia* to each other, and further to the sequences found from the databases, are shown in Table 10.

TABLE 10

The highest homology sequences to the deduced amino acid sequences of the cbh/cel7 genes from *Thermoascus aurantiacus* ALKO4242, *Chaetomium thermophilum* ALKO4265 and *Acremonium thermophilum* ALKO4245.

| Organism, enzyme and accession number | Identity, (%) |
|---|---|
| * *Thermoascus aurantiacus* Cel7A | 100.0 |
| *Thermoascus aurantiacus*, AY840982 | 99.6 |
| *Thermoascus aurantiacus*, AX657575 | 99.1 |
| *Thermoascus aurantiacus*, AF421954 | 97.8 |
| *Talaromyces emersonii*, AY081766 | 79.5 |
| *Chaetomidium pingtungium*, AX657623 | 76.4 |
| *Trichophaea saccata*, AX657607 | 73.4 |
| * *Acremonium thermophilum* Cel7A (core) | 70.6 |
| *Emericella nidulans*, AF420020 (core) | 70.4 |
| * *Chaetomium thermophilum* Cel7A (core) | 66.4 |
| * *Chaetomium thermophilum* Cel7A | 100.0 |
| *Chaetomium thermophilum*, AY861347 | 91.9 |
| *Chaetomium thermophilum*, AX657571 | 91.7 |
| *Scytalidium thermophilum*, AX657627 | 74.7 |
| *Thielavia australiensis*, AX657577 | 74.6 |
| *Acremonium thermophilum*, AX657569 | 72.3 |
| *Exidia glandulosa*, AX657613 | 68.0 |
| * *Acremonium thermophilum* Cel7A | 66.9 |
| * *Thermoascus aurantiacus* Cel7A (core) | 66.4 |
| *Exidia glandulosa*, AX657615 | 60.8 |
| *Chaetomium pingtungium*, AX657623 | 60.7 |

TABLE 10-continued

The highest homology sequences to the deduced amino acid sequences of the cbh/cel7 genes from *Thermoascus aurantiacus* ALKO4242, *Chaetomium thermophilum* ALKO4265 and *Acremonium thermophilum* ALKO4245.

| Organism, enzyme and accession number | Identity, (%) |
|---|---|
| * *Acremonium thermophilum* Cel7B (core) | 60.2 |
| * *Acremonium thermophilum* Cel7B | 100.0 |
| *Oryza sativa*, AK108948 | 66.1 |
| *Exidia glandulosa*, AX657615 | 65.0 |
| *Acremonium thermophilum*, AX657569 (core) | 64.8 |
| *Thermoascus aurantiacus*, AX657575 | 64.8 |
| * *Acremonium thermophilum* Cel7A | 64.6 |
| * *Thermoascus aurantiacus* Cel7A | 64.4 |
| *Trichophaea saccata*, AX657607 | 63.6 |
| * *Chaetomium thermophilum* Cel7A (core) | 60.2 |
| * *Acremonium thermophilum* Cel7A | 100.0 |
| *Exidia glandulosa*, AX657613 | 77.9 |
| *Exidia glandulosa*, AX657615 | 77.9 |
| *Acremonium thermophilum*, AX657569 | 77.5 |
| *Thielavia australiensis*, AX657577 | 71.0 |
| * *Thermoascus aurantiacus* Cel7A (core) | 70.6 |
| *Scytalidium thermophilum*, AX657627 | 67.5 |
| *Chaetomium thermophilum*, AX657571 | 67.5 |
| *Chaetomium pingtungium*, AX657623 | 67.3 |
| * *Chaetomium thermophilum* Cel7A | 66.9 |
| * *Acremonium thermophilum* Cel7B (core) | 64.6 |

The alignment was made using Needleman-Wunsch global alignment (EMBLO-SUM62, Gap penalty 10.0, Extend penalty 0.5).
* indicates an amino acid sequence derived from one of the cellobiohydrolase genes cloned in this work. 'Core' indicates alignment without the CBD.

Example 14

Production of Recombinant CBH/Cel7 Proteins in *Trichoderma Reesei*

Expression plasmids were constructed for production of the recombinant CBH/Cel7 proteins from *Thermoascus aurantiacus* (Ta Cel7A), *Chaetomium thermophilum* (Ct Cel7A) and *Acremonium thermophilum* (At Cel7A, At Cel7B; at early phase of the work these proteins had the temporary codes At CBH_C and At CBH_A, respectively). The expression plasmids constructed are listed in Table 11. The recombinant cbh/cel7 genes, including their own signal sequences, were exactly fused to the *T. reesei* cbh1 (cel7A) promoter by PCR. The transcription termination was ensured by the *T. reesei* cel7A terminator and the *A. nidulans amdS* marker gene was used for selection of the transformants as described in Paloheimo et al. (2003). The linear expression cassettes (FIG. 2), were isolated from the vector backbones after EcoRI digestion and were transformed into *T. reesei* A96 and A98 protoplasts (both strains have the genes encoding the four major cellulases CBHI/Cel7A, CBHII/Cel6A, EGI/Cel7B and EGII/Cel5A deleted). The transformations were performed as in Penttilä et al. (1987) with the modifications described in Karhunen et al. (1993), selecting with acetamide as a sole nitrogen source. The transformants were purified on selection plates through single conidia prior to sporulating them on PD.

TABLE 11

The expression cassettes constructed to produce CBH/Cel7 proteins of *Thermoascus aurantiacus* ALKO4242 (Ta Cel7A), *Chaetomium thermophilum* ALKO4265 (Ct Cel7A), and *Acremonium thermophilum* ALKO4245 (At Cel7A, At Cel7B) in *Trichoderma reesei*.

| CBH/Cel7 | Expression plasmid | Size of the expr. cassette [a] | cel7A terminator [b] |
|---|---|---|---|
| Ta Cel7A | pALK1851 | 9.0 kb | 245 bp (XbaI) |
| Ct Cel7A | pALK1857 | 9.2 kb | 240 bp (HindIII) |
| At Cel7B | pALK1860 | 9.4 kb | 361 bp (EcoRI) |
| At Cel7A | pALK1865 | 9.5 kb | 427 bp (EcoRV) |

Figure 2:
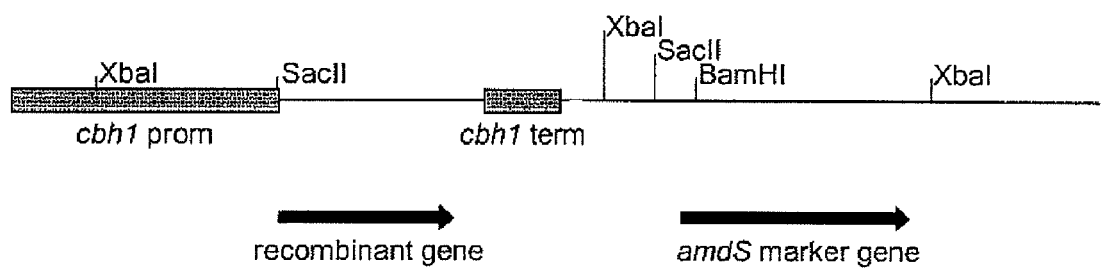
FIG. 2. Schematic picture of the expression cassettes used in the transformation of *Trichoderma reesei* protoplasts for producing the recombinant fungal proteins. The recombinant genes were under the control of *T. reesei* cbh1 (cel7A) promoter (cbh1 prom) and the termination of the transcription was ensured by using *T. reesei* cbh1 terminator sequence (cbh1 term). The amdS gene was included as a transformation marker.

The overall structure of the expression cassettes was as described in FIG. 2. The cloned cbh/cel7 genes were exactly fused to the *T. reesei* cbh1/cel7A promoter.
[a] The expression cassette for *T. reesei* transformation was isolated from the vector backbone by using EcoRI digestion.
[b] The number of the nucleotides from the genomic cbh1/cel7A terminator region after the STOP codon. The restriction site at the 3'-end, used in excising the genomic gene fragment, is included in the parenthesis.

The CBH/Cel7 production of the transformants was analysed from the culture supernatants of the shake flask cultivations (50 ml). The transformants were grown for 7 days at 28° C. in a complex lactose-based cellulase-inducing medium (Joutsjoki et al. 1993) buffered with 5% $KH_2PO_4$. The cellobiohydrolase activity was assayed using 4-methylumbelliferyl-β-D-lactoside (MUL) substrate according to van Tilbeurgh et al., 1988. The genotypes of the chosen transformants were confirmed by using Southern blots in which several genomic digests were included and the respective expression cassette was used as a probe. Heterologous expression of the Ta Cel7A, Ct Cel7A, At Cel7A and At Cel7B proteins was analyzed by SDS-PAGE with subsequent Coomassive staining. The findings that no cellobiohydrolase activity or heterologous protein production in SDS-PAGE could be detected for the At Cel7B transformants containing integrated expression cassette, suggest that At Cel7B is produced below detection levels in *Trichoderma* using the described experimental design.

Figure 3A:
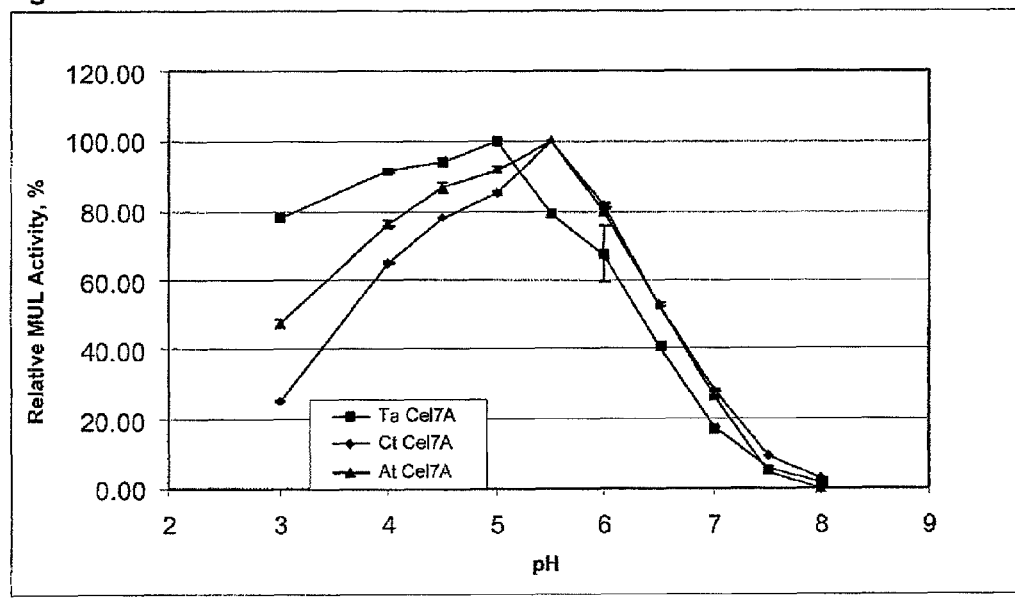
FIG. 3. A) pH optima of the recombinant CBH/Cel7 protein preparations from *Thermoascus aurantiacus* ALKO4242, *Chaetomium thermophilum* ALKO4265 and *Acremonium thermophilum* ALKO4245 determined on 4-methylumbelliferyl-β-D-lactoside (MUL) at 50° C., 10 min. The results are given as mean (±SD) of three separate measurements. B) Thermal stability of recombinant CBH/Cel7 protein preparations from *Thermoascus aurantiacus* ALKO4242, *Chaetomium thermophilum* ALKO4265 and *Acremonium thermophilum* ALKO4245 determined on 4-methylumbelliferyl-β-D-lactoside (MUL) at the optimum pH for 60 min. The results are given as mean (±SD) of three separate measurements. Both reactions contained BSA (100 µg/ml) as a stabilizer.
Figure 3B:
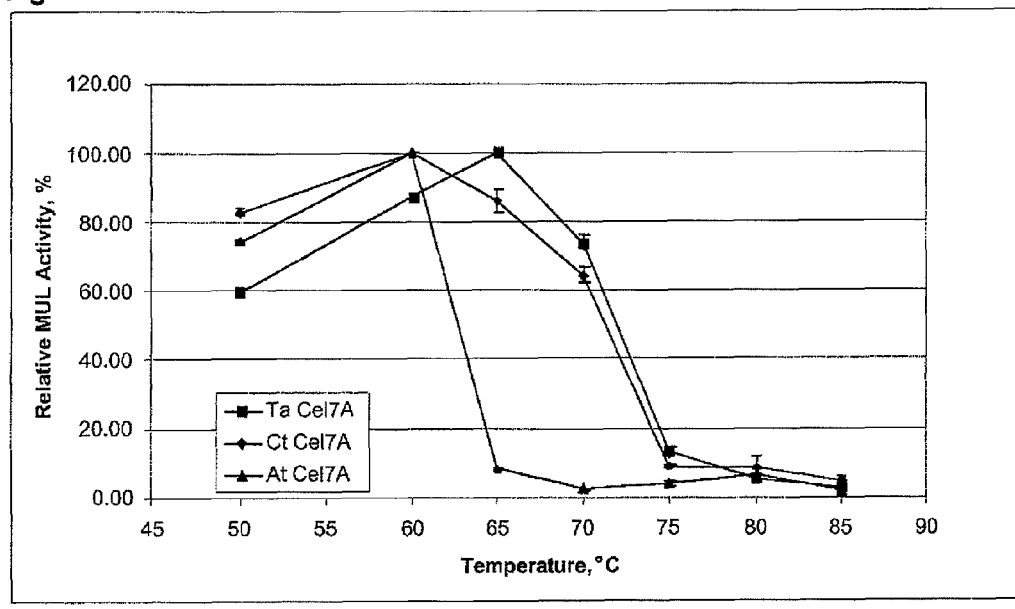

The recombinant CBH/Cel7 enzyme preparations were characterized in terms of pH optimum and thermal stability. The pH optimum of the recombinant CBH/Cel7 proteins from *Thermoascus aurantiacus*, *Chaetomium thermophilum*, and *Acremonium thermophilum* were determined in the universal McIlvaine buffer within a pH range of 3.0-8.0 using 4-methylumbelliferyl-β-D-lactoside (MUL) as a substrate (FIG. 3A). The pH optimum for Ct Cel7A and At Cel7A enzymes is at 5.5, above which the activity starts to gradually drop. The pH optimum of the recombinant crude Ta Cel7A is at 5.0 (FIG. 3A). Thermal stability of the recombinant Cel7 enzymes was determined by measuring the MUL activity in universal McIlvaine buffer at the optimum pH with reaction time of 1 h. As shown from the results Ta Cel7A and Ct Cel7A retained more than 60% of their activities at 70° C., whereas At Cel7A showed to be clearly less stable at the higher temperatures (≧65° C.) (FIG. 3 B).

The chosen CBH/Cel7 transformants were cultivated in lab bioreactors at 28° C. in the medium indicated above for 3-4 days with pH control 4.4±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

Example 15

Production of the Recombinant *Thermoascus Aurantiacus* Cel7A+CBD Fusion Proteins in *T. Reesei*

*Thermoascus aurantiacus* Cel7A (AF478686, Hong et al., 2003b; SEQ ID. NO: 1) was fused to linker and CBD of Trichoderma reesei CBHI/Cel7A (AR088330, Srisodsuk et al. 1993) (=Tr CBD) followed by the production of the fusion protein (SEQ ID NO: 28 corresponding nucleic acid SEQ ID. NO: 27) in the *T. reesei* as was described in FI20055205/U.S. Ser. No. 11/119,526; filed Apr. 29, 2005. In addition, *Thermoascus aurantiacus* Cel7A was fused to linker and CBD of *Chaetomium thermophilum* Cel7A (SEQ ID. NO: 7) (Ct CBD). For that purpose, the coding sequence of the linker and the CBD of *Chaetomium thermophilum* Cel7A were synthesized by PCR using following primers:

```
5'-TTAAACATATGTTATCTACTCCAACATCAAGGTCGGACCCATCGGCT
C-GACCGTCCCTGGCCTTGAC-3' (forward sequence)
And
5'-TATATGCGGCCGCAAGCTTTACCATCAAGTTACTCCAGCAAATCAGG
G-AACTG-3' (reverse sequence).
```

The PCR reaction mixture contained 1×DyNAzyme™ EXT reaction buffer (Finnzymes, Finland), 15 mM $Mg^2$, 0.2 mM dNTPs, 2 μM of each primer, 0.6 units of DyNAzyme™ EXT DNA polymerase (Finnzymes, Finland), and approximately 75 ng/30 μl of template DNA, containing full-length cel7A gene from the *Chaetomium thermophilum*. The conditions for the PCR reaction were the following: 2 min initial denaturation at 98° C., followed by 30 cycles of 30 sec at 98° C., 30 sec annealing at 68° C. (±4° C. gradient), 30 sec extension at 72° C. and a final extension at 72° C. for 10 min. The specific DNA fragment in PCR reaction was obtained at annealing temperature range from 64° C. to 68.5° C. The synthesized CBD fragment of the *Chaetomium thermophilum* was ligated after *Thermoascus aurantiacus* cel7A gene resulting in a junction point of GPIGST between the domains. The PCR amplified fragment in the plasmid was confirmed by sequencing (SEQ ID. NO: 29). The constructed fusion cel7A gene was exactly fused to the *T. reesei* cbh1 (cel7A) promoter. The transcription termination was ensured by the *T. reesei* cel7A terminator and the *A. nidulans* amdS marker gene was used for selection of the transformants as described in Paloheimo et al. (2003).

The linear expression cassette was isolated from the vector backbone after NotI digestion and was transformed to *T. reesei* A96 protoplasts. The transformations were performed as in Penttilä et al. (1987) with the modifications described in Karhunen et al. (1993), selecting with acetamide as a sole nitrogen source. The transformants were purified on selection plates through single conidia prior to sporulating them on PD.

*Thermoascus aurantiacus* Cel7A+CBD (SEQ ID. NO: 28 and 30) production of the transformants was analyzed from the culture supernatants of the shake flask cultivations (50 ml). The transformants were grown for 7 days in a complex cellulase-inducing medium (Joutsjoki et al. 1993) buffered with 5% $KH_2PO_4$ at pH 5.5. The cellobiohydrolase activity was assayed using 4-methylumbelliferyl-β-D-lactoside (MUL) substrate according to van Tilbeurgh et al., 1988. The genotypes of the chosen transformants were confirmed by using Southern blots in which several genomic digests were included and the expression cassette was used as a probe. The SDS-PAGE analyses showed that the recombinant *Thermoascus aurantiacus* Cel7A+CBD enzymes were produced as stable fusion proteins in *T. reesei*.

The chosen transformant producing the Ta Cel7A+Tr CBD fusion protein (SEQ ID. NO: 28) was also cultivated in 2 liter bioreactor at 28° C. in the medium indicated above for 3-4 days with pH control 4.4±0.2 ($NH_3$/$H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

Example 16

Comparison of the Michaelis-Menten and Cellobiose Inhibition Constants of Purified Recombinant Cellobiohydrolases The Michaelis-Menten and cellobiose inhibition constants were determined from the cellobiohydrolases produced heterologously in *T. reesei* (Examples 14 and 15). The enzymes were purified as described in Example 2. Protein concentrations of purified enzymes were measured by their absorption at 280 nm using a theoretical molar extinction co-efficient, which were calculated from the amino acid sequences (Gill and von Hippel, 1989).

Kinetic constants (Km and kcat values) and cellobiose inhibition constant (Ki) for Tr CBHI/Cel7A, Ta CBH/Cel7A, At CBH/Cel7A and Ct CBH/Cel7A, were measured using CNPLac (2-Chloro-4-nitrophenyl-β-D-lactoside) as substrate at ambient temperature (22° C.) in 50 mM sodium phosphate buffer, pH 5.7. For the determination of the inhibition constant (Ki), eight different substrate concentrations (31-4000 μM) in the presence of a range of five inhibitor concentrations (0-100 μM or 0-400 μM), which bracket the Ki value, were used. All experiments were performed in microtiter plates and the total reaction volume was 200 μl. The initial rates were in each case measured by continuous monitoring the release of the chloro-nitrophenolate anion (CNP, 2-Chloro-4-nitrophenolate) through measurements at 405 nm using Varioscan (Thermolabsystems) microtiter plate reader. The results were calculated from CNP standard curve (from 0 to 100 μM). Enzyme concentrations used were: Tr CBHI/Cel7A 2.46 μM, Ta CBH/Cel7A 1.58 μM, Ct CBH/Cel7A 0.79 μM and At CBH/Cel7A 3 μM. The Km and kcat constants were calculated from the fitting of the Michaelis-Menten equation using the programme of Origin. Lineweaver-Burk plots, replots (LWB slope versus [Glc2; cellobiose]) and Hanes plots were used to distinguish between competitive and mixed type inhibition and to determine the inhibition constants (Ki).

The results from the kinetic measurements are shown in Table 12 and Table 13. As can be seen, Ct CBH/Cel7A has clearly the higher turnover number (kcat) on CNPLac and also the specificity constant (kcat/Km) is higher as compared to CBHI/Cel7A of *T. reesei*. Cellobiose (Glc2) is a competitive inhibitor for all the measured cellulases, and the Tr CBHI/Cel7A (used as a control) has the strongest inhibition (i.e. the lowest Ki value) by cellobiose. The At CBH/Cel7A had over 7-fold higher inhibition constant as compared to that of Tr CBHI/Cel7A. These results indicate that all three novel cellobiohydrolases could work better on cellulose hydrolysis due to decreased cellobiose inhibition as compared to *Trichoderma reesei* Cel7A cellobiohydrolase I.

TABLE 12

Comparison of the cellobiose inhibition constants of four GH family 7 cellobiohydrolases, measured on CNPLac in 50 mM sodium phosphate buffer pH 5.7, at 22° C.

| Enzyme | Ki (μM) | Type of inhibition |
|---|---|---|
| Ct Cel7A | 39 | competitive |
| Ta Cel7A | 107 | competitive |

TABLE 12-continued

Comparison of the cellobiose inhibition constants of
four GH family 7 cellobiohydrolases, measured on CNPLac
in 50 mM sodium phosphate buffer pH 5.7, at 22° C.

| Enzyme | Ki (μM) | Type of inhibition |
|---|---|---|
| At Cel7A | 141 | competitive |
| Tr Cel7A | 19 | competitive |

TABLE 13

Comparison of the Michaelis-Menten kinetic constants
of *Chaetomium thermophilum* cellobiohydrolase Cel7A
to CBHI/Cel7A of *T. reesei*, measured on CNPLac in
50 mM sodium phosphate buffer pH 5.7, at 22° C.

| Enzyme | kcat (min$^{-1}$) | Km (μM) | kcat/Km (min$^{-1}$ M$^{-1}$) |
|---|---|---|---|
| Ct Cel7A | 18.8 | 1960 | 9.5 103 |
| Tr Cel7A | 2.6 | 520 | 5.0 103 |

Example 17

Hydrolysis of Crystalline Cellulose (Avicel) by the Recombinant Cellobiohydrolases The purified recombinant cellobiohydrolases Ct Cel7A, Ta Cel7A, Ta Cel7A+Tr CBD, Ta Cel7A+Ct CBD, At Cel7A as well as the core version of Ct Cel7A (see below) were tested in equimolar amounts in crystalline cellulose hydrolysis at two temperatures, 45° C. and 70° C.; the purified *T. reesei* Tr Cel7A and its core version (see below) were used as comparison. The crystalline cellulose (Ph 101, Avicel; Fluka, Bucsh, Switzerland) hydrolysis assays were performed in 1.5 ml tube scale 50 mM sodium acetate, pH 5.0. Avicel was shaken at 45° C. or at 70° C., with the enzyme solution (1.4 μM), and the final volume of the reaction mixture was 325 μl. The hydrolysis was followed up to 24 hours taking samples at six different time points and stopping the reaction by adding 163 μl of stop reagent containing 9 vol of 94% ethanol and 1 vol of 1 M glycine (pH 11). The solution was filtered through a Millex GV13 0.22 μm filtration unit (Millipore, Billerica, Mass., USA). The formation of soluble reducing sugars in the supernatant was determined by para-hydroxybenzoicacidhydrazide (PAHBAH) method (Lever, 1972) using a cellobiose standard curve (50 to 1600 μM cellobiose). A freshly made 0.1 M PAHBAH (Sigma-Aldrich, St. Louis, Mo., USA) in 0.5 M NaOH (100 μl) solution was added to 150 μl of the filtered sample and boiled for 10 minutes after which the solution was cooled on ice. The absorbance of the samples at 405 nm was measured.

The core versions of the cellobiohydrolases harboring a CBD in their native form were obtained as follows: Ct Cel7A and Tr Cel7A were exposed to proteolytic digestion to remove the cellulose-binding domain. Papain (Papaya Latex, 14 U/mg, Sigma) digestion of the native cellobiohydrolases was performed at 37° C. for 24 h in a reaction mixture composed of 10 mM L-cystein and 2 mM EDTA in 50 mM sodium acetate buffer (pH 5.0) with addition of papain (two papain concentrations were tested: of one fifth or one tenth amount of papain of the total amount of the Cel7A in the reaction mixture). The resultant core protein was purified with DEAE Sepharose FF (Pharmacia, Uppsala, Sweden) anion exchange column as described above. The product was analysed in SDS-PAGE.

Figure 4A:
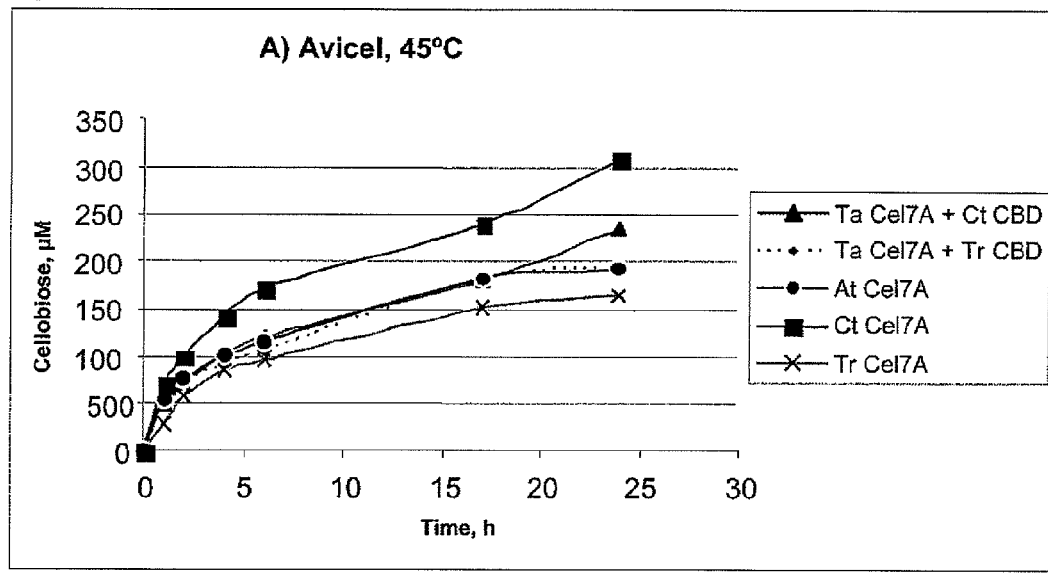
FIG. 4. Crystalline cellulose (Avicel) hydrolysis by the purified recombinant cellobiohydrolases at 45° C. Substrate concentration 1% (w/v), pH 5.0, enzyme concentration 1.4 µM. A) Cellobiohydrolases harboring a CBD, B) cellobiohydrolases (core) without a CBD.
Figure 4B:
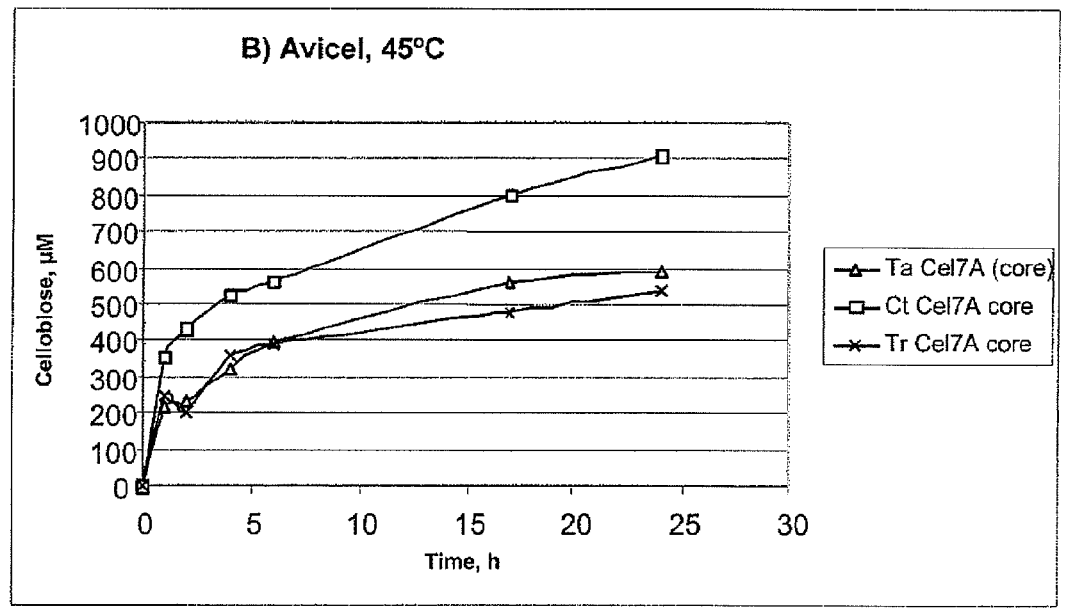
Figure 5A:
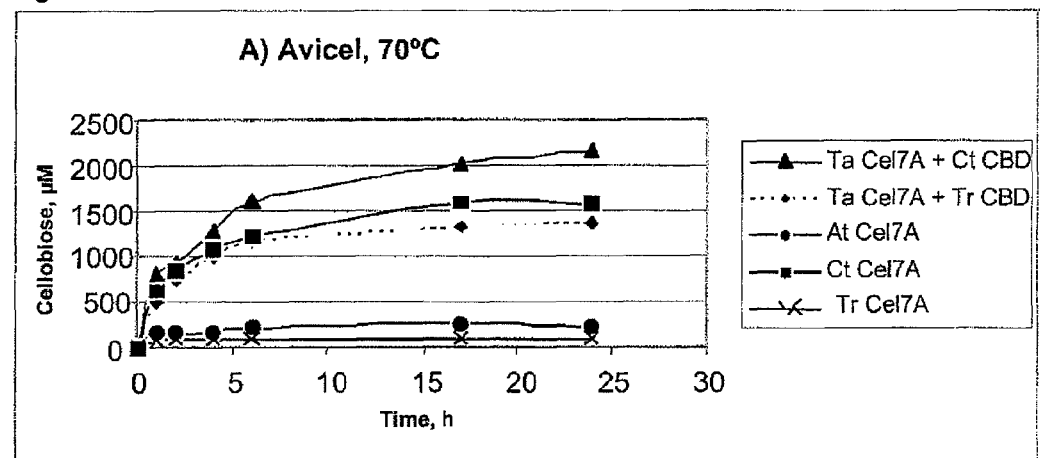
FIG. 5. Crystalline cellulose (Avicel) hydrolysis by the purified recombinant cellobiohydrolases at 70° C. Substrate concentration 1% (w/v), pH 5.0, enzyme concentration 1.4 µM. A) Cellobiohydrolases harboring a CBD, B) cellobiohydrolases (core) without a CBD.
Figure 5B:
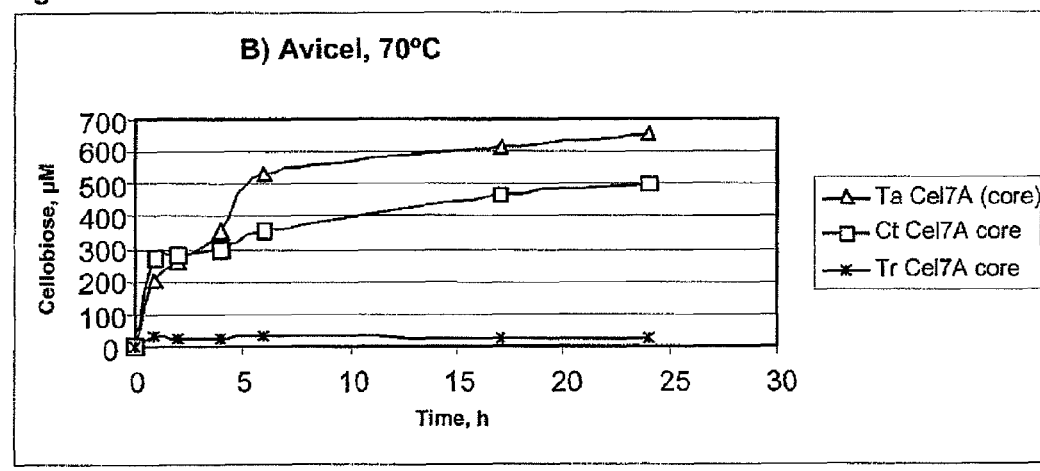

The hydrolysis results at 45° C. and 70° C. are shown in FIG. 4 and FIG. 5, respectively. The results show clearly that all the cellobiohydrolases show faster and more complete hydrolysis at both temperatures as compared to the state-of-art cellobiohydrolase *T. reesei* Cel7A. At 70° C. the thermostable cellobiohydrolases from *Thermoascus aurantiacus* ALKO4242 and *Chaetomium thermophilum* ALKO4265 are superior as compared to the *T. reesei* Cel7A, also in the case where the *Thermoascus* Cel7A core is linked to the CBD of *T. reesei* Cel7A (Ta Cel7A+Tr CBD). It was surprising that the cellobiohydrolases isolated and cloned in this work are superior, when harboring a CBD, in the rate and product formation in crystalline cellulose hydrolysis also at the conventional hydrolysis temperature of 45° C. when compared to the state-of-art cellobiohydrolase *T. reesei* Cel7A (CBHI) at the same enzyme concentration. The results are also in agreement with those enzyme preparations (At Cel7A and Ct Cel7A), which were purified from the original hosts and tested in Avicel hydrolysis (50° C., 24 h) (Example 2, Table 1).

Example 18

Cloning of *Acremonium Thermophilum* ALKO4245, *Chaetomium Thermophilum* ALKO4261, and *Thermoascus Aurantiacus* ALKO4242 Endoglucanase Genes Standard molecular biology methods were used as described in Example 13. The construction of the *Acremonium*, *Chaetomium*, and *Thermoascus* genomic libraries has been described in Example 12.

The peptides derived from the purified *Acremonium* and *Chaetomium* endoglucanases shared homology with several endoglucanases of glycosyl hydrolase family 45 such as *Melanocarpus albomyces* Cel45A endoglucanase (AJ515703) and *Humicola insolens* endoglucanase (A35275), respectively. Peptides derived from the *Thermoascus* endoglucanase shared almost 100% identity with the published *Thermoascus aurantiacus* EG1 endoglucanase sequence (AF487830). To amplify a probe for screening of the *Acremonium* and *Chaetomium* genomic libraries, degenerate primers were designed on the basis of the peptide sequences. The order of the peptides in the protein sequence and the corresponding sense or anti-sense nature of the primers was deduced from the comparison with the homologous published endoglucanases. Primer sequences and the corresponding peptides are listed in Table 14. Due to almost 100% identity of the *Thermoascus* peptides with the published sequence, the endoglucanase gene was amplified by PCR directly from the genomic DNA.

TABLE 14

Oligonucleotides synthesized and used as PCR
primers to amplify a probe for screening of
*Acremonium thermophilum* cel45A (EG_40) and
*Chaetomium thermophilum* cel7B (EG_54)
gene from the corresponding genomic libraries.

| Protein | Peptide | Primer location[a] | Primer sequence[b] |
|---|---|---|---|
| At EG_40 | Peptide 5 WFQNADN[c] | 1-6 | TAYTGGGAYTGYTGYAARCC RTTRTCNGCRTTYTGRAACCA |
| Ct EG_54 | Peptide 7 | 3-7 | GCAAGCTTCGRCARAARTCRT CRTT[d] |

TABLE 14-continued

Oligonucleotides synthesized and used as PCR primers to amplify a probe for screening of Acremonium thermophilum cel45A (EG_40) and Chaetomium thermophilum cel7B (EG_54) gene from the corresponding genomic libraries.

| Protein Peptide | Primer location[a] | Primer sequence[b] |
|---|---|---|
| Peptide 2 | 5-9 | GGAATTCGAYCARACNGARCARTA[e] |

[a]Amino acids of the peptide used for designing the primer sequence
[b]N = A, C, G, or T; R = A or G; Y = C or T
[c]Peptide not derived from the purified Acremonium EG_40 protein, but originates from the M. albomyces Cel45A sequence (AJ515703) homologous to EG_40.
[d]A HindIII restriction site was added to the 5' end of the oligonucleotide
[e]An EcoRI restriction site was added to the 5' end of the oligonucleotide The *Acremonium thermophilum* cel45A gene specific probe to screen the genomic library was amplified with the forward (TAYTGGGAYTGYTGYAARCC) and reverse (RTTRTCNGCRTTYTGRAACCA) primers using genomic DNA as a template. The PCR reaction mixtures contained 50 mM Tris-HCl, pH 9.0, 15 mM $(NH_4)_2SO_4$, 0.1% Triton X-100, 1.5 mM $MgCl_2$, 0.1 mM dNTPs, 0.5 μg each primer, 1 unit of Dynazyme EXT DNA polymerase (Finnzymes, Finland) and approximately 0.5 μg of *Acremonium* genomic DNA. The conditions for PCR reactions were the following: 5 min initial denaturation at 95° C., followed by 30 cycles of 1 min at 95° C., 1 min annealing at 50-60° C., 2 min extension at 72° C. and a final extension at 72° C. for 10 min. For amplification of the *Chaetomium thermophilum* cel7B gene (coding for Ct EG_54) specific probe, a forward primer (GGAATTCGAYCARACNGARCARTA) and a reverse primer (GCAAGCTTCGRCARAARTCRTCRTT) were used. The PCR reaction mixtures contained 10 mM Tris-HCl, pH 8.8, 50 mM KCl, 0.1% Triton X-100, 1.5 mM $MgCl_2$, 0.2 mM dNTPs, 250 pmol each primer, 2 unit of Dynazyme II DNA polymerase (Finnzymes, Finland) and approximately 2 μg of *Chaetomium* genomic DNA. The conditions for PCR reaction were as described above, except that annealing was performed at 45-50° C.

Two PCR products were obtained from the *Acremonium* PCR reaction. DNA fragments of about 0.6 kb and 0.8 kb were isolated from agarose gel and were cloned into the pCR4-TOPO® TA vector (Invitrogen, USA) resulting in plasmids pALK1710 and pALK1711, respectively. The DNA products were characterized by sequencing and by performing Southern blot hybridizations to the genomic *Acremonium* DNA digested with several restriction enzymes. The hybridization patterns obtained with the two fragments in stringent washing conditions suggest that two putative endoglucanase genes could be screened from the *Acremonium* genomic library. The deduced amino acid sequences of both PCR products have homology to several published endoglucanase sequences of glycosyl hydrolase family 45 (BLAST program, National Center for Biotechnology Information; Altschul et al., 1990).

One PCR product of expected size (estimated from the homologous *Humicola insolens* endoglucanase sequence, A35275) was obtained from the *Chaetomium* PCR reaction. This DNA fragment of about 0.7 kb was cloned into the pCR4-TOPO® TA vector (Invitrogen, USA) resulting in plasmid pALK2005 and analyzed as described above. The deduced amino acid sequence of the PCR product has homology to several published cellulase sequences of glycosyl hydrolase family 7 (BLAST program, version 2.2.9 at NCBI, National Center for Biotechnology Information; Altschul et al., 1990).

The insert from plasmids pALK1710, pALK1711, and pALK2005 was isolated by restriction enzyme digestion and labeled with digoxigenin according to the supplier's instructions (Roche, Germany). About $1-2 \times 10^5$ plaques from the amplified *Acremonium* or *Chaetomium* genomic library were screened. The temperature for hybridisation was 68° C. and the filters were washed 2×5 min at RT using 2×SSC–0.1% SDS followed by 2×15 min at 68° C. using 0.1×SSC–0.1% SDS. Several positive plaques were obtained, of which five to six strongly hybridizing plaques were purified from each screening. Phage DNAs were isolated and analysed by Southern blot hybridization. Restriction fragments hybridizing to the probe were subcloned into the pBluescript II KS+ vector (Stratagene, USA) and the relevant parts were sequenced. In all cases the subcloned phage fragment contains the full-length gene of interest. Table 15 summarises the information of the probes used for screening of the endoglucanase genes, phage clones from which the genes were isolated, chosen restriction fragments containing the full-length genes with their promoter and terminator regions, names of plasmids containing the subcloned phage fragment, and the deposit numbers in the Deutsche Sammlung von Mikroorganismen and Zellkulturen GmbH culture collection (DSM) for *E. coli* strains carrying these plasmids.

TABLE 15

Probes used for cloning of endoglucanase gene, phage clone and the subclone chosen, plasmid name and the corresponding deposit number of the *E. coli* strain.

| Gene | Genomic library | Probe used in screening | Phage clone | Subcloned fragment | Plasmid | E. coli deposit no. |
|---|---|---|---|---|---|---|
| At cel45A | A. thermophilum ALKO4245 | pALK1710 | P24 | 5.5 kb SmaI | pALK1908 | DSM 17324 |
| At cel45B | A. thermophilum ALKO4245 | pALK1711 | P41 | 6.0 kb XhoI | pALK1904 | DSM 17323 |
| Ct cel7B | C. thermophilum ALKO4261 | pALK2005 | P55 | 5.1 kb BamHI | pALK2010 | DSM 17729 |

*Thermoascus aurantiacus* cel5A gene (coding for EG_28) (SEQ ID NO: 9) was amplified directly from the isolated genomic DNA by PCR reaction. The forward (ATTAAC-CGCGGACTGCGCATCATGAAGCTCG-GCTCTCTCGTGCTC) and reverse (AACTGAGGCATA-GAAACTGACGTCATATT) primers that were used for amplification were designed on the basis of the published *T. aurantiacus* eg1 gene (AF487830). The PCR reaction mixtures contained 1× Phusion HF buffer, 0.3 mM dNTPs, 0.5

µM of each primer, 2 units of Phusion™ DNA polymerase (Finnzymes, Finland) and approximately 0.25 µg of *Thermoascus* genomic DNA. The conditions for PCR reactions were the following: 5 min initial denaturation at 95° C., followed by 25 cycles of 30 s at 95° C., 30 s annealing at 57-67° C., 2.5 min extension at 72° C. and a final extension at 72° C. for 5 min. The amplified 1.3 kb product containing the exact gene (from START to STOP codon) was cloned as a SacII-PstI fragment into the pBluescript II KS+ vector. Two independent clones were sequenced and one clone was selected and designated as pALK1926. The deposit number of the *E. coli* strain containing pALK1926 in the Deutsche Sammlung von Mikroorganismen and Zellkulturen GmbH culture collection is DSM 17326.

Relevant information of the genes and the deduced protein sequences (SEQ ID NO: 9-16) are summarized in Table 16 and Table 17, respectively. Peptide sequences of the purified *Acremonium* EG_40 (gene At cel45A), *Chaetomium* EG_54 (gene Ct cel7B), and *Thermoascus* EG_28 (gene Ta cel5A) endoglucanases were found in the corresponding deduced amino acid sequences of the cloned genes confirming that appropriate genes were cloned.

TABLE 16

Summary of the endoglucanase genes isolated from *Acremonium thermophilum, Chaetomium thermophilum*, and *Thermoascus aurantiacus*.

| Endoglucanase gene | Length with introns (bp) [a] | Coding region (bp) [b] | No of introns | Lengths of introns (bp) | SEQ ID NO: |
|---|---|---|---|---|---|
| At cel45A | 1076 | 891 | 2 | 59, 123 | 11 |
| At cel45B | 1013 | 753 | 2 | 155, 102 | 13 |
| Ct cel7B | 1278 | 1275 | — | — | 15 |
| Ta cel5A | 1317 | 1005 | 5 | 55, 60, 59, 74, 61 | 9 |

[a] The STOP codon is included.
[b] The STOP codon is not included.

TABLE 17

Summary of the deduced endoglucanase sequences of *Acremonium thermophilum, Chaetomium thermophilum*, and *Thermoascus aurantiacus*.

| Endoglucanase protein | No of aas | Length of ss NN/HMM [a] | CBD [b] | Predicted MW (Da, ss not incl) [c] | Predicted pI (ss not incl) | Putative N-glycosylation sites [d] | SEQ ID NO: |
|---|---|---|---|---|---|---|---|
| At EG_40 | 297 | 21/21 | Yes, K265 to L297 | 28625 | 4.79 | 2 | 12 |
| At EG_40_like | 251 | 20/20 | No | 23972 | 6.11 | 2 | 14 |
| Ct EG_54 | 425 | 17/17 | No | 45358 | 5.44 | 1 | 16 |
| Ta EG_28 | 335 | 30 [e] | No | 33712 | 4.30 | 1 | 10 | ss, signal sequence.
[a] The prediction of the signal sequence was made using the program SignalP V3.0 (Nielsen et al., 1997; Bendtsen et al., 2004); the NN value was obtained using neural networks and HMM value using hidden Markov models.
[b] Presence of a cellulose binding domain in the protein, the amino acids of the C-terminal CBD are indicated (numbering according to the full length polypeptide)
[c] The predicted signal sequence is not included. Prediction was made using the Compute pI/MW tool at ExPASy server (Gasteiger et al., 2003).
[d] The putative N-glycosylation sites N-X-S/T were predicted using the program NetNGlyc 1.0 (Gupta et al., 2004).
[e] According to Hong et al. 2003a The deduced protein sequences of *Acremonium* EG_40 (At Cel45A) and EG_40_like (At Cel45B), *Chaetomium* EG_54 (Ct Cel7B), and *Thermoascus* EG_28 (Ta Cel5A) endoglucanases share homology with cellulases of glycosyl hydrolase family 45 (*Acremonium*), family 7 (*Chaetomium*), and family 5 (*Thermoascus*), thus identifying the isolated genes as members of these gene families. The closest homologies of the *Acremonium* endoglucanases EG_40/Cel45A and EG_40_like/Cel45B are endoglucanases of *Thielavia terrestris* (CQ827970, 77.3% identity) and *Myceliophthora thermophile* (AR094305, 66.9% identity), respectively (Table 18). The two isolated *Acremonium* family 45 endoglucanases share only an identity of 53.7% with each other. Of these enzymes only EG_40/Cel45A contains a cellulose binding domain (CBD).

The closest homology for the predicted protein sequence of *Chaetomium* EG_54/Cel7B endoglucanase is found in the *Melanocarpus albomyces* Cel7A cellulase sequence (AJ515704). The identity between these two protein sequences is 70.6%.

The protein sequence of the isolated *Thermoascus aurantiacus* endoglucanase is completely identical with that of the published *T. aurantiacus* EGI (AF487830, Table 18). The closest homology was found in a β-glucanase sequence of *Talaromyces emersonii* (AX254752, 71.1% identity).

TABLE 18

Comparison of the deduced *Acremonium thermophilum* EG_40, EG_40_like/Cel45B, *Chaetomium thermophilum* EG_54/Cel7B, and *Thermoascus aurantiacus* EG_28/Cel5A endoglucanases with their homologous counterparts.

| Organism, enzyme, and accession number | Identity (%) |
| --- | --- |
| *Acremonium thermophilum* EG_40 | 100.0 |
| *Thielavia terrestris* EG45, CQ827970 | 77.3 |
| *Melanocarpus albomyces* Cel45A, AJ515703 | 75.3 |
| *Neurospora crassa*, hypothetical XM_324477 | 68.9 |
| *Humicola grisea* var *thermoidea*, EGL3, AB003107 | 67.5 |
| *Humicola insolens* EG5, A23635 | 67.3 |
| *Myceliophthora thermophila* fam 45, AR094305 | 57.9 |
| * *Acremonium thermophilum* EG_40_like | 53.7 |
| *Acremonium thermophilum* EG_40_like | 100.0 |
| *Myceliophthora thermophila* fam 45, AR094305 | 66.9 |
| *Magnaporthe grisea* 70-15 hypothetical, XM_363402 | 61.9 |
| *Thielavia terrestris* EG45, CQ827970 | 56.8 |
| * *Acremonium thermophilum* EG_40 | 53.7 |
| *Melanocarpus albomyces* Cel45A, AJ515703 | 52.8 |
| *Chaetomium thermophilum* EG_54 | 100.0 |
| *Melanocarpus albomyces* Cel7A, AJ515704 | 70.6 |
| *Humicola grisea* var *thermoidea* EGI, D63516 | 68.8 |
| *Humicola insolens* EGI, AR012244 | 67.7 |
| *Myceliophthora thermophila* EGI, AR071934 | 61.7 |
| *Fusarium oxysporum* var *lycopercisi* EGI, AF29210 | 53.5 |
| *Fusarium oxysporum* EGI, AR012243 | 52.6 |
| *Thermoascus aurantiacus* EG_28 | 100.0 |
| *Thermoascus aurantiacus* EG, AX812161 | 100.0 |
| *Thermoascus aurantiacus* EGI, AY055121 | 99.4 |
| *Talaromyces emersonii* β-glucanase, AX254752 | 71.1 |
| *Talaromyces emersonii* EG, AF440003 | 70.4 |
| *Aspergillus niger* EG, A69663 | 70.1 |
| *Aspergillus niger* EG, A62441 | 69.9 |
| *Aspergillus niger* EG, AF331518 | 69.6 |
| *Aspergillus aculeatus* EGV, AF054512 | 68.5 |

The alignment was performed using the Needle programme of the EMBOSS programme package.
* indicates an endoglucanase encoded by a gene cloned in this work.

Example 19

Production of Recombinant Endoglucanases in *Trichoderma Reesei*

Expression plasmids were constructed for production of the recombinant *Acremonium* EG_40/Cel45A, EG_40 like/Cel45B, and *Thermoascus* EG_28/Cel5A proteins as described in Example 14. Linear expression cassettes (Table 19) were isolated from the vector backbone by restriction enzyme digestion, transformed into *T. reesei* A96 and transformants purified as described in Example 14.

TABLE 19

The expression cassettes constructed for production of *Acremonium thermophilum* EG_40/Cel45A, EG_40_like/Cel45B, and *Thermoascus aurantiacus* EG_28/Cel5A endoglucanases in *Trichoderma reesei*.

| Endoglucanase | Expression plasmid | Size of the expression cassette[a] | Heterologous terminator[b] |
| --- | --- | --- | --- |
| At EG_40 | pALK1920 | 10.9 kb NotI | 156 bp (HindIII) |
| At EG_40_like | pALK1921 | 8.6 kb EcoRI | 282 bp (SspI) |
| Ta EG_28 | pALK1930 | 8.6 kb NotI | none |

The schematic structure of the expression cassettes is described in FIG. 2.
[a] The expression cassette for *T. reesei* transformation was isolated from the vector backbone by EcoRI or NotI digestion.
[b] The number of nucleotides after the STOP codon of the cloned gene that are included in the expression cassette are indicated. The restriction site at the 3'-region of the gene that was used in construction of the expression cassette is indicated in parenthesis.

The endoglucanase production of the transformants was analyzed from the culture supernatants of shake flask cultivations (50 ml). Transformants were grown as in Example 14 and the enzyme activity of the recombinant protein was measured from the culture supernatant as the release of reducing sugars from carboxymethylcellulose (2% (w/v) CMC) at 50° C. in 50 mM citrate buffer pH 4.8 essentially as described by Bailey and Nevalainen 1981; Haakana et al. 2004. Production of the recombinant proteins was also detected from culture supernatants by SDS-polyacrylamide gel electrophoresis. *Acremonium* EG_40-specific polyclonal antibodies were produced in rabbits (University of Helsinki, Finland). The expression of EG_40 was verified by Western blot analysis with anti-EG_40 antibodies using the ProtoBlot Western blot AP system (Promega). The genotypes of the chosen transformants were analysed by Southern blotting using the expression cassette as a probe.

Figure 6A:
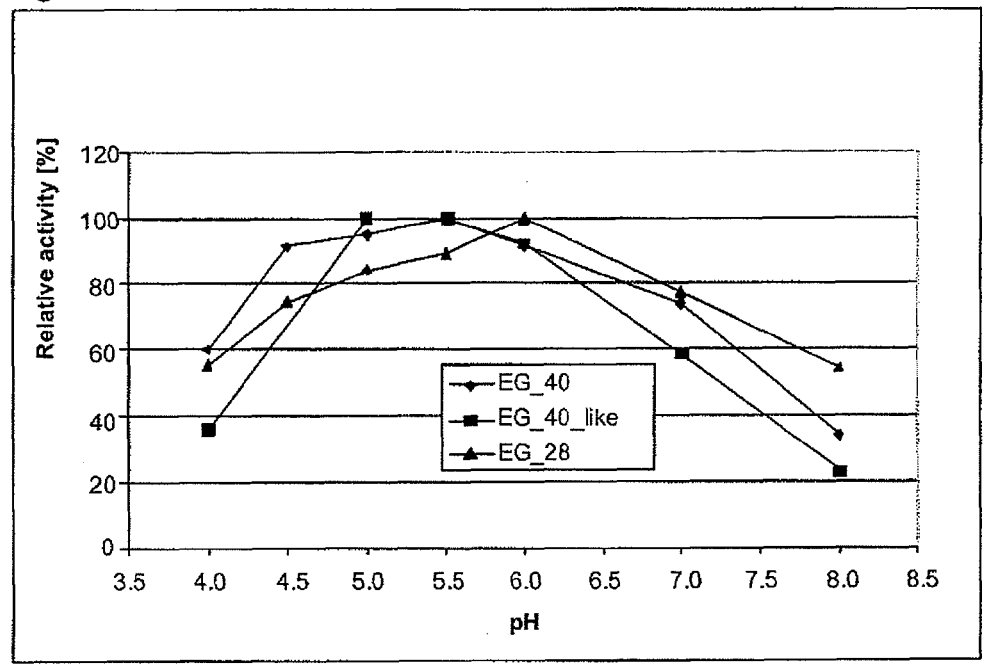
FIG. 6. A) The pH dependency of the heterologously produced *Acremonium* EG_40/Cel45A, EG_40_like/Cel45B and *Thermoascus* EG_28/Cel5A activity was determined with CMC substrate in a 10 min reaction at 50° C. B) Temperature optimum of the *Acremonium* EG_40/Cel45A, EG_40_like/Cel45B and *Thermoascus* EG_28/Cel5A was determined at pH 5.5, 4.8, and 6.0, respectively. The reaction containing CMC as substrate was performed for 60 min, except for EG_28/Cel5A for 10 min. BSA (100 µg/ml) was added as a stabilizer.
Figure 6B:
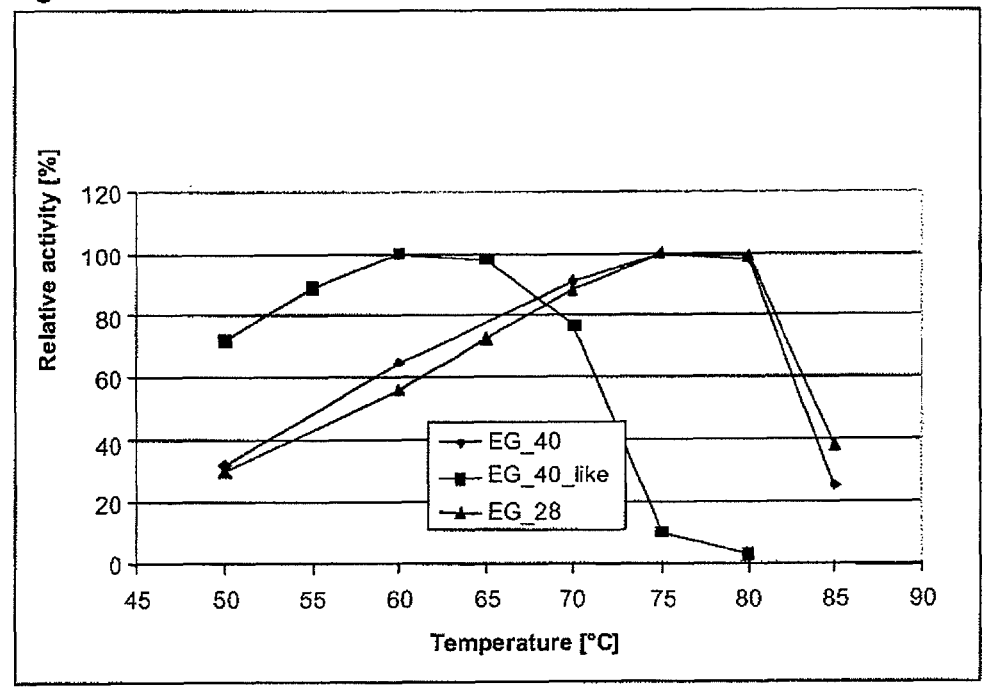

The pH optimum of the heterologously produced endoglucanases was determined in the universal McIlvaine's buffer within a pH range of 4.0-8.0 using carboxymethylcellulose as substrate. As shown in FIG. 6 A the broadest pH range (4.5-6.0) is that of the *Acremonium* EG_40/Cel45A protein, the optimum being at pH 5.5. The pH optima for the other heterologously produced endoglucanases are pH 5.0-5.5 and 6.0 for *Acremonium* EG_40_like/Cel45B and *Thermoascus* EG_28/Cel5A, respectively. The optimal temperature for enzymatic activity of these endoglucanases was determined at the temperature range of 50-85° C. as described above. The highest activity of the enzymes was determined to be at 75° C., 60° C., and 75° C. for the *Acremonium* EG_40/Cel45A, EG_40 like/Cel45B, and *Thermoascus* EG_28/Cel5A, respectively (FIG. 6 B).

The chosen transformants were cultivated, as described in Example 14, in a 2 liter bioreactor for four days (28° C., pH 4.2) to obtain material for the application tests.

Example 20

Cloning of *Acremonium Thermophilum* ALKO4245, *Chaetomium Thermophilum* ALKO4261, and *Thermoascus Aurantiacus* ALKO4242 Beta-Glucosidase Genes Standard molecular biology methods were used as described in Example 13. The construction of the *Acremonium*, *Chaetomium*, and *Thermoascus* genomic libraries has been described in Example 12.

The peptides derived from the purified *Acremonium*, *Chaetomium*, and *Thermoascus* β-glucosidases shared homology with several β-glucosidases of glycosyl hydrolase family 3 such as *Acremonium cellulolyticus* (BD168028), *Trichoderma viride* (AY368687), and *Talaromyces emersonii* (AY072918) β-glucosidases, respectively. To amplify a probe for screening of the *Acremonium*, *Chaetomium*, or *Thermoascus* genomic libraries, degenerate primers were designed on the basis of the peptide sequences. The order of the peptides in the protein sequence and the corresponding sense or antisense nature of the primers was deduced from the comparison with the homologous published β-glucosidases. Primer sequences and the corresponding peptides are listed in Table 20.

TABLE 20

Oligonucleotides synthesized and used as PCR primers to amplify a probe for screening of Acremonium thermophilum cel3A (βG_101), Chaetomium thermophilum cel3A (βG_76), and Thermoascus aurantiacus cel3A (βG_81) gene from the corresponding genomic libraries.

| Protein | Peptide | Primer location[a] | Primer Sequence |
|---|---|---|---|
| At βG_101 | EKVNLT[c] Peptide 4 | 6-11 | GARAARGTNAAYCTNAC YTTRCCRTTRTTSGGRGTR TA |
| Ct βG_76 | Peptide 6 Peptide 1 | 4-9 3-8 | TNTGYCTNCARGAYGG TCRAARTGSCGRTARTCRA TRAASAG |
| Ta βG-81 | Peptide 3 Peptide 1 | 1-5 2-7 | AARGGYGTSGAYGTSCAR YTTRCCCCASGTRAASGG |

[a]Amino acids of the peptide used for designing the primer sequence
[b]To reduce degeneracy, some codons were chosen according to fungal preference. N = A, C, G, or T; R = A or G; S = C or G; Y = C or T
[c]Peptide not derived from the purified Acremonium βG_101 protein, but originates from the A. cellulolyticus β-glucosidase sequence (BD168028) homologous to βG_101.

The probes for screening genomic libraries constructed were amplified with the listed primer combinations (Table 20) using Acremonium, Chaetomium, or Thermoascus genomic DNA as template. The PCR reaction mixtures contained 50 mM Tris-HCl, pH 9.0, 15 mM $(NH_4)_2SO_4$, 0.1% Triton X-100, 1.5 mM $MgCl_2$, 0.1-0.2 mM dNTPs, 0.25 μg each primer, 1 unit of Dynazyme EXT DNA polymerase (Finnzymes, Finland) and approximately 0.5 μg of genomic DNA. The conditions for PCR reactions were the following: 5 min initial denaturation at 95° C., followed by 30 cycles of 1 min at 95° C., 1 min annealing at 40° C. (Acremonium DNA as a template), at 50° C. (Chaetomium DNA as a template), or at 63° C. (Thermoascus DNA as a template), 2-3 min extension at 72° C. and a final extension at 72° C. for 5-10 min.

Specific PCR products of expected size (estimated from the homologous β-glucosidase sequences BD168028, AY072918, and AY368687) were isolated from the agarose gel. DNA fragments of about 1.8 kb (Acremonium), 1.5 kb (Chaetomium), and 1.52 kb (Thermoascus) were cloned into the pCR4-TOPO® TA vector (Invitrogen, USA) resulting in plasmids pALK1924, pALK1935, and pALK1713, respectively. The DNA products were characterized by sequencing and by performing Southern blot hybridizations to the genomic DNA digested with several restriction enzymes. The hybridization patterns in stringent washing conditions suggest that one putative β-glucosidase gene could be isolated from the Acremonium, Chaetomium, and Thermoascus genomic library. The deduced amino acid sequences of all three PCR products have homology to several published β-glucosidase sequences of glycosyl hydrolase family 3 (BLAST program, National Center for Biotechnology Information; Altschul et al., 1990).

The insert from plasmids pALK1713, pALK1924, and pALK1935 was isolated by restriction enzyme digestion and labeled with digoxigenin according to the supplier's instructions (Roche, Germany). About $1-2 \times 10^5$ plaques from the amplified Acremonium, Chaetomium, or Thermoascus genomic library were screened as described in Example 18. Several positive plaques were obtained, of which five to six strongly hybridizing plaques were purified from each screening. Phage DNAs were isolated and analysed by Southern blot hybridization. Restriction fragments hybridizing to the probe were subcloned into the pBluescript II KS+ vector (Stratagene, USA) and the relevant parts were sequenced. In all cases the subcloned phage fragment contains the full-length gene of interest. Table 21 summarises the information of the probes used for screening of the β-glucosidase genes, phage clones from which the genes were isolated, chosen restriction fragments containing the full-length genes with their promoter and terminator regions, names of plasmids containing the subcloned phage fragment, and the deposit numbers in the Deutsche Sammlung von Mikroorganismen and Zellkulturen GmbH culture collection (DSM) for E. coli strains carrying these plasmids.

TABLE 21

Probes used for cloning of β-glucosidase gene, phage clone and the subclone chosen, plasmid name and the corresponding deposit number of the E. coli strain.

| Gene | Genomic library | Probe used in screening | Phage clone | Subcloned fragment | Plasmid | E. coli deposit no. |
|---|---|---|---|---|---|---|
| At cel3A | A. thermophilum ALKO4245 | pALK1924 | P44 | 6.0 kb HindIII | pALK1925 | DSM 17325 |
| Ct cel3A | C. thermophilum ALKO4261 | pALK1935 | P51 | 7.0 kb XbaI | pALK2001 | DSM 17667 |
| Ta cel3A | T. aurantiacus ALKO4242 | pALK1713 | P21 | 5.3 kb BamHI | pALK1723 | DSM 16725 |

Relevant information of the genes and deduced protein sequences (SEQ ID NO: 21-26) are summarized in Table 22 and Table 23, respectively. Peptide sequences of the purified Acremonium βG_101 (At Cel3A), Chaetomium βG_76 (Ct Cel3A), and Thermoascus βG_81 (Ta Cel3A) proteins were found in the corresponding deduced amino acid sequences of the cloned genes confirming that appropriate genes were cloned.

TABLE 22

Summary of the β-glucosidase genes isolated from *Acremonium thermophilum*, *Chaetomium thermophilum*, and *Thermoascus aurantiacus*.

| β-glucosidase gene | Length with introns (bp) [a] | Coding region bp) [b] | No of introns | Lengths of introns (bp) | SEQ ID NO: |
|---|---|---|---|---|---|
| At cel3A | 2821 | 2583 | 3 | 92, 74, 69 | 23 |
| Ct cel3A | 2257 | 2202 | 1 | 52 | 25 |
| Ta cel3A | 3084 | 2529 | 7 | 134, 67, 56, 64, 59, 110, 62 | 21 |

[a] The STOP codon is included.
[b] The STOP codon is not included.

TABLE 23

Summary of the deduced β-glucosidase sequences of *Acremonium thermophilum*, *Chaetomium thermophilum*, and *Thermoascus aurantiacus*.

| β-glucosidase protein | No of aas | Length of ss NN/HMM[a] | CBD[b] | Predicted MW (Da, ss not incl)[c] | Predicted pI ss not incl) | Putative N-glycosylation sites[d] | SEQ ID NO: |
|---|---|---|---|---|---|---|---|
| At βG_101 | 861 | 19/18 | No | 91434 | 5.46 | 8 | 24 |
| Ct βG_76 | 734 | 20/20 | No | 76457 | 6.3 | 2 | 26 |
| Ta βG_81 | 843 | 19/19 | No | 89924 | 4.95 | 8 | 22 | ss, signal sequence.
[a] The prediction of the signal sequence was made using the program SignalP V3.0 (Nielsen et al., 1997; Bendtsen et al, 2004); the NN value was obtained using neural networks and HMM value using hidden Markov models.
[b] Presence of a cellulose binding domain in the protein.
[c] The predicted signal sequence is not included. Prediction was made using the Compute pI/MW tool at ExPASy server (Gasteiger et al., 2003).
[d] The putative N-glycosylation sites N-X-S/T were predicted using the program NetNGlyc 1.0 (Gupta et al., 2004).

The deduced protein sequences of *Acremonium* βG_101/Cel3A, *Chaetomium* βG_76/Cel3A, and *Thermoascus* βG_81/Cel3A β-glucosidases share homology with enzymes of glycosyl hydrolase family 3, thus identifying that the isolated genes belong to this gene family. The closest counterparts of the *Acremonium*, *Chaetomium*, and *Thermoascus* β-glucosidases are those of *Magnaporthe grisea* (β-glucosidase, AY849670), *Neurospora crassa* (hypothetical, XM_324308), and *Talaromyces emersonii* (β-glucosidase, AY072918), respectively (Table 24). The highest sequence identity (73.2%) found was that of *C. thermophilum* βG 76/Cel3A to *N. crassa* hypothetical protein indicating that novel enzymes genes were cloned.

TABLE 24

Comparison of the deduced *Acremonium thermophilum* βG_101/Cel3A, *Chaetomium thermophilum* βG_76/Cel3A, and *Thermoascus aurantiacus* βG_81/Cel3A β-glucosidases with their homologous counterparts.

| Organism, enzyme, and accession number | Identity (%) |
|---|---|
| * *Acremonium thermophilum* βG_101 | 100.0 |
| *Magnaporthe grisea* β-glucosidase, AY849670 | 73.1 |
| *Neurospora crassa* hypothetical, XM_330871 | 71.1 |
| *Trichoderma reesei* Cel3B, AY281374 | 65.2 |
| * *Thermoascus aurantiacus* βG_81 | 62.2 |
| *Aspergillus aculeatus* β-glucosidase, D64088 | 59.5 |
| *Talaromyces emersonii* β-glucosidase, AY072918 | 58.9 |
| *Aspergillus oryzae*, AX616738 | 58.2 |
| *Acremonium cellulolyticus* β-glucosidase, BD168028 | 57.2 |
| * *Chaetomium thermophilum* βG_76 | 40.9 |
| *Chaetomium thermophilum* βG_76 | 100.0 |
| *Neurospora crassa*, hypothetical XM_324308 | 76.9 |
| *Magnaporthe grisea*, hypothetical XM_364573 | 70.2 |
| *Trichoderma viridae* BGI, AY368687 | 65.8 |

TABLE 24-continued

Comparison of the deduced *Acremonium thermophilum* βG_101/Cel3A, *Chaetomium thermophilum* βG_76/Cel3A, and *Thermoascus aurantiacus* βG_81/Cel3A β-glucosidases with their homologous counterparts.

| Organism, enzyme, and accession number | Identity (%) |
|---|---|
| *Acremonium cellulolyticus* β-glucosidase, BD168028 | 41.2 |
| * *Acremonium thermophilum* βG_101 | 40.9 |
| *Trichoderma reesei* Cel3B, AY281374 | 40.0 |
| * *Thermoascus aurantiacus* βG_81 | 39.9 |
| * *Thermoascus aurantiacus* βG_81 | 100.0 |
| *Talaromyces emersonii* β-glucosidase, AY072918 | 73.2 |
| *Aspergillus oryzae*, AX616738 | 69.5 |
| *Aspergillus aculeatus* β-glucosidase, D64088 | 68.0 |
| *Acremonium cellulolyticus* β-glucosidase, BD168028 | 65.7 |
| * *Acremonium thermophilum* βG_101 | 62.2 |
| *Trichoderma reesei* Cel3B, AY281374 | 57.9 |
| * *Chaetomium thermophilum* βG_76 | 39.9 |

The alignment was performed with the Needle programme of the EMBOSS programme package.
* indicates a β-glucosidase encoded by a gene cloned in this work.

Example 21

Production of Recombinant Beta-Glucosidases in *Trichoderma Reesei*

Expression plasmids were constructed for production of the recombinant *Acremonium* βG_101/Cel3A, *Chaetomium* βG_76/Cel3A, and *Thermoascus* βG_81/Cel3A proteins as described in Example 14. Linear expression cassettes (Table 25) were isolated from the vector backbone by restriction enzyme digestion, transformed into *T. reesei* A96 or A33 (both strains have the genes encoding the four major cellulases CBHI/Cel7A, CBHII/Cel6A, EGI/Cel7B and EGII/Cel5A deleted) and transformants purified as described in Example 14.

TABLE 25

The expression cassettes constructed for production of *Acremonium thermophilum* βG_101/Cel3A, *Chaetomium thermophilum* βG_76/Cel3A, and *Thermoascus aurantiacus* βG_81/Cel3A β-glucosidases in *Trichoderma reesei*.

| β-glucosidase | Expression plasmid | Size of the expression cassette[a] | Heterologous terminator[b] |
|---|---|---|---|
| At βG_101 | pALK1933 | 10.5 kb NotI | 300 bp (HindIII) |
| Ct βG_76 | pALK2004 | 10.1 kb EcoRI | 528 bp (XbaI) |
| Ta βG_81 | pALK1914 | 10.9 kB EcoRI | 452 bp (ApoI) |

The schematic structure of the expression cassettes is described in FIG. 2.
[a]The expression cassette for *T. reesei* transformation was isolated from the vector backbone by EcoRI or NotI digestion.
[b]The number of nucleotides after the STOP codon of the cloned gene that are included in the expression cassette are indicated. The restriction site at the 3'-region of the gene that was used in construction of the expression cassette is indicated in parenthesis.

The beta-glucosidase production of the transformants was analyzed from the culture supernatants of shake flask cultivations (50 ml). Transformants were grown as in Example 14 and the enzyme activity of the recombinant protein was measured from the culture supernatant using 4-nitrophenyl-β-D-glucopyranoside substrate as described by Bailey and Nevalainen 1981. Production of the recombinant proteins was also detected from culture supernatants by SDS-polyacrylamide gel electrophoresis. In addition, the expression of *Thermoascus* βG_81 was verified by Western blot analysis with anti-βG_81 antibodies as described in Example 19. The genotypes of the chosen transformants were analysed by Southern blotting using the expression cassette as a probe.

Figure 7A:
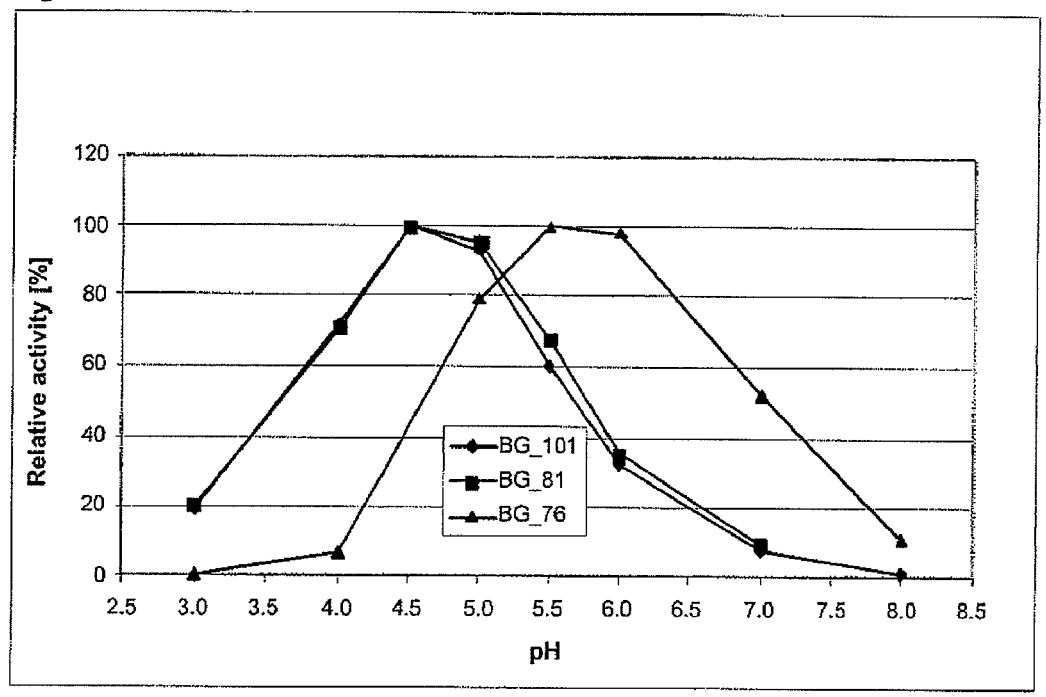
FIG. 7. A) The pH dependency of the heterologously produced *Acremonium* BG_101/Cel3A, *Chaetomium* BG_76/Cel3A, and Thermoascus BG_81/Cel3A activity was determined with 4-nitrophenyl-β-D-glucopyranoside substrate in a 10 min reaction at 50° C. B) Temperature optimum of the *Acremonium* βG_101/Cel3A, *Chaetomium* βG_76/Cel3A, and *Thermoascus* βG_81/Cel3A was determined at pH 4.5, 5.5, and 4.5, respectively. The reaction containing 4-nitrophenyl-β-D-glucopyranosid as substrate was performed for 60 min, BSA (100 µg/ml) was added as a stabilizer.
Figure 7B:
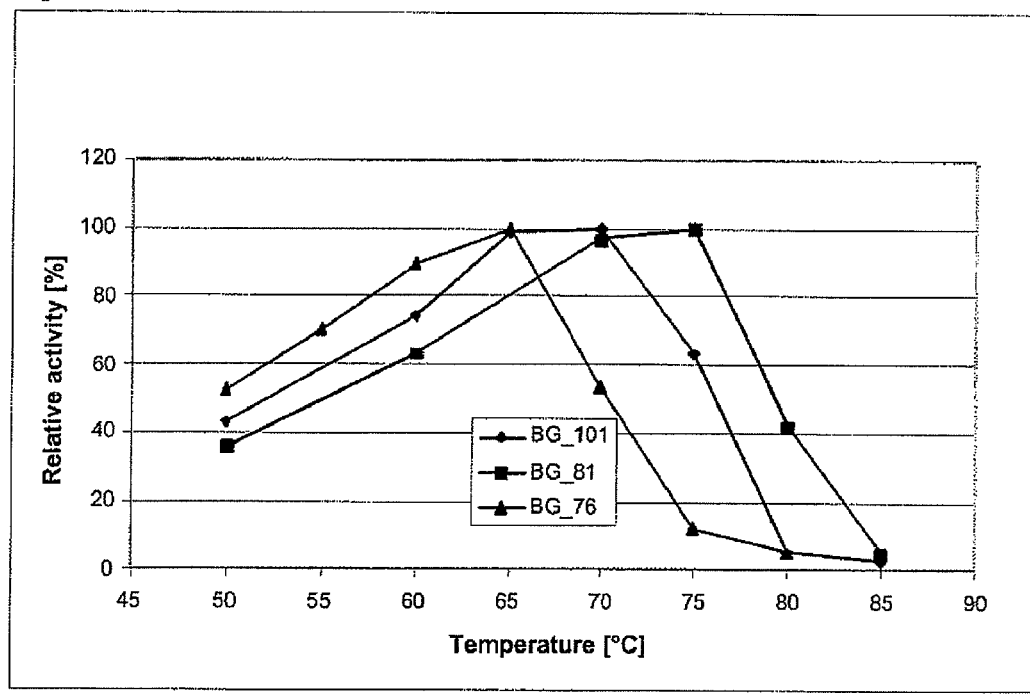

The pH optimum of the heterologously produced β-glucosidases was determined in the universal McIlvaine's buffer within a pH range of 3.0-8.0 using 4-nitrophenyl-β-D-glucopyranoside as substrate. The pH optima for the *Acremonium* βG_101, *Chaetomium* βG_76, and *Thermoascus* βG_81 are pH 4.5, 5.5, and 4.5, respectively (FIG. 7A). The optimal temperature for enzymatic activity of these β-glucosidases was determined at the temperature range of 50-85° C. as described above. The highest activity of the enzymes was determined to be at 70° C., 65° C., and 75° C. for the *Acremonium* βG_101/Cel3A, *Chaetomium* βG_76/Cel3A, and *Thermoascus* βG_81/Cel3A, respectively (FIG. 7B).

The chosen transformants were cultivated, as described in Example 14, in a 2 liter bioreactor for four days (28° C., pH 4.2) to obtain material for the application tests.

Example 22

Cloning of *Acremonium Thermophilum* ALKO4245 and *Thermoascus Aurantiacus* ALKO4242 Xylanase Genes Standard molecular biology methods were used as described in Example 13. The construction of the *Acremonium* genomic library has been described in Example 12.

The peptides derived from the purified *Acremonium* xylanase shared homology with xylanases of the glycosyl hydrolase family 10 such as *Humicola grisea* XYNI (AB001030). All peptides derived from the *Thermoascus* xylanase were completely identical with the published *Thermoascus aurantiacus* XYNA sequence (AJ132635) thus identifying the purified protein as the same enzyme. Due to this the *Thermoascus* xylanase gene was amplified by PCR from the genomic DNA.

To amplify a probe for screening of the *Acremonium* xylanase gene from the genomic library, degenerate primers were designed on the basis of the peptide sequences (Example 11, Table 5). The order of the peptides in the protein sequence and the corresponding sense or antisense nature of the primers was deduced from the comparison with the homologous *Humicola insolens* XYNI sequence (AB001030). The sense primer sequence (GAYGGYGAYGCSACYTAYATG) is based on Peptide 3 (amino acids 2-8) and anti-sense primer (YTTYTGRTCR-TAYTCSAGRTTRTA) on Peptide 1 (amino acids 4-11).

A PCR product of expected size (estimated from the homologous *Humicola insolens* XYNI sequence AB001030) was obtained from the reaction. This DNA fragment of about 0.7 kb was cloned into the pCR4-TOPO® TA vector (Invitrogen, USA) resulting in plasmid pALK1714, and was characterized by sequencing. The deduced amino acid sequence of the PCR product has homology to several published xylanase sequences of glycosyl hydrolase family 10 (BLAST program, National Center for Biotechnology Information; Altschul et al., 1990).

The insert from plasmid pALK1714 was isolated by restriction enzyme digestion and labeled with digoxigenin according to the supplier's instructions (Roche, Germany). About 1-2×10⁵ plaques from the amplified *Acremonium* genomic library were screened as described in Example 18. Several positive plaques were obtained, of which five strongly hybridizing plaques were purified. Phage DNAs were isolated and analysed by Southern blot hybridization. A 3.0 kb XbaI restriction fragment hybridizing to the probe was subcloned into the pBluescript II KS+vector (Stratagene, USA) resulting in plasmid pALK1725. Relevant parts of pALK1725 were sequenced and found to contain the full-length *Acremonium thermophilum* xyn10A gene (SEQ ID NO: 19). The deposit number of the *E. coli* strain containing pALK1725 in the Deutsche Sammlung von Mikroorganismen and Zellkulturen GmbH culture collection is DSM 16726.

*Thermoascus aurantiacus* xyn10A gene (SEQ ID NO: 17) was amplified directly from the isolated genomic DNA by PCR reaction. The forward (TTATACCGCGGGAAGC-CATGGTTCGACCAACGATCCTAC) and reverse (TTAT-AGGATCCACCGGTCTATACTCACTGCTG-CAGGTCCTG) primers that were used in the amplification of the gene were designed on the basis of the published *T. aurantiacus* xynA gene (AJ132635). The PCR reaction mixtures contained 50 mM Tris-HCl, pH 9.0, 15 mM (NH$_4$)$_2$SO$_4$, 0.1% Triton X-100, 1.5 mM MgCl$_2$, 0.3 mM dNTPs, 1 μM each primer, 1 unit of Dynazyme EXT DNA polymerase (Finnzymes, Finland) and approximately 0.5 μg of *Thermoascus* genomic DNA. The conditions for PCR reactions were the following: 5 min initial denaturation at 95° C., followed by 30 cycles of 1 min at 95° C., 1 min annealing at 60-66° C., 3 min extension at 72° C. and a final extension at 72° C. for 10 min. The amplified 1.9 kb product containing the exact gene (from START to STOP codon) was cloned as a SacII-BamHI fragment into the pBluescript II KS+ vector. Three independent clones were sequenced and one clone was selected and designated as pALK1715. The deposit number of the *E. coli* strain containing pALK1715 in the Deutsche Sammlung von Mikroorganismen and Zellkulturen GmbH culture collection is DSM 16724.

Relevant information of the genes and deduced protein sequences (SEQ ID NO: 17-20) are summarized in Table 26 and Table 27, respectively. Peptide sequences of the purified *Acremonium* XYN_60 and *Thermoascus* XYN_30 proteins were found in the corresponding deduced amino acid sequences of the cloned genes (At xyn10A and Ta xyn10A, respectively) confirming that appropriate genes were cloned.

TABLE 26

Summary of the xylanase genes isolated from *Acremonium thermophilum* and *Thermoascus aurantiacus*.

| Xylanase gene | Length with introns (bp) [a] | Coding region (bp) [b] | No of introns | Lengths of introns (bp) | SEQ ID NO: |
|---|---|---|---|---|---|
| At xyn 10A | 1471 | 1248 | 2 | 135, 85 | 19 |
| Ta xyn 10A | 1913 | 987 | 10 | 73, 74, 68, 103, 69, 65, 93, 66, 100, 212 | 17 |

[a] The STOP codon is included.
[b] The STOP codon is not included.

TABLE 27

Summary of the deduced xylanase sequences of *Acremonium thermophilum* and *Thermoascus aurantiacus*.

| Xylanase protein | No of aas | Length of ss NN/HMM [a] | CBD [b] | Predicted MW (Da, ss not incl) [c] | Predicted pI (ss not incl) | Putative N-glycosylation sites [d] | SEQ ID NO: |
|---|---|---|---|---|---|---|---|
| At XYN_60 | 416 | 19/19 | Yes, W385 to L416 | 42533 | 6.32 | 1-2 | 20 |
| Ta XYN_30 | 329 | 26 [e] | No | 32901 | 5.81 | 0 | 18 | ss, signal sequence.
[a] The prediction of the signal sequence was made using the program SignalP V3.0 (Nielsen et al., 1997; Bendtsen et al, 2004); the NN value was obtained using neural networks and HMM value using hidden Markov models.
[b] Presence of a carbohydrate binding domain CBD, the amino acids of the C-terminal CBD are indicated (numbering according to the full length polypeptide)
[c] The predicted signal sequence is not included. Prediction was made using the Compute pI/MW tool at ExPASy server (Gasteiger et al., 2003).
[d] The putative N-glycosylation sites N-X-S/T were predicted using the program NetNGlyc 1.0 (Gupta et al., 2004).
[e] According to Lo Leggio et al., 1999

The deduced protein sequences of *Acremonium* and *Thermoascus* xylanases share homology with several enzymes of glycosyl hydrolase family 10, identifying the corresponding genes as members of family 10 xylanases. The closest counterpart for the *Acremonium* XYN_60/Xyn10A found is the *Humicola grisea* XYLI (AB001030) showing 67.1% identity with XYN_60 (Table 28). The predicted protein sequence of the isolated *Thermoascus aurantiacus* XYN_30/Xyn10A xylanase is completely identical with that of the published *T. aurantiacus* XYNA (P23360, Table 28). The closest homology was found in a xylanase sequence of *Aspergillus niger* (A62445, 69.7% identity).

TABLE 28

Comparison of the deduced *Acremonium thermophilum* XYN_60/Xyn10A and *Thermoascus aurantiacus* XYN_30/Xyn10A xylanases with their homologous counterparts.

| Organism, enzyme, and accession number | Identity (%) |
|---|---|
| * *Thermoascus aurantiacus* XYN_30 | 100.0 |
| *Thermoascus aurantiacus* XynA, P23360 | 100.0 |
| *Thermoascus aurantiacus* XynA, AF127529 | 99.4 |
| *Aspergillus niger* xylanase, A62445 | 69.7 |
| *Aspergillus aculeatus* xylanase, AR137844 | 69.9 |
| *Aspergillus terreus* fam 10 xyn, DQ087436 | 65.0 |
| *Aspergillus sojae*, XynXI AB040414 | 63.8 |
| *Penicillium chrysogenum* xylanase, AY583585 | 62.5 |
| * *Acremonium thermophilum* XYN_60 | 100.0 |
| *Humicola grisea* XYL I, AB001030 | 67.1 |
| *Magnaporthe grisea* 70-15, hypothetical XM_364947 | 63.8 |
| *Aspergillus aculeatus* xylanase, AR149839 | 53.7 |

TABLE 28-continued

Comparison of the deduced *Acremonium thermophilum* XYN_60/Xyn10A and *Thermoascus aurantiacus* XYN_30/Xyn10A xylanases with their homologous counterparts.

| Organism, enzyme, and accession number | Identity (%) |
|---|---|
| *Talaromyces emersonii* xylanase, AX403831 | 51.8 |
| *Gibberella zeae* xylanase, AY575962 | 51.4 |
| *Magnaporthe grisea* XYL5, AY144348 | 48.5 |
| *Talaromyces emersonii*, AX172287 | 46.9 |

The alignment was performed using the Needle programme of the EMBOSS programme package.
* indicates a xylanase encoded by a gene cloned in this work.

Example 23

Production of Recombinant Xylanases in *Trichoderma Reesei*

Expression plasmids were constructed for production of the recombinant *Acremonium* XYN_60/Xyn10A and *Thermoascus* XYN_30/Xyn10A proteins as described in Example 14. Linear expression cassettes (Table 29) were isolated from the vector backbone by restriction enzyme digestion, transformed into *T. reesei* A96, and transformants purified as described in Example 14.

TABLE 29

The expression cassettes constructed for production of *Acremonium thermophilum* XYN_60/Xyn10A and *Thermoascus aurantiacus* XYN_30/Xyn10A xylanases in *Trichoderma reesei*.

| Xylanase | Expression plasmid | Size of the expression cassette [a] | Heterologous terminator [b] |
|---|---|---|---|
| At XYN_60 | pALK1912 | 9.0 kb | 150 bp (BamHI) |
| Ta XYN_30 | pALK1913 | 9.3 kb | none |

The schematic structure of the expression cassettes is described in FIG. 2.
[a] The expression cassette for *T. reesei* transformation was isolated from the vector backbone by EcoRI digestion.
[b] The number of nucleotides after the STOP codon of the cloned gene that are included in the expression cassette are indicated. The restriction site at the 3'-region of the gene that was used in construction of the expression cassette is indicated in parenthesis.

The xylanase production of the transformants was analyzed from the culture supernatants of shake flask cultivations (50 ml). Transformants were grown as in Example 14 and the enzyme activity of the recombinant protein was measured from the culture supernatant as the release of reducing sugars from birch xylan (1% w/v) at 50° C. in 50 mM citrate buffer pH 5.3 as described by Bailey and Poutanen 1989. Production of the recombinant protein was also analyzed from culture supernatant by SDS-polyacrylamide gel electrophoresis. In addition, the expression of both xylanases was determined by Western blot analysis with anti-XYN_30 or anti-XYN_60 antibodies as described in Example 19. The genotypes of the chosen transformants were analysed by Southern blotting using the expression cassette as a probe.

Figure 8A:
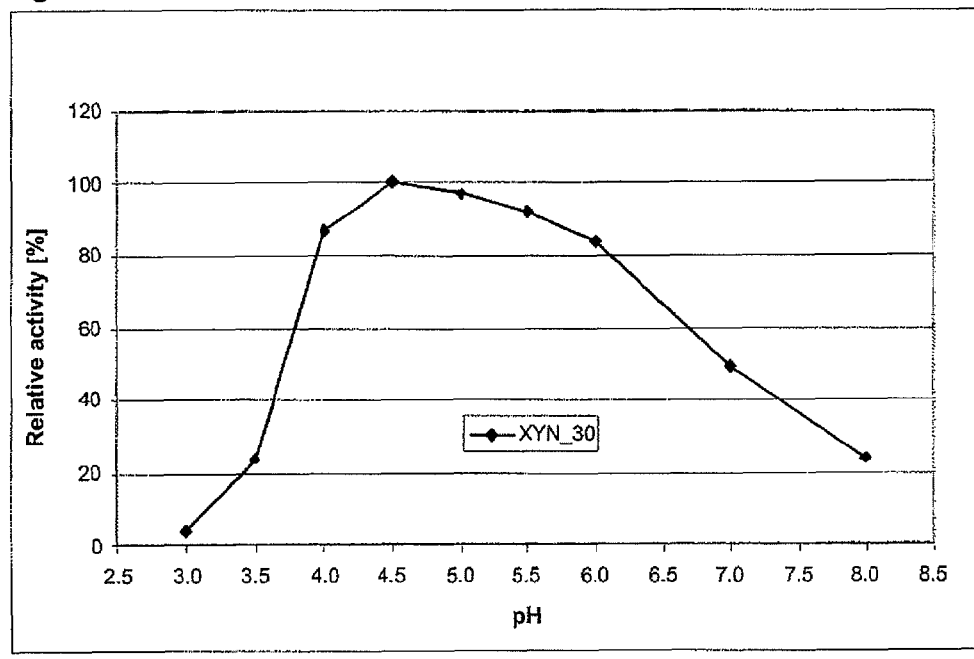
FIG. 8. A) The pH dependency of the heterologously produced *Thermoascus XYN_30/Xyn10A* xylanase activity was determined with birch xylan substrate in a 10 min reaction at 50° C. B) Temperature optimum of XYN_30/Xyn10A was determined at pH 5.3 in a 60 min reaction, BSA (100 µg/ml) was added as a stabilizer.
Figure 8B:
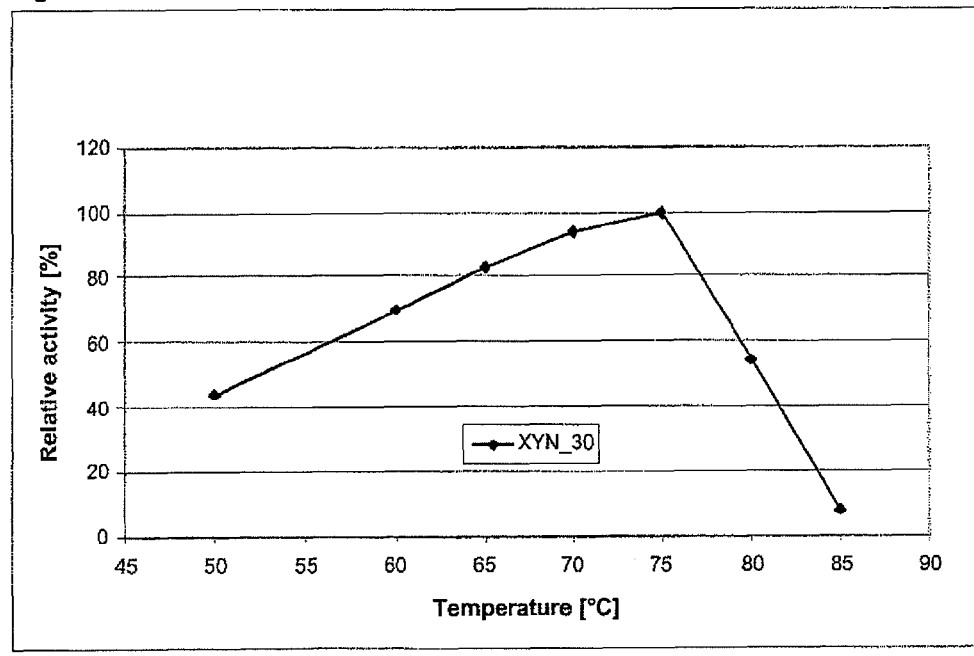

*Thermoascus* XYN_30/Xyn10A was produced in *T. reesei* and the pH optimum of the heterologously produced protein was determined in the universal McIlvaine's buffer within a pH range of 3.0-8.0 using birch xylan as substrate (FIG. 8A). The optimal pH was determined to be 4.5. The temperature optimum for the enzymatic activity of XYN_30 was determined to be 75° C. (FIG. 8B).

The chosen transformants were cultivated, as described in Example 14, in a 2 liter bioreactor for four days (28° C., pH 4.2) to obtain material for the application tests.

Example 24

Performance of the Recombinant Cellobiohydrolases in the Hydrolysis

The performance of the purified recombinant cellobiohydrolases was evaluated in the hydrolysis studies with purified *T. reesei* enzymes. Hydrolysis was carried out with controlled mixtures of purified enzymes on several pre-treated substrates. Culture filtrates of *T. reesei*, containing different cloned CBH/Cel7 enzymes were obtained as described in Examples 14 and 15, and the CBH enzymes were purified by affinity chromatography as described in Example 2. In addition, pure *T. reesei* cellulases (purified as described by Suurnäkki et al., 2000) were used in the enzyme mixtures. The cellobiohydrolases used in the experiment were:

*Thermoascus aurantiacus* ALKO4242 CBH (Ta Cel7A)
*Thermoascus aurantiacus* ALKO4242 CBH (Ta Cel7A) with genetically attached CBD of *Trichoderma reesei* (Ta Cel7A+Tr CBD)
*Thermoascus aurantiacus* ALKO4242 CBH (Ta Cel7A) with genetically attached CBD of *Chaetomium thermophilum* (Ta Cel7A+Ct CBD)
*Acremonium thermophilum* ALKO4245 CBH (At Cel7A)
*Chaetomium thermophilum* ALKO4265 CBH (Ct Cel7A).

Each CBH/Cel7 to be tested (dosage 14.5 mg/g dry matter of substrate) was used either together with EGII/Cel5A of *T. reesei* (3.6 mg/g) or with a mixture containing *T. reesei* EGI/Cel7B (1.8 mg/g), EGII/Cel5A (1.8 mg/g), xylanase pI 9 (Tenkanen et al. 1992) (5000 nkat/g) and acetyl xylan esterase (AXE) (Sundberg and Poutanen, 1991) (250 nkat/g). All mixtures were supplemented with additional β-glucosidase from a commercial enzyme preparation Novozym 188 (176 nkat/g d.w.). Triplicate tubes containing the enzyme mixture and 10 mg (dry matter)/ml of the substrate suspended in 0.05 M sodium acetate were incubated in mixing by magnetic stirring at 45° C. for 48 h. Reference samples with inactivated enzymes and corresponding substrates were also prepared. The release of hydrolysis products was measured as reducing sugars with DNS method using glucose as standard (Table 30).

The following substrates were used in the experiment:
Crystalline cellulose (Avicel)
Washed steam pre-treated spruce fibre (impregnation with 3% w/w SO$_2$ for 20 min, followed by steam pre-treatment at 215° C. for 5 min), dry matter 25.9% (SPRUCE).
Washed wet oxidized corn stover fibre (WOCS).
Washed steam pre-treated willow fibre (pre-treatment for 14 min at 210° C.), dry matter 23.0% (WILLOW).

TABLE 30

Hydrolysis products with CBH enzymes (45° C., pH 5.0).

| | Enzymes | Substrates | | | |
|---|---|---|---|---|---|
| CBH | Additional enzymes | Avicel | SPRUCE | WOCS | WILLOW |
| Ta Cel7A | EGII, bG | 2.0 | 2.0 | 2.8 | 2.0 |
| Ta Cel7A + Tr CBD | EGII, bG | 5.8 | 4.0 | 4.4 | 4.0 |
| Ta Cel7A + Ct CBD | EGII, bG | 4.9 | 3.7 | 4.6 | 3.7 |
| At Cel7A | EGII, bG | 5.3 | 3.3 | 4.5 | 3.3 |
| Ct Cel7A | EGII, bG | 6.0 | 2.6 | 3.4 | 2.6 |
| Cel7A of *T. reesei* | EGII, bG | 4.7 | 2.9 | 2.9 | 2.9 |
| Ta Cel7A | EGII, EGI, XYL, AXE, bG | nd | nd | 4.3 | 2.8 |
| Ta Cel7A + Tr CBD | EGII, EGI, XYL, AXE, bG | nd | nd | 7.2 | 5.9 |
| Ta Cel7A + Ct CBD | EGII, EGI, XYL, AXE, bG | nd | nd | 7.2 | 5.6 |
| At Cel7A | EGII, EGI, XYL, AXE, bG | nd | nd | 6.4 | 5.4 |
| Ct Cel7A | EGII, EGI, XYL, AXE, bG | nd | nd | 5.6 | 4.0 |
| Cel7A of *T. reesei* | EGII, EGI, XYL, AXE, bG | nd | nd | 6.0 | 4.1 |

Reaction products after 48 h hydrolysis as reducing sugars (mg/ml), measured glucose as standard. Abbreviations: CBH = cellobiohydrolase; EGI = endoglucanase I (Cel7B) of *T. reesei*, EGII = endoglucanase II (Cel5A) of *T. reesei*; bG = β-glucosidase (from Novozym 188); XYL = xylanase pI 9 (XYN II) of *T. reesei*, AXE = acetyl xylan esterase of *T. reesei*; nd = not done.

In Table 30 the different cellobiohydrolases have been compared based on the same protein dosage in the hydrolysis. The results show that on cellulosic substrates (Avicel and spruce fibre) Cel7A of *Thermoascus aurantiacus* with genetically attached CBD showed clearly higher hydrolysis than *T. reesei* CBHI/Cel7A. Without CBD, *T. aurantiacus* Cel7A was less efficient on these substrates. The performance of *Acremonium thermophilum* and *Chaetomium thermophilum* cellobiohydrolases was also better than that of *T. reesei* CBHI/Cel7A on several substrates; in particular, *C. thermophilum* Cel7A showed high efficiency on pure cellulose (Avicel).

In the case of substrates containing notable amounts of hemicellulose (willow and corn stover) the CBH/Cel7 enzymes clearly needed additionally both hemicellulases and endoglucanases to perform efficiently. If no additional hemicellulases were present, Cel7A of *T. aurantiacus* with genetically attached CBD showed again clearly highest hydrolysis. With the most important hemicellulose-degrading enzymes (xylanase, acetyl xylan esterase and EGI) Cel7A of *T. aurantiacus* with genetically attached CBD performed again with highest efficiency. *A. thermophilum* Cel7A was more efficient than *T. reesei* enzyme and *C. thermophilum* Cel7A produced hydrolysis products on the same level than *T. reesei* CBHI/Cel7A. The cellulose binding domain of *T. reesei* seemed to give slightly better efficiency than CBD of *C. thermophilum* in the hydrolytic performance of *T. aurantiacus* Cel7A, even though the difference was rather small.

It can be concluded that when CBHI/Cel7A was replaced in the mixture of *Trichoderma* enzymes by the herein produced cellobiohydrolases, the hydrolysis efficiency as judged by this experimental arrangements was clearly improved in the case of *T. aurantiacus* Cel7A with genetically attached CBD, and also improved in the case of *A. thermophilum* Cel7A and *C. thermophilum* Cel7A. Considering also the better temperature stability of the herein produced cellobiohydrolases, the results indicate that the performance of cellulase enzyme mixtures in higher temperatures than 45° C. can be clearly improved by using the herein produced cellobiohydrolases.

Example 25

Performance of the Recombinant Endoglucanases in the Hydrolysis

The preparations containing the endoglucanases were compared in hydrolysis studies mixed with the purified CBH/Cel7 and CBH/Cel6 enzymes on several pre-treated substrates. Culture filtrates of *T. reesei*, containing different cloned endoglucanase enzymes were obtained as described in Example 19. The enzymes were enriched by removing thermolabile proteins from the mixtures by a heat treatment (60° C., 2 h, pH 5) and the supernatant was used for the hydrolysis studies. In addition, pure *T. reesei* cellulases (purified as described by Suurnäkki et al., 2000) were used in the enzyme mixtures. The endoglucanases used in the experiment were:
  *Acremonium thermophilum* ALKO4245 endoglucanase At EG_40/Cel45A (ALKO4245 EG_40)
  *Acremonium thermophilum* ALKO4245 endoglucanase At EG_40 like/Cel45B (ALKO4245 EG_40_like)
  *Thermoascus aurantiacus* ALKO4242 endoglucanase Ta EG_28/Cel5A (ALKO4242 EG_28).
The following substrates were used in the experiment:
  Washed steam pre-treated spruce fibre (impregnation with 3% SO₂ for 20 min, followed by steam pre-treatment at 215° C. for 5 min), dry matter 25.9% (SPRUCE).

Steam exploded corn stover fibre (steam pre-treatment at 210° C. for 5 min), dry matter 31.0% (SECS).

The endoglucanases to be studied (dosage 840 nkat/g dry matter, based on endoglucanase activity against HEC according to IUPAC, 1987) were used either with cellobiohydrolases of *T. reesei* (CBHI/Cel7A, 8.1 mg/g d.m. and CBHII/Cel6A, 2.0 mg/g d.m.) or with *Thermoascus aurantiacus* Cel7A with genetically attached CBD of *T. reesei* (10.1 mg/g d.m.). Purified (Suurnäkki et al., 2000) EGI (Cel7B) and EGII (Cel5A) of *T. reesei* were also included in the experiments for comparison. All mixtures were supplemented with additional β-glucosidase from Novozym 188 (to make the total β-glucosidase dosage 560 nkat/g d.w., the relatively high dosage was used to compensate the differences in the background activities of the different EG preparations). Triplicate tubes were incubated in mixing at 45° C. for 48 h and reference samples with inactivated enzymes and corresponding substrates were prepared. The release of hydrolysis products was measured as reducing sugars with DNS method using glucose as standard (Table 31).

TABLE 31

Hydrolysis products with different endoglucanase preparations when used together with cellobiohydrolases from *T. reesei* or with *T. aurantiacus* Cel7A harbouring CBD of *T. reesei*.

| Enzymes | | Substrate | |
|---|---|---|---|
| Endoglucanase | CBH/Cel7 | SPRUCE | SECS |
| no added EG | CBHI and CBHII of *T. reesei* | 2.4 | 3.2 |
| EGI | CBHI and CBHII of *T. reesei* | 3.5 | 4.6 |
| EGII | CBHI and CBHII of *T. reesei* | 3.8 | 3.5 |
| At EG_40 | CBHI and CBHII of *T. reesei* | 4.9 | 4.3 |
| At EG_40like | CBHI and CBHII of *T. reesei* | 4.5 | 4.8 |
| Ta EG_28 | CBHI and CBHII of *T. reesei* | 3.0 | 3.9 |
| no added EG | *T. aurantiacus* Cel7A + Tr CBD | 1.8 | 2.1 |
| EGI | *T. aurantiacus* Cel7A + Tr CBD | nd. | 4.2 |
| EGII | *T. aurantiacus* Cel7A + Tr CBD | 3.2 | nd. |
| At EG_40 | *T. aurantiacus* Cel7A + Tr CBD | 4.8 | 4.0 |
| Ta EG_28 | *T. aurantiacus* Cel7A + Tr CBD | 1.5 | nd. |

Reaction products after 48 h hydrolysis (45° C., pH 5.0) as reducing sugars (mg/ml), measured glucose as standard. Abbreviations: CBHI = cellobiohydrolase I (Cel7A) of *T. reesei*; CBHII = cellobiohydrolase II (Cel6A) of *T. reesei*; EGI = endoglucanase I (Cel7B) of *T. reesei*, EGII = endoglucanase II (Cel5A) of *T. reesei*; bG = β-glucosidase (from Novozym 188); nd. = not done.

In Table 31 the different endoglucanases have been compared based on the same activity dosage in the hydrolysis. This may favour enzymes with low specific activity against the substrate (hydroxyethyl cellulose) used in the assay and underestimate the efficiency of enzymes with high specific activity against hydroxyethyl cellulose. In any case, the results show that *Acremonium thermophilum* endoglucanases perform very well in the hydrolysis when affecting together with both cellobiohydrolases used in the mixture. *A. thermophilum* endoglucanases have similar performance to *T. reesei* EGI/Cel7B which is a very efficient enzyme on hemicellulose-containing corn stover substrate due to its strong xylanase side activity. *T. aurantiacus* endoglucanase Cel5A (ALKO4242 EG_28) showed lower hydrolysis than *T. reesei* enzymes.

It can be concluded that the endoglucanases from *A. thermophilum* perform with comparable or enhanced efficiency when compared to the corresponding *Trichoderma* enzymes in the hydrolysis as judged by this experimental arrangement. Considering also the temperature stability of the herein described endoglucanases, the results indicate that the performance of cellulase enzyme mixtures in higher temperatures than 45° C. can be improved by using the herein described endoglucanases.

Example 26

Hydrolysis of Steam Pre-Treated Spruce at High Temperatures

Washed steam exploded spruce fibre (impregnation with 3% w/w $SO_2$ for 20 min, followed by steam pre-treatment at 215° C. for 5 min), with dry matter of 25.9% was suspended in 5 ml of 0.05 M sodium acetate buffer in the consistency of 10 mg/ml. This substrate was hydrolysed using different enzyme mixtures in test tubes with magnetic stirring in the water bath adjusted in different temperatures for 72 h. For each sample point, a triplicate of test tubes was withdrawn from hydrolysis, boiled for 10 min in order to terminate the enzyme hydrolysis, centrifuged, and the supernatant was analysed for reaction products from hydrolysis. The blanks containing the substrate alone (only buffer added instead of enzymes) were also incubated in the corresponding conditions.

A mixture of thermophilic cellulases was prepared using the following components:

Thermophilic CBH/Cel7 preparation containing *Thermoascus aurantiacus* ALKO4242 Cel7A with genetically attached CBD of *T. reesei* CBHI/Cel7A. The protein preparation was produced as described in Example 15 and purified according to Example 2 resulting in the purified Ta Cel7A+Tr CBD preparation with protein content of 5.6 mg/ml.

Thermophilic endoglucanase preparation containing *Acremonium thermophilum* ALKO4245 endoglucanase At EG_40/Cel45A. The protein was produced in *T. reesei* as described in Example 19. In order to enrich the thermophilic components, the spent culture medium was heat treated (60° C. for 2 hours). The preparation obtained contained protein 4.9 mg/ml and endoglucanase activity (according to IUPAC, 1987) 422 nkat/ml.

Thermophilic β-glucosidase preparation prepared as described in Example 21 containing *Thermoascus aurantiacus* ALKO4242 β-glucosidase Ta βG_81/Cel3A. In order to enrich the thermophilic components, the fermentor broth was heat treated (65° C. for 2 hours). The preparation obtained contained 4.3 mg/ml protein and β-glucosidase activity of 6270 nkat/ml (according to Bailey and Linko, 1990).

These enzyme preparations were combined as follows (per 10 ml of mixture): CBH/Cel7-preparation 4.51 ml, endoglucanase preparation 5.19 ml and β-glucosidase preparation 0.29 ml. This mixture was used as "MIXTURE 1" of the thermophilic enzymes.

As a comparison and reference, a state-of art mixture of commercial *Trichoderma reesei* enzymes was constructed combining (per 10 ml): 8.05 ml Celluclast 1.5 L FG (from Novozymes A/S) and 1.95 ml Novozym 188 (from Novozymes A/S). This was designated as "*T. REESEI* ENZYMES."

Enzymes were dosed on the basis of the FPU activity of the mixtures: "MIXTURE 1" using the dosage of 5.5 FPU per 1 gram of dry matter in the spruce substrate, and "*T. REESEI* ENZYMES" using 5.8 FPU per 1 gram of dry matter in the spruce substrate.

Figure 9:
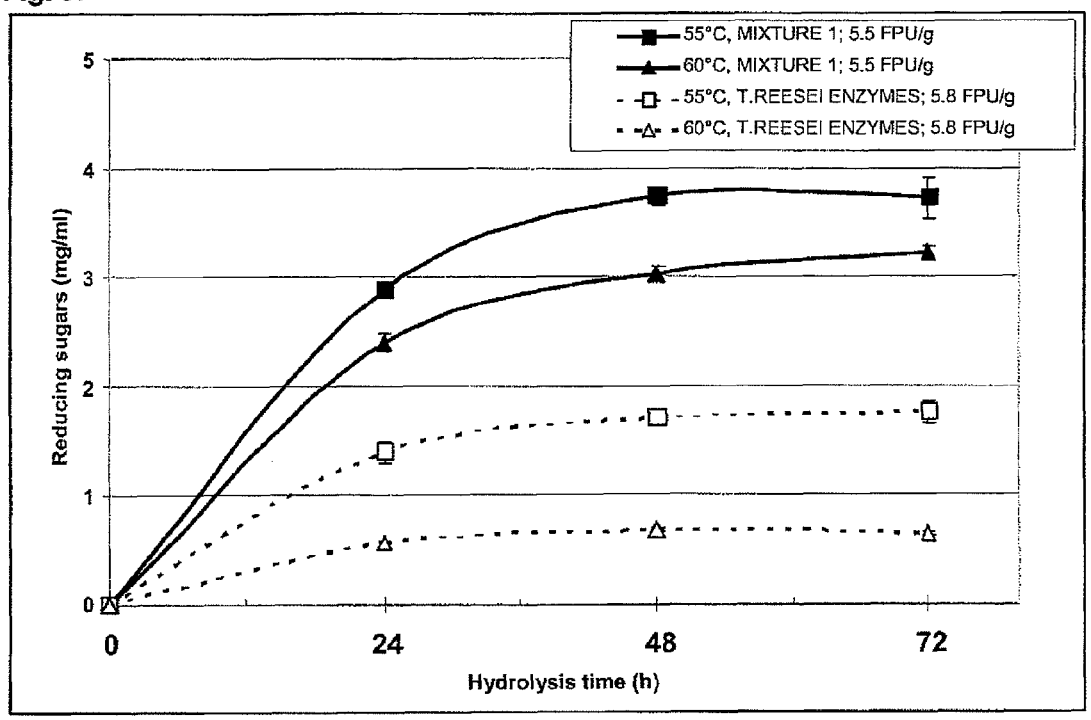
FIG. 9. Hydrolysis of washed steam exploded spruce fibre (10 mg/ml) with a mixture of thermophilic enzymes (MIXTURE 1) and *T. reesei* enzymes at 55 and 60° C. Enzyme dosage is given by FPU/g dry matter of substrate, FPU assayed at 50° C., pH 5. Hydrolysis was carried out for 72 h at pH 5, with mixing. The results are given as mean (±SD) of three separate measurements.

Samples were taken from the hydrolysis after 24, 48 and 72 h and treated as described above. The hydrolysis products were quantified using the assay for reducing sugars (Bernfeld, 1955), using glucose as standard. The amount of hydrolysis products as reducing sugars is presented in FIG. 9.

The results clearly show better performance of the herein described enzymes as compared to the state-of-art *Trichoderma* enzymes in 55° C. and 60° C. on the spruce substrate. On the basis of HPLC analysis the maximum yield of sugars from the substrate would be 5.67 mg per 10 mg of dry spruce substrate. Because of the relatively low dosage of enzyme the final sugar yields were clearly lower. For thermostable enzymes the sugar yield based on reducing sugar assay was 66% and 57% of theoretical in 55° C. and 60° C., respectively. For state-of art *Trichoderma* enzymes it was only 31% and 11% in 55° C. and 60° C., respectively.

Example 27

Hydrolysis of Steam Pre-Treated Corn Stover at High Temperatures

Steam exploded corn stover fibre (treatment at 195° C. for 5 min), with dry matter of 45.3% was suspended in 5 ml of 0.05 M sodium acetate buffer in the consistency of 10 mg/ml. The treatments and measurements were performed as described in Example 26.

A mixture of herein described thermophilic cellulases was constructed using the following components:

Thermophilic CBH preparation containing *Thermoascus aurantiacus* ALKO4242 Cel7A with genetically attached CBD of *T. reesei* CBHI/Cel7A (Ta Cel7A+Tr CBD, Example 15). The protein content of the preparation was 31 mg/ml.

Thermophilic endoglucanase preparation containing *Acremonium thermophilum* ALKO4245 endoglucanase At EG_40/Cel45A was obtained as described in Example 19. The concentrated enzyme preparation contained endoglucanase activity (according to IUPAC, 1987) of 2057 nkat/ml.

Thermophilic β-glucosidase preparation containing *Thermoascus aurantiacus* ALKO 4242 β-glucosidase Ta βG_81/Cel3A was obtained as described in Example 21 containing β-glucosidase activity (according to Bailey and Linko, 1990) of 11500 nkat/ml.

Thermophilic xylanase product containing an AM24 xylanase originating from *Nonomuraea flexuosa* DSM43186. The product was prepared by using a recombinant *Trichoderma reesei* strain that had been transformed with the expression cassette pALK1502, as described in WO2005/100557. The solid product was dissolved in water to make a 10% solution and an enzyme preparation with xylanase activity (assayed according to Bailey et al., 1992) of 208000 nkat/ml was obtained.

These enzyme preparations were combined as follows (per 10 ml of mixture): CBH/Cel7 preparation 7.79 ml, endoglucanase preparation 0.96 ml, β-glucosidase preparation 1.14 ml and xylanase preparation 0.31 ml. This mixture was used as "MIXTURE 2" of the thermophilic enzymes.

As a comparison and reference, a state-of art mixture of commercial *Trichoderma reesei* enzymes was constructed by combining (per 10 ml) 8.05 ml Celluclast 1.5 L FG (from Novozymes A/S) and 1.95 ml Novozym 188 (from Novozymes A/S). This was designated as "*T. REESEI* ENZYMES."

Figure 10:
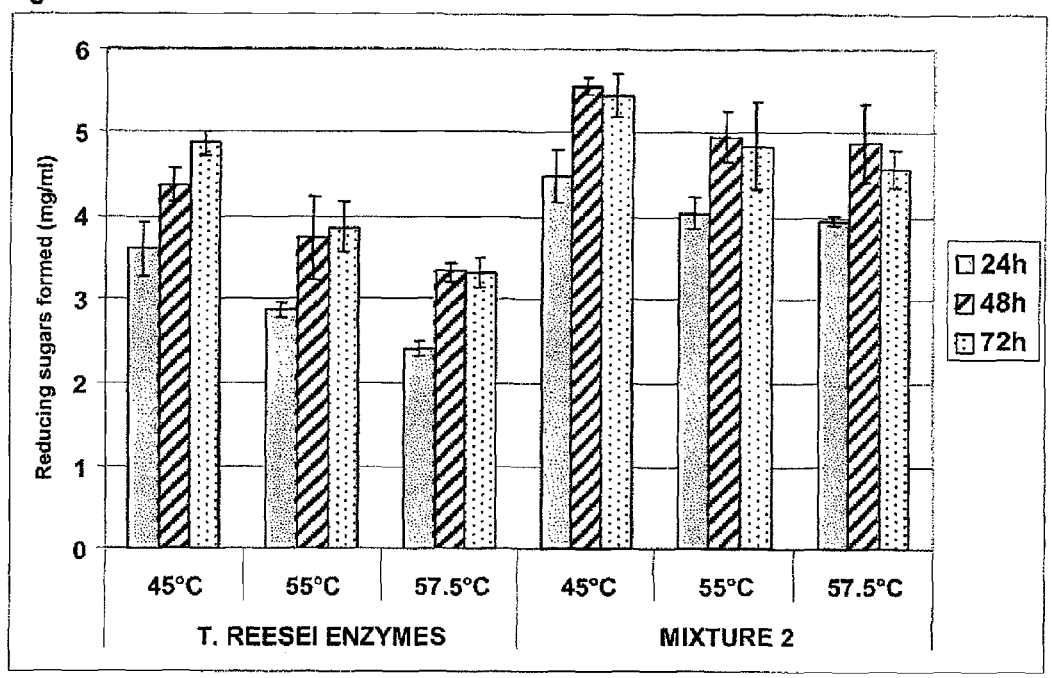
FIG. 10. Hydrolysis of steam exploded corn stover (10 mg/ml) with a mixture of thermophilic enzymes (MIXTURE 2) and *T. reesei* enzymes at 45, 55 and 57.5° C. Enzyme dosage was for "MIXTURE 2" 5 FPU/g dry matter of substrate and for *T. reesei* enzymes 5 FPU/g dry matter Celluclast supplemented with 100 nkat/g dry matter Novozym 188 (filter paper activity was assayed at 50° C., pH 5). Hydrolysis was carried out for 72 h at pH 5, with mixing. The results are given as mean (±SD) of three separate measurements. The substrate contained soluble reducing sugars (ca 0.7 mg/ml). This background sugar content was subtracted from the reducing sugars formed during the hydrolysis.

Samples were taken from the hydrolysis after 24, 48 and 72 h and treated as described above. The hydrolysis products were quantified using the assay for reducing sugars (Bernfeld, 1955), using glucose as standard. The results from the substrate blanks were subtracted from the samples with enzymes, and the concentration of hydrolysis products as reducing sugars is presented in FIG. 10.

The results clearly show better performance of the herein described enzymes as compared to the state-of-art *Trichoderma* enzymes. In 45° C. the mixture of thermophilic enzymes showed more efficient hydrolysis as compared to *T. reesei* enzymes: The hydrolysis was faster and higher sugar yields were also obtained. On the basis of HPLC analysis the maximum yield of sugars (including free soluble sugars in the unwashed substrate that was used) from the substrate would be 5.73 mg per 10 mg of dry substrate. Thus, the hydrolysis by the MIXTURE 2 enzymes was nearly complete within 48 hours. In 55° C. and 57.5° C. the herein described thermophilic enzymes showed also clearly better performance in the hydrolysis as compared to the state-of art *Trichoderma* enzymes.

Example 28

Hydrolysis of Pre-Treated Corn Stover at High Temperatures Using Mixture with a Thermostable Xylanase The procedure explained in Example 27 was repeated except that the xylanase product XT 02026A3 was replaced by thermophilic xylanase preparation containing *Thermoascus aurantiacus* ALKO4242 xylanase Ta XYN_30/Xyn10A produced in *T. reesei*. The fermentor broth, produced as described in Example 23 contained xylanase activity of 132 000 nkat/ml (assayed according to Bailey et al., 1992).

These enzyme preparations were combined as follows (per 10 ml of mixture): CBH/Cel7-preparation 7.64 ml, endoglucanase preparation 0.96 ml, β-glucosidase preparation 1.15 ml and xylanase preparation 0.25 ml. This mixture was used as "MIXTURE 3" of the thermophilic enzymes.

As a comparison and reference, a state-of-art mixture of commercial *Trichoderma reesei* enzymes was constructed by combining (per 10 ml) 8.05 ml Celluclast 1.5 L FG (from Novozymes A/S) and 1.95 ml Novozym 188 (from Novozymes A/S). This was designated as "*T. REESEI* ENZYMES."

Figure 11:
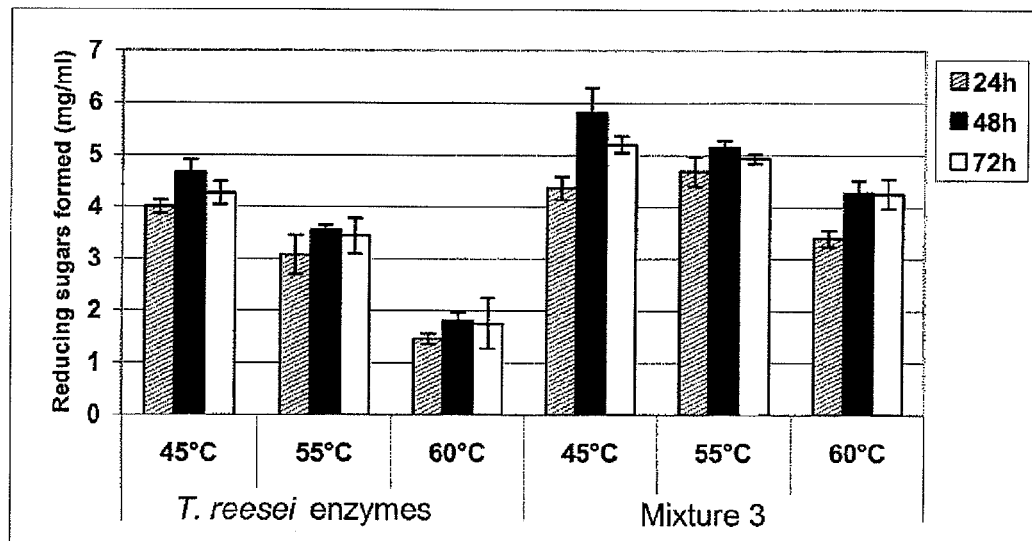
FIG. 11. Hydrolysis of steam exploded corn stover (10 mg/ml) with a mixture of thermophilic enzymes containing a new thermophilic xylanase from *Thermoascus aurantiacus* (MIXTURE 3) and *T. reesei* enzymes at 45, 55 and 60° C. Enzyme dosage was for "MIXTURE 3" 5 FPU/g dry matter of substrate and for *T. reesei* enzymes 5 FPU/g dry matter Celluclast supplemented with 100 nkat/g dry matter Novozym 188 (filter paper activity was assayed at 50° C., pH 5). Hydrolysis was carried out for 72 h at pH 5, with mixing. The results are given as mean (±SD) of three separate measurements. The substrate contained soluble reducing sugars (ca 0.7 mg/ml). This background sugar content was subtracted from the reducing sugars formed during the hydrolysis.

Samples were taken from the hydrolysis after 24, 48 and 72 h and treated as described above. The hydrolysis products were quantified using the assay for reducing sugars (Bernfeld, 1955), using glucose as standard. The results from the substrate blanks were subtracted from the samples with enzymes, and the concentration of hydrolysis products as reducing sugars is presented in FIG. 11.

The results clearly show better performance of the mixture of the herein described enzymes as compared to the state-of-art *Trichoderma* enzymes. In 45° C. the mixture of thermophilic enzymes showed more efficient hydrolysis as compared to *T. reesei* enzymes. In 55° C. and 60° C. the herein described thermophilic enzymes showed clearly better performance in the hydrolysis as compared to the state-of art *Trichoderma* enzymes. The performance of the new enzyme mixture at 60° C. was at the same level than the performance of state-of-art enzymes at 45° C.

Example 29

Figure 12:
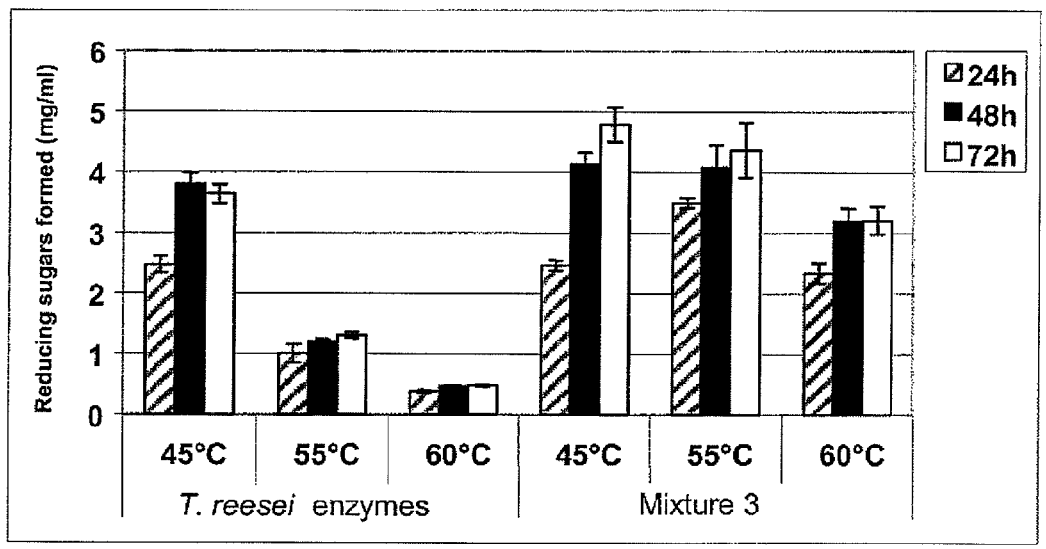
FIG. 12. Hydrolysis of steam exploded spruce fibre (10 mg/ml) with a mixture of thermophilic enzymes containing a new thermophilic xylanase XYN_30/Xyn10A from *Thermoascus aurantiacus* (MIXTURE 3) and *T. reesei* enzymes at 45, 55 and 60° C. Enzyme dosage for "MIXTURE 3" was 5 FPU/g dry matter of substrate and for *T. reesei* enzymes 5 FPU/g dry matter Celluclast supplemented with 100 nkat/g dry matter Novozym 188 (filter paper activity was assayed at 50° C., pH 5). Hydrolysis was carried out for 72 h at pH 5, with mixing. The results are given as mean (±SD) of three separate measurements.

Hydrolysis of Pre-Treated Spruce at High Temperatures Using Mixture with a Thermostable Xylanase Procedure as described in Example 28 was repeated with washed steam exploded spruce fibre (impregnation with 3% w/w $SO_2$ for 20 min, followed by steam pretreatment at 215° C. for 5 min, with dry matter of 25.9%) as substrate using hydrolysis temperatures 45° C., 55° C. and 60° C. Samples were taken from the hydrolysis after 24, 48 and 72 h and treated as described above. The hydrolysis products were quantified using the assay for reducing sugars (Bernfeld, 1955), using glucose as standard. The results from the substrate blanks were subtracted from the samples with enzymes, and the concentration of hydrolysis products as reducing sugars is presented in FIG. 12.

The results clearly show better performance of the mixture of herein described enzymes as compared to the state-of-art *Trichoderma* enzymes in all the temperatures studied. At 45° C. the mixture of thermophilic enzymes showed more efficient hydrolysis as compared to *T. reesei* enzymes, evidently due to the better stability in long term hydrolysis. At 55° C. the efficiency of the mixture of herein described enzymes was still on the same level than at 45° C., whereas the state-of-art mixture was inefficient with the substrate used in this temperature. At 60° C. the herein described thermophilic enzymes showed decreased hydrolysis although the hydrolysis was nearly at the same level as the performance of the state-of-art enzymes at 45° C.

Example 30

Evaluation of Glucose Inhibition of β-Glucosidases from *Acremonium Thermophilium* ALKO4245, *Chaetomium Thermophilum* ALKO4261 and *Thermoascus Aurantiacus* ALKO4242

The culture filtrates produced by *Acremonium thermophilium* ALKO4245, *Chaetomium thermophilum* ALKO4261 and *Thermoascus aurantiacus* ALKO4242 strains are described in Example 1. The β-glucosidase activities (measured according to Bailey and Linko, 1990) of these preparations were 21.4 nkat/ml, 5.6 nkat/ml and 18.6 nkat/ml, respectively. For comparison, commercial enzymes Celluclast 1.5 L (β-glucosidase 534 nkat/ml) and Novozym 188 (β-glucosidase 5840 nkat/ml) were also included in the experiment.

Figure 13:
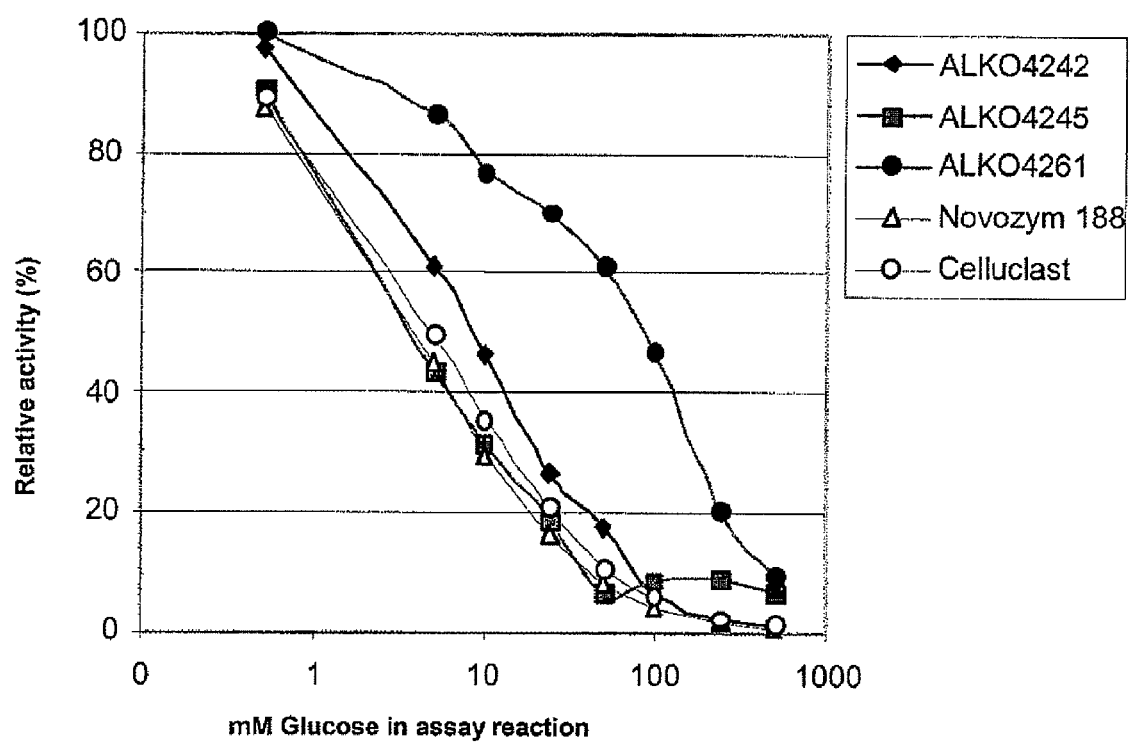
FIG. 13. The effect of glucose on activity of different β-glucosidase preparations. The standard assay using p-nitrophenyl-β-D-glucopyranoside as substrate was carried out in the presence of glucose in the assay mixture. The activity is presented as percentage of the activity obtained without glucose.

In order to evaluate the sensitivity of the different β-glucosidases towards glucose inhibition, the standard activity assay procedure was performed in the presence of different concentrations of glucose. The substrate (p-nitrophenyl-β-D-glucopyranoside) solutions for β-glucosidase activity assay were supplemented by glucose so that the glucose concentration in the assay mixture was adjusted to the values from 0 to 0.5 M. Except this glucose addition the assay was performed using the standard procedure (Bailey and Linko, 1990). The activities in the presence of varying glucose concentrations as a percentage of the activity without glucose are presented in FIG. 13.

The results show that β-glucosidases from *C. thermophilum* and *T. aurantiacus* were affected less by glucose inhibition than the β-glucosidases present in the commercial enzymes: *Aspergillus*-derived β-glucosidase in Novozym 188 or *Trichoderma*-derived β-glucosidase in Celluclast 1.5 L. *A. thermophilum* enzyme showed behaviour comparable to *T. reesei* enzyme of Celluclast. Especially *C. thermophilum* enzyme was clearly less affected by high glucose concentration. Thus, these results indicate that considering glucose inhibition the use of the new β-glucosidases, especially from strains *Acremonium thermophilium* ALKO4242 and *Chaetomium thermophilum* ALKO4261, would give clear advantages in hydrolysis in industrial conditions with high glucose concentration.

Example 31

Filter Paper Activity of Enzyme Mixtures in High Temperatures

Filter paper activity of enzyme preparations was measured according to the method of IUPAC (1987) as described in the procedure except enzyme reaction was performed at temperatures from 50° C. to 70° C. The calculated FPU activity is based on the amount of enzyme required to hydrolyse 4% of filter paper substrate in 1 h under the experimental conditions. The FPU activity is considered to represent the total overall cellulase activity of an enzyme preparation.

The enzyme mixtures were MIXTURE 2 prepared as described in Example 27, MIXTURE 3 prepared as described in Example 28, and MIXTURE 4. MIXTURE 4 was prepared by combining enzyme preparations described in Example 27 as follows (per 10 ml of mixture): CBH/Cel7-preparation 7.84 ml, endoglucanase preparation 0.99 ml and β-glucosidase preparation 1.17 ml.

The enzyme mixtures used as reference, representing the state-of art-mixtures, were:

"*T. REESEI* ENZYMES A" prepared as preparation "*T. REESEI* ENZYMES" described in Example 26.

"*T. REESEI* ENZYMES B" was constructed combining (per 10 ml) 8.05 ml Econase CE (a commercial *T. reesei* cellulase preparation from AB Enzymes Oy, Rajamäki, Finland) and 1.95 ml Novozym 188 (from Novozymes A/S).

Figure 14:
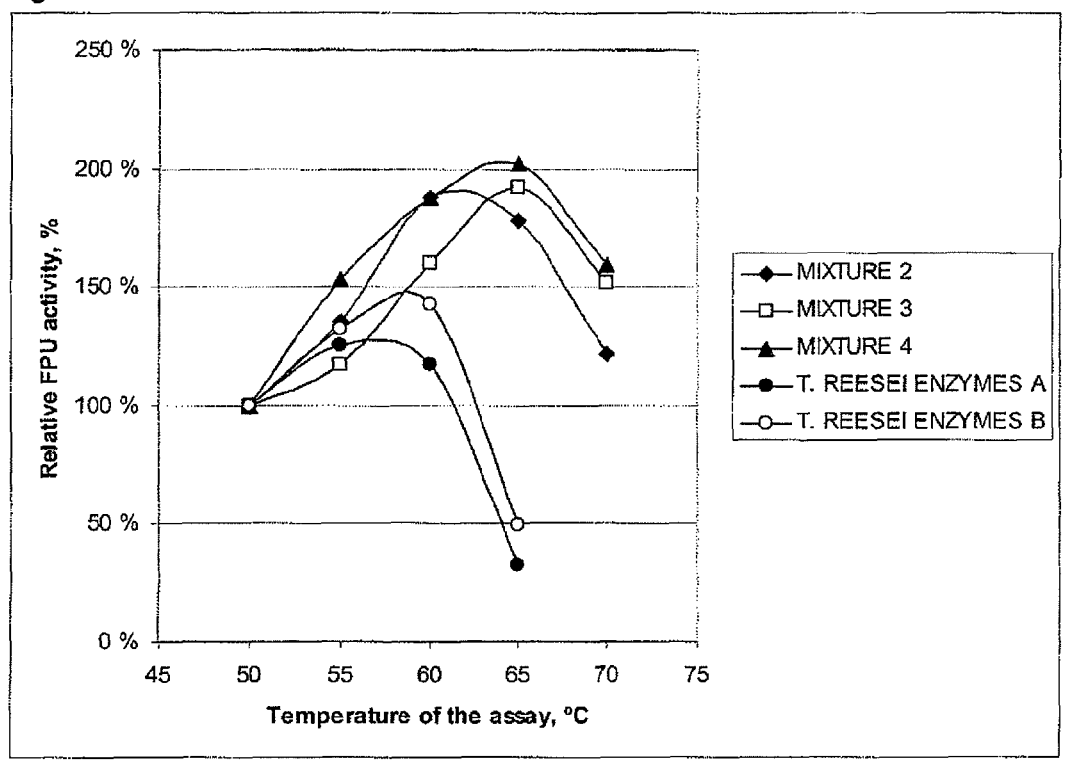
FIG. 14. FPU activities of the enzyme mixtures at temperatures from 50° C. to 70° C., presented as a percentage of the activity under the standard conditions (50° C., 1 h).

The FPU activities measured for the enzyme preparations at different temperatures are presented in FIG. 14 as percentages of the activity under standard (IUPAC, 1987) conditions (at 50° C.).

Results clearly show that the mixtures of the invention show higher overall cellulase activity in elevated (60-70° temperatures as compared to the state-of art mixtures based on enzymes from *Trichoderma* and *Aspergillus*.

Example 32

Use of the Novel Beta-Glucosidases in Preparation of Sophorose

A high concentration starch hydrolysate mixture (Nutriose 74/968, Roquette) was treated with *Thermoascus aurantiacus* βG_81/Cel3A enriched enzyme preparation produced as described in Example 21 to produce a sugar mixture containing appreciable amounts of cellulase inducer (sophorose) to overcome the glucose repression.

Figure 15:
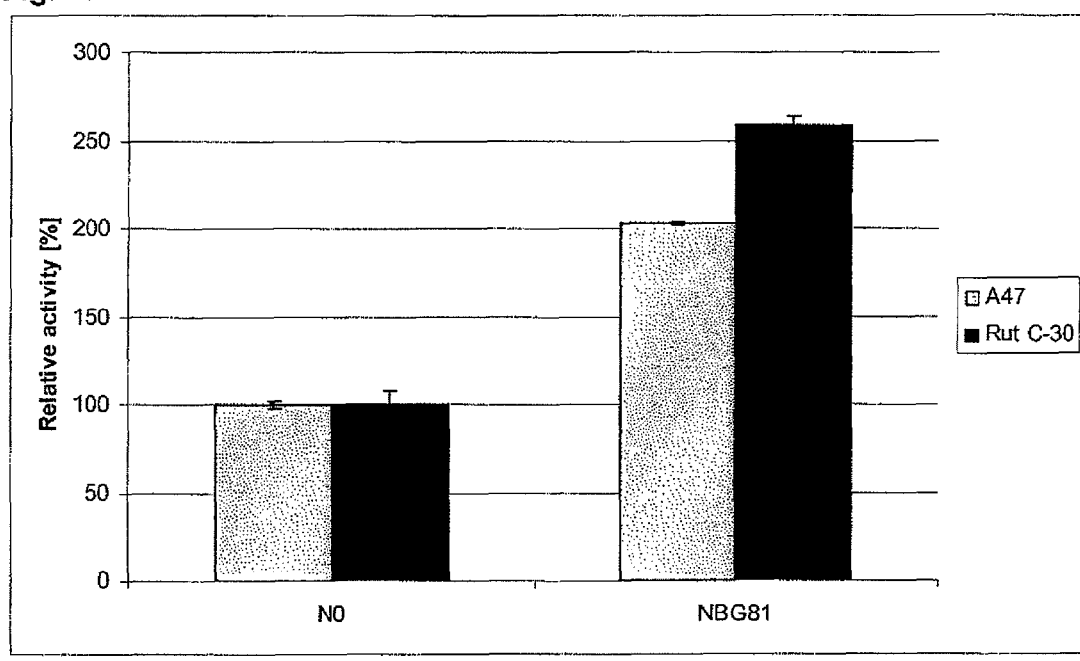
FIG. 15. The relative cellulase activity of two different *T. reesei* strains grown in media containing untreated Nutriose (N0) or BG_81/Cel3A pretreated Nutriose (NBG81) as a carbon source.

The Ta βG_81/Cel3A enriched enzyme preparation was added to a 70% (w/w) Nutriose solution to a final concentration of 1 g total protein/liter. The container of the mixture was incubated in a water bath at 65° C. for 3 days with constant stirring and used as a carbon source in a shake flask medium for two different *Trichoderma*-strains (A47 and Rut-C30). The effect of the enzyme treatment was measured as an endoglucanase activity formed during a 7 days shake flask cultivation. As a reference cultivations were performed under the same conditions with untreated Nutriose as a carbon source. More than two-fold increase in the activities was obtained in the shake flask cultivations performed on Ta βG_81/Cel3A pretreated Nutriose media with the strains tested. Results are shown in FIG. 15.

List of deposited organisms

| Strain | Plasmid contained | Deposition authority | Deposition date | Deposition number |
| --- | --- | --- | --- | --- |
| *Acremonium thermophilum* ALKO4245 | — | CBS[1] | 20 Sep. 2004 | CBS 116240 |
| *Thermoascus aurantiacus* ALKO4242 | — | CBS[1] | 20 Sep. 2004 | CBS 116239 |
| *Chaetomium thermophilum* ALKO4265 | — | CBS[2] | Nov. 8, 1995 | CBS 730.95[4] |
| *Escherichia coli* | pALK1635 | DSMZ[3] | 16 Sep. 2004 | DSM 16723 |
| *Escherichia coli* | pALK1642 | DSMZ | 16 Sep. 2004 | DSM 16727 |
| *Escherichia coli* | pALK1646 | DSMZ | 16 Sep. 2004 | DSM 16728 |
| *Escherichia coli* | pALK1861 | DSMZ | 16 Sep. 2004 | DSM 16729 |
| *Escherichia coli* | pALK1715 | DSMZ | 16 Sep. 2004 | DSM 16724 |
| *Escherichia coli* | pALK1723 | DSMZ | 16 Sep. 2004 | DSM 16725 |
| *Escherichia coli* | pALK1725 | DSMZ | 16 Sep. 2004 | DSM 16726 |
| *Escherichia coli* | pALK1904 | DSMZ | 13 May 2005 | DSM 17323 |
| *Escherichia coli* | pALK1908 | DSMZ | 13 May 2005 | DSM 17324 |
| *Escherichia coli* | pALK1925 | DSMZ | 13 May 2005 | DSM 17325 |
| *Escherichia coli* | pALK1926 | DSMZ | 13 May 2005 | DSM 17326 |
| *Escherichia coli* | pALK2001 | DSMZ | 18 Oct. 2005 | DSM 17667 |
| *Escherichia coli* | pALK2010 | DSMZ | 18 Nov. 2005 | DSM 17729 |

[1]the Centralbureau Voor Schimmelcultures at Uppsalalaan 8, 3584 CT, Utrecht, the Netherlands
[2]the Centralbureau Voor Schimmelcultures at Oosterstraat 1, 3742 SK BAARN, The Netherlands
[3]Deutsche Sammlung von Mikroorganismen und Zellkulturen GmbH (DSMZ), Mascheroder Weg 1 b, D-38124 Braunschweig, Germany
[4][After termination of the current deposit period, samples will be stored under agreements as to make the strain available beyond the enforceable time of the patent.]

References

Altschul S., Gish W., Miller W., Myers E. W. and Lipman D. J., (1990) "Basic local alignment search tool," *J. Mol. Biol.* 215: 403-410.

Badger, P.C. (2002) "Ethanol from cellulose: a general review," In: *Trends in New Crops and New Uses*, J. Janick and A. Whipkey (eds.). ASHS Press, Alexandria, Va., USA, pp. 17-21.

Bailey M. J. and K. M. H. Nevalainen (1981) "Induction, isolation and testing of stable *Trichoderma reesei* mutants with improved production of solubilizing cellulose," *Enz. Microbiol. Technol.*, 3:153-157.

Bailey, M. J., Biely, P. and Poutanen, K. (1992) "Interlaboratory testing for assay of xylanase activity," *J. Biotechnol.*, 23:257-270.

Bailey, M. J. and Linko, M. (1990) "Production of β-galactosidase by *Aspergillus oryzae* in submerged bioreactor cultivation," *J. Biotechnol.*, 16:57-66.

Bailey M. J. and Poutanen K. (1989) "Production of xylanases by strains of *Aspergillus,*" *Appl. Microbiol. Biotechnol.*, 30:5-10.

Bailey M., Siika-aho M., Valkeajärvi A. and Penttilä M. (1993) "Hydrolytic properties of two cellulases of *Trichoderma reesei* expressed in yeast," *Biotehnol. Appl. Biochem.*, 17:65-76.

Bendtsen J. D., Nielsen H., von Heijne G. and Brunak S. (2004) "Improved prediction of signal peptides: SignalP 3.0," *J. Mol. Biol.*, 340:783-795.

Bernfeld, B. (1955) "Amylases, α and β," In: *Methods in Enzymology*, vol. 1, Eds. Colowick, S. P. and Kaplan, N. O. Academic Press, New York, pp. 149-158.

Biely P., Vrsanska M., Tenkanen M., Kluepfel D. (1997) "Endo-beta-1,4-xylanase families: differences in catalytic properties," *Journal of Biotechnology*, 57:151-166.

Coen, D. M. (2001) "The polymerase chain reaction," In: *Current Protocols in Molecular Biology*, Ausubel, F. M., Brent, R., Kingston, R. E., More, D. D., Seidman, J. G., Smith, K. and Struhl, K. (eds.), John Wiley & Sons. Inc., Hoboken, USA.

Gasteiger, E., Gattiker A., Hoogland C., Ivanyi I., Appel R. D. and Bairoch A. (2003) "ExPASy: the proteiomics server for in-depth protein knowledge and analysis," *Nucleic Acids Res.*, 31:3784-3788.

Gellissen, G. (ed.) (2005) "Production of recombinant proteins," *Novel Microbial and Eukaryotic Expression Systems*, Wiley-VCH Verlag Gmbh & Co. Weinheim, Germany.

Gill, S. C, and von Hippel, P. H. (1989) "Calculation of protein extinction coefficients from amino acid sequence data," *Anal. Biochem.*, 182:319-326.

Gupta, R., E. Jung and S. Brunak. (2004) "Prediction of N-glycosylation sites in human proteins," in preparation: www.cbs.dtu.dk/services/NetNGlyc/.

Haakana H., Miettinen-Oinonen A., Joutsjoki V., Mäntylä A., Suominen P, and Vehmaanperä J. (2004) "Cloning of cellulase genes from Melanocarpus albomyces and their efficient expression in *Trichoderma reesei,*" *Enz. Microbiol. Technol.*, 34:159-167.

Henrissat B. (1991) "A classification of glycosyl hydrolases based on amino acid sequence similarities," *Biochem. J.*, 280:309-316.

Henrissat B. and Bairoch A. (1993) "New families in the classification of glycosyl hydrolases based on amino acid sequence similarities," *Biochem. J.*, 293:781-788.

Henrissat B. and Bairoch A. (1996) "Updating the sequence-based classification of glycosyl hydrolases," *Biochem. J.*, 316:695-696.

Henrissat B., Teeri T. T. and Warren R. A. J. (1998) "A scheme for designating enzymes that hydrolyse the polysaccharides in the cell wall of plants," *FEBS Letters*, 425:352-354.

Hong J., H. Tamaki, K. Yamamoto, and Kumagai H. (2003a) "Cloning of a gene encoding a thermo-stabile endo-β-1,4-glucanase from *Thermoascus aurantiacus* and its expression in yeast," *Biotech. Letters*, 25:657-661.

Hong J., Tamaki H., Yamamoto K. and Kumagai H. (2003b) "Cloning of a gene encoding thermostable cellobiohydrolase from *Thermoascus aurantiacus* and its expression in yeast," *Appl. Microbiol. Biotechnol.*, 63:42-50.

IUPAC (International Union of Pure and Applied Chemistry) (1987) "Measurement of cellulase activities," *Pure and Appl. Chem.*, 59:257-268.

Joutsjoki, V. V., Torkkeli T. K. and Nevalainen K. M. H. (1993) "Transformation of *Trichoderma reesei* with the Hormoconis resinae glucoamylase P (gamP) gene: production of a heterologous glucoamylase by *Trichoderma reesei,*" *Curr. Genet.*, 24:223-228.

Karhunen T., Mäntylä A., Nevalainen K. M. H. and Suominen P. L. (1993) "High frequency one-step gene replacement in *Trichoderma reesei*. I. Endoglucanase I overproduction," *Mol. Gen. Genet.*, 241:515-522.

Kurabi A., Berlin A, Gilkes N., Kilburn D., Markov A., Skomarovsky A., Gusakov A., Okunev O., Sinitsyn A., Gregg D. Xie D. and Saddler J. (2005) "Enzymatic hydrolysis of steam-exploded and ethanol organosolv-pretreated Douglas-Fir by novel and commercial fungal cellulases," *Appl. Biochem and Biotechn*. Vol. 121-124:219-229.

Lever, M. (1972) "A new reaction for colorimetric determination of carbohydrates," *Anal. Biochem.*, 47:276-279.

Lo Leggio, L., Kalogiannis S., Bhat M. K., and Pickersgill R. W. (1999) "High resolution structure and sequence of the *T. aurantiacus* xylanase I: implications for evolution of thermostability in family 10 xylanases and enzymes with (beta) alpha-barrel architecture," *Proteins* 36(3):295-306.

Lowry, O., Rosenbrough, N., Farr, A. and Randall, R. (1951) "Protein measurement with the Folin phenol reagent," *J. Biol. Chem.* 193:265-275.

Needleman S. and Wunsch C. (1970) "A general method applicable to the search for similarities in the amino acid sequence of two proteins," *Journal of Molecular Biology*, 48:443-453.

Nielsen H., Engelbrecht J., Brunak S, and von Heijne G. (1997) "Identification of prokaryotic and eykaryotic signal peptides and prediction of their cleavage sites," *Protein Engineering*, 10:1-6.

Paloheimo M., Mäntylä A., Kallio J., and Suominen P. (2003) "High-yield production of a bacterial xylanase in the filamentous fungus *Trichoderma reesei* requires a carrier polypeptide with an intact domain structure," *Appl. Env. Microbiol.*, 69:7073-7082.

Parry N., Beever D., Owen E., Nerinckx W. Claeyssens M, Van Beeumen J. and Bhat M. (2002) "Biochemical characterization and mode of action of a thermostable endoglucanase purified from *Thermoascus aurantiacus,*" *Arch. of Biochem. and Biophys.*, 404:243-253.

Penttilä M., Nevalainen H., Rättö M., Salminen E. and Knowles J. (1987) "A versatile transformation system for the cellulolytic filamentous fungus *Trichoderma reesei,*" *Gene*, 61:155-164.

Raeder U. and Broda P. (1985) "Rapid preparation of DNA from filamentous fungi," *Lett. Appl. Microbiol.*, 1:17-20.

Rice P, Longden I and Bleasby A. (2000). "EMBOSS: The European Molecular Biology Open Software Suite," *Trends in Genetics*, 16:276-277.

Sambrook J., Fritsch E. F. and Maniatis T. (1989) *Molecular Cloning, A Laboratory Manual*, Cold Spring Harbor Laboratory, New York, US.

Sambrook J. and Russell D. W. (2001) *Molecular Cloning, A Laboratory Manual*, Cold Spring Harbor Laboratory, New York, US.

Srisodsuk M, Reinikainen T, Penttilä M and Teeri T. (1993) "Role of the interdomain linker peptide of *Trichoderma reesei* cellobiohydrolase I in its interaction with crystalline cellulose," *J. Biol. Chem.*, Oct. 5, 268(28):20756-20761.

Sundberg, M., and Poutanen, K. (1991) "Purification and properties of two acetylxylan esterases of *Trichoderma reesei*," *Biotechnol. Appl. Biochem.*, 13:1-11.

Suurnäkki, A., Tenkanen M., Siika-aho, M., Niku-Paavola, M.-L., Viikari, L. and Buchert, J. (2000) "*Trichoderma reesei* cellulases and their core domains in the hydrolysis and modification of chemical pulp," *Cellulose* 7:189-209.

Tenkanen, M., Puls, J. and Poutanen, K (1992) Two major xylanases of *Trichoderma reesei*. Enzyme Microbiol. Technol. 14: 566-574.

Tomme, P. McRae, S., Wood, T. and Claeyssens, M. (1988) "Chromatographic separation of cellulolytic enzymes," *Methods in Enzymol.*, 160:187-192.

Tuohy M., Walsh J., Murray P., Claeyssens M., Cuffe M., Savage A. and Coughan M. (2002) "Kinetic parameters and mode of action of cellobiohydrolases produced by *Talaromyces emersonii*," *Biochem. Biophys. Acta,* 1596:366-380 (abstract).

Van Petegem et at (2002) "Atomic resolution structure of major endoglucanase from *Thermoascus aurantiacus*," *Biochem. and Biophys. Res. Comm.,* 296:161-166.

Van Tilbeurgh, H., Loonties, F., de Bruyne, C. and Claeyssens, M. (1988) "Fluorogenic and chromogenic glycosides as substrates and ligands of carbohydrases," *Methods Enzymol.,* 160:45-59.

Wyman, C. E. (2001) "Twenty years of trials, tribulations, and research progress in bioethanol technology," *Applied Biochemistry and Biotechnology,* 91-93: 5-21.

The invention claimed is:

1. A recombinant polypeptide having cellobiohydrolase activity comprising
an amino acid sequence having at least 90% identity to the amino acid sequence of SEQ ID NO:6 or amino acids 18 to 523 of SEQ ID NO:6.

2. The polypeptide of claim 1 comprising
an amino acid sequence having at least 95% identity to the amino acid sequence of SEQ ID NO: 6 or amino acids 18 to 523 of SEQ ID NO:6.

3. The polypeptide of claim 1, which is encoded by a polynucleotide selected from the group consisting of:
a) the nucleotide sequence of SEQ ID NO: 5, and
b) a nucleotide sequence that is degenerate of the nucleotide sequence of SEQ ID NO: 5 as a result of the genetic code thereto.

4. The polypeptide of claim 3, which is encoded by the sequence comprised in SEQ ID NO: 5.

5. The polypeptide of claim 3, which is encoded by a plasmid carried by an *Escherichia coli* strain deposited under accession number DSM 16729.

6. An enzyme preparation comprising a polypeptide of claim 1.

7. The enzyme preparation of claim 6, which is in the form of spent culture medium, powder, granules, or liquid.

8. The enzyme preparation of claim 6, which further comprises at least one other enzyme activity being a member selected from the group consisting of endoglucanase, beta-glucosidase, xylanase and other enzyme activities.

9. The enzyme preparation of claim 6, which further comprises additives.

10. The enzyme preparation of claim 6, comprising cellobiohydrolase, endoglucanase and beta-glucosidase, wherein said cellobiohydrolase comprises an amino acid sequence having at least 90% identity to the amino acid sequence of SEQ ID NO: 6 or amino acids 18 to 523 of SEQ ID NO:6.

11. The enzyme preparation of claim 10, wherein said cellobiohydrolase is obtained from *Acremonium thermophilum*.

12. The enzyme preparation of claim 11, wherein the cellobiohydrolase is obtained from *Acremonium thermophilum* CBS 116240.

13. The enzyme preparation of claim 10, wherein the enzymes are recombinant enzymes produced in a strain from the genus *Trichoderma* or *Aspergillus*.

14. The enzyme preparation of claim 10, wherein the endoglucanase comprises an amino acid sequence having at least 90% identity to the amino acid sequence of SEQ ID NO: 10, amino acids 31 to 335 of SEQ ID NO: 10, SEQ ID NO: 12, amino acids 22 to 297 of SEQ ID NO: 12, SEQ ID NO: 14, amino acids 21 to 251 of SEQ ID NO: 14, SEQ ID NO: 16, or amino acids 18 to 425 of SEQ ID NO: 16.

15. The enzyme preparation of claim 14, wherein the endoglucanase is encoded by a gene obtainable from *Thermoascus aurantiacus, Acremonium thermophilum*, or *Chaetomium thermophilum*.

16. The enzyme preparation of claim 10, wherein the beta-glucosidase comprises an amino acid sequence having at least 90% identity to the amino acid sequence of SEQ ID NO: 22, amino acids 20 to 843 of SEQ ID NO: 22, SEQ ID NO: 24, amino acids 19 to 861 of SEQ ID NO: 24, amino acids 20 to 861 of SEQ ID NO: 24, SEQ ID NO: 26, or amino acids 21 to 734 of SEQ ID NO: 26.

17. The enzyme preparation of claim 16, wherein the beta-glucosidase is obtained from *Thermoascus aurantiacus, Acremonium thermophilum*, or *Chaetomium thermophilum*.

18. The enzyme preparation of claim 10, further comprising a xylanase.

19. The enzyme preparation of claim 18, wherein the xylanase comprises an amino acid sequence having at least 90% identity to the amino acid sequence of SEQ ID NO: 18, amino acids 27 to 329 of SEQ ID NO: 18, SEQ ID NO: 20, or amino acids 20 to 416 of SEQ ID NO: 20.

20. The enzyme preparation of claim 19, wherein the xylanase is obtained from *Thermoascus aurantiacus* or *Acremonium thermophilum*.

21. The enzyme preparation of claim 20, wherein the xylanase is obtained from *Thermoascus aurantiacus* CBS 116239, or *Acremonium thermophilum* CBS 116240.

22. The enzyme preparation of claim 10, wherein at least one of the enzymes is encoded by a plasmid carried by an Escherichia coli strain deposited under accession number DSM 16723, DSM 16728, DSM 16729, DSM 16727, DSM 17326, DSM 17324, DSM 17323, DSM 17729, DSM 16724, DSM 16726, DSM 16725, DSM 17325 or DSM 17667.

23. The enzyme preparation of claim 10, which is in the form of spent culture medium, powder, granules, or liquid.

24. The enzyme preparation of claim 13, wherein the enzymes are recombinant enzymes produced in a strain from the genus *Trichoderma* or *Aspergillus*.

25. The enzyme preparation of claim 16, wherein the beta-glucosidase is obtained from *Thermoascus aurantiacus* CBS 116239, *Acremonium thermophilum* CBS 116240, or *Chaetomium thermophilum* CBS 730.95.

26. The enzyme preparation of claim 14, wherein the endoglucanase is encoded by a gene from *Thermoascus aurantiacus* CBS 116239, *Acremonium thermophilum* CBS 116240, or *Chaetomium thermophilum* CBS 730.95.

27. A method for preparing the polypeptide of claim 1 said method comprising transforming a host cell with a vector encoding said polypeptide, and culturing said host cell under conditions enabling expression of said polypeptide, and optionally recovering and purifying the polypeptide produced.

28. A method of treating cellulosic material with a spent culture medium of at least one microorganism capable of producing the polypeptide of claim 1 said method comprising reacting the cellulosic material with the spent culture medium to obtain hydrolysed cellulosic material.

29. A method for treating cellulosic material with cellobiohydrolase, endoglucanase and beta-glucosidase, whereby said cellobiohydrolase comprises the polypeptide of claim 1.

* * * * *

SEQUENCE LISTING

```
<160> NUMBER OF SEQ ID NOS: 30

<210> SEQ ID NO 1
<211> LENGTH: 3192
<212> TYPE: DNA
<213> ORGANISM: Thermoascus aurantiacus
<220> FEATURE:
<221> NAME/KEY: CDS
<222> LOCATION: (1514)..(2122)
<220> FEATURE:
<221> NAME/KEY: Intron
<222> LOCATION: (2123)..(2187)
<220> FEATURE:
<221> NAME/KEY: CDS
<222> LOCATION: (2188)..(2949)

<400> SEQUENCE: 1
ctagaccttt atcctttcat ccgaccagac ttcccctttg accttggcgc cctgttgact      60
acctacctac ctaggtaggt aacgtcgtcg accctcttga atgatcctcg tcacactgca     120
aacatccgaa acatacggca aaagatgatt gggcatggat gcaggagaca tcgaatgagg     180
gcttagaagg aaatgaaaac ctgggaccag gacgctaggt acgatgaaat ccgccaatgg     240
tgaaacttta agtcgtgcct acagcacagg ctctgtgaag attgcgctgt tcagacttaa     300
tcttctcatc acagtccaag tctttatgaa aaggaaaaga gagagaagag cgctatttcg     360
agctgtcggc ctcataggga gacagtcgag cataccagcg gtatcgacgt tagactcaac     420
caagaataat gacgagaata aacacagaag tcaaccttga actgtatatc agggttccag     480
cagcagatag ttacttgcat aaagacaact ccccgagggc tctctgcata caccaggatg     540
ttccggaatt attcactgct cgtttccgac gtggcgtcag tgatccgtct ccacagaacc     600
tctacctggg gaataaccca ggggaggaat ctgcaagtaa gaacttaata ccaatccccg     660
gggctgccgg ggtgaatcaa atctcccgcg ggaaattaaa cccatacgat gtttttgcac     720
cacatgcatg cttggcacga tttctccgca agggagtcac agagaaagac atatttcgca     780
tactactgtg actctgcaga gttacatatc actcaggata cattgcagat cattgtccga     840
gcatcaaaca tggacctgca ggatcaacgg cccgacaaaa cacaagtggc taaagctggg     900
ggatgcccga acccgctgcg caatatcatt gatggatgtt cccccacatt tttaaaacat     960
cgacggatcg gcccgcatac taatccttt atcaaccaaa agttccactc gactagaaa     1020 aaaaaggcca aggccactaa ttgcagtcgg atactggtct tttcgccgtc caacaccttc    1080
atccatgatc cccttagcca ccaatgcccc acataataca tgttgacata ggtacgtagc    1140
tctgttatcc aatcgcatcc gaacctcttt aacggacccc tcctacacac cttatcctaa    1200
```

-continued

```
cttcaggaga ctgttgccca ttggggattg aggaggtccg ggttgcagga tgcgttctag    1260
gctaaattct cggccggtag ccatctcgaa tctctcgtga agccttcatc tgaacggttg    1320
gcggcccgtc aagccgatga ccatgggttc ctgatagagc ttgtgcctga ccggccttgg    1380
cggcatagac gagctgaaca catcaggtat gaacagatca gatataaagt cggattgagt    1440
cctagtacga agcaatccgc caccaccaaa tcaagcaacg agcgacagca ataacaatat    1500
caatcgaatc gca atg tat cag cgc gct ctt ctc ttc tct ttc ttc ctc      1549
              Met Tyr Gln Arg Ala Leu Leu Phe Ser Phe Phe Leu
                1               5                   10 gcc gcc gcc cgc gcg cag cag gcc ggt acc gta acc gca gag aat cac      1597
Ala Ala Ala Arg Ala Gln Gln Ala Gly Thr Val Thr Ala Glu Asn His
        15                  20                  25 cct tcc ctg acc tgg cag caa tgc tcc agc ggc ggt agt tgt acc acg      1645
Pro Ser Leu Thr Trp Gln Gln Cys Ser Ser Gly Gly Ser Cys Thr Thr
    30                  35                  40 cag aat gga aaa gtc gtt atc gat gcg aac tgg cgt tgg gtc cat acc      1693
Gln Asn Gly Lys Val Val Ile Asp Ala Asn Trp Arg Trp Val His Thr
45                  50                  55                  60 acc tct gga tac acc aac tgc tac acg ggc aat acg tgg gac acc agt      1741
Thr Ser Gly Tyr Thr Asn Cys Tyr Thr Gly Asn Thr Trp Asp Thr Ser
                65                  70                  75 atc tgt ccc gac gac gtg acc tgc gct cag aat tgt gcc ttg gat gga      1789
Ile Cys Pro Asp Asp Val Thr Cys Ala Gln Asn Cys Ala Leu Asp Gly
            80                  85                  90 gcg gat tac agt ggc acc tat ggt gtt acg acc agt ggc aac gcc ctg      1837
Ala Asp Tyr Ser Gly Thr Tyr Gly Val Thr Thr Ser Gly Asn Ala Leu
        95                  100                 105 aga ctg aac ttt gtc acc caa agc tca ggg aag aac att ggc tcg cgc      1885
Arg Leu Asn Phe Val Thr Gln Ser Ser Gly Lys Asn Ile Gly Ser Arg
    110                 115                 120 ctg tac ctg ctg cag gac gac acc act tat cag atc ttc aag ctg ctg      1933
Leu Tyr Leu Leu Gln Asp Asp Thr Thr Tyr Gln Ile Phe Lys Leu Leu
125                 130                 135                 140 ggt cag gag ttt acc ttc gat gtc gac gtc tcc aat ctc cct tgc ggg      1981
Gly Gln Glu Phe Thr Phe Asp Val Asp Val Ser Asn Leu Pro Cys Gly
                145                 150                 155 ctg aac ggc gcc ctc tac ttt gtg gcc atg gac gcc gac ggc gga ttg      2029
Leu Asn Gly Ala Leu Tyr Phe Val Ala Met Asp Ala Asp Gly Gly Leu
            160                 165                 170 tcc aaa tac cct ggc aac aag gca ggc gct aag tat ggc act ggt tac      2077
Ser Lys Tyr Pro Gly Asn Lys Ala Gly Ala Lys Tyr Gly Thr Gly Tyr
        175                 180                 185 tgc gac tct cag tgc cct cgg gat ctc aag ttc atc aac ggt cag          2122
Cys Asp Ser Gln Cys Pro Arg Asp Leu Lys Phe Ile Asn Gly Gln
    190                 195                 200 gtacgtcaga agtgataact agccagcaga gcccatgaat cattaactaa cgctgtcaaa    2182 tacag gcc aat gtt gaa ggc tgg cag ccg tct gcc aac gac cca aat gcc    2232
      Ala Asn Val Glu Gly Trp Gln Pro Ser Ala Asn Asp Pro Asn Ala
          205                 210                 215 ggc gtt ggt aac cac ggt tcc tgc tgc gct gag atg gat gtc tgg gaa      2280
Gly Val Gly Asn His Gly Ser Cys Cys Ala Glu Met Asp Val Trp Glu
220                 225                 230 gcc aac agc atc tct act gcg gtg acg cct cac cca tgc gac acc ccc      2328
Ala Asn Ser Ile Ser Thr Ala Val Thr Pro His Pro Cys Asp Thr Pro
    235                 240                 245                 250 ggc cag acc atg tgc cag gga gac gac tgt ggt gga acc tac tcc tcc      2376
Gly Gln Thr Met Cys Gln Gly Asp Asp Cys Gly Gly Thr Tyr Ser Ser
            255                 260                 265
```

| | | | | | | | | | | | | | | | |
|---|---|---|---|---|---|---|---|---|---|---|---|---|---|---|---|
| act | cga | tat | gct | ggt | acc | tgc | gac | cct | gat | ggc | tgc | gac | ttc | aat | cct | 2424 |
| Thr | Arg | Tyr | Ala | Gly | Thr | Cys | Asp | Pro | Asp | Gly | Cys | Asp | Phe | Asn | Pro |
| | | | 270 | | | | 275 | | | | 280 |

```
act cga tat gct ggt acc tgc gac cct gat ggc tgc gac ttc aat cct      2424
Thr Arg Tyr Ala Gly Thr Cys Asp Pro Asp Gly Cys Asp Phe Asn Pro
            270             275             280 tac cgc cag ggc aac cac tcg ttc tac ggc ccc ggg cag atc gtc gac      2472
Tyr Arg Gln Gly Asn His Ser Phe Tyr Gly Pro Gly Gln Ile Val Asp
            285             290             295 acc agc tcc aaa ttc acc gtc gtc acc cag ttc atc acc gac gac ggg      2520
Thr Ser Ser Lys Phe Thr Val Val Thr Gln Phe Ile Thr Asp Asp Gly
300             305             310 acc ccc tcc ggc acc ctg acg gag atc aaa cgc ttc tac gtc cag aac      2568
Thr Pro Ser Gly Thr Leu Thr Glu Ile Lys Arg Phe Tyr Val Gln Asn
315             320             325             330 ggc aag gta atc ccc cag tcg gag tcg acg atc agc ggc gtc acc ggc      2616
Gly Lys Val Ile Pro Gln Ser Glu Ser Thr Ile Ser Gly Val Thr Gly
                335             340             345 aac tca atc acc acc gag tat tgc acg gcc cag aag gcc gcc ttc ggc      2664
Asn Ser Ile Thr Thr Glu Tyr Cys Thr Ala Gln Lys Ala Ala Phe Gly
            350             355             360 gac aac acc ggc ttc ttc acg cac ggc ggg ctt cag aag atc agt cag      2712
Asp Asn Thr Gly Phe Phe Thr His Gly Gly Leu Gln Lys Ile Ser Gln
            365             370             375 gct ctg gct cag ggc atg gtc ctc gtc atg agc ctg tgg gac gat cac      2760
Ala Leu Ala Gln Gly Met Val Leu Val Met Ser Leu Trp Asp Asp His
380             385             390 gcc gcc aac atg ctc tgg ctg gac agc acc tac ccg act gat gcg gac      2808
Ala Ala Asn Met Leu Trp Leu Asp Ser Thr Tyr Pro Thr Asp Ala Asp
395             400             405             410 ccg gac acc cct ggc gtc gcg cgc ggt acc tgc ccc acg acc tcc ggc      2856
Pro Asp Thr Pro Gly Val Ala Arg Gly Thr Cys Pro Thr Thr Ser Gly
            415             420             425 gtc ccg gcc gac gtt gag tcg cag tac ccc aat tca tat gtt atc tac      2904
Val Pro Ala Asp Val Glu Ser Gln Tyr Pro Asn Ser Tyr Val Ile Tyr
            430             435             440 tcc aac atc aag gtc gga ccc atc aac tcg acc ttc acc gcc aac          2949
Ser Asn Ile Lys Val Gly Pro Ile Asn Ser Thr Phe Thr Ala Asn
            445             450             455 taagtaagta actggcactc taccaccgag agcttcgtga agatacaggg gtggttggga    3009
gattgtcgtg tacaggggac atgcgatgct caaaaatcta catcagtttg ccaattgaac    3069
catgaaaaaa agggggagat caaagaagtc tgtcaaagga gggggctgt ggcagcttaa     3129 gccttgttgt agatcgagtc gacgccctat agtgagtcgt attagagctc gcggccgcga    3189
gct                                                                   3192

<210> SEQ ID NO 2
<211> LENGTH: 457
<212> TYPE: PRT
<213> ORGANISM: Thermoascus aurantiacus

<400> SEQUENCE: 2

Met Tyr Gln Arg Ala Leu Leu Phe Ser Phe Phe Leu Ala Ala Ala Arg
1               5                   10                  15

Ala Gln Gln Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Ser Gly Tyr
    50                  55                  60

Thr Asn Cys Tyr Thr Gly Asn Thr Trp Asp Thr Ser Ile Cys Pro Asp
65                  70                  75                  80
```

Asp Val Thr Cys Ala Gln Asn Cys Ala Leu Asp Gly Ala Asp Tyr Ser
            85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
            115                 120                 125

Gln Asp Asp Thr Thr Tyr Gln Ile Phe Lys Leu Leu Gly Gln Glu Phe
130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Leu Ser Lys Tyr Pro
            165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Gln Pro Ser Ala Asn Asp Pro Asn Ala Gly Val Gly Asn His Gly
            210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
            245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
            275                 280                 285

Ser Phe Tyr Gly Pro Gly Gln Ile Val Asp Thr Ser Lys Phe Thr
            290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
            325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
            355                 360                 365

Thr His Gly Gly Leu Gln Lys Ile Ser Gln Ala Leu Ala Gln Gly Met
370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
            405                 410                 415

Ala Arg Gly Thr Cys Pro Thr Thr Ser Gly Val Pro Ala Asp Val Glu
            420                 425                 430

Ser Gln Tyr Pro Asn Ser Tyr Val Ile Tyr Ser Asn Ile Lys Val Gly
            435                 440                 445

Pro Ile Asn Ser Thr Phe Thr Ala Asn
        450                 455

<210> SEQ ID NO 3
<211> LENGTH: 3055
<212> TYPE: DNA
<213> ORGANISM: Acremonium thermophilum
<220> FEATURE:
<221> NAME/KEY: CDS

```
<222> LOCATION: (972)..(1595)
<220> FEATURE:
<221> NAME/KEY: Intron
<222> LOCATION: (1596)..(1729)
<220> FEATURE:
<221> NAME/KEY: CDS
<222> LOCATION: (1730)..(2290)
<220> FEATURE:
<221> NAME/KEY: Intron
<222> LOCATION: (2291)..(2412)
<220> FEATURE:
<221> NAME/KEY: CDS
<222> LOCATION: (2413)..(2540)
<220> FEATURE:
<221> NAME/KEY: Intron
<222> LOCATION: (2541)..(2627)
<220> FEATURE:
<221> NAME/KEY: CDS
<222> LOCATION: (2628)..(2691)

<400> SEQUENCE: 3
```

| | | |
|---|---|---|
| gaattcggat cacaccgaga gcttcgcgat ggccagctgt ctcagcttgt acccgtctac | 60 | |
| caacgttccg catcttcgtt accttgatag ctcgcgtttg ctggactgct ttgtgagggg | 120 | |
| actgtgccac gcctgggaga cgggtgccgt accatcggtt actgcgcaga ctgaaaccg | 180 | |
| tcgttgccga aacagccagg caggaagcct gtccaccttc atgtatcttc atatggaccc | 240 | |
| cagcgcgccc ctctctttct cctcatttct tgcccaccac gatggacacc atgccaatct | 300 | |
| atttcttgat cccttgactc ctcagccccc cagcagtccg acaatgtaca gtgatgggca | 360 | |
| tctcttctg tacatacgtc ccctctcgcg gtgtccacgc gcggccgggg atgcctggga | 420 | |
| cggagtgcca cccgcaggga cgagacttg gctgatgggg tgcggtgcat ggtggcacaa | 480 | |
| gagatccagg cccccgatc tcgttctcgc acgtatcctt ccccgccgg cgatgcccaa | 540 | |
| gtgggaagtc ttcggagcgg cacccaggcc atcttgccg atgcccggca cggctctggc | 600 | |
| ggttgccttc atctatcgtg gctgcacatc cgccgtgccc ccattgggaa agcaggcttt | 660 | |
| gttcttcccg tctgtcgatc gtctcccacc tacccctccct cctcgcaagg gcttaccctg | 720 | |
| gccctcact gctgcttcac ctcactgctg cttccccgca atgccccctc gcccccccc | 780 | |
| cccccctctc ctttgcagta cagatctaca taatatcgag acgccccca agctgtttct | 840 | |
| ctggcacagc cctctcgcgc gtggtgcaag agcaagtcag agtatcaatt ccccccatctc | 900 | |
| tcatctcagc ccttctgccg tggtccaccc gacattctgg gcccgtagcc aagaccgatc | 960 | |

```
cgcctctcac c atg cac aag cgg gcg gcc acc ctc tcc gcc ctc gtc gtc           1010
              Met His Lys Arg Ala Ala Thr Leu Ser Ala Leu Val Val
              1               5                   10 gcc gcc gcc ggc ttc gcc cgc ggc cag ggc gtg ggc acg cag cag acg           1058
Ala Ala Ala Gly Phe Ala Arg Gly Gln Gly Val Gly Thr Gln Gln Thr
 15                  20                  25 gag acg cac ccc aag ctc acc ttc cag aag tgc tcc gcc gcc ggc agc           1106
Glu Thr His Pro Lys Leu Thr Phe Gln Lys Cys Ser Ala Ala Gly Ser
30                  35                  40                  45 tgc acg acc cag aac ggc gag gtg gtc atc gac gcc aac tgg cgc tgg           1154
Cys Thr Thr Gln Asn Gly Glu Val Val Ile Asp Ala Asn Trp Arg Trp
                50                  55                  60 gtg cac gac aag aac ggc tac acc aac tgc tac acg ggc aac gag tgg           1202
Val His Asp Lys Asn Gly Tyr Thr Asn Cys Tyr Thr Gly Asn Glu Trp
             65                  70                  75 aac acc acc atc tgc gcc gac gcc gcc tcg tgc gcc agc aac tgc gtc           1250
Asn Thr Thr Ile Cys Ala Asp Ala Ala Ser Cys Ala Ser Asn Cys Val
         80                  85                  90 gtc gac ggc gcc gac tac cag ggc acc tac ggc gcc tcc acc tcc ggc           1298
Val Asp Gly Ala Asp Tyr Gln Gly Thr Tyr Gly Ala Ser Thr Ser Gly
```

```
                    95                  100                 105
aac gcc ctg acc ctc aag ttc gtc acc aag ggc agc tac gcc acc aac        1346
Asn Ala Leu Thr Leu Lys Phe Val Thr Lys Gly Ser Tyr Ala Thr Asn
110                 115                 120                 125 atc ggc tcg cgc atg tac ctg atg gcc agc ccc acc aag tac gcc atg        1394
Ile Gly Ser Arg Met Tyr Leu Met Ala Ser Pro Thr Lys Tyr Ala Met
                130                 135                 140 ttc acc ctg ctg ggc cac gag ttc gcc ttc gac gtc gac ctg agc aag        1442
Phe Thr Leu Leu Gly His Glu Phe Ala Phe Asp Val Asp Leu Ser Lys
            145                 150                 155 ctg ccc tgc ggc ctc aac ggc gcc gtc tac ttc gtc agc atg gac gag        1490
Leu Pro Cys Gly Leu Asn Gly Ala Val Tyr Phe Val Ser Met Asp Glu
        160                 165                 170 gac ggc ggc acc agc aag tac ccc tcc aac aag gcc ggc gcc aag tac        1538
Asp Gly Gly Thr Ser Lys Tyr Pro Ser Asn Lys Ala Gly Ala Lys Tyr
    175                 180                 185 ggc acg ggc tac tgc gac tcg cag tgt ccg cgc gac ctc aag ttt atc        1586
Gly Thr Gly Tyr Cys Asp Ser Gln Cys Pro Arg Asp Leu Lys Phe Ile
190                 195                 200                 205 gac ggc aag gtgagaaccc gcactagcgt cccgccttcc gtgtccctcc                1635
Asp Gly Lys ttttgccttc ttcgaccgcc ctcttccctg cgggccaggg tcgctggggt gctgtcctcc      1695
tttctggtgg gcagcggtgc tgatcccgcg ccag gcc aac tcg gcc agc tgg cag      1750
                                    Ala Asn Ser Ala Ser Trp Gln
                                                210                 215 ccc tcg tcc aac gac cag aac gcc ggc gtg ggc ggc atg ggc tcg tgc        1798
Pro Ser Ser Asn Asp Gln Asn Ala Gly Val Gly Gly Met Gly Ser Cys
                220                 225                 230 tgc gcc gag atg gac atc tgg gag gcc aac tcc gtc tcc gcc gcc tac        1846
Cys Ala Glu Met Asp Ile Trp Glu Ala Asn Ser Val Ser Ala Ala Tyr
            235                 240                 245 acg ccg cac ccg tgc cag aac tac cag cag cac agc tgc agc ggc gac        1894
Thr Pro His Pro Cys Gln Asn Tyr Gln Gln His Ser Cys Ser Gly Asp
        250                 255                 260 gac tgc ggc ggc acc tac tcg gcc acc cgc ttc gcc ggc gac tgc gac        1942
Asp Cys Gly Gly Thr Tyr Ser Ala Thr Arg Phe Ala Gly Asp Cys Asp
    265                 270                 275 ccg gac ggc tgc gac tgg aac gcc tac cgc atg ggc gtg cac gac ttc        1990
Pro Asp Gly Cys Asp Trp Asn Ala Tyr Arg Met Gly Val His Asp Phe
280                 285                 290                 295 tac ggc aac ggc aag acc gtc gac acc ggc aag aag ttc tcc atc gtc        2038
Tyr Gly Asn Gly Lys Thr Val Asp Thr Gly Lys Lys Phe Ser Ile Val
                300                 305                 310 acc cag ttc aag ggc tcc ggc tcc acc ctg acc gag atc aag cag ttc        2086
Thr Gln Phe Lys Gly Ser Gly Ser Thr Leu Thr Glu Ile Lys Gln Phe
            315                 320                 325 tac gtc cag gac ggc agg aag atc gag aac ccc aac gcc acc tgg ccc        2134
Tyr Val Gln Asp Gly Arg Lys Ile Glu Asn Pro Asn Ala Thr Trp Pro
        330                 335                 340 ggc ctc gag ccc ttc aac tcc atc acc ccg gac ttc tgc aag gcc cag        2182
Gly Leu Glu Pro Phe Asn Ser Ile Thr Pro Asp Phe Cys Lys Ala Gln
    345                 350                 355 aag cag gtc ttc ggc gac ccc gac cgc ttc aac gac atg ggc ggc ttc        2230
Lys Gln Val Phe Gly Asp Pro Asp Arg Phe Asn Asp Met Gly Gly Phe
360                 365                 370                 375 acc aac atg gcc aag gcc ctg gcc aac ccc atg gtc ctg gtg ctg tcg        2278
Thr Asn Met Ala Lys Ala Leu Ala Asn Pro Met Val Leu Val Leu Ser
                380                 385                 390 ctg tgg gac gac gtgagccatt ttcgcattct ctcctgactc tcctccgctg            2330
Leu Trp Asp Asp
```

```
Leu Trp Asp Asp
        395 ccatcaccac ctcttccacc accgccacga gggtgtagct tgatctccgc tgactgacgt    2390 gtgcccacac ccccgtttct ag cac tac tcc aac atg ctg tgg ctc gac tct    2442
                          His Tyr Ser Asn Met Leu Trp Leu Asp Ser
                                          400                 405 acc tac ccg acc gac gcc gat ccc agc gcg ccc ggc aag gga cgt ggc    2490
Thr Tyr Pro Thr Asp Ala Asp Pro Ser Ala Pro Gly Lys Gly Arg Gly
                410                 415                 420 acc tgc gac acc agc agc ggc gtg cca agc gac gtg gag tcg aag aat    2538
Thr Cys Asp Thr Ser Ser Gly Val Pro Ser Asp Val Glu Ser Lys Asn
            425                 430                 435 gg  gtgagtcgga tcttctgcat gcggcccgtt ttccgagcat tgcttggggt         2590
Gly cctccctcag gctgacacac gcgcgccttc gatacag c gat gcg acc gtc atc     2643
                                            Asp Ala Thr Val Ile
                                                        440 tac tcc aac atc aag ttt ggg ccg ctg gac tcc acc tac acg gct tcc    2691
Tyr Ser Asn Ile Lys Phe Gly Pro Leu Asp Ser Thr Tyr Thr Ala Ser
        445                 450                 455 tgagcagccg ctttgggttc ggtggggccg aagcacaaca agtgtgtgcg tagctgagat    2751
gatggccgat ctctgtcctt tgtctcctag tgtctctctt atcgaacaac ccccgacct    2811 gcagcgtcgg cgggcatcgt atagtctggt gtaactgtat atagctctgt gcgtgtgaat    2871
cgaacgagca ccgacgaaat gtggtgtttc atgctatcgt acatgctctt gcgagatctg    2931
aagtcgtcaa ttagacattg ccaccatcca acttggcgac tgtccacccg gtccatttgt    2991
atcactggct cttccgagac ccggtctctc tcacaccgta atcactgcaa gcagagttga    3051
attc                                                                 3055

<210> SEQ ID NO 4
<211> LENGTH: 459
<212> TYPE: PRT
<213> ORGANISM: Acremonium thermophilum

<400> SEQUENCE: 4

Met His Lys Arg Ala Ala Thr Leu Ser Ala Leu Val Val Ala Ala
1               5                   10                  15

Gly Phe Ala Arg Gly Gln Gly Val Gly Thr Gln Thr Glu Thr His
            20                  25                  30

Pro Lys Leu Thr Phe Gln Lys Cys Ser Ala Ala Gly Ser Cys Thr Thr
        35                  40                  45

Gln Asn Gly Glu Val Val Ile Asp Ala Asn Trp Arg Trp Val His Asp
    50                  55                  60

Lys Asn Gly Tyr Thr Asn Cys Tyr Thr Gly Asn Glu Trp Asn Thr Thr
65                  70                  75                  80

Ile Cys Ala Asp Ala Ala Ser Cys Ala Ser Asn Cys Val Val Asp Gly
                85                  90                  95

Ala Asp Tyr Gln Gly Thr Tyr Gly Ala Ser Thr Ser Gly Asn Ala Leu
            100                 105                 110

Thr Leu Lys Phe Val Thr Lys Gly Ser Tyr Ala Thr Asn Ile Gly Ser
        115                 120                 125

Arg Met Tyr Leu Met Ala Ser Pro Thr Lys Tyr Ala Met Phe Thr Leu
    130                 135                 140

Leu Gly His Glu Phe Ala Phe Asp Val Asp Leu Ser Lys Leu Pro Cys
145                 150                 155                 160
```

```
Gly Leu Asn Gly Ala Val Tyr Phe Val Ser Met Asp Glu Asp Gly Gly
                165                 170                 175

Thr Ser Lys Tyr Pro Ser Asn Lys Ala Gly Ala Lys Tyr Gly Thr Gly
            180                 185                 190

Tyr Cys Asp Ser Gln Cys Pro Arg Asp Leu Lys Phe Ile Asp Gly Lys
        195                 200                 205

Ala Asn Ser Ala Ser Trp Gln Pro Ser Ser Asn Asp Gln Asn Ala Gly
    210                 215                 220

Val Gly Gly Met Gly Ser Cys Cys Ala Glu Met Asp Ile Trp Glu Ala
225                 230                 235                 240

Asn Ser Val Ser Ala Ala Tyr Thr Pro His Pro Cys Gly Asn Tyr Gln
                245                 250                 255

Gln His Ser Cys Ser Gly Asp Asp Cys Gly Gly Thr Tyr Ser Ala Thr
            260                 265                 270

Arg Phe Ala Gly Asp Cys Asp Pro Asp Gly Cys Asp Trp Asn Ala Tyr
        275                 280                 285

Arg Met Gly Val His Asp Phe Tyr Gly Asn Gly Lys Thr Val Asp Thr
    290                 295                 300

Gly Lys Lys Phe Ser Ile Val Thr Gln Phe Lys Gly Ser Gly Ser Thr
305                 310                 315                 320

Leu Thr Glu Ile Lys Gln Phe Tyr Val Gln Asp Gly Arg Lys Ile Glu
                325                 330                 335

Asn Pro Asn Ala Thr Trp Pro Gly Leu Glu Pro Phe Asn Ser Ile Thr
            340                 345                 350

Pro Asp Phe Cys Lys Ala Gln Lys Gln Val Phe Gly Asp Pro Asp Arg
        355                 360                 365

Phe Asn Asp Met Gly Gly Phe Thr Asn Met Ala Lys Ala Leu Ala Asn
    370                 375                 380

Pro Met Val Leu Val Leu Ser Leu Trp Asp Asp His Tyr Ser Asn Met
385                 390                 395                 400

Leu Trp Leu Asp Ser Thr Tyr Pro Thr Asp Ala Asp Pro Ser Ala Pro
                405                 410                 415

Gly Lys Gly Arg Gly Thr Cys Asp Thr Ser Ser Gly Val Pro Ser Asp
            420                 425                 430

Val Glu Ser Lys Asn Gly Asp Ala Thr Val Ile Tyr Ser Asn Ile Lys
        435                 440                 445

Phe Gly Pro Leu Asp Ser Thr Tyr Thr Ala Ser
    450                 455

<210> SEQ ID NO 5
<211> LENGTH: 3401
<212> TYPE: DNA
<213> ORGANISM: Acremonium thermophilum
<220> FEATURE:
<221> NAME/KEY: CDS
<222> LOCATION: (891)..(1299)
<220> FEATURE:
<221> NAME/KEY: Intron
<222> LOCATION: (1300)..(1387)
<220> FEATURE:
<221> NAME/KEY: CDS
<222> LOCATION: (1388)..(1442)
<220> FEATURE:
<221> NAME/KEY: Intron
<222> LOCATION: (1443)..(1495)
<220> FEATURE:
<221> NAME/KEY: CDS
<222> LOCATION: (1496)..(1643)
<220> FEATURE:
<221> NAME/KEY: Intron
<222> LOCATION: (1644)..(1697)
```

```
<220> FEATURE:
<221> NAME/KEY: CDS
<222> LOCATION: (1698)..(1928)
<220> FEATURE:
<221> NAME/KEY: Intron
<222> LOCATION: (1929)..(2014)
<220> FEATURE:
<221> NAME/KEY: CDS
<222> LOCATION: (2015)..(2740)

<400> SEQUENCE: 5
ctcgagtttc cctggtcggc cactctctgc tcatctcgct ctgcgcccct ggatgtgccg      60
tgtgtccagt cgtgtatctc ttgactgcac gacgtgttcc tcgcgactcg tctcgcgccg     120
gtggatgccc gtccactcat ttgtccgtct actgggtcag cctctcgtct cgaacgagct     180
tccacggccc actccccgga caacctcggc tctggatggc cctcctcccc ctccgtgtct     240
cccctcctgc ggggtccgtc gtgccctggc tgcatgctcc acatcgcttg atcacgctgc     300
gagccaccgc agagcccat ctccaaagcg accgtggcag cactacctct gtttctggga      360
tggggcccac gtcgatggcc tggcatccct gccaccctc ctccatcccc ctgacctcac      420
tcccaaccga taggagaagt ggtcatgggc acgaccccgt gcacgtcttg gactcgacga     480
gcttgatcgg gccggaagcc gtcaacgacg ggggagccgt gtcttgccac gcgtggccgt     540
ccttcgacag tggacagcga gaaaactggt ggggaagagg gctgctacag tcttgtcttg     600
cgaggcccga cgctcctagt ccgagaacca cctacgtgtt tctcgcgaag acggggccag     660
cttagcggcc aaatttgccc cccgggccta gggtctagcg atggggatga tgaactggtg     720
tcgacgatgt ctatataacg acggcgatct cctgtctctg agatcccatc ctttcatctc     780
caacccactt catcccttcc tctctctctc ccctcccctt ctctgacata ccgagtcctc     840
agaagcctcg tccgtcgtca cctattctca cttccccgcg aactccggcc atg tat        896
                                                         Met Tyr
                                                          1 acc aag ttc gcc gcc ctc gcc gcc ctc gtg gcc acc gtc cgc ggc cag       944
Thr Lys Phe Ala Ala Leu Ala Ala Leu Val Ala Thr Val Arg Gly Gln
        5                  10                  15 gcc gcc tgc tcg ctc acc gcc gag acc cac ccg tcg ctg cag tgg cag       992
Ala Ala Cys Ser Leu Thr Ala Glu Thr His Pro Ser Leu Gln Trp Gln
 20                  25                  30 aag tgc acc gcg ccc ggc agc tgc acc acc gtc agc ggc cag gtc acc      1040
Lys Cys Thr Ala Pro Gly Ser Cys Thr Thr Val Ser Gly Gln Val Thr
35                  40                  45                  50 atc gac gcc aac tgg cgc tgg ctg cac cag acc aac agc agc acc aac      1088
Ile Asp Ala Asn Trp Arg Trp Leu His Gln Thr Asn Ser Ser Thr Asn
                55                  60                  65 tgc tac acc ggc aac gag tgg gac acc agc atc tgc agc tcc gac acc      1136
Cys Tyr Thr Gly Asn Glu Trp Asp Thr Ser Ile Cys Ser Ser Asp Thr
            70                  75                  80 gac tgc gcc acc aag tgc tgc ctc gac ggc gcc gac tac acc ggc acc      1184
Asp Cys Ala Thr Lys Cys Cys Leu Asp Gly Ala Asp Tyr Thr Gly Thr
        85                  90                  95 tac ggc gtc acc gcc agc ggc aac tcg ctc aac ctc aag ttc gtc acc      1232
Tyr Gly Val Thr Ala Ser Gly Asn Ser Leu Asn Leu Lys Phe Val Thr
   100                 105                 110 cag ggg ccc tac tcc aag aac atc ggc tcg cgc atg tac ctc atg gag      1280
Gln Gly Pro Tyr Ser Lys Asn Ile Gly Ser Arg Met Tyr Leu Met Glu
115                 120                 125                 130 tcg gag tcc aag tac cag g gtgagcatat agatcacatc tttcgtcact            1329
Ser Glu Ser Lys Tyr Gln
                135
```

```
tgcgtccgtt tcgcacggca agcggtccag acgctaacgg gacggttctc ttctctag          1387 gc ttc act ctc ctc ggt cag gag ttt acc ttt gac gtg gac gtc tcc            1434
   Gly Phe Thr Leu Leu Gly Gln Glu Phe Thr Phe Asp Val Asp Val Ser
           140                 145                 150 aac ctc gg gtaggtgatg acttctcccg catgagaaga gctctgctaa                   1482
Asn Leu Gly
        155 ccgtgttgtc cag c tgc ggt ctg aac gga gcg ctc tac ttc gtg tcc atg         1532
                 Cys Gly Leu Asn Gly Ala Leu Tyr Phe Val Ser Met
                                 160                 165 gac ctc gac ggc ggc gtg tcc aag tac acc acc aac aag gcc ggc gcc           1580
Asp Leu Asp Gly Gly Val Ser Lys Tyr Thr Thr Asn Lys Ala Gly Ala
        170                 175                 180 aag tac ggc acc ggc tac tgc gac tcc cag tgc ccg cgg gat ctc aag           1628
Lys Tyr Gly Thr Gly Tyr Cys Asp Ser Gln Cys Pro Arg Asp Leu Lys
        185                 190                 195 ttc atc aac ggc cag gtgggtcgag agaccctctt ccctctcag tgaacgatgt           1683
Phe Ile Asn Gly Gln
200 ctgaccctct ctag gcc aac atc gac ggc tgg caa ccg tcg tcc aac gac          1733
                 Ala Asn Ile Asp Gly Trp Gln Pro Ser Ser Asn Asp
                                 205                 215 gcc aac gcc ggc ctc ggg aac cac ggc agc tgc tgc tcc gag atg gac          1781
Ala Asn Ala Gly Leu Gly Asn His Gly Ser Cys Cys Ser Glu Met Asp
        220                 225                 230 atc tgg gag gcc aac aag gtc tcc gcc gcc tac acg ccg cac ccc tgc          1829
Ile Trp Glu Ala Asn Lys Val Ser Ala Ala Tyr Thr Pro His Pro Cys
        235                 240                 245 acc acc atc ggc cag acc atg tgc acc ggc gac gac tgc ggc ggc acc          1877
Thr Thr Ile Gly Gln Thr Met Cys Thr Gly Asp Asp Cys Gly Gly Thr
        250                 255                 260 tat tcg tcg gac cgc tat gcc ggc atc tgc gac ccc gac ggt tgc gat          1925
Tyr Ser Ser Asp Arg Tyr Ala Gly Ile Cys Asp Pro Asp Gly Cys Asp
265                 270                 275                 280 ttt gtaggttctt tctctcgccg ctccctgacg acctatatgt gtgaagggac               1978
Phe gcacagaaaa gacaaggtca agctgacca gagcag aac tcg tac cgc atg ggc            2032
                                       Asn Ser Tyr Arg Met Gly
                                                     285 gac acc agc ttc tac ggc ccc ggc aag acg gtc gac acc ggc tcc aag          2080
Asp Thr Ser Phe Tyr Gly Pro Gly Lys Thr Val Asp Thr Gly Ser Lys
        290                 295                 300 ttc acc gtc gtg acc cag ttc ctc acg ggc tcc gac ggc aac ctc agc          2128
Phe Thr Val Val Thr Gln Phe Leu Thr Gly Ser Asp Gly Asn Leu Ser
        305                 310                 315 gag atc aag cgc ttc tac gtg cag aac ggc aag gtc atc ccc aac tcc          2176
Glu Ile Lys Arg Phe Tyr Val Gln Asn Gly Lys Val Ile Pro Asn Ser
320                 325                 330                 335 gag tcc aag atc gcc ggc gtc tcc ggc aac tcc atc acc acc gac ttc          2224
Glu Ser Lys Ile Ala Gly Val Ser Gly Asn Ser Ile Thr Thr Asp Phe
                340                 345                 350 tgc acc gcc cag aag acc gcc ttc ggc gac acc aac gtc ttc gag gag          2272
Cys Thr Ala Gln Lys Thr Ala Phe Gly Asp Thr Asn Val Phe Glu Glu
        355                 360                 365 cgc ggc ggc ctc gcc cag atg ggc aag gcc ctg gcc gag ccc atg gtc          2320
Arg Gly Gly Leu Ala Gln Met Gly Lys Ala Leu Ala Glu Pro Met Val
        370                 375                 380 ctg gtc ctg tcc gtc tgg gac gac cac gcc gtc aac atg ctc tgg ctc          2368
Leu Val Leu Ser Val Trp Asp Asp His Ala Val Asn Met Leu Trp Leu
        385                 390                 395
```

```
gac tcc acc tac ccc acc gac agc acc aag ccc ggc gcc gcc cgc ggc      2416
Asp Ser Thr Tyr Pro Thr Asp Ser Thr Lys Pro Gly Ala Ala Arg Gly
400                 405                 410                 415 gac tgc ccc atc acc tcc ggc gtg ccc gcc gac gtc gag tcc cag gcg      2464
Asp Cys Pro Ile Thr Ser Gly Val Pro Ala Asp Val Glu Ser Gln Ala
                420                 425                 430 ccc aac tcc aac gtc atc tac tcc aac atc cgc ttc ggc ccc atc aac      2512
Pro Asn Ser Asn Val Ile Tyr Ser Asn Ile Arg Phe Gly Pro Ile Asn
            435                 440                 445 tcc acc tac acc ggc acc ccc agc ggc ggc aac ccc ccc ggc ggc ggg      2560
Ser Thr Tyr Thr Gly Thr Pro Ser Gly Gly Asn Pro Pro Gly Gly Gly
        450                 455                 460 acc acc acc acc acc acc acc acc tcc aag ccc tcc ggc ccc acc          2608
Thr Thr Thr Thr Thr Thr Thr Thr Ser Lys Pro Ser Gly Pro Thr
465                 470                 475 acc acc acc aac ccc tcg ggt ccg cag cag acg cac tgg ggt cag tgc      2656
Thr Thr Thr Asn Pro Ser Gly Pro Gln Gln Thr His Trp Gly Gln Cys
480                 485                 490                 495 ggc ggc cag gga tgg acc ggc ccc acg gtc tgc cag agc ccc tac acc      2704
Gly Gly Gln Gly Trp Thr Gly Pro Thr Val Cys Gln Ser Pro Tyr Thr
                500                 505                 510 tgc aag tac tcc aac gac tgg tac tcg cag tgc ctg taagccataa           2750
Cys Lys Tyr Ser Asn Asp Trp Tyr Ser Gln Cys Leu
            515                 520 gcccccctgta cgttcggaag acggtggcaa cagacaaacc cctcccccga gcacacccccc  2810 cagggatcta aggggggttgt ggttaagaca taagaatgcg ccgtggcttg cctacgcca   2870 cggtcatgaa agtgcagtga aaatgggggc aagagtcgga aaaagtgagt ttgcttgcaa    2930
gggagagagg atgtcgagag gtgatgactt cgtttgtaca tagttggctc ttcgtgattg   2990
ggaacgggag gagtgtcggg gggagccctc cagactcctt ggcctctccg ctcgttccat   3050
ctttctcagt acatatacat ctgcattttc atccacgtct ctggcgtctc tggatgtgaa   3110
cgaatccgac aactggtggg ctgagatgaa tcgcaaggag agtatcttgc gaggatatca   3170
cagtcagaaa gtagcatttg agccactact aaaaggtcaa ccagtatgcg aagcttagca   3230
attatataca gcagctcaac ttcagaacga agtattgcat gtggcagaga atcttgggaa   3290
atgagccatg aagacctcgt cgagagagta cctctcaccg ccaaataacc agctagcggg   3350
ttgggagagg agcaatagga cgagcgcgat ggacagatat acgaactcga g            3401

<210> SEQ ID NO 6
<211> LENGTH: 523
<212> TYPE: PRT
<213> ORGANISM: Acremonium thermophilum

<400> SEQUENCE: 6

Met Tyr Thr Lys Phe Ala Ala Leu Ala Ala Leu Val Ala Thr Val Arg
1               5                   10                  15

Gly Gln Ala Ala Cys Ser Leu Thr Ala Glu Thr His Pro Ser Leu Gln
                20                  25                  30

Trp Gln Lys Cys Thr Ala Pro Gly Ser Cys Thr Thr Val Ser Gly Gln
            35                  40                  45

Val Thr Ile Asp Ala Asn Trp Arg Trp Leu His Gln Thr Asn Ser Ser
        50                  55                  60

Thr Asn Cys Tyr Thr Gly Asn Glu Trp Asp Thr Ser Ile Cys Ser Ser
65                  70                  75                  80

Asp Thr Asp Cys Ala Thr Lys Cys Cys Leu Asp Gly Ala Asp Tyr Thr
                85                  90                  95
```

```
Gly Thr Tyr Gly Val Thr Ala Ser Gly Asn Ser Leu Asn Leu Lys Phe
            100                 105                 110

Val Thr Gln Gly Pro Tyr Ser Lys Asn Ile Gly Ser Arg Met Tyr Leu
            115                 120                 125

Met Glu Ser Glu Ser Lys Tyr Gln Gly Phe Thr Leu Leu Gly Gln Glu
            130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Leu Asp Gly Gly Val Ser Lys Tyr
                165                 170                 175

Thr Thr Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Ala Asn Ile Asp
            195                 200                 205

Gly Trp Gln Pro Ser Ser Asn Asp Ala Asn Ala Gly Leu Gly Asn His
210                 215                 220

Gly Ser Cys Cys Ser Glu Met Asp Ile Trp Glu Ala Asn Lys Val Ser
225                 230                 235                 240

Ala Ala Tyr Thr Pro His Pro Cys Thr Thr Ile Gly Gln Thr Met Cys
                245                 250                 255

Thr Gly Asp Asp Cys Gly Gly Thr Tyr Ser Ser Asp Arg Tyr Ala Gly
            260                 265                 270

Ile Cys Asp Pro Asp Gly Cys Asp Phe Asn Ser Tyr Arg Met Gly Asp
            275                 280                 285

Thr Ser Phe Tyr Gly Pro Gly Lys Thr Val Asp Thr Gly Ser Lys Phe
            290                 295                 300

Thr Val Val Thr Gln Phe Leu Thr Gly Ser Asp Gly Asn Leu Ser Glu
305                 310                 315                 320

Ile Lys Arg Phe Tyr Val Gln Asn Gly Lys Val Ile Pro Asn Ser Glu
                325                 330                 335

Ser Lys Ile Ala Gly Val Ser Gly Asn Ser Ile Thr Thr Asp Phe Cys
            340                 345                 350

Thr Ala Gln Lys Thr Ala Phe Gly Asp Thr Asn Val Phe Glu Glu Arg
            355                 360                 365

Gly Gly Leu Ala Gln Met Gly Lys Ala Leu Ala Glu Pro Met Val Leu
            370                 375                 380

Val Leu Ser Val Trp Asp Asp His Ala Val Asn Met Leu Trp Leu Asp
385                 390                 395                 400

Ser Thr Tyr Pro Thr Asp Ser Thr Lys Pro Gly Ala Ala Arg Gly Asp
                405                 410                 415

Cys Pro Ile Thr Ser Gly Val Pro Ala Asp Val Glu Ser Gln Ala Pro
            420                 425                 430

Asn Ser Asn Val Ile Tyr Ser Asn Ile Arg Phe Gly Pro Ile Asn Ser
            435                 440                 445

Thr Tyr Thr Gly Thr Pro Ser Gly Gly Asn Pro Pro Gly Gly Gly Thr
            450                 455                 460

Thr Thr Thr Thr Thr Thr Thr Thr Ser Lys Pro Ser Gly Pro Thr Thr
465                 470                 475                 480

Thr Thr Asn Pro Ser Gly Pro Gln Gln Thr His Trp Gly Gln Cys Gly
                485                 490                 495

Gly Gln Gly Trp Thr Gly Pro Thr Val Cys Gln Ser Pro Tyr Thr Cys
            500                 505                 510

Lys Tyr Ser Asn Asp Trp Tyr Ser Gln Cys Leu
```

<210> SEQ ID NO 7
<211> LENGTH: 3649
<212> TYPE: DNA
<213> ORGANISM: Chaetomium thermophilum
<220> FEATURE:
<221> NAME/KEY: CDS
<222> LOCATION: (1290)..(2879)
<220> FEATURE:
<221> NAME/KEY: Intron
<222> LOCATION: (2880)..(2943)
<220> FEATURE:
<221> NAME/KEY: CDS
<222> LOCATION: (2944)..(2949)

<400> SEQUENCE: 7

```
tctagagctg tcgacgcggc cgcgtaatac gactcactat agggcgaaga attcggatcg      60
gactagagct cgtcacgggc tcgcgccgac gaggcgatga ggacgaaggg ccgacataat     120 ccgtactta cgctacatga cgactctcga aaattgtaaa gggccggcat ttcggagcga     180
gtgctgcgag ggcgcattcg cggcgtacct ggaattcctg gaatggtaag caatggccag     240
caatgggcca ggtatggacc agcttgaatc ctggttgcgg cgtcaccagg cccagcatgg     300
tgcccagaat ggcccaccgt ggcccatcgt cctaagaaac aagctgcgtc ccgcgatcca     360
aaaacgtcgt cttcggcgca cgtcctccgt ggtcccccg gctggacacc ctggctggcc     420
ctccaatgag cggcatttgc ccctgtcgag cgtgtcggca accttaatcg actccatctc     480
tcggctccac gccgtccatc ctgtcctcga cctcgtcatc tgtgctcccc ttgccctccc     540
ttgcccttcc ttgcctccgc acgacgtgc cacaatgtga ccctgctgcc cggagcgccc     600
agcgccatgc accgtttggg cttgtcgccg tgtcgccagt ctccatcgag cgattcgacc     660
gtgtgcctct ctccaccagc gttccccgcg ctctccatag tccatgctac ttcgagccgt     720
tgcctcacaa gctgccagcg gcatggctct gtcggtctcg cctctccttt tcccgtgaag     780
cgctgccata caattctccg tctgccccag tccttgaggc gccgctattc ccaatcggcc     840
atggcactgg ccagcccgat ccatgttcga tcgagcttcg acgggccgtg agccgtctgc     900
acggaggagc ttgcgagcct gcgaacctgg cggacctgga gaagcctggc ccatctccct     960
ggatggagat actgggtgcg ctagcaccac ggcgtgccac ggccaagctc cggccgaccc    1020
ggaggcggga agagggttgc gttgctgtct tcggcggctg tcagggcaaa gggtaatcgt    1080
caatgtggga aaaggggctc atctccatga gattcatgac tcggacatcg tctatataag    1140
tcgagtcccc catcctccaa cagccgattc tgctcctcat cccatcacca ccctcgtcca    1200
caaccacgca gttgtgtaca tcaaaacaag ttcgctccct ttacatcttc accacaacaa    1260
cagcacatcc tctcctttcg gctttcaag atg atg tat aag aag ttc gcc gct     1313
                                  Met Met Tyr Lys Lys Phe Ala Ala
                                   1               5 ctc gcc gcc ctc gtg gct ggc gcc tcc gcc cag cag gct tgc tcc ctc     1361
Leu Ala Ala Leu Val Ala Gly Ala Ser Ala Gln Gln Ala Cys Ser Leu
         10                  15                  20 acc gct gag aac cac cct agc ctc acc tgg aag cgc tgc acc tct ggc     1409
Thr Ala Glu Asn His Pro Ser Leu Thr Trp Lys Arg Cys Thr Ser Gly
 25                  30                  35                  40 ggc agc tgc tcg acc gtg aac ggc gcc gtc acc atc gat gcc aac tgg     1457
Gly Ser Cys Ser Thr Val Asn Gly Ala Val Thr Ile Asp Ala Asn Trp
                 45                  50                  55 cgc tgg act cac acc gtc tcc ggc tcg acc aac tgc tac acc ggc aac     1505
Arg Trp Thr His Thr Val Ser Gly Ser Thr Asn Cys Tyr Thr Gly Asn
             60                  65                  70
```

```
cag tgg gat acc tcc ctc tgc act gat ggc aag agc tgc gcc cag acc    1553
Gln Trp Asp Thr Ser Leu Cys Thr Asp Gly Lys Ser Cys Ala Gln Thr
         75                  80                  85 tgc tgc gtc gat ggc gct gac tac tct tcg acc tat ggt atc acc acc    1601
Cys Cys Val Asp Gly Ala Asp Tyr Ser Ser Thr Tyr Gly Ile Thr Thr
         90                  95                 100 agc ggt gac tcc ctg aac ctc aag ttc gtc acc aag cac cag tac ggc    1649
Ser Gly Asp Ser Leu Asn Leu Lys Phe Val Thr Lys His Gln Tyr Gly
105                 110                 115                 120 acc aac gtc ggc tcc cgt gtc tat ctg atg gag aac gac acc aag tac    1697
Thr Asn Val Gly Ser Arg Val Tyr Leu Met Glu Asn Asp Thr Lys Tyr
                125                 130                 135 cag atg ttc gag ctc ctc ggc aac gag ttc acc ttc gat gtc gat gtc    1745
Gln Met Phe Glu Leu Leu Gly Asn Glu Phe Thr Phe Asp Val Asp Val
            140                 145                 150 tcc aac ctg ggc tgc ggt ctc aac ggc gcc ctc tac ttc gtt tcc atg    1793
Ser Asn Leu Gly Cys Gly Leu Asn Gly Ala Leu Tyr Phe Val Ser Met
                155                 160                 165 gat gct gat ggt ggc atg agc aaa tac tct ggc aac aag gct ggc gcc    1841
Asp Ala Asp Gly Gly Met Ser Lys Tyr Ser Gly Asn Lys Ala Gly Ala
170                 175                 180 aag tac ggt acc ggc tac tgc gat gct cag tgc ccg cgc gac ctc aag    1889
Lys Tyr Gly Thr Gly Tyr Cys Asp Ala Gln Cys Pro Arg Asp Leu Lys
185                 190                 195                 200 ttc atc aac ggc gag gcc aac gtt ggg aac tgg acc ccc tcg acc aac    1937
Phe Ile Asn Gly Glu Ala Asn Val Gly Asn Trp Thr Pro Ser Thr Asn
                205                 210                 215 gat gcc aac gcc ggc ttc ggc cgc tat ggc agc tgc tgc tct gag atg    1985
Asp Ala Asn Ala Gly Phe Gly Arg Tyr Gly Ser Cys Cys Ser Glu Met
            220                 225                 230 gat gtc tgg gag gcc aac aac atg gct act gcc ttc act cct cac cct    2033
Asp Val Trp Glu Ala Asn Asn Met Ala Thr Ala Phe Thr Pro His Pro
                235                 240                 245 tgc acc acc gtt ggc cag agc cgc tgc gag gcc gac acc tgc ggt ggc    2081
Cys Thr Thr Val Gly Gln Ser Arg Cys Glu Ala Asp Thr Cys Gly Gly
250                 255                 260 acc tac agc tct gac cgc tat gct ggt gtt tgc gac cct gat ggc tgc    2129
Thr Tyr Ser Ser Asp Arg Tyr Ala Gly Val Cys Asp Pro Asp Gly Cys
265                 270                 275                 280 gac ttc aac gcc tac cgc caa ggc gac aag acc ttc tac ggc aag ggc    2177
Asp Phe Asn Ala Tyr Arg Gln Gly Asp Lys Thr Phe Tyr Gly Lys Gly
                285                 290                 295 atg act gtc gac acc aac aag aag atg acc gtc gtc acc cag ttc cac    2225
Met Thr Val Asp Thr Asn Lys Lys Met Thr Val Val Thr Gln Phe His
            300                 305                 310 aag aac tcg gct ggc gtc ctc agc gag atc aag cgc ttc tac gtc cag    2273
Lys Asn Ser Ala Gly Val Leu Ser Glu Ile Lys Arg Phe Tyr Val Gln
                315                 320                 325 gac ggc aag atc att gcc aac gct gag tcc aag atc ccc ggc aac ccc    2321
Asp Gly Lys Ile Ile Ala Asn Ala Glu Ser Lys Ile Pro Gly Asn Pro
330                 335                 340 gga aac tcc att acc cag gag tat tgc gat gcc cag aag gtc gcc ttc    2369
Gly Asn Ser Ile Thr Gln Glu Tyr Cys Asp Ala Gln Lys Val Ala Phe
345                 350                 355                 360 agt aac acc gat gac ttc aac cgc aag ggc ggt atg gct cag atg agc    2417
Ser Asn Thr Asp Asp Phe Asn Arg Lys Gly Gly Met Ala Gln Met Ser
                365                 370                 375 aag gcc ctc gca ggc ccc atg gtc ctg gtc atg tcc gtc tgg gat gac    2465
Lys Ala Leu Ala Gly Pro Met Val Leu Val Met Ser Val Trp Asp Asp
            380                 385                 390
```

```
cac tac gcc aac atg ctc tgg ctc gac tcg acc tac ccc atc gac cag    2513
His Tyr Ala Asn Met Leu Trp Leu Asp Ser Thr Tyr Pro Ile Asp Gln
            395                 400                 405 gcc ggc gcc ccc ggc gcc gag cgc ggt gct tgc ccg acc acc tcc ggt    2561
Ala Gly Ala Pro Gly Ala Glu Arg Gly Ala Cys Pro Thr Thr Ser Gly
    410                 415                 420 gtc cct gcc gag atc gag gcc cag gtc ccc aac agc aac gtc atc ttc    2609
Val Pro Ala Glu Ile Glu Ala Gln Val Pro Asn Ser Asn Val Ile Phe
425                 430                 435                 440 tcc aac atc cgt ttc ggc ccc atc ggc tcg acc gtc cct ggc ctt gac    2657
Ser Asn Ile Arg Phe Gly Pro Ile Gly Ser Thr Val Pro Gly Leu Asp
                445                 450                 455 ggc agc aac ccc ggc aac ccg acc acc acc gtc gtt cct ccc gct tct    2705
Gly Ser Asn Pro Gly Asn Pro Thr Thr Thr Val Val Pro Pro Ala Ser
            460                 465                 470 acc tcc acc tcc cgt ccg acc agc agc act agc tct ccc gtt tcg acc    2753
Thr Ser Thr Ser Arg Pro Thr Ser Ser Thr Ser Ser Pro Val Ser Thr
    475                 480                 485 ccg act ggc cag ccc ggc ggc tgc acc acc cag aag tgg ggc cag tgc    2801
Pro Thr Gly Gln Pro Gly Gly Cys Thr Thr Gln Lys Trp Gly Gln Cys
490                 495                 500 ggc ggt atc ggc tac acc ggc tgc act aac tgc gtt gct ggc acc acc    2849
Gly Gly Ile Gly Tyr Thr Gly Cys Thr Asn Cys Val Ala Gly Thr Thr
505                 510                 515                 520 tgc act cag ctc aac ccc tgg tac agc cag gtatgtttct cttccccctt     2899
Cys Thr Gln Leu Asn Pro Trp Tyr Ser Gln
                525                 530 ctagactcgc ttggatttga cagttgctaa catctgctca acag tgc ctg           2949
                                              Cys Leu taaacaactc gcttcgtccg cacgacggag gagggccatg agaaagaatg ggcaacatag  3009
attctttgcg cggttgtgga ctacttgggt attttctgga tgtacatagt tttatcacgt  3069
catgaggctg tcatgtgggg atgtgtatct ttttcgcttc ttcgtacata aatttacgca  3129
ttgagctttt cacccccaa aaacagttcc ctgatttgct ggagtaactt gatggtaaag   3189
cttggtcata agctcttcaa tggaaaaaac gatacagtca tgccttgaca catcctccca  3249
aagtcttcgt ccatgacatc acggtcgatc cttaagcaca agttcaataa ccccatgtgg  3309
cgttgccttg tcctgaaaca cagatgagat cttcagccca gccgcatcgg ccacttcctt  3369
gaactgagcc aacgagcgtt ccttcccgcc gattgagagc atcgcatagt ccttgaaggc  3429
tgcatagaga ggaataggg gcttgtttcc ggtagttggg ctgccggaac tcggatctgt   3489
tggcgcaagg gggtcagggt tgatctgctc ggcgatgagg acgcgtccat cggggtttgt  3549
tagtgcacga gcgacattgc gcaggatggt gactgccaca gggtcggagt aatcgcggag  3609
gatgtggcgg aggtagtaga ccagtgcacc tggaatcgat                       3649

<210> SEQ ID NO 8
<211> LENGTH: 532
<212> TYPE: PRT
<213> ORGANISM: Chaetomium thermophilum

<400> SEQUENCE: 8

Met Met Tyr Lys Lys Phe Ala Ala Leu Ala Ala Leu Val Ala Gly Ala
1               5                   10                  15

Ser Ala Gln Gln Ala Cys Ser Leu Thr Ala Glu Asn His Pro Ser Leu
            20                  25                  30

Thr Trp Lys Arg Cys Thr Ser Gly Gly Ser Cys Ser Thr Val Asn Gly
        35                  40                  45
```

```
Ala Val Thr Ile Asp Ala Asn Trp Arg Trp Thr His Thr Val Ser Gly
     50                  55                  60
Ser Thr Asn Cys Tyr Thr Gly Asn Gln Trp Asp Thr Ser Leu Cys Thr
 65                  70                  75                  80
Asp Gly Lys Ser Cys Ala Gln Thr Cys Cys Val Asp Gly Ala Asp Tyr
                 85                  90                  95
Ser Ser Thr Tyr Gly Ile Thr Thr Ser Gly Asp Ser Leu Asn Leu Lys
                100                 105                 110
Phe Val Thr Lys His Gln Tyr Gly Thr Asn Val Gly Ser Arg Val Tyr
             115                 120                 125
Leu Met Glu Asn Asp Thr Lys Tyr Gln Met Phe Glu Leu Leu Gly Asn
         130                 135                 140
Glu Phe Thr Phe Asp Val Asp Val Ser Asn Leu Gly Cys Gly Leu Asn
145                 150                 155                 160
Gly Ala Leu Tyr Phe Val Ser Met Asp Ala Asp Gly Gly Met Ser Lys
                165                 170                 175
Tyr Ser Gly Asn Lys Ala Gly Ala Lys Tyr Gly Thr Gly Tyr Cys Asp
                180                 185                 190
Ala Gln Cys Pro Arg Asp Leu Lys Phe Ile Asn Gly Glu Ala Asn Val
            195                 200                 205
Gly Asn Trp Thr Pro Ser Thr Asn Asp Ala Asn Ala Gly Phe Gly Arg
        210                 215                 220
Tyr Gly Ser Cys Cys Ser Glu Met Asp Val Trp Glu Ala Asn Asn Met
225                 230                 235                 240
Ala Thr Ala Phe Thr Pro His Pro Cys Thr Thr Val Gly Gln Ser Arg
                245                 250                 255
Cys Glu Ala Asp Thr Cys Gly Gly Thr Tyr Ser Ser Asp Arg Tyr Ala
                260                 265                 270
Gly Val Cys Asp Pro Asp Gly Cys Asp Phe Asn Ala Tyr Arg Gln Gly
            275                 280                 285
Asp Lys Thr Phe Tyr Gly Lys Gly Met Thr Val Asp Thr Asn Lys Lys
        290                 295                 300
Met Thr Val Val Thr Gln Phe His Lys Asn Ser Ala Gly Val Leu Ser
305                 310                 315                 320
Glu Ile Lys Arg Phe Tyr Val Gln Asp Gly Lys Ile Ile Ala Asn Ala
                325                 330                 335
Glu Ser Lys Ile Pro Gly Asn Pro Gly Asn Ser Ile Thr Gln Glu Tyr
                340                 345                 350
Cys Asp Ala Gln Lys Val Ala Phe Ser Asn Thr Asp Asp Phe Asn Arg
            355                 360                 365
Lys Gly Gly Met Ala Gln Met Ser Lys Ala Leu Ala Gly Pro Met Val
        370                 375                 380
Leu Val Met Ser Val Trp Asp Asp His Tyr Ala Asn Met Leu Trp Leu
385                 390                 395                 400
Asp Ser Thr Tyr Pro Ile Asp Gln Ala Gly Ala Pro Gly Ala Glu Arg
                405                 410                 415
Gly Ala Cys Pro Thr Thr Ser Gly Val Pro Ala Glu Ile Glu Ala Gln
            420                 425                 430
Val Pro Asn Ser Asn Val Ile Phe Ser Asn Ile Arg Phe Gly Pro Ile
        435                 440                 445
Gly Ser Thr Val Pro Gly Leu Asp Gly Ser Asn Pro Gly Asn Pro Thr
450                 455                 460
Thr Thr Val Val Pro Pro Ala Ser Thr Ser Thr Ser Arg Pro Thr Ser
```

-continued

```
                 465                 470                 475                 480
Ser Thr Ser Ser Pro Val Ser Thr Pro Thr Gly Gln Pro Gly Gly Cys
                485                 490                 495

Thr Thr Gln Lys Trp Gly Gln Cys Gly Gly Ile Gly Tyr Thr Gly Cys
            500                 505                 510

Thr Asn Cys Val Ala Gly Thr Thr Cys Thr Gln Leu Asn Pro Trp Tyr
        515                 520                 525

Ser Gln Cys Leu
    530

<210> SEQ ID NO 9
<211> LENGTH: 1339
<212> TYPE: DNA
<213> ORGANISM: Thermoascus aurantiacus
<220> FEATURE:
<221> NAME/KEY: CDS
<222> LOCATION: (17)..(122)
<220> FEATURE:
<221> NAME/KEY: Intron
<222> LOCATION: (123)..(177)
<220> FEATURE:
<221> NAME/KEY: CDS
<222> LOCATION: (178)..(236)
<220> FEATURE:
<221> NAME/KEY: Intron
<222> LOCATION: (237)..(296)
<220> FEATURE:
<221> NAME/KEY: CDS
<222> LOCATION: (297)..(449)
<220> FEATURE:
<221> NAME/KEY: Intron
<222> LOCATION: (450)..(508)
<220> FEATURE:
<221> NAME/KEY: CDS
<222> LOCATION: (509)..(573)
<220> FEATURE:
<221> NAME/KEY: Intron
<222> LOCATION: (574)..(647)
<220> FEATURE:
<221> NAME/KEY: CDS
<222> LOCATION: (648)..(745)
<220> FEATURE:
<221> NAME/KEY: Intron
<222> LOCATION: (746)..(806)
<220> FEATURE:
<221> NAME/KEY: CDS
<222> LOCATION: (807)..(1330)

<400> SEQUENCE: 9
ccgcggactg cgcatc atg aag ctc ggc tct ctc gtg ctc gct ctc agc gca         52
               Met Lys Leu Gly Ser Leu Val Leu Ala Leu Ser Ala
                 1               5                  10 gct agg ctt aca ctg tcg gcc cct ctc gca gac agg aag cag gag acc          100
Ala Arg Leu Thr Leu Ser Ala Pro Leu Ala Asp Arg Lys Gln Glu Thr
    15                  20                  25 aag cgt gcg aaa gta ttc caa t gttcgtaaca tccacgtctg gcttgctggc          152
Lys Arg Ala Lys Val Phe Gln
    30                  35 ttactggcaa ctgacaatgg cgaag gg ttc ggt tca aac gag tcc ggt gct          203
                              Trp Phe Gly Ser Asn Glu Ser Gly Ala
                                                         40 gaa ttc gga agc cag aac ctt cca gga gtc gag gtcagcatgc ctgtactctc       256
Glu Phe Gly Ser Gln Asn Leu Pro Gly Val Glu
45                  50                  55 tgcattatat taatatctca agaggcttac tctttcgcag gga aag gat tat ata         311
                                              Gly Lys Asp Tyr Ile
                                                              60 tgg cct gat ccc aac acc att gac aca ttg atc agc aag ggg atg aac         359
Trp Pro Asp Pro Asn Thr Ile Asp Thr Leu Ile Ser Lys Gly Met Asn
```

```
                    Trp Pro Asp Pro Asn Thr Ile Asp Thr Leu Ile Ser Lys Gly Met Asn
                                        65                  70                  75 atc ttt cgt gtc ccc ttt atg atg gag aga ttg gtt ccc aac tca atg         407
Ile Phe Arg Val Pro Phe Met Met Glu Arg Leu Val Pro Asn Ser Met
                80                  85                  90 acc ggc tct ccg gat ccg aac tac ctg gca gat ctc ata gcg                 449
Thr Gly Ser Pro Asp Pro Asn Tyr Leu Ala Asp Leu Ile Ala
                95                  100                 105 gtacatttca attccaccat gtttggagct gtcttcgttg tgctgacatt taatggtag        508 act gta aat gca atc acc cag aaa ggt gcc tac gcc gtc gtc gat cct        556
Thr Val Asn Ala Ile Thr Gln Lys Gly Ala Tyr Ala Val Val Asp Pro
                110                 115                 120 cat aac tac ggc aga ta  gtgaggtccc cggttctggt attgctgctg                603
His Asn Tyr Gly Arg Tyr
            125 tatatctaag tagatatgtg tttctaacat ttccacgatt tcag c tac aat tct          657
                                                   Tyr Asn Ser
                                                       130 ata atc tcg agc cct tcc gat ttc cag acc ttc tgg aaa acg gtc gcc        705
Ile Ile Ser Ser Pro Ser Asp Phe Gln Thr Phe Trp Lys Thr Val Ala
                135                 140                 145 tca cag ttt gct tcg aat cca ctg gtc atc ttc gac act a gtaagctgaa       755
Ser Gln Phe Ala Ser Asn Pro Leu Val Ile Phe Asp Thr
                150                 155                 160 cacccgaaat taactgagtc tgagcatgtc tgacaagacg atccatgaaa g at   aac       811
                                                             Asn Asn gaa tac cac gat atg gac cag acc tta gtc ctc aat ctc aac cag gcc        859
Glu Tyr His Asp Met Asp Gln Thr Leu Val Leu Asn Leu Asn Gln Ala
                165                 170                 175 gct atc gac ggc atc cgt tcc gcc gga gcc act tcc cag tac atc ttt        907
Ala Ile Asp Gly Ile Arg Ser Ala Gly Ala Thr Ser Gln Tyr Ile Phe
                180                 185                 190 gtc gag ggc aat tcg tgg acc ggg gca tgg acc tgg acg aac gtg aac        955
Val Glu Gly Asn Ser Trp Thr Gly Ala Trp Thr Trp Thr Asn Val Asn
195                 200                 205                 210 gat aac atg aaa agc ctg acc gac cca tct gac aag atc ata tac gag        1003
Asp Asn Met Lys Ser Leu Thr Asp Pro Ser Asp Lys Ile Ile Tyr Glu
                215                 220                 225 atg cac cag tac ctg gac tct gac gga tcc ggg aca tca gcg acc tgc        1051
Met His Gln Tyr Leu Asp Ser Asp Gly Ser Gly Thr Ser Ala Thr Cys
                230                 235                 240 gta tct tcg acc atc ggt caa gag cga atc acc agc gca acg caa tgg        1099
Val Ser Ser Thr Ile Gly Gln Glu Arg Ile Thr Ser Ala Thr Gln Trp
                245                 250                 255 ctc agg gcc aac ggg aag aag ggc atc atc ggc gag ttt gcg ggc gga        1147
Leu Arg Ala Asn Gly Lys Lys Gly Ile Ile Gly Glu Phe Ala Gly Gly
                260                 265                 270 gcc aac gac gtc tgc gag acg gcc atc acg ggc atg ctg gac tac atg        1195
Ala Asn Asp Val Cys Glu Thr Ala Ile Thr Gly Met Leu Asp Tyr Met
275                 280                 285                 290 gcc cag aac acg gac gtc tgg act ggc gcc atc tgg tgg gcg gcc ggg        1243
Ala Gln Asn Thr Asp Val Trp Thr Gly Ala Ile Trp Trp Ala Ala Gly
                295                 300                 305 ccg tgg tgg gga gac tac ata ttc tcc atg gag ccg gac aat ggc atc        1291
Pro Trp Trp Gly Asp Tyr Ile Phe Ser Met Glu Pro Asp Asn Gly Ile
                310                 315                 320 gcg tat cag cag ata ctt cct att ttg act ccg tat ctt tgactgcag          1339
Ala Tyr Gln Gln Ile Leu Pro Ile Leu Thr Pro Tyr Leu
                325                 330                 335
```

<210> SEQ ID NO 10
<211> LENGTH: 335
<212> TYPE: PRT
<213> ORGANISM: Thermoascus aurantiacus

<400> SEQUENCE: 10

Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
            20                  25                  30

Val Phe Gln Trp Phe Gly Ser Asn Glu Ser Gly Ala Glu Phe Gly Ser
        35                  40                  45

Gln Asn Leu Pro Gly Val Glu Gly Lys Asp Tyr Ile Trp Pro Asp Pro
    50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
            100                 105                 110

Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
    130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
            180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
    210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
            260                 265                 270

Gly Gly Ala Asn Asp Val Cys Glu Thr Ala Ile Thr Gly Met Leu Asp
        275                 280                 285

Tyr Met Ala Gln Asn Thr Asp Val Trp Thr Gly Ala Ile Trp Trp Ala
    290                 295                 300

Ala Gly Pro Trp Trp Gly Asp Tyr Ile Phe Ser Met Glu Pro Asp Asn
305                 310                 315                 320

Gly Ile Ala Tyr Gln Gln Ile Leu Pro Ile Leu Thr Pro Tyr Leu
                325                 330                 335

<210> SEQ ID NO 11
<211> LENGTH: 2334
<212> TYPE: DNA
<213> ORGANISM: Acremonium thermophilum
<220> FEATURE:
<221> NAME/KEY: misc_feature
<222> LOCATION: (13)..(13)
<223> OTHER INFORMATION: N = unknown

```
<220> FEATURE:
<221> NAME/KEY: CDS
<222> LOCATION: (715)..(797)
<220> FEATURE:
<221> NAME/KEY: Intron
<222> LOCATION: (798)..(856)
<220> FEATURE:
<221> NAME/KEY: CDS
<222> LOCATION: (857)..(1105)
<220> FEATURE:
<221> NAME/KEY: Intron
<222> LOCATION: (1106)..(1228)
<220> FEATURE:
<221> NAME/KEY: CDS
<222> LOCATION: (1229)..(1787)

<400> SEQUENCE: 11
```

| | |
|---|---|
| tctgtctctt gtntcagaac agatctcctg gcggcctgct ttgccggtcc gaattgcgat | 60 |
| cgatgcaacg tcgattgcat acgagctaag cccgtctcgt gataaccgca agggtcttc | 120 |
| cgagtttctg tctgcgaccc aggcattttc cgatttgtgt gcggggaccc aactgtcttc | 180 |
| tggggagtac ctggtgacaa agcacagat aaacagatgg atgacggtat tgctgtgata | 240 |
| tcgccgtggc gctgaatcct ttctcttcgc taccaagata tttattcccc gttgtgaaat | 300 |
| cttctattca gcccatccca tccggcaaca cgcatctgct tttcgttccg gcattccgat | 360 |
| acctggttcc tggagtgcct accgagcctc gcttcctggg atcgggcgtt gcaccccgcc | 420 |
| aaaccctatg ccccaaacgg tacggacaag gatgccggac cccggttttg tccagaaagg | 480 |
| ttgcattcct acccacctcg ctggagccac aacatgcaga tcaccgcccg agggaggaca | 540 |
| tgtgtggtgc agggacgttg caactctgc tgtgtctgaa gtatatgagg ccgatggttc | 600 |
| tccttgcaca aagcagagaa tggagtagcc agctcctcct caccagagtc gcctttgcag | 660 |
| cgtctcggca ttgcaggctc cccatcgtca gcatttcact tctcagcaac gaac atg | 717 |
| | Met |
| | 1 |
| cgc tcc tca ccc ttt ctc cgc gca gct ctg gct gcc gct ctg cct ctg | 765 |
| Arg Ser Ser Pro Phe Leu Arg Ala Ala Leu Ala Ala Ala Leu Pro Leu | |
|     5                   10                  15 | |
| agc gcc cat gcc ctc gac gga aag tcg acg ag gtatgccaat cctcgtacct | 817 |
| Ser Ala His Ala Leu Asp Gly Lys Ser Thr Arg | |
|         20                  25 | |
| ctgccctctg tagaaacaag tgaccgactg caaagacag a tac tgg gac tgc tgc | 872 |
| | Tyr Trp Asp Cys Cys |
| |        30 |
| aag ccg tcc tgc ggc tgg ccg gga aag gcc tcg gtg aac cag ccc gtc | 920 |
| Lys Pro Ser Cys Gly Trp Pro Gly Lys Ala Ser Val Asn Gln Pro Val | |
|     35                  40                  45 | |
| ttc tcg tgc tcg gcc gac tgg cag cgc atc agc gac ttc aac gcg aag | 968 |
| Phe Ser Cys Ser Ala Asp Trp Gln Arg Ile Ser Asp Phe Asn Ala Lys | |
| 50                  55                  60                  65 | |
| tcg ggc tgc gac gga ggc tcc gcc tac tcg tgc gcc gac cag acg ccc | 1016 |
| Ser Gly Cys Asp Gly Gly Ser Ala Tyr Ser Cys Ala Asp Gln Thr Pro | |
|             70                  75                  80 | |
| tgg gcg gtc aac gac aac ttc tcg tac ggc ttc gca gcc acg gcc atc | 1064 |
| Trp Ala Val Asn Asp Asn Phe Ser Tyr Gly Phe Ala Ala Thr Ala Ile | |
|         85                  90                  95 | |
| gcc ggc ggc tcc gag tcc agc tgg tgc tgc gcc tgc tat gc | 1105 |
| Ala Gly Gly Ser Glu Ser Ser Trp Cys Cys Ala Cys Tyr Ala | |
|     100                 105                 110 | |
| gtgagttctc tgcaagccgc ttcccacccc cgctttctgt gcaggccgct tcccccctac | 1165 |
| ccacccactt ccccccccc gcctctgtga tcgggcatcc gagctaagtt gcgtgtcgtc | 1225 |

```
cag a ctc acc ttc aac tcg ggc ccc gtc gcg ggc aag acc atg gtg gtg      1274
    Leu Thr Phe Asn Ser Gly Pro Val Ala Gly Lys Thr Met Val Val
            115                 120                 125 cag tcg acc agc acc ggc ggc gac ctg ggc agc aac cag ttc gac ctc        1322
Gln Ser Thr Ser Thr Gly Gly Asp Leu Gly Ser Asn Gln Phe Asp Leu
        130                 135                 140 gcc atc ccc ggc ggc ggc gtg ggc atc ttc aac ggc tgc gcc tcc cag        1370
Ala Ile Pro Gly Gly Gly Val Gly Ile Phe Asn Gly Cys Ala Ser Gln
145                 150                 155 ttc ggc ggc ctc ccc ggc gcc cag tac ggc ggc atc agc gac cgc agc        1418
Phe Gly Gly Leu Pro Gly Ala Gln Tyr Gly Gly Ile Ser Asp Arg Ser
    160                 165                 170 cag tgc tcg tcc ttc ccc gcg ccg ctc cag ccg ggc tgc cag tgg cgc        1466
Gln Cys Ser Ser Phe Pro Ala Pro Leu Gln Pro Gly Cys Gln Trp Arg
175                 180                 185                 190 ttc gac tgg ttc cag aac gcc gac aac ccc acc ttc acc ttc cag cgc        1514
Phe Asp Trp Phe Gln Asn Ala Asp Asn Pro Thr Phe Thr Phe Gln Arg
                195                 200                 205 gtg cag tgc ccg tcc gag ctc acg tcc cgc acg ggc tgt aag cgc gac        1562
Val Gln Cys Pro Ser Glu Leu Thr Ser Arg Thr Gly Cys Lys Arg Asp
            210                 215                 220 gac gac gcc agc tat ccc gtc ttc aac ccg cct agc ggt ggc tcc ccc        1610
Asp Asp Ala Ser Tyr Pro Val Phe Asn Pro Pro Ser Gly Gly Ser Pro
        225                 230                 235 agc acc acc agc acc acc agc tcc ccg tcc ggt ccc acg ggc aac            1658
Ser Thr Thr Ser Thr Thr Ser Ser Pro Ser Gly Pro Thr Gly Asn
    240                 245                 250 cct cct gga ggc ggt ggc tgc act gcc cag aag tgg gcc cag tgc ggc        1706
Pro Pro Gly Gly Gly Gly Cys Thr Ala Gln Lys Trp Ala Gln Cys Gly
255                 260                 265                 270 ggc act ggc ttc acg ggc tgc acc acc tgc gtc tcg ggc acc acc tgc        1754
Gly Thr Gly Phe Thr Gly Cys Thr Thr Cys Val Ser Gly Thr Thr Cys
                275                 280                 285 cag gtg cag aac cag tgg tat tcc cag tgt ctg tgagcgggag ggttgttggg      1807
Gln Val Gln Asn Gln Trp Tyr Ser Gln Cys Leu
            290                 295 gtccgtttcc ctagggctga ggctgacgtg aactgggtcc tcttgtccgc cccatcacgg      1867
gttcgtattc gcgcgcttag ggagaggagg atgcagtttg aggggccac attttgaggg       1927 ggacgcagtc tggggtcgaa gcttgtcggt tagggctgcc gtgacgtggt agagcagatg      1987
ggaccaagtg cggagctagg caggtgggtg gttgtggtgg tggcttacct tctgtaacgc      2047
aatggcatct catctcactc gcctgctccc tgattggtgg ctctgttcgg cctggcgctt     2107
tttgggaccg ctggctggaa tggattgctc cggaacgcca ggttgagctg ggctggcgcg     2167
agtagattgg ccgctccgag ctgcaaccat aataaaattt tcggaccctg taagccgcac    2227
ccgaccaggt ctccattggc ggacatgcac gacgtccttc gcaggcacgg cctgcccgcc    2287
tctgatcacc cgcagttttc gtaccgtcag accagataca agccccg                  2334

<210> SEQ ID NO 12
<211> LENGTH: 297
<212> TYPE: PRT
<213> ORGANISM: Acremonium thermophilum
<221> NAME/KEY: misc_feature
<222> LOCATION: (13)..(13)

<400> SEQUENCE: 12

Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
```

```
                20                  25                  30
Cys Lys Pro Ser Cys Gly Trp Pro Gly Lys Ala Ser Val Asn Gln Pro
            35                  40                  45

Val Phe Ser Cys Ser Ala Asp Trp Gln Arg Ile Ser Asp Phe Asn Ala
 50                  55                  60

Lys Ser Gly Cys Asp Gly Gly Ser Ala Tyr Ser Cys Ala Asp Gln Thr
 65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
                100                 105                 110

Thr Phe Asn Ser Gly Pro Val Ala Gly Lys Thr Met Val Val Gln Ser
            115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
                180                 185                 190

Trp Phe Gln Asn Ala Asp Asn Pro Thr Phe Thr Phe Gln Arg Val Gln
                195                 200                 205

Cys Pro Ser Glu Leu Thr Ser Arg Thr Gly Cys Lys Arg Asp Asp Asp
            210                 215                 220

Ala Ser Tyr Pro Val Phe Asn Pro Pro Ser Gly Gly Ser Pro Ser Thr
225                 230                 235                 240

Thr Ser Thr Thr Thr Ser Ser Pro Ser Gly Pro Thr Gly Asn Pro Pro
                245                 250                 255

Gly Gly Gly Gly Cys Thr Ala Gln Lys Trp Ala Gln Cys Gly Gly Thr
                260                 265                 270

Gly Phe Thr Gly Cys Thr Thr Cys Val Ser Gly Thr Thr Cys Gln Val
            275                 280                 285

Gln Asn Gln Trp Tyr Ser Gln Cys Leu
            290                 295

<210> SEQ ID NO 13
<211> LENGTH: 2033
<212> TYPE: DNA
<213> ORGANISM: Acremonium thermophilum
<220> FEATURE:
<221> NAME/KEY: CDS
<222> LOCATION: (259)..(702)
<220> FEATURE:
<221> NAME/KEY: Intron
<222> LOCATION: (703)..(857)
<220> FEATURE:
<221> NAME/KEY: CDS
<222> LOCATION: (858)..(888)
<220> FEATURE:
<221> NAME/KEY: Intron
<222> LOCATION: (889)..(990)
<220> FEATURE:
<221> NAME/KEY: CDS
<222> LOCATION: (991)..(1268)

<400> SEQUENCE: 13
ctcgaggaga ggaaccgagt ttgaaagatg ctatatatcg atagactacc ggcgtcgcct      60
cgccctgtcc gctctcttgc attccccctg ttgatgagac gagacaaaat tcctggttag     120
```

-continued

```
aaaagatccg tcgccgagat tcaccagtg gtaagtccg agaattggtc attcgacgtt       180
caatatgagt gtcaaagcta tgggtcctaa caaagaagga agcaagagct ttaaagagac     240
agaataacag cagcaaag atg cgt ctc cca cta ccg act ctg ctc gcc ctc      291
                    Met Arg Leu Pro Leu Pro Thr Leu Leu Ala Leu
                    1               5                   10 ttg ccc tac tac ctc gaa gtg tcc gct cag ggg gca tcc gga acc ggc      339
Leu Pro Tyr Tyr Leu Glu Val Ser Ala Gln Gly Ala Ser Gly Thr Gly
            15                  20                  25 acg aca aca cgt tac tgg gat tgc tgc aag ccg agc tgc gcg tgg cct      387
Thr Thr Thr Arg Tyr Trp Asp Cys Cys Lys Pro Ser Cys Ala Trp Pro
        30                  35                  40 ctg aag ggc aat tcg ccc agc ccg gtg cag act tgc gac aag aat gac      435
Leu Lys Gly Asn Ser Pro Ser Pro Val Gln Thr Cys Asp Lys Asn Asp
    45                  50                  55 agg ccg ctg aac gat ggg gga aac acc aag tcc ggc tgc gac aac ggt      483
Arg Pro Leu Asn Asp Gly Gly Asn Thr Lys Ser Gly Cys Asp Asn Gly
60                  65                  70                  75 ggc ggg gcc ttc atg tgc tca tcc cag agt ccc tgg gcc gtc aat gag      531
Gly Gly Ala Phe Met Cys Ser Ser Gln Ser Pro Trp Ala Val Asn Glu
                80                  85                  90 acc acc agc tac ggc tgg gca gcc gtt cgt atc gcc ggc agt acc gag      579
Thr Thr Ser Tyr Gly Trp Ala Ala Val Arg Ile Ala Gly Ser Thr Glu
            95                  100                 105 tcg gcc tgg tgc tgt gcc tgc tac gag ctc acc ttc acc agt ggg ccc      627
Ser Ala Trp Cys Cys Ala Cys Tyr Glu Leu Thr Phe Thr Ser Gly Pro
        110                 115                 120 gtc agt gga aag aag ctc ata gtc cag gcc acg aac act ggt gga gac      675
Val Ser Gly Lys Lys Leu Ile Val Gln Ala Thr Asn Thr Gly Gly Asp
    125                 130                 135 ctt ggg agc aac cac ttt gac ctt gcg gtatgtgggg ttttctttc             722
Leu Gly Ser Asn His Phe Asp Leu Ala
140                 145 ttcatcatcg ctctcaccat ggattcctcg gcgcaaggac caagattgag aagcgtcaat    782
gccgggttgg acacgggagc cgggatagga acacagaggc cgtttaagac cgtcagctga    842
cagcagagca attag att ccc gga ggt ggt gtt ggt cag tcc aat g           888
                Ile Pro Gly Gly Gly Val Gly Gln Ser Asn
                    150                 155 gtaggttcct tccctgaagt accggcaaca gcctgtgcgt tgctgtatac ccctttaat     948 catagcatct tcctgctgga tacaagccaa cccattttct ag ct tgc acg aac        1001
                                                  Ala Cys Thr Asn
                                                  160 cag tat ggt gcg ccc ccg aac ggc tgg ggc gac agg tat ggt ggc gtg      1049
Gln Tyr Gly Ala Pro Pro Asn Gly Trp Gly Asp Arg Tyr Gly Gly Val
        165                 170                 175 cac tcg cgg agc gac tgc gac agc ttc ccc gcg gcg ctc aag gcc ggc      1097
His Ser Arg Ser Asp Cys Asp Ser Phe Pro Ala Ala Leu Lys Ala Gly
    180                 185                 190 tgc tac tgg cga ttc gac tgg ttc cag ggc gcc gac aac ccg tcc gtg      1145
Cys Tyr Trp Arg Phe Asp Trp Phe Gln Gly Ala Asp Asn Pro Ser Val
195                 200                 205                 210 agc ttc aaa cag gta gcc tgc ccg gca gcc atc aca gct aag agc ggc      1193
Ser Phe Lys Gln Val Ala Cys Pro Ala Ala Ile Thr Ala Lys Ser Gly
                215                 220                 225 tgt act cgc cag aac gat gcc atc aac gag act ccg act ggg ccc agc      1241
Cys Thr Arg Gln Asn Asp Ala Ile Asn Glu Thr Pro Thr Gly Pro Ser
            230                 235                 240 act gtg cct acc tac acc gcg tca ggc tgaaagtcgg ctggggcacc            1288
Thr Val Pro Thr Tyr Thr Ala Ser Gly
```

```
                    245                 250
attgcccagg tgatggttgg gcatgtgtta gtctcactca ccagggacat ttgtcgcgac    1348
ctgatcatag gcgccagggg agttgaaagg ggttgccgta cgagaagaca ttttgtcgcc    1408
gtcttactcc cagccacttc tgtacatatt caatgacatt acatagcccg caaatatgtt    1468
catatatcgt ggccgcccaa accgccccgg tttgcttagg ctggagctga agtggctcgc    1528
cgatggctgt caaaggcagt cggaatattc ctcgttgctt cggcaacacg gtagctgctt    1588
gaaccgtacc cagcattaga acaccccccg ccgagggctt gctacgtcaa tggcggggtc    1648 tccaaccccct gcgcggcaca aaaccaacca cgccctcgtc ttttatgatg tcctcgctca    1708
aacgtcccgt gacgacactc cgctcatggt ctggtcctct gatgtagaag gggtaggtca    1768
gccgatggtc gtcaccgtcg tcaatgcttc cctcaagctt cttgcggcct ttatcctcca    1828
actcttccca catgagaact ccatctttcc gccttttcac aaagccactg ccctccttgt    1888
caagggccaa aaaccaacgc cgctgatgaa tgcttccgat cgtgtttgac gcgcccgggg    1948
tatgcatttg gttcggcgca cttttttcgt cctccagctc ccttaactcc cgttccatct    2008
gagagggtga ctcgtctact cgact                                         2033

<210> SEQ ID NO 14
<211> LENGTH: 251
<212> TYPE: PRT
<213> ORGANISM: Acremonium thermophilum

<400> SEQUENCE: 14

Met Arg Leu Pro Leu Pro Thr Leu Leu Ala Leu Leu Pro Tyr Tyr Leu
1               5                   10                  15

Glu Val Ser Ala Gln Gly Ala Ser Gly Thr Gly Thr Thr Thr Arg Tyr
            20                  25                  30

Trp Asp Cys Cys Lys Pro Ser Cys Ala Trp Pro Leu Lys Gly Asn Ser
        35                  40                  45

Pro Ser Pro Val Gln Thr Cys Asp Lys Asn Asp Arg Pro Leu Asn Asp
    50                  55                  60

Gly Gly Asn Thr Lys Ser Gly Cys Asp Asn Gly Gly Ala Phe Met
65                  70                  75                  80

Cys Ser Ser Gln Ser Pro Trp Ala Val Asn Glu Thr Thr Ser Tyr Gly
                85                  90                  95

Trp Ala Ala Val Arg Ile Ala Gly Ser Thr Glu Ser Ala Trp Cys Cys
            100                 105                 110

Ala Cys Tyr Glu Leu Thr Phe Thr Ser Gly Pro Val Ser Gly Lys Lys
        115                 120                 125

Leu Ile Val Gln Ala Thr Asn Thr Gly Gly Asp Leu Gly Ser Asn His
    130                 135                 140

Phe Asp Leu Ala Ile Pro Gly Gly Val Gly Gln Ser Asn Ala Cys
145                 150                 155                 160

Thr Asn Gln Tyr Gly Ala Pro Pro Asn Gly Trp Gly Asp Arg Tyr Gly
                165                 170                 175

Gly Val His Ser Arg Ser Asp Cys Asp Ser Phe Pro Ala Ala Leu Lys
            180                 185                 190

Ala Gly Cys Tyr Trp Arg Phe Asp Trp Phe Gln Gly Ala Asp Asn Pro
        195                 200                 205

Ser Val Ser Phe Lys Gln Val Ala Cys Pro Ala Ala Ile Thr Ala Lys
    210                 215                 220

Ser Gly Cys Thr Arg Gln Asn Asp Ala Ile Asn Glu Thr Pro Thr Gly
225                 230                 235                 240
```

```
Pro Ser Thr Val Pro Thr Tyr Thr Ala Ser Gly
            245                 250

<210> SEQ ID NO 15
<211> LENGTH: 2800
<212> TYPE: DNA
<213> ORGANISM: Chaetomium thermophilum
<220> FEATURE:
<221> NAME/KEY: misc_feature
<222> LOCATION: (2786)..(2786)
<223> OTHER INFORMATION: N = unknown
<220> FEATURE:
<221> NAME/KEY: CDS
<222> LOCATION: (768)..(2042)

<400> SEQUENCE: 15
ggatccaaga ccgatcccga ggattctcgg attatgtttg catctcaccc tccgaaaccg      60
catgaaaaat tgaaatgggc aactgtcgct gtgtttaatg ctttgcacat catgggatca     120
tgttcacccg ctctaatctc tcatcctcca gatcctatct atcctccgca tctagccggc     180
ttcttgcttg tgatccaaag ccctgatccc acgcggcttc tagacgcttt agaaattaca     240
ccgaatctcc ccatgcccct cttgcaatat cttcccgacc aggaacttcg ggtgctcaac     300
atccgcgagc ttgacgacga ccttcttgg ccggcttggc atgcgactct gttcgggact     360
caatgcaact ctgggccctt caatgccgcg catgaccgtt actgaggctt agccgcccca     420
atcgcttggc acggtacctt gcagacggaa tcccgggccc gttgtccgat ctgctttggt     480
tccggtagag aagcctcgga ggaagagaca cacggacaca acgattgcgg ccccaatgc      540 gctgctccta attgaggctc cgaggtcgtg tgccgtgtgg agaggccgcg actgggtctg     600
gggtgcggag gattgcggag atgaagataa tctgggtgca accgtggata cataaaaggg     660
agtagttctc ccctctgtga aaccttcttc cccaggattc tcctcgcctc taagagtcca     720
aagtcattca agacatccta cagcggggtc agtgagattc cataatc atg act cgc        776
                                                    Met Thr Arg
                                                    1 aag ttc gca ctc gtt ccc ctc ctt ctg ggt ctt gcc tcg gcc cag aaa        824
Lys Phe Ala Leu Val Pro Leu Leu Leu Gly Leu Ala Ser Ala Gln Lys
  5              10                  15 ccc ggc aac act cca gaa gtc cac ccc aag atc acc act tac cgc tgc        872
Pro Gly Asn Thr Pro Glu Val His Pro Lys Ile Thr Thr Tyr Arg Cys
 20              25                  30                  35 agc cac cgc cag gga tgc cgc ccg gag acg aac tac atc gtc ctc gac        920
Ser His Arg Gln Gly Cys Arg Pro Glu Thr Asn Tyr Ile Val Leu Asp
             40                  45                  50 tcc ctc acc cat ccc gtg cac cag ttg aac tcc aac gcg aac tgc ggc        968
Ser Leu Thr His Pro Val His Gln Leu Asn Ser Asn Ala Asn Cys Gly
         55                  60                  65 gac tgg ggt aac ccg ccc ccg cgc agc gtc tgc cct gat gtc gag acc       1016
Asp Trp Gly Asn Pro Pro Pro Arg Ser Val Cys Pro Asp Val Glu Thr
     70                  75                  80 tgc gcg cag aat tgc atc atg gag ggc atc caa gac tac tcc acc tac       1064
Cys Ala Gln Asn Cys Ile Met Glu Gly Ile Gln Asp Tyr Ser Thr Tyr
 85                  90                  95 ggc gtg acc acc tct ggc tct tcc ctt cgc ctg aag cag atc cac cag       1112
Gly Val Thr Thr Ser Gly Ser Ser Leu Arg Leu Lys Gln Ile His Gln
100                 105                 110                 115 ggc cgc gtc acc tct cct cgt gtc tac ctc ctc gac aag acg gag cag       1160
Gly Arg Val Thr Ser Pro Arg Val Tyr Leu Leu Asp Lys Thr Glu Gln
                120                 125                 130 cag tat gag atg atg cgt ctc acc ggc ttc gag ttc act ttc gac gtc       1208
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Gln | Tyr | Glu | Met | Met | Arg | Leu | Thr | Gly | Phe | Glu | Phe | Thr | Phe | Asp | Val |      |
|     |     |     | 135 |     |     |     | 140 |     |     |     |     | 145 |     |     |     |      |

```
gac acc acc aag ctc ccc tgc ggc atg aac gct gcg ctc tat ctc tcc    1256
Asp Thr Thr Lys Leu Pro Cys Gly Met Asn Ala Ala Leu Tyr Leu Ser
        150                 155                 160 gag atg gac gct acc ggc gct cgc tcc cgc ctc aac cct ggc ggt gcc    1304
Glu Met Asp Ala Thr Gly Ala Arg Ser Arg Leu Asn Pro Gly Gly Ala
165                 170                 175 tac tac ggc acg ggt tac tgc gat gca cag tgc ttc gtc acc ccc ttc    1352
Tyr Tyr Gly Thr Gly Tyr Cys Asp Ala Gln Cys Phe Val Thr Pro Phe
180                 185                 190                 195 atc aat ggc atc ggc aac atc gag ggc aag ggc tcg tgc tgc aac gag    1400
Ile Asn Gly Ile Gly Asn Ile Glu Gly Lys Gly Ser Cys Cys Asn Glu
        200                 205                 210 atg gac att tgg gag gcc aac tcg cgt agt cag tcc att gct ccg cac    1448
Met Asp Ile Trp Glu Ala Asn Ser Arg Ser Gln Ser Ile Ala Pro His
        215                 220                 225 ccc tgc aac aag cag ggt ctg tac atg tgc tcc ggc cag gag tgc gag    1496
Pro Cys Asn Lys Gln Gly Leu Tyr Met Cys Ser Gly Gln Glu Cys Glu
        230                 235                 240 ttc gac ggc gtc tgc gac gag tgg gga tgc aca tgg aac ccg tac aag    1544
Phe Asp Gly Val Cys Asp Glu Trp Gly Cys Thr Trp Asn Pro Tyr Lys
245                 250                 255 gtc aac gtt acc gac tac tat ggc cgc ggt ccg cag ttc aag gtc gac    1592
Val Asn Val Thr Asp Tyr Tyr Gly Arg Gly Pro Gln Phe Lys Val Asp
260                 265                 270                 275 acg acc cgt ccc ttc acc gtc atc aca cag ttt cca gcc gac cag aac    1640
Thr Thr Arg Pro Phe Thr Val Ile Thr Gln Phe Pro Ala Asp Gln Asn
        280                 285                 290 ggc aag ctg acg tcg atc cat cgc atg tat gtg caa gat ggc aag ttg    1688
Gly Lys Leu Thr Ser Ile His Arg Met Tyr Val Gln Asp Gly Lys Leu
        295                 300                 305 atc gag gcg cat acc gtc aac ctg ccg ggt tat cct caa gtg aac gcg    1736
Ile Glu Ala His Thr Val Asn Leu Pro Gly Tyr Pro Gln Val Asn Ala
        310                 315                 320 ctg aac gat gac ttc tgc cgt gcc acg gga gcc gcg acg aag tat ctt    1784
Leu Asn Asp Asp Phe Cys Arg Ala Thr Gly Ala Ala Thr Lys Tyr Leu
325                 330                 335 gaa ctg ggt gcc act gcg ggt atg ggc gag gct ctg agg cgt ggt atg    1832
Glu Leu Gly Ala Thr Ala Gly Met Gly Glu Ala Leu Arg Arg Gly Met
340                 345                 350                 355 gtg ctg gct atg agc atc tgg tgg gat gag agc ggc ttc atg aac tgg    1880
Val Leu Ala Met Ser Ile Trp Trp Asp Glu Ser Gly Phe Met Asn Trp
                360                 365                 370 ctt gat agc ggc gag tct ggg ccg tgc aac ccg aac gag ggt aac cca    1928
Leu Asp Ser Gly Glu Ser Gly Pro Cys Asn Pro Asn Glu Gly Asn Pro
        375                 380                 385 cag aac att cgc cag att gag ccc gag ccg gag gtt acc tat agc aac    1976
Gln Asn Ile Arg Gln Ile Glu Pro Glu Pro Glu Val Thr Tyr Ser Asn
        390                 395                 400 ctg cgc tgg ggt gag att ggg tcg act tat aag cac aat ctg aag ggc    2024
Leu Arg Trp Gly Glu Ile Gly Ser Thr Tyr Lys His Asn Leu Lys Gly
405                 410                 415 ggg tgg act ggc agg aac taagtgttgg ggattagagc ctgtgattgg          2072
Gly Trp Thr Gly Arg Asn
420                 425 atacctgtgg gttaaacggg gctcggtttg agagggttgt tgaaatttat ttctcgtaca  2132
tagttggcgt cttggcgaat atatgccccc aggactttga tccagtcttc gtccatttct  2192
ctgtgactta gttggtgcaa gtatcattgt tatgtcctgg gtgagacaaa gcaatctctt  2252
```

-continued

```
cagtggtcat gggtaaataa tctacaggct gtgaatggcg ttgcgtcagc ctcattaact    2312
taaacgattg gactcccctt ttcctaatca tcgccgttgc cgtgtaactc tcctagatct    2372
cttgttgtat atggcttcaa ctcgaagtga agaaaaatgg atacggcgac ctctttgtgc    2432
caattttctt gctgttcttc cggtattgac cctcggcaag acaactatgg ccaatattct    2492
gttatagtcg gcagttagtg ttgtgtcgta caagtcgtgc gggagcaata ctcaacagcc    2552
gcccttaata tggttattta cgccacgacg cacttcatta cacggctttg gggggtatat    2612
attccgttca actctatccc tcattcggtg tgattgaacg tctccaacag tgaaagtata    2672
agtctgacaa aaatgcccaa ccgccatgcc actgatgatc ctgttgagat gctcgtggtc    2732
tataacatcc tgtctaagtg ttacctccct aatgttagcc ccagttctgc tctncttgtc    2792
tcgacagc                                                              2800
```

<210> SEQ ID NO 16
<211> LENGTH: 425
<212> TYPE: PRT
<213> ORGANISM: Chaetomium thermophilum
<221> NAME/KEY: misc_feature
<222> LOCATION: (2786)..(2786)

<400> SEQUENCE: 16

```
Met Thr Arg Lys Phe Ala Leu Val Pro Leu Leu Leu Gly Leu Ala Ser
1               5                   10                  15

Ala Gln Lys Pro Gly Asn Thr Pro Glu Val His Pro Lys Ile Thr Thr
            20                  25                  30

Tyr Arg Cys Ser His Arg Gln Gly Cys Arg Pro Glu Thr Asn Tyr Ile
        35                  40                  45

Val Leu Asp Ser Leu Thr His Pro Val His Gln Leu Asn Ser Asn Ala
    50                  55                  60

Asn Cys Gly Asp Trp Gly Asn Pro Pro Arg Ser Val Cys Pro Asp
65                  70                  75                  80

Val Glu Thr Cys Ala Gln Asn Cys Ile Met Glu Gly Ile Gln Asp Tyr
                85                  90                  95

Ser Thr Tyr Gly Val Thr Thr Ser Gly Ser Ser Leu Arg Leu Lys Gln
            100                 105                 110

Ile His Gln Gly Arg Val Thr Ser Pro Arg Val Tyr Leu Leu Asp Lys
        115                 120                 125

Thr Glu Gln Gln Tyr Glu Met Met Arg Leu Thr Gly Phe Glu Phe Thr
    130                 135                 140

Phe Asp Val Asp Thr Thr Lys Leu Pro Cys Gly Met Asn Ala Ala Leu
145                 150                 155                 160

Tyr Leu Ser Glu Met Asp Ala Thr Gly Ala Arg Ser Arg Leu Asn Pro
                165                 170                 175

Gly Gly Ala Tyr Tyr Gly Thr Gly Tyr Cys Asp Ala Gln Cys Phe Val
            180                 185                 190

Thr Pro Phe Ile Asn Gly Ile Gly Asn Ile Glu Gly Lys Gly Ser Cys
        195                 200                 205

Cys Asn Glu Met Asp Ile Trp Glu Ala Asn Ser Arg Ser Gln Ser Ile
    210                 215                 220

Ala Pro His Pro Cys Asn Lys Gln Gly Leu Tyr Met Cys Ser Gly Gln
225                 230                 235                 240

Glu Cys Glu Phe Asp Gly Val Cys Asp Glu Trp Gly Cys Thr Trp Asn
                245                 250                 255

Pro Tyr Lys Val Asn Val Thr Asp Tyr Tyr Gly Arg Gly Pro Gln Phe
```

```
                         260                 265                 270
Lys Val Asp Thr Thr Arg Pro Phe Thr Val Ile Thr Gln Phe Pro Ala
        275                 280                 285

Asp Gln Asn Gly Lys Leu Thr Ser Ile His Arg Met Tyr Val Gln Asp
        290                 295                 300

Gly Lys Leu Ile Glu Ala His Thr Val Asn Leu Pro Gly Tyr Pro Gln
305                 310                 315                 320

Val Asn Ala Leu Asn Asp Asp Phe Cys Arg Ala Thr Gly Ala Ala Thr
                325                 330                 335

Lys Tyr Leu Glu Leu Gly Ala Thr Ala Gly Met Gly Glu Ala Leu Arg
            340                 345                 350

Arg Gly Met Val Leu Ala Met Ser Ile Trp Trp Asp Glu Ser Gly Phe
            355                 360                 365

Met Asn Trp Leu Asp Ser Gly Glu Ser Gly Pro Cys Asn Pro Asn Glu
        370                 375                 380

Gly Asn Pro Gln Asn Ile Arg Gln Ile Glu Pro Glu Pro Glu Val Thr
385                 390                 395                 400

Tyr Ser Asn Leu Arg Trp Gly Glu Ile Gly Ser Thr Tyr Lys His Asn
                405                 410                 415

Leu Lys Gly Gly Trp Thr Gly Arg Asn
            420                 425

<210> SEQ ID NO 17
<211> LENGTH: 1943
<212> TYPE: DNA
<213> ORGANISM: Thermoascus aurantiacus
<220> FEATURE:
<221> NAME/KEY: CDS
<222> LOCATION: (13)..(256)
<220> FEATURE:
<221> NAME/KEY: Intron
<222> LOCATION: (257)..(329)
<220> FEATURE:
<221> NAME/KEY: CDS
<222> LOCATION: (330)..(370)
<220> FEATURE:
<221> NAME/KEY: Intron
<222> LOCATION: (371)..(444)
<220> FEATURE:
<221> NAME/KEY: CDS
<222> LOCATION: (445)..(493)
<220> FEATURE:
<221> NAME/KEY: Intron
<222> LOCATION: (494)..(561)
<220> FEATURE:
<221> NAME/KEY: CDS
<222> LOCATION: (562)..(683)
<220> FEATURE:
<221> NAME/KEY: Intron
<222> LOCATION: (684)..(786)
<220> FEATURE:
<221> NAME/KEY: CDS
<222> LOCATION: (787)..(932)
<220> FEATURE:
<221> NAME/KEY: Intron
<222> LOCATION: (933)..(1001)
<220> FEATURE:
<221> NAME/KEY: CDS
<222> LOCATION: (1002)..(1090)
<220> FEATURE:
<221> NAME/KEY: Intron
<222> LOCATION: (1091)..(1155)
<220> FEATURE:
<221> NAME/KEY: CDS
<222> LOCATION: (1156)..(1174)
<220> FEATURE:
<221> NAME/KEY: Intron
<222> LOCATION: (1175)..(1267)
<220> FEATURE:
```

```
<221> NAME/KEY: CDS
<222> LOCATION: (1268)..(1295)
<220> FEATURE:
<221> NAME/KEY: Intron
<222> LOCATION: (1296)..(1361)
<220> FEATURE:
<221> NAME/KEY: CDS
<222> LOCATION: (1362)..(1451)
<220> FEATURE:
<221> NAME/KEY: Intron
<222> LOCATION: (1452)..(1551)
<220> FEATURE:
<221> NAME/KEY: CDS
<222> LOCATION: (1552)..(1617)
<220> FEATURE:
<221> NAME/KEY: Intron
<222> LOCATION: (1618)..(1829)
<220> FEATURE:
<221> NAME/KEY: CDS
<222> LOCATION: (1830)..(1922)

<400> SEQUENCE: 17
```

| | |
|---|---|
| ccgcgggaag cc atg gtt cga cca acg atc cta ctt act tca ctc ctg cta<br>              Met Val Arg Pro Thr Ile Leu Leu Thr Ser Leu Leu Leu<br>              1              5                10 | 51 |
| gct ccc ttc gca gct gcg agc cct atc ctc gag gaa cgc caa gct gca<br>Ala Pro Phe Ala Ala Ala Ser Pro Ile Leu Glu Glu Arg Gln Ala Ala<br> 15                    20                  25 | 99 |
| cag agt gtc gac caa ctg atc aag gct cgc ggc aag gtg tac ttt ggc<br>Gln Ser Val Asp Gln Leu Ile Lys Ala Arg Gly Lys Val Tyr Phe Gly<br>30                35                  40                  45 | 147 |
| gtc gcc acg gac caa aac cgg ctg acg acc ggc aag aat gcg gct atc<br>Val Ala Thr Asp Gln Asn Arg Leu Thr Thr Gly Lys Asn Ala Ala Ile<br>                50                  55                  60 | 195 |
| atc cag gct gat ttc ggc cag gtc acg ccg gag aat agt atg aaa tgg<br>Ile Gln Ala Asp Phe Gly Gln Val Thr Pro Glu Asn Ser Met Lys Trp<br>           65                  70                  75 | 243 |
| gac gct act gaa c gtgcgtgaga aagataattt gattttttc ttctatgacc<br>Asp Ala Thr Glu<br>           80 | 296 |
| gctcggaccg ttctgactag gtttataata tag ct tct caa gga aac ttc aac<br>                                                     Pro Ser Gln Gly Asn Phe Asn<br>                                                                85 | 349 |
| ttt gcc ggt gct gat tac ctt gtacgtacat acgaccactt gacgtttctt<br>Phe Ala Gly Ala Asp Tyr Leu<br> 90                 95 | 400 |
| gcacgcaact gcgattgagg agaagatact aatcttcttg aaag gtc aat tgg gcc<br>                                                                      Val Asn Trp Ala | 456 |
| cag caa aat gga aag ctg atc cgt ggc cat act ctt g gttagtagaa<br>Gln Gln Asn Gly Lys Leu Ile Arg Gly His Thr Leu<br>100                105                 110 | 503 |
| cgccaacctg cttccctaac ttactgaaga aggaaaaccg aattgaccgt ccccaag | 561 |
| ta tgg cac tcg cag ctg ccc tcg tgg gtg agc tcc atc acc gac aag<br>Val Trp His Ser Gln Leu Pro Ser Trp Val Ser Ser Ile Thr Asp Lys<br>               115                  120                  125 | 608 |
| aat acg ctg acc aac gtg atg aaa aat cac atc acc acc ttg atg acc<br>Asn Thr Leu Thr Asn Val Met Lys Asn His Ile Thr Thr Leu Met Thr<br>          130                 135                  140 | 656 |
| cgg tac aag ggc aag atc cgt gca tgg gtcagtcatc ctaccctaag<br>Arg Tyr Lys Gly Lys Ile Arg Ala Trp<br> 145                  150 | 703 |
| ctgcgtttca atgaagagac aaataagaac acacgtattt gcccgggcgt ttcagaatca | 763 |
| gaactgacag aatcactgaa tag gac gtg gtg aac gag gca ttc aac gag gat<br>                                             Asp Val Val Asn Glu Ala Phe Asn Glu Asp | 816 |

```
                                    155                       160
ggc tcc ctc cgc cag act gtc ttc ctc aac gtc atc ggg gag gat tac      864
Gly Ser Leu Arg Gln Thr Val Phe Leu Asn Val Ile Gly Glu Asp Tyr
        165                     170                 175 atc ccg att gct ttc cag acc gcc cgc gcc gct gac ccg aat gcc aag      912
Ile Pro Ile Ala Phe Gln Thr Ala Arg Ala Ala Asp Pro Asn Ala Lys
        180                 185                 190 ctg tac atc aac gat tac aa gtaagattta aggctcagtg atattccatt          962
Leu Tyr Ile Asn Asp Tyr Asn
195             200 tagtgtgaga agcattgctt atgagcatct gtattacag c ctc gac agt gcc tcg    1017
                                             Leu Asp Ser Ala Ser
                                                             205 tac ccc aag acg cag gcc att gtc aac cgc gtc aag caa tgg cgt gca     1065
Tyr Pro Lys Thr Gln Ala Ile Val Asn Arg Val Lys Gln Trp Arg Ala
                210                 215                 220 gct gga gtc ccg att gac ggc ata g gtatgtctct ctttctgttt             1110
Ala Gly Val Pro Ile Asp Gly Ile
                225             230 gtgatgtgac cgatttgaaa ccagtctaac gttagctggg tctag ga tcg caa acg    1166
                                                    Gly Ser Gln Thr cac ctc ag gtaaataatc gggaatgcct cggagaataa aagagaaaaa              1214
His Leu Ser
235 aaatgattgt cttatcagat cgtatcgact gactcatggc ttgtccaaaa tag c gct    1271
                                                              Ala ggt cag gga gcc ggt gtt cta caa taagtgcccc cctcccctat tttttactat   1325
Gly Gln Gly Ala Gly Val Leu Gln
240                 245 tattgcgaga gcggaatagg ctgacaaccc caaacg gct ctt ccg ctc ctt gct    1379
                                        Ala Leu Pro Leu Leu Ala
                                                            250 agt gcc gga act ccc gag gtc gct atc acg gaa ctg gac gtg gct ggt    1427
Ser Ala Gly Thr Pro Glu Val Ala Ile Thr Glu Leu Asp Val Ala Gly
            255                 260                 265 gct agc ccg acg gat tac gtc aat gtatgtacct cgttgtccct atccccttg    1481
Ala Ser Pro Thr Asp Tyr Val Asn
270                 275 gatactttgt ataattatta tcttcccgga gcctgttgat cagatctgac gatcatttct  1541
cgttttttag gtc gtg aac gct tgc ctc aac gtg cag tcc tgc gtg ggc     1590
                Val Val Asn Ala Cys Leu Asn Val Gln Ser Cys Val Gly
                                280                 285 atc acc gtc tgg ggc gtg gca gat ccg gtaagcgcgg ttcttccgta          1637
Ile Thr Val Trp Gly Val Ala Asp Pro
290                 295 ctccgtaccc aactagagtt cgggctgtca cgtcatgtct tagtcgtctt cagtcaggcc  1697
aaggccaaga cacaggacct gaaacgggca ggcagcagct gctagcagcc caagaagcag  1757
ccacatgatg catgattatt attattatat ctccgagttc tgggctaacg attggtgata  1817
ataaataaat ag gac tca tgg cgt gct agc acg acg cct ctc ctc ttc gac  1868
              Asp Ser Trp Arg Ala Ser Thr Thr Pro Leu Leu Phe Asp
                  300                 305                 310 ggc aac ttc aac ccg aag ccg gcg tac aac gcc att gtg cag gac ctg    1916
Gly Asn Phe Asn Pro Lys Pro Ala Tyr Asn Ala Ile Val Gln Asp Leu
                315                 320                 325 cag cag tgagtataga ccggtggatc c                                    1943
Gln Gln
```

<210> SEQ ID NO 18
<211> LENGTH: 329
<212> TYPE: PRT
<213> ORGANISM: Thermoascus aurantiacus

<400> SEQUENCE: 18

Met Val Arg Pro Thr Ile Leu Leu Thr Ser Leu Leu Leu Ala Pro Phe
1               5                   10                  15

Ala Ala Ala Ser Pro Ile Leu Glu Glu Arg Gln Ala Gln Ser Val
            20                  25                  30

Asp Gln Leu Ile Lys Ala Arg Gly Lys Val Tyr Phe Gly Val Ala Thr
            35                  40                  45

Asp Gln Asn Arg Leu Thr Thr Gly Lys Asn Ala Ala Ile Ile Gln Ala
        50                  55                  60

Asp Phe Gly Gln Val Thr Pro Glu Asn Ser Met Lys Trp Asp Ala Thr
65                  70                  75                  80

Glu Pro Ser Gln Gly Asn Phe Asn Phe Ala Gly Ala Asp Tyr Leu Val
                85                  90                  95

Asn Trp Ala Gln Gln Asn Gly Lys Leu Ile Arg Gly His Thr Leu Val
            100                 105                 110

Trp His Ser Gln Leu Pro Ser Trp Val Ser Ser Ile Thr Asp Lys Asn
        115                 120                 125

Thr Leu Thr Asn Val Met Lys Asn His Ile Thr Thr Leu Met Thr Arg
130                 135                 140

Tyr Lys Gly Lys Ile Arg Ala Trp Asp Val Val Asn Glu Ala Phe Asn
145                 150                 155                 160

Glu Asp Gly Ser Leu Arg Gln Thr Val Phe Leu Asn Val Ile Gly Glu
                165                 170                 175

Asp Tyr Ile Pro Ile Ala Phe Gln Thr Ala Arg Ala Ala Asp Pro Asn
            180                 185                 190

Ala Lys Leu Tyr Ile Asn Asp Tyr Asn Leu Asp Ser Ala Ser Tyr Pro
        195                 200                 205

Lys Thr Gln Ala Ile Val Asn Arg Val Lys Gln Trp Arg Ala Ala Gly
210                 215                 220

Val Pro Ile Asp Gly Ile Gly Ser Gln Thr His Leu Ser Ala Gly Gln
225                 230                 235                 240

Gly Ala Gly Val Leu Gln Ala Leu Pro Leu Leu Ala Ser Ala Gly Thr
                245                 250                 255

Pro Glu Val Ala Ile Thr Glu Leu Asp Val Ala Gly Ala Ser Pro Thr
            260                 265                 270

Asp Tyr Val Asn Val Val Asn Ala Cys Leu Asn Val Gln Ser Cys Val
        275                 280                 285

Gly Ile Thr Val Trp Gly Val Ala Asp Pro Asp Ser Trp Arg Ala Ser
290                 295                 300

Thr Thr Pro Leu Leu Phe Asp Gly Asn Phe Asn Pro Lys Pro Ala Tyr
305                 310                 315                 320

Asn Ala Ile Val Gln Asp Leu Gln Gln
                325

<210> SEQ ID NO 19
<211> LENGTH: 2955
<212> TYPE: DNA
<213> ORGANISM: Acremonium thermophilum
<220> FEATURE:
<221> NAME/KEY: CDS
<222> LOCATION: (1335)..(1671)
<220> FEATURE:
<221> NAME/KEY: Intron -continued

```
<222> LOCATION: (1672)..(1806)
<220> FEATURE:
<221> NAME/KEY: CDS
<222> LOCATION: (1807)..(2032)
<220> FEATURE:
<221> NAME/KEY: Intron
<222> LOCATION: (2033)..(2117)
<220> FEATURE:
<221> NAME/KEY: CDS
<222> LOCATION: (2118)..(2802)

<400> SEQUENCE: 19
tctagagctg tcgacgcggc cgcgtaatac gactcactat agggcgaaga attcggatca      60
cgtttgcttc agcaagtcgt tcgctacgac accacgtcca tgatggaggc cctgattcaa     120
tcataccaag gacggggcat gatggctgat ggctggactc gaagtgagtg gcccgtggct     180
gaattttcct tcccgttctc tacagtcctt ccctcagcga cacatccgca gttttgacag     240
cggaaatcgt caggatgctc cgccttctct cgcaacctga gtgcccaggc gtctcggcca     300
ccgtctctta tatatggccg ctgggtccgc ctttcgatcg ttttcgatt tggtctctcc      360
tagttccctc agctgacccg ggatatcgct tgtggctccg aaacctcacc atcccagacg     420
agcaagttct ccgcagtcca cctcagctca tccggccctt ggtagcatcg cagcgacccc     480
agacgaaggc accaaagaag catactatat attaggctaa atcgagcccc acgtggaata     540
tttgccatcg aggaggggtg gttgggcttc ttgtcctcgc aggtgctgcg cctgtaccta     600
cctggtgctc cagctggtgc tcccgctggt gctgttccag tcgccgtctg gccccaatgc     660
tctgtatctc ggttcgtccc gcactccttt cgccaagcgc taccaatgct ttgacgaacc     720
cggtaaattt gcagtggacc tgcagctggg caaacccgca gtgggaacca cagacctggt     780
tcgttcgaca cactccaatc gcaaccccgc ccgcgcaaac cttgcaccac atgtcgcccc     840
tttcccagtt gggtccctga agacacggag ccacttccgt gatcgtcggc tccccaagcc     900
gacagtcgga cgctgcaata ggatgccagc accgtggat ccaagggcca gtgaccccaa      960
ctctttcgcg gtattctggc cctcccaaag gtatgccagg acttccctgt ctttgctacc    1020
accagctctc ctccacggcg gaacggatac gccgtctcgc cggctcttgc tcgacaacat    1080
gcgagggggc gcgaaggcta ggttgtgacg atgcgacggt gcgatgtcac catttggcag    1140
tgatgttttc cgttgtcccc ttctccaccc tgcgccgttt cctcaaagac gcccaaccca    1200
taaatacgat gcgacgccaa ccttcatgtg ttcgtggcat cttgcctgac cagtctcagc    1260
aagaaacctg tggcggcgcg attgtcttga ccttctgatt gaaaacggat ctgcgtcctc    1320
```

| | | | | | | | | | | | |
|---|---|---|---|---|---|---|---|---|---|---|---|
| ctcgatagcc gacc | atg | cgc | gcc | aag | caa | ctc | ctg | gcg | gcc | ggc | ctg | ctg | 1370 |
| | Met | Arg | Ala | Lys | Gln | Leu | Leu | Ala | Ala | Gly | Leu | Leu | |
| | 1 | | | 5 | | | | | 10 | | | | |

| gcc | ccc | gcg | tcc | gtc | tcg | gcc | cag | ctc | aac | agc | ctc | gcc | gtg | gcg | gct | 1418 |
|---|---|---|---|---|---|---|---|---|---|---|---|---|---|---|---|---|
| Ala | Pro | Ala | Ser | Val | Ser | Ala | Gln | Leu | Asn | Ser | Leu | Ala | Val | Ala | Ala | |
| | 15 | | | | 20 | | | | | 25 | | | | | | |

| ggc | ctc | aag | tac | ttc | ggc | acg | gcc | gtg | cgg | gag | gcc | aac | gtc | aac | ggc | 1466 |
|---|---|---|---|---|---|---|---|---|---|---|---|---|---|---|---|---|
| Gly | Leu | Lys | Tyr | Phe | Gly | Thr | Ala | Val | Arg | Glu | Ala | Asn | Val | Asn | Gly | |
| 30 | | | | | 35 | | | | | 40 | | | | | | |

| gac | gcc | acc | tac | atg | tcg | tac | gtc | aac | aac | aag | tcc | gag | ttc | ggc | cag | 1514 |
|---|---|---|---|---|---|---|---|---|---|---|---|---|---|---|---|---|
| Asp | Ala | Thr | Tyr | Met | Ser | Tyr | Val | Asn | Asn | Lys | Ser | Glu | Phe | Gly | Gln | |
| 45 | | | | 50 | | | | | 55 | | | | | 60 | | |

| gtg | acg | ccc | gag | aac | ggc | cag | aag | tgg | gat | tcc | acc | gag | ccc | agc | cag | 1562 |
|---|---|---|---|---|---|---|---|---|---|---|---|---|---|---|---|---|
| Val | Thr | Pro | Glu | Asn | Gly | Gln | Lys | Trp | Asp | Ser | Thr | Glu | Pro | Ser | Gln | |
| | | | | 65 | | | | | 70 | | | | | 75 | | |

| ggc | cag | ttc | agc | tac | agc | cag | ggc | gac | atc | gtc | ccc | ggc | gtc | gcg | aag | 1610 |
|---|---|---|---|---|---|---|---|---|---|---|---|---|---|---|---|---|
| Gly | Gln | Phe | Ser | Tyr | Ser | Gln | Gly | Asp | Ile | Val | Pro | Gly | Val | Ala | Lys | |
| | 80 | | | | | 85 | | | | | 90 | | | | | |

```
aag aac ggc cag gtg ctg cgc tgc cac acc ctg gtg tgg tac agc cag      1658
Lys Asn Gly Gln Val Leu Arg Cys His Thr Leu Val Trp Tyr Ser Gln
             95                 100                 105 ctc ccc agc tgg g gtcagtgact ctctctttct ctctgtcttt ctctttgtct         1711
Leu Pro Ser Trp
    110 ttctctcttt ctctctctct ctctctctct ctctctctct ctctctccca tccagcatcg    1771 actgctgatc ttgctgacca gaagctcgtg tgcag tg  tca tcc gga agt tgg        1823
                                           Val Ser Ser Gly Ser Trp
                                                       115 acc cgc gcg acg ctt cag tcc gtc atc gag acg cac atc tcg aac gtg      1871
Thr Arg Ala Thr Leu Gln Ser Val Ile Glu Thr His Ile Ser Asn Val
        120                 125                 130 atg ggc cac tac aag ggc cag tgc tac gcc tgg gac gtg gtc aac gag      1919
Met Gly His Tyr Lys Gly Gln Cys Tyr Ala Trp Asp Val Val Asn Glu
135                 140                 145                 150 gcc atc aac gac gac ggc acg tgg cgg acc agc gtc ttc tac aac acc      1967
Ala Ile Asn Asp Asp Gly Thr Trp Arg Thr Ser Val Phe Tyr Asn Thr
                155                 160                 165 ttc aac acc gac tac ctg gcc att gcc ttc aac gcc gcg aag aag gcc      2015
Phe Asn Thr Asp Tyr Leu Ala Ile Ala Phe Asn Ala Ala Lys Lys Ala
            170                 175                 180 gat gcg ggc gcg aag ct  gtaggtgtcg gcctttacgt tgccgcagcg              2062
Asp Ala Gly Ala Lys Leu
            185 cacctccgcg acatgagccc cagagcgcgt ggctaatagt tcctcacgca cgcag g       2118 tac tac aac gac tac aat ctc gag tac aac ggc gcc aag acc aac acg      2166
Tyr Tyr Asn Asp Tyr Asn Leu Glu Tyr Asn Gly Ala Lys Thr Asn Thr
        190                 195                 200 gcc gtg cag ctg gtg cag atc gtg cag cag gcc ggc gcg ccc atc gac      2214
Ala Val Gln Leu Val Gln Ile Val Gln Gln Ala Gly Ala Pro Ile Asp
205                 210                 215                 220 ggg gtg ggc ttc cag ggc cac ctg atc gtg ggg tca acg ccg tcg cgc      2262
Gly Val Gly Phe Gln Gly His Leu Ile Val Gly Ser Thr Pro Ser Arg
                225                 230                 235 agc tcc ctg gcc acg gcg ctg aag cgc ttc acg gcg ctt ggc ctg gag      2310
Ser Ser Leu Ala Thr Ala Leu Lys Arg Phe Thr Ala Leu Gly Leu Glu
            240                 245                 250 gtg gcg tac acg gag ctg gac atc cgg cac tcg agc ctg ccg ccg tcg      2358
Val Ala Tyr Thr Glu Leu Asp Ile Arg His Ser Ser Leu Pro Pro Ser
        255                 260                 265 tcg gcg gcg ctg gcg acg cag ggc aac gac ttc gcc agc gtg gtg ggc      2406
Ser Ala Ala Leu Ala Thr Gln Gly Asn Asp Phe Ala Ser Val Val Gly
270                 275                 280 tcg tgc ctc gac gtg gcg ggc tgc gtg ggc atc acc atc tgg ggg ttc      2454
Ser Cys Leu Asp Val Ala Gly Cys Val Gly Ile Thr Ile Trp Gly Phe
285                 290                 295                 300 acg gac aag tac agc tgg gtg ccc gac acg ttc ccc ggc tcg ggc gcg      2502
Thr Asp Lys Tyr Ser Trp Val Pro Asp Thr Phe Pro Gly Ser Gly Ala
                305                 310                 315 gcg ctg ctg tac gac gcg aac tac agc aag aag ccg gcg tgg acg tcg      2550
Ala Leu Leu Tyr Asp Ala Asn Tyr Ser Lys Lys Pro Ala Trp Thr Ser
            320                 325                 330 gtc tcg tcg gtg ctg gcg gcc aag gcg acg aac ccg ccc ggc ggc ggg      2598
Val Ser Ser Val Leu Ala Ala Lys Ala Thr Asn Pro Pro Gly Gly Gly
        335                 340                 345 aac cca ccc ccc gtc acc acc acg acc acg acc acg acc acg tcg aag      2646
Asn Pro Pro Pro Val Thr Thr Thr Thr Thr Thr Thr Thr Thr Ser Lys
350                 355                 360
```

```
ccg tcg cag ccc acc acc acg acc acg acc acc agc ccg cag ggt ccg    2694
Pro Ser Gln Pro Thr Thr Thr Thr Thr Thr Thr Ser Pro Gln Gly Pro
365                 370                 375                 380 cag cag acg cac tgg ggc cag tgc ggc ggg atc ggc tgg acg ggg ccg    2742
Gln Gln Thr His Trp Gly Gln Cys Gly Gly Ile Gly Trp Thr Gly Pro
                385                 390                 395 cag tcg tgc cag agc ccg tgg acg tgc cag aag cag aac gac tgg tac    2790
Gln Ser Cys Gln Ser Pro Trp Thr Cys Gln Lys Gln Asn Asp Trp Tyr
400                 405                 410 tct cag tgc ctg tgaccaccac ggctgaccag ctgccattcc gaccacgggg         2842
Ser Gln Cys Leu
        415 cccggactac aaaaagaggg gacggtgtaa ataaagagcc gaacgggtct acgtacactg   2902 ttttgacctt ttctccgcag acgtatatta tcaattatag ttggatttct aga         2955

<210> SEQ ID NO 20
<211> LENGTH: 416
<212> TYPE: PRT
<213> ORGANISM: Acremonium thermophilum

<400> SEQUENCE: 20

Met Arg Ala Lys Gln Leu Leu Ala Ala Gly Leu Leu Ala Pro Ala Ser
1               5                   10                  15

Val Ser Ala Gln Leu Asn Ser Leu Ala Val Ala Ala Gly Leu Lys Tyr
            20                  25                  30

Phe Gly Thr Ala Val Arg Glu Ala Asn Val Asn Gly Asp Ala Thr Tyr
        35                  40                  45

Met Ser Tyr Val Asn Asn Lys Ser Glu Phe Gly Gln Val Thr Pro Glu
    50                  55                  60

Asn Gly Gln Lys Trp Asp Ser Thr Glu Pro Ser Gln Gly Gln Phe Ser
65                  70                  75                  80

Tyr Ser Gln Gly Asp Ile Val Pro Gly Val Ala Lys Lys Asn Gly Gln
                85                  90                  95

Val Leu Arg Cys His Thr Leu Val Trp Tyr Ser Gln Leu Pro Ser Trp
            100                 105                 110

Val Ser Ser Gly Ser Trp Thr Arg Ala Thr Leu Gln Ser Val Ile Glu
        115                 120                 125

Thr His Ile Ser Asn Val Met Gly His Tyr Lys Gly Gln Cys Tyr Ala
    130                 135                 140

Trp Asp Val Val Asn Glu Ala Ile Asn Asp Asp Gly Thr Trp Arg Thr
145                 150                 155                 160

Ser Val Phe Tyr Asn Thr Phe Asn Thr Asp Tyr Leu Ala Ile Ala Phe
                165                 170                 175

Asn Ala Ala Lys Lys Ala Asp Ala Gly Ala Lys Leu Tyr Tyr Asn Asp
            180                 185                 190

Tyr Asn Leu Glu Tyr Asn Gly Ala Lys Thr Asn Thr Ala Val Gln Leu
        195                 200                 205

Val Gln Ile Val Gln Gln Ala Gly Ala Pro Ile Asp Gly Val Gly Phe
    210                 215                 220

Gln Gly His Leu Ile Val Gly Ser Thr Pro Ser Arg Ser Ser Leu Ala
225                 230                 235                 240

Thr Ala Leu Lys Arg Phe Thr Ala Leu Gly Leu Glu Val Ala Tyr Thr
                245                 250                 255

Glu Leu Asp Ile Arg His Ser Ser Leu Pro Pro Ser Ser Ala Ala Leu
            260                 265                 270
```

```
Ala Thr Gln Gly Asn Asp Phe Ala Ser Val Val Gly Ser Cys Leu Asp
        275                 280                 285

Val Ala Gly Cys Val Gly Ile Thr Ile Trp Gly Phe Thr Asp Lys Tyr
290                 295                 300

Ser Trp Val Pro Asp Thr Phe Pro Gly Ser Gly Ala Ala Leu Leu Tyr
305                 310                 315                 320

Asp Ala Asn Tyr Ser Lys Lys Pro Ala Trp Thr Ser Val Ser Ser Val
                325                 330                 335

Leu Ala Ala Lys Ala Thr Asn Pro Pro Gly Gly Gly Asn Pro Pro Pro
                340                 345                 350

Val Thr Thr Thr Thr Thr Thr Thr Thr Ser Lys Pro Ser Gln Pro
                355                 360                 365

Thr Thr Thr Thr Thr Thr Thr Ser Pro Gln Gly Pro Gln Gln Thr His
370                 375                 380

Trp Gly Gln Cys Gly Gly Ile Gly Trp Thr Gly Pro Gln Ser Cys Gln
385                 390                 395                 400

Ser Pro Trp Thr Cys Gln Lys Gln Asn Asp Trp Tyr Ser Gln Cys Leu
                405                 410                 415
```

<210> SEQ ID NO 21
<211> LENGTH: 5092
<212> TYPE: DNA
<213> ORGANISM: Thermoascus aurantiacus
<220> FEATURE:
<221> NAME/KEY: CDS
<222> LOCATION: (669)..(728)
<220> FEATURE:
<221> NAME/KEY: Intron
<222> LOCATION: (729)..(872)
<220> FEATURE:
<221> NAME/KEY: CDS
<222> LOCATION: (873)..(1015)
<220> FEATURE:
<221> NAME/KEY: Intron
<222> LOCATION: (1016)..(1082)
<220> FEATURE:
<221> NAME/KEY: CDS
<222> LOCATION: (1083)..(1127)
<220> FEATURE:
<221> NAME/KEY: Intron
<222> LOCATION: (1128)..(1183)
<220> FEATURE:
<221> NAME/KEY: CDS
<222> LOCATION: (1184)..(1236)
<220> FEATURE:
<221> NAME/KEY: Intron
<222> LOCATION: (1237)..(1300)
<220> FEATURE:
<221> NAME/KEY: CDS
<222> LOCATION: (1301)..(1717)
<220> FEATURE:
<221> NAME/KEY: Intron
<222> LOCATION: (1718)..(1776)
<220> FEATURE:
<221> NAME/KEY: CDS
<222> LOCATION: (1777)..(2489)
<220> FEATURE:
<221> NAME/KEY: Intron
<222> LOCATION: (2490)..(2599)
<220> FEATURE:
<221> NAME/KEY: CDS
<222> LOCATION: (2600)..(3469)
<220> FEATURE:
<221> NAME/KEY: Intron
<222> LOCATION: (3470)..(3531)
<220> FEATURE:
<221> NAME/KEY: CDS
<222> LOCATION: (3532)..(3759)

<400> SEQUENCE: 21

```
ggatccgtcc gcggacacag gcagagagac ggcacgggga ctcgacctga tcctcccagg    60
gcggggtgtt gtttgtggcg agggagcgat gctgatgttc ttccagctcc gttgctacct   120
tcccacggcc atttagccgg cggacggcat gtaacatgtc aaacatgtgg gctcggcagt   180
gggggcgtga gacgcagcac ctgacccggc ggcgcgcgc ttgcagggtc caggacagc    240 cggccgtggt cgtttgcggg gaaggcgaca cagacgactt ggcgcggccc gccggaaggc   300
gaggaatcat gagtgcgacg gagacatggc aagaccacgg ccttcctggc gaagaagaag   360
atgaataatc gcaggggcag tgtggcatgg accgcacggc cgccagggac ctgccccgtg   420
aggtttctcg ggtgtttcca ctggttccat cgctgggggc gatcccgagc ccgtgtgccc   480
gtgtaactat tattgacgat caacatgcca tggccagcca gcttctataa taatcatata   540
taacaccccc cgttctcccg ctgccttgct ccgtggtctt cctggtcctg cttgaggttc   600
acgagtctcc ttgcatggtc aactcgtcct ctgcttcatc cgctgcttga ctccgtacct   660 cagcaacc atg agg ctt ggg tgg ctg gag ctg gcc gtc gcg gcg gcc gca    710
         Met Arg Leu Gly Trp Leu Glu Leu Ala Val Ala Ala Ala Ala
           1               5                  10 acc gtc gcc agc gcc aag gtgcgtcaga ccctcccccg gatcgacctt             758
Thr Val Ala Ser Ala Lys
 15              20 taggtgcttc ttcagcaagt gcgcgccggc cgcgacatcc gccgccgctg ccctcaccga    818
cgcagcaccc atatgcagca ggagagaagg catctctgac gaaagctccc ccag gat      875
                                                               Asp gac ttg gcc tac tcg ccg cct ttc tac ccg tcg cca tgg atg aac gga     923
Asp Leu Ala Tyr Ser Pro Pro Phe Tyr Pro Ser Pro Trp Met Asn Gly
         25                  30                  35 aac gga gag tgg gcg gag gcc tac cgc agg gct gtc gac ttc gtc tcg     971
Asn Gly Glu Trp Ala Glu Ala Tyr Arg Arg Ala Val Asp Phe Val Ser
     40                  45                  50 cag ctg acc ctc gcg gag aag gtc aac ctg acg acc ggt gtc gg         1015
Gln Leu Thr Leu Ala Glu Lys Val Asn Leu Thr Thr Gly Val Gly
         55                  60                  65 gtgagtccat tgacctctac cgagcccccg ttccatgtcc attgagcaat tggctgacgt   1075 cttgaag c tgg atg cag gag aaa tgt gtc ggt gaa acg ggc agc att ccg   1125
          Trp Met Gln Glu Lys Cys Val Gly Glu Thr Gly Ser Ile Pro
             70                  75                  80 ag gtaggctcac ttcccaatgc cgctgcaaag gaggtgtcta aactggaata aatcag     1183
Arg a ctg ggg ttc cgt gga ctg tgc ctc caa gac tcg ccc ctt ggt gtc aga   1232
  Leu Gly Phe Arg Gly Leu Cys Leu Gln Asp Ser Pro Leu Gly Val Arg
     85                  90                  95 ttt g gtaggtcttt caacagagaa caagggtcgt cgcgggagag atgctgatcg        1286
Phe
100 atacctactt ttag ct gac tac gtt tct gcc ttc ccc gcc ggt gtc aat      1335
               Ala Asp Tyr Val Ser Ala Phe Pro Ala Gly Val Asn
                              105                 110 gtc gct gca acg tgg gat aag aac ctc gcc tac ctt cgt ggg aag gcg     1383
Val Ala Ala Thr Trp Asp Lys Asn Leu Ala Tyr Leu Arg Gly Lys Ala
         115                 120                 125 atg ggt gag gaa cac cgt ggt aag ggc gtc gac gtc cag ctg gga cct     1431
Met Gly Glu Glu His Arg Gly Lys Gly Val Asp Val Gln Leu Gly Pro
         130                 135                 140 gtc gcc ggc cct ctt ggc aga cac ccc gac ggt ggc aga aac tgg gag     1479
Val Ala Gly Pro Leu Gly Arg His Pro Asp Gly Gly Arg Asn Trp Glu
145                 150                 155                 160
```

```
                                            -continued
ggt ttc tct cct gac ccc gtc ctg acc ggt gtg ctt atg gcg gag acg      1527
Gly Phe Ser Pro Asp Pro Val Leu Thr Gly Val Leu Met Ala Glu Thr
            165                 170                 175 atc aag ggt atc cag gat gcc ggt gtg att gct tgc gcc aag cac ttc      1575
Ile Lys Gly Ile Gln Asp Ala Gly Val Ile Ala Cys Ala Lys His Phe
        180                 185                 190 att ggt aac gag atg gag cac ttc cgg caa gcc ggt gag gct gtt ggc      1623
Ile Gly Asn Glu Met Glu His Phe Arg Gln Ala Gly Glu Ala Val Gly
    195                 200                 205 tat ggt ttc gat att acc gag agt gtc agc tca aat atc gac gac aag      1671
Tyr Gly Phe Asp Ile Thr Glu Ser Val Ser Ser Asn Ile Asp Asp Lys
210                 215                 220 acg ctt cac gag ctg tac ctt tgg ccc ttt gcg gat gct gtt cgc g        1717
Thr Leu His Glu Leu Tyr Leu Trp Pro Phe Ala Asp Ala Val Arg
225                 230                 235 gtaagcagtc cccccctcat aggtgattgt acatgtgtat ttctgactcg ctttcaaag     1776 ct ggc gtt ggt tcg ttc atg tgc tcc tac aac cag gtt aac aac agc      1823
   Ala Gly Val Gly Ser Phe Met Cys Ser Tyr Asn Gln Val Asn Asn Ser
   240                 245                 250                 255 tac agc tgc tcg aac agc tac ctc cta aac aag ttg ctc aaa tcg gag     1871
Tyr Ser Cys Ser Asn Ser Tyr Leu Leu Asn Lys Leu Leu Lys Ser Glu
                260                 265                 270 ctt gat ttt cag ggc ttc gtg atg agt gac tgg gga gcg cac cac agc     1919
Leu Asp Phe Gln Gly Phe Val Met Ser Asp Trp Gly Ala His His Ser
            275                 280                 285 ggc gtt gga gct gcc ctg gct ggc ctt gac atg tcg atg cca gga gac     1967
Gly Val Gly Ala Ala Leu Ala Gly Leu Asp Met Ser Met Pro Gly Asp
        290                 295                 300 acc gcc ttt ggt acc ggc aaa tcc ttc tgg gga acc aac ctg acc atc     2015
Thr Ala Phe Gly Thr Gly Lys Ser Phe Trp Gly Thr Asn Leu Thr Ile
    305                 310                 315 gcc gtt ctc aac ggt act gtt ccg gaa tgg cgt gtg gat gac atg gct     2063
Ala Val Leu Asn Gly Thr Val Pro Glu Trp Arg Val Asp Asp Met Ala
320                 325                 330                 335 gtt cgc atc atg gcg gcc ttt tac aag gtt ggt cgc gac cgt tac cag     2111
Val Arg Ile Met Ala Ala Phe Tyr Lys Val Gly Arg Asp Arg Tyr Gln
                340                 345                 350 gtg ccg gtc aac ttc gac tcg tgg acg aag gat gaa tac ggt tac gag     2159
Val Pro Val Asn Phe Asp Ser Trp Thr Lys Asp Glu Tyr Gly Tyr Glu
            355                 360                 365 cac gca ctg gtt ggc cag aac tat gtc aag gtc aat gac aag gtg gat     2207
His Ala Leu Val Gly Gln Asn Tyr Val Lys Val Asn Asp Lys Val Asp
        370                 375                 380 gtt cgt gcc gac cat gcg gac atc atc cgt caa att ggg tct gct agt     2255
Val Arg Ala Asp His Ala Asp Ile Ile Arg Gln Ile Gly Ser Ala Ser
385                 390                 395 gtt gtc ctt ctt aag aac gat gga gga ctc cca ttg acc ggc tat gaa     2303
Val Val Leu Leu Lys Asn Asp Gly Gly Leu Pro Leu Thr Gly Tyr Glu
400                 405                 410                 415 aag ttc acc gga gtt ttt gga gag gat gcc gga tcg aac cgt tgg ggc     2351
Lys Phe Thr Gly Val Phe Gly Glu Asp Ala Gly Ser Asn Arg Trp Gly
                420                 425                 430 gct gac ggc tgc tct gat cgt ggt tgc gac aac ggc acg ttg gca atg     2399
Ala Asp Gly Cys Ser Asp Arg Gly Cys Asp Asn Gly Thr Leu Ala Met
            435                 440                 445 ggt tgg ggc agt ggc act gct gac ttc ccc tac ctt gtc act ccc gag     2447
Gly Trp Gly Ser Gly Thr Ala Asp Phe Pro Tyr Leu Val Thr Pro Glu
        450                 455                 460 cag gca atc cag aat gaa atc ctt tcc aag ggg aag ggg tta              2489
Gln Ala Ile Gln Asn Glu Ile Leu Ser Lys Gly Lys Gly Leu
```

```
                465                 470                 475
gtgagtgctg tcaccgacaa tggtgccctt gaccagatgg aacaggttgc gtctcaggcc       2549
aggtattcct tcctccgtat ccctagcaat cgaatctcca ctgactttag gac agc         2605
                                                        Asp Ser gtt tct atc gtt ttc gtc aac gcc gac tct ggt gaa ggc tac atc aac       2653
Val Ser Ile Val Phe Val Asn Ala Asp Ser Gly Glu Gly Tyr Ile Asn
480                 485                 490                 495 gtt gat ggc aac gaa ggt gat cgg aag aac ctc acc ctc tgg aaa gga       2701
Val Asp Gly Asn Glu Gly Asp Arg Lys Asn Leu Thr Leu Trp Lys Gly
                500                 505                 510 ggc gag gag gtg atc aag act gtt gca gcc aac tgc aac aac acc att       2749
Gly Glu Glu Val Ile Lys Thr Val Ala Ala Asn Cys Asn Asn Thr Ile
            515                 520                 525 gtt gtg atg cac act gtg gga cct gtc ttg atc gat gag tgg tat gac       2797
Val Val Met His Thr Val Gly Pro Val Leu Ile Asp Glu Trp Tyr Asp
        530                 535                 540 aac ccc aac gtc acc gcc atc gtc tgg gcc ggt ctt cca ggc cag gag       2845
Asn Pro Asn Val Thr Ala Ile Val Trp Ala Gly Leu Pro Gly Gln Glu
    545                 550                 555 agc ggc aac agt ctc gtc gat gtg ctc tac ggc cgt gtc agc ccc gga       2893
Ser Gly Asn Ser Leu Val Asp Val Leu Tyr Gly Arg Val Ser Pro Gly
560                 565                 570                 575 gga aag acg ccg ttt acg tgg gga aag act cgc gag tcg tac ggc gct       2941
Gly Lys Thr Pro Phe Thr Trp Gly Lys Thr Arg Glu Ser Tyr Gly Ala
                580                 585                 590 cct ctg ctc acc aaa ccc aac aac ggc aag ggt gct ccc cag gac gac       2989
Pro Leu Leu Thr Lys Pro Asn Asn Gly Lys Gly Ala Pro Gln Asp Asp
            595                 600                 605 ttc acc gag ggc gtc ttc atc gac tac aga agg ttc gac aag tac aac       3037
Phe Thr Glu Gly Val Phe Ile Asp Tyr Arg Arg Phe Asp Lys Tyr Asn
        610                 615                 620 gag acg ccc atc tat gag ttc ggg ttt ggt ctg agt tat act act ttt       3085
Glu Thr Pro Ile Tyr Glu Phe Gly Phe Gly Leu Ser Tyr Thr Thr Phe
    625                 630                 635 gaa tac tcg aac atc tac gtc cag ccc ctt aac gca cga cct tac acc       3133
Glu Tyr Ser Asn Ile Tyr Val Gln Pro Leu Asn Ala Arg Pro Tyr Thr
640                 645                 650                 655 cca gcc tcc ggc agc acc aag gcg gct cct acc ttt ggg aat atc agc       3181
Pro Ala Ser Gly Ser Thr Lys Ala Ala Pro Thr Phe Gly Asn Ile Ser
                660                 665                 670 acg gac tat gca gat tac ttg tac cct gag gat ata cac aag gtc cca       3229
Thr Asp Tyr Ala Asp Tyr Leu Tyr Pro Glu Asp Ile His Lys Val Pro
            675                 680                 685 tta tac atc tat cct tgg ctt aac acg acg gac ccc gaa gaa gtc ctc       3277
Leu Tyr Ile Tyr Pro Trp Leu Asn Thr Thr Asp Pro Glu Glu Val Leu
        690                 695                 700 cgg cga tcc cga ctt acg gaa atg aag gcc gag gac tac atc cca tct       3325
Arg Arg Ser Arg Leu Thr Glu Met Lys Ala Glu Asp Tyr Ile Pro Ser
    705                 710                 715 ggc gcg act gat gga tct cct cag ccc atc ctt ccg gca ggt ggt gct       3373
Gly Ala Thr Asp Gly Ser Pro Gln Pro Ile Leu Pro Ala Gly Gly Ala
720                 725                 730                 735 cct ggt ggc aac ccg ggt ctc tat gat gag atg tac agg gta tct gca       3421
Pro Gly Gly Asn Pro Gly Leu Tyr Asp Glu Met Tyr Arg Val Ser Ala
                740                 745                 750 atc atc acc aac acc ggt aac gtt gtt ggt gat gag gtt cct cag ctg       3469
Ile Ile Thr Asn Thr Gly Asn Val Val Gly Asp Glu Val Pro Gln Leu
            755                 760                 765 gtgagtttcg cagtctcatt gatatatgtc tttcgagttg gtcactgacc cgcgatctat    3529
```

```
ag tat gtc tct ctt ggt ggt cca gat gac ccc aag gtc gtg ctc cgc     3576
   Tyr Val Ser Leu Gly Gly Pro Asp Asp Pro Lys Val Val Leu Arg
           770                 775                 780 aac ttt gac cgc atc acg ctc cac ccc ggc caa cag aca atg tgg acc     3624
Asn Phe Asp Arg Ile Thr Leu His Pro Gly Gln Gln Thr Met Trp Thr
        785                 790                 795 acg aca ttg acg cga cgc gat atc tcg aac tgg gac cct gcc tcc cag     3672
Thr Thr Leu Thr Arg Arg Asp Ile Ser Asn Trp Asp Pro Ala Ser Gln
    800                 805                 810 aat tgg gtt gtg acc aaa tat ccc aag aca gtc tac atc ggc agc tct     3720
Asn Trp Val Val Thr Lys Tyr Pro Lys Thr Val Tyr Ile Gly Ser Ser
815                 820                 825                 830 tcg cgg aaa ctg cac ctg cag gca ccg ctt ccc cct tac tgaggtttta     3769
Ser Arg Lys Leu His Leu Gln Ala Pro Leu Pro Pro Tyr
                835                 840 tccggaagga ggaagtaaaa acacaatgtt ttagttgtac aggcgtcttt cgtttgtgat    3829
tatccatagg catatcaaga ccactttggg ttatatatat atatatatat ataagcggcc    3889
gaggaaaggc aatgggtagc atggttcaag gggaggaacc gtcttgaaac tactctcaat    3949
ttctttcagt agatagtgca ctccggttga gtcccaaata tagttttaat aatggtaaat    4009
ggttcagaaa aagaaaatgt agaggtttca aacacgctag ttgaccctga taggaattga    4069
gcatgaatgc ctacacattc caagtcgtgt tagcgagtcg atagccgatg aacctattcc    4129
gtaggttgag gttcacccta caaataagcc aggatttaag taaatacctg ctcgtgaaat    4189
ctacaacgca tcagatcaga ggaaaattca aatggcagaa gtgcgagcac ctcggtgaga    4249
agagatcgag ctgtcgaagt cggctggaac acaggtaaag agaagtaata caattcattg    4309
attttacat cgtttaacat gtagaaggta tctaaaatag taagtccaga tatgggccat     4369
ggagatcgcc tcggcgatct tcgggagtat ctcgggagac gcacatgacc gcgcttaacc    4429
ctgtcggttg gacccgagtc cgaccgacgt catcagcgca gcgcaggtca ggctgcgcgc    4489
aacgtcaatg ccagggggtg ctgggacagt tgcatatcaa tcgatcagtc aattaaagca    4549
tctgctttcc acgttctttt tttatcacct ttcacttccc ctgtcccact tgccttggga    4609
ttgttgagcc caaagaagaa ggagaagaaa atgggctcga caccccggaa cgggtggtcg    4669
acgagcacat catcagcagc gtcttattat caacattccc aaccaccggc cctcgttctc    4729
ctcgtctacc cgctcactct cctcctcggc tccctgtaca gagccatttc ccccaccgcg    4789
cgggtgaggc acgatgctgc agaccctgct ctggccccga ccatagcgtc cgacatcaac    4849
ctgtcccagt catcccggta ttcccattcc catagcaaca gcaacagccc ggtcaattac    4909
ttcgcccgca aggacaacat ctttaacgtc tacttcgtca agatcggctg gttctggacg    4969
accctcgcct tcctcacgtt actcctcacc cagcctgcct acacaaacgc cggtcccctg    5029
cgcgcccgac gcaccctcca agccctgtcc cgctacgcca tcgtcaccct actacctgga    5089
tcc                                                                  5092
```

<210> SEQ ID NO 22
<211> LENGTH: 843
<212> TYPE: PRT
<213> ORGANISM: Thermoascus aurantiacus

<400> SEQUENCE: 22

```
Met Arg Leu Gly Trp Leu Glu Leu Ala Val Ala Ala Ala Ala Thr Val
1               5                   10                  15

Ala Ser Ala Lys Asp Asp Leu Ala Tyr Ser Pro Pro Phe Tyr Pro Ser
            20                  25                  30
```

```
Pro Trp Met Asn Gly Asn Gly Glu Trp Ala Glu Ala Tyr Arg Arg Ala
         35                  40                  45

Val Asp Phe Val Ser Gln Leu Thr Leu Ala Glu Lys Val Asn Leu Thr
 50                  55                  60

Thr Gly Val Gly Trp Met Gln Glu Lys Cys Val Gly Glu Thr Gly Ser
 65                  70                  75                  80

Ile Pro Arg Leu Gly Phe Arg Gly Leu Cys Leu Gln Asp Ser Pro Leu
                 85                  90                  95

Gly Val Arg Phe Ala Asp Tyr Val Ser Ala Phe Pro Ala Gly Val Asn
             100                 105                 110

Val Ala Ala Thr Trp Asp Lys Asn Leu Ala Tyr Leu Arg Gly Lys Ala
             115                 120                 125

Met Gly Glu Glu His Arg Gly Lys Gly Val Asp Val Gln Leu Gly Pro
 130                 135                 140

Val Ala Gly Pro Leu Gly Arg His Pro Asp Gly Gly Arg Asn Trp Glu
145                 150                 155                 160

Gly Phe Ser Pro Asp Pro Val Leu Thr Gly Val Leu Met Ala Glu Thr
                 165                 170                 175

Ile Lys Gly Ile Gln Asp Ala Gly Val Ile Ala Cys Ala Lys His Phe
                 180                 185                 190

Ile Gly Asn Glu Met Glu His Phe Arg Gln Ala Gly Glu Ala Val Gly
             195                 200                 205

Tyr Gly Phe Asp Ile Thr Glu Ser Val Ser Ser Asn Ile Asp Asp Lys
             210                 215                 220

Thr Leu His Glu Leu Tyr Leu Trp Pro Phe Ala Asp Ala Val Arg Ala
225                 230                 235                 240

Gly Val Gly Ser Phe Met Cys Ser Tyr Asn Gln Val Asn Asn Ser Tyr
                 245                 250                 255

Ser Cys Ser Asn Ser Tyr Leu Leu Asn Lys Leu Leu Lys Ser Glu Leu
             260                 265                 270

Asp Phe Gln Gly Phe Val Met Ser Asp Trp Gly Ala His His Ser Gly
             275                 280                 285

Val Gly Ala Ala Leu Ala Gly Leu Asp Met Ser Met Pro Gly Asp Thr
290                 295                 300

Ala Phe Gly Thr Gly Lys Ser Phe Trp Gly Thr Asn Leu Thr Ile Ala
305                 310                 315                 320

Val Leu Asn Gly Thr Val Pro Glu Trp Arg Val Asp Asp Met Ala Val
                 325                 330                 335

Arg Ile Met Ala Ala Phe Tyr Lys Val Gly Arg Asp Arg Tyr Gln Val
             340                 345                 350

Pro Val Asn Phe Asp Ser Trp Thr Lys Asp Glu Tyr Gly Tyr Glu His
             355                 360                 365

Ala Leu Val Gly Gln Asn Tyr Val Lys Val Asn Asp Lys Val Asp Val
 370                 375                 380

Arg Ala Asp His Ala Asp Ile Ile Arg Gln Ile Gly Ser Ala Ser Val
385                 390                 395                 400

Val Leu Leu Lys Asn Asp Gly Gly Leu Pro Leu Thr Gly Tyr Glu Lys
                 405                 410                 415

Phe Thr Gly Val Phe Gly Glu Asp Ala Gly Ser Asn Arg Trp Gly Ala
             420                 425                 430

Asp Gly Cys Ser Asp Arg Gly Cys Asp Asn Gly Thr Leu Ala Met Gly
             435                 440                 445

Trp Gly Ser Gly Thr Ala Asp Phe Pro Tyr Leu Val Thr Pro Glu Gln
```

```
            450              455              460
Ala Ile Gln Asn Glu Ile Leu Ser Lys Gly Lys Gly Leu Asp Ser Val
465              470              475              480

Ser Ile Val Phe Val Asn Ala Asp Ser Gly Glu Gly Tyr Ile Asn Val
                485              490              495

Asp Gly Asn Glu Gly Asp Arg Lys Asn Leu Thr Leu Trp Lys Gly Gly
            500              505              510

Glu Glu Val Ile Lys Thr Val Ala Asn Cys Asn Asn Thr Ile Val
            515              520              525

Val Met His Thr Val Gly Pro Val Leu Ile Asp Glu Trp Tyr Asp Asn
530              535              540

Pro Asn Val Thr Ala Ile Val Trp Ala Gly Leu Pro Gly Gln Glu Ser
545              550              555              560

Gly Asn Ser Leu Val Asp Val Leu Tyr Gly Arg Val Ser Pro Gly Gly
                565              570              575

Lys Thr Pro Phe Thr Trp Gly Lys Thr Arg Glu Ser Tyr Gly Ala Pro
            580              585              590

Leu Leu Thr Lys Pro Asn Asn Gly Lys Gly Ala Pro Gln Asp Asp Phe
            595              600              605

Thr Glu Gly Val Phe Ile Asp Tyr Arg Arg Phe Asp Lys Tyr Asn Glu
610              615              620

Thr Pro Ile Tyr Glu Phe Gly Phe Gly Leu Ser Tyr Thr Thr Phe Glu
625              630              635              640

Tyr Ser Asn Ile Tyr Val Gln Pro Leu Asn Ala Arg Pro Tyr Thr Pro
                645              650              655

Ala Ser Gly Ser Thr Lys Ala Ala Pro Thr Phe Gly Asn Ile Ser Thr
            660              665              670

Asp Tyr Ala Asp Tyr Leu Tyr Pro Glu Asp Ile His Lys Val Pro Leu
            675              680              685

Tyr Ile Tyr Pro Trp Leu Asn Thr Thr Asp Pro Glu Glu Val Leu Arg
690              695              700

Arg Ser Arg Leu Thr Glu Met Lys Ala Glu Asp Tyr Ile Pro Ser Gly
705              710              715              720

Ala Thr Asp Gly Ser Pro Gln Pro Ile Leu Pro Ala Gly Gly Ala Pro
                725              730              735

Gly Gly Asn Pro Gly Leu Tyr Asp Glu Met Tyr Arg Val Ser Ala Ile
            740              745              750

Ile Thr Asn Thr Gly Asn Val Val Gly Asp Glu Val Pro Gln Leu Tyr
            755              760              765

Val Ser Leu Gly Gly Pro Asp Asp Pro Lys Val Val Leu Arg Asn Phe
770              775              780

Asp Arg Ile Thr Leu His Pro Gly Gln Gln Thr Met Trp Thr Thr Thr
785              790              795              800

Leu Thr Arg Arg Asp Ile Ser Asn Trp Asp Pro Ala Ser Gln Asn Trp
                805              810              815

Val Val Thr Lys Tyr Pro Lys Thr Val Tyr Ile Gly Ser Ser Ser Arg
            820              825              830

Lys Leu His Leu Gln Ala Pro Leu Pro Pro Tyr
            835              840

<210> SEQ ID NO 23
<211> LENGTH: 3510
<212> TYPE: DNA
<213> ORGANISM: Acremonium thermophilum
<220> FEATURE:
```

-continued

```
<221> NAME/KEY: CDS
<222> LOCATION: (391)..(447)
<220> FEATURE:
<221> NAME/KEY: Intron
<222> LOCATION: (448)..(539)
<220> FEATURE:
<221> NAME/KEY: CDS
<222> LOCATION: (540)..(685)
<220> FEATURE:
<221> NAME/KEY: Intron
<222> LOCATION: (686)..(759)
<220> FEATURE:
<221> NAME/KEY: CDS
<222> LOCATION: (760)..(1148)
<220> FEATURE:
<221> NAME/KEY: Intron
<222> LOCATION: (1149)..(1217)
<220> FEATURE:
<221> NAME/KEY: CDS
<222> LOCATION: (1218)..(3208)

<400> SEQUENCE: 23
gcaggtagct acgacattcg acggtccacg cccagtggcg tctgctcggc cgtctgggaa     60
ccatgcacgc ccgcctctta ggtcgagcga ggtataacat actatctgca cggctaccta    120
tatattacgt cgatgtcacc cgcaggatgc gagcaccatt acttcgtgtc tcacccgccc    180
ttccgctccg catctcgtga acctaaaccc acgcgggcac actgcttctt gtgagagcct    240
ctacccgttc cacaagagcc atagctagag agagaagggc agccaaggga ccggtcaagc    300
ggcgctcttc atcgcaccaa tctcgacaac ccggcagacg tcaccaccgg ctcccgccgc    360
acgacgtcac acgggactga ctacgaagac atg agg cag gcc ctt gtt tcg ctg     414
                                  Met Arg Gln Ala Leu Val Ser Leu
                                   1               5 gcc ttg ctg gcc agc agc cct gtt tcg gcg gcg gtgaccgcca gggacgccca    467
Ala Leu Leu Ala Ser Ser Pro Val Ser Ala Ala
        10                  15 ggtatggtcc caactgctct tcctccccgt ttcctcctct accggtgctg acaacgacaa    527
tagctgcacc ag cga gaa ctc gcc act tcc gac cct ttc tat cct tcg cca    578
              Arg Glu Leu Ala Thr Ser Asp Pro Phe Tyr Pro Ser Pro
               20                  25                  30 tgg atg aac cct gaa gcc aat ggc tgg gag gac gcc tac gcc aag gcc     626
Trp Met Asn Pro Glu Ala Asn Gly Trp Glu Asp Ala Tyr Ala Lys Ala
         35                  40                  45 aag gcg ttc gtt tcc cag ctg acg ctc ttg gaa aag gtc aac ctg acg     674
Lys Ala Phe Val Ser Gln Leu Thr Leu Leu Glu Lys Val Asn Leu Thr
     50                  55                  60 act ggc atc gg gtgagtcttg ttctctcctg tagaaccgcc taccagaaga           725
Thr Gly Ile Gly
65 cattcaggaa gtgctaatga tgggcggttg acag c tgg caa gga gga caa tgc     778
                                       Trp Gln Gly Gly Gln Cys
                                                70 gtg ggc aac gtc ggt tcc gtc ccg cgt ctc ggc ctt cgc agc ctg tgc     826
Val Gly Asn Val Gly Ser Val Pro Arg Leu Gly Leu Arg Ser Leu Cys
 75                  80                  85                  90 atg cag gac tcc ccc gtg ggt atc cgc ttt ggg gac tac gtc tcc gtc     874
Met Gln Asp Ser Pro Val Gly Ile Arg Phe Gly Asp Tyr Val Ser Val
                 95                 100                 105 ttc ccc tct ggt cag acc acg gct gcc acc ttc gac aag ggt ctg atg     922
Phe Pro Ser Gly Gln Thr Thr Ala Ala Thr Phe Asp Lys Gly Leu Met
            110                 115                 120 aac cgt cgc ggc aat gcc atg ggc cag gag cac aaa gga aag ggt gtc     970
Asn Arg Arg Gly Asn Ala Met Gly Gln Glu His Lys Gly Lys Gly Val
        125                 130                 135
```

```
aac gtc ctg ctc ggc ccg gtc gct ggc ccc att ggc cgt acg ccc gag    1018
Asn Val Leu Leu Gly Pro Val Ala Gly Pro Ile Gly Arg Thr Pro Glu
    140             145             150 ggg gga cga aac tgg gag ggc ttc tcc ccc gac ccc gtc cta acg ggt    1066
Gly Gly Arg Asn Trp Glu Gly Phe Ser Pro Asp Pro Val Leu Thr Gly
155             160             165                 170 att gcc ttg gcc gaa acg atc aag gga atc cag gat gct ggt gtc att    1114
Ile Ala Leu Ala Glu Thr Ile Lys Gly Ile Gln Asp Ala Gly Val Ile
                175             180             185 gct tgc gcc aag cat ttc atc gcg aac gaa cag g gtgcgtgatg           1158
Ala Cys Ala Lys His Phe Ile Ala Asn Glu Gln
            190             195 gaacgcggga cgtgctctga tgcaaaccca cgagcactga ccacgctttc ctcgaacag   1217 aa  cac ttc cgc cag tcc ggc gag gcc cag ggc tac ggc ttt gac atc    1264
Glu His Phe Arg Gln Ser Gly Glu Ala Gln Gly Tyr Gly Phe Asp Ile
            200             205             210 tcc gag tcg ctg tcg tcc aac atc gac gac aag acc atg cac gag ctg    1312
Ser Glu Ser Leu Ser Ser Asn Ile Asp Asp Lys Thr Met His Glu Leu
    215             220             225 tat ctg tgg ccc ttc gcc gac ggc gtg cgt gcc ggc gtc ggc gcc atc    1360
Tyr Leu Trp Pro Phe Ala Asp Gly Val Arg Ala Gly Val Gly Ala Ile
230             235             240             245 atg tgc tcg tac aac cag atc aac aac tcg tac ggg tgc cag aac tcc    1408
Met Cys Ser Tyr Asn Gln Ile Asn Asn Ser Tyr Gly Cys Gln Asn Ser
            250             255             260 aag acc ctg aac aac ctg ctc aag aac gag ctc ggc ttc cag ggc ttc    1456
Lys Thr Leu Asn Asn Leu Leu Lys Asn Glu Leu Gly Phe Gln Gly Phe
    265             270             275 gtc atg agc gac tgg cag gcc cag cac acc ggc gcg gcc agc gcc gtc    1504
Val Met Ser Asp Trp Gln Ala Gln His Thr Gly Ala Ala Ser Ala Val
            280             285             290 gcc ggc ctg gac atg acc atg ccc ggc gac acc agc ttc aac acc ggc    1552
Ala Gly Leu Asp Met Thr Met Pro Gly Asp Thr Ser Phe Asn Thr Gly
    295             300             305 ctc agc tac tgg ggc acg aac ctc acc ctc gcc gtc ctg aac ggc acc    1600
Leu Ser Tyr Trp Gly Thr Asn Leu Thr Leu Ala Val Leu Asn Gly Thr
310             315             320             325 gtc ccc gag tac cgc atc gac gac atg gtc atg cgc atc atg gcc gcc    1648
Val Pro Glu Tyr Arg Ile Asp Asp Met Val Met Arg Ile Met Ala Ala
            330             335             340 ttc ttc aag acc ggc cag acc ctg gac ctg ccg ccc atc aac ttc gac    1696
Phe Phe Lys Thr Gly Gln Thr Leu Asp Leu Pro Pro Ile Asn Phe Asp
    345             350             355 tcg tgg acc acc gac acc ttc ggc ccg ctc cac ttc gcc gtc aac gag    1744
Ser Trp Thr Thr Asp Thr Phe Gly Pro Leu His Phe Ala Val Asn Glu
            360             365             370 gac cgc cag cag atc aac tgg cac gtc aac gtc cag gac aac cat ggc    1792
Asp Arg Gln Gln Ile Asn Trp His Val Asn Val Gln Asp Asn His Gly
    375             380             385 agc ctc atc cgc gag atc gcg gcc aag gga acc gtc ctg ctg aag aac    1840
Ser Leu Ile Arg Glu Ile Ala Ala Lys Gly Thr Val Leu Leu Lys Asn
390             395             400             405 acc ggg tcc ctc ccg ctc aac aag ccc aag ttc ctc gtc gtg gtc ggc    1888
Thr Gly Ser Leu Pro Leu Asn Lys Pro Lys Phe Leu Val Val Gly
            410             415             420 gac gac gcg ggc ccc aac ccg gcg gga ccc aac gcc tgc ccc gac cgc    1936
Asp Asp Ala Gly Pro Asn Pro Ala Gly Pro Asn Ala Cys Pro Asp Arg
    425             430             435 gga tgc gac gtc ggc acc ctc ggc atg gcc tgg ggc tcc ggc tcg gcc    1984
```

|     |     |     |     |     |     |     |     |     |     |     |     |      |
| --- | --- | --- | --- | --- | --- | --- | --- | --- | --- | --- | --- | ---  |
| Gly | Cys | Asp | Val | Gly | Thr | Leu | Gly | Met | Ala | Trp | Gly | Ser  | Gly | Ser | Ala |
|     |     | 440 |     |     |     | 445 |     |     |     |     | 450 |      |

```
aac ttc ccc tac ctg atc acc ccg gac gcc gcg ctg cag gcg cag gcg      2032
Asn Phe Pro Tyr Leu Ile Thr Pro Asp Ala Ala Leu Gln Ala Gln Ala
        455                 460                 465 atc aag gac ggc acc cgc tac gag agc gtg ctg tcc aac tac cag ctc      2080
Ile Lys Asp Gly Thr Arg Tyr Glu Ser Val Leu Ser Asn Tyr Gln Leu
470                 475                 480                 485 gac cag acc aag gcg ctg gtc acc cag gcc aac gcc acg gcc atc gtc      2128
Asp Gln Thr Lys Ala Leu Val Thr Gln Ala Asn Ala Thr Ala Ile Val
                490                 495                 500 ttc gtc aac gcc gac tcg ggc gag ggc tac atc aac gtc gac ggc aac      2176
Phe Val Asn Ala Asp Ser Gly Glu Gly Tyr Ile Asn Val Asp Gly Asn
            505                 510                 515 gag ggc gac cgc aag aac ctc acg ctc tgg cac gac ggc gac gcc ctg      2224
Glu Gly Asp Arg Lys Asn Leu Thr Leu Trp His Asp Gly Asp Ala Leu
        520                 525                 530 atc aag agc gtg gcc ggc tgg aac ccg aac acc atc gtc gtc atc cac      2272
Ile Lys Ser Val Ala Gly Trp Asn Pro Asn Thr Ile Val Val Ile His
535                 540                 545 tcg acc ggc ccc gtc ctc gtg acc gac tgg tac gac cac ccc aac atc      2320
Ser Thr Gly Pro Val Leu Val Thr Asp Trp Tyr Asp His Pro Asn Ile
550                 555                 560                 565 acc gcc atc ctg tgg gcc ggc gtg ccc ggg cag gag tcc ggc aac gcc      2368
Thr Ala Ile Leu Trp Ala Gly Val Pro Gly Gln Glu Ser Gly Asn Ala
                570                 575                 580 atc acc gac gtc ctc tac gga aaa gtc aac ccg tcg ggc cgc agc ccc      2416
Ile Thr Asp Val Leu Tyr Gly Lys Val Asn Pro Ser Gly Arg Ser Pro
            585                 590                 595 ttc acc tgg ggt ccg acc cgc gag agc tac ggc acc gac gtc ctc tac      2464
Phe Thr Trp Gly Pro Thr Arg Glu Ser Tyr Gly Thr Asp Val Leu Tyr
        600                 605                 610 act ccc aac aac ggc aag ggc gcg ccg cag cag gcc ttc tcc gag ggc      2512
Thr Pro Asn Asn Gly Lys Gly Ala Pro Gln Gln Ala Phe Ser Glu Gly
    615                 620                 625 gtc ttc atc gac tac cgc cac ttc gac cgc acc aac gcg tcc gtc atc      2560
Val Phe Ile Asp Tyr Arg His Phe Asp Arg Thr Asn Ala Ser Val Ile
630                 635                 640                 645 tac gag ttc ggc cac ggc ctc agc tac acg acg ttc cag tac agc aac      2608
Tyr Glu Phe Gly His Gly Leu Ser Tyr Thr Thr Phe Gln Tyr Ser Asn
                650                 655                 660 atc cag gtg gtc aag tcc aac gcc ggc gcg tac aag ccc acg acg ggc      2656
Ile Gln Val Val Lys Ser Asn Ala Gly Ala Tyr Lys Pro Thr Thr Gly
            665                 670                 675 acg acc atc ccc gcg ccc acg ttt ggc agc ttc tcc aag gac ctc aag      2704
Thr Thr Ile Pro Ala Pro Thr Phe Gly Ser Phe Ser Lys Asp Leu Lys
        680                 685                 690 gac tac ctc ttc ccg tcg gac cag ttc cgc tac atc acc cag tac atc      2752
Asp Tyr Leu Phe Pro Ser Asp Gln Phe Arg Tyr Ile Thr Gln Tyr Ile
    695                 700                 705 tac ccg tac ctc aac tcc acc gac ccg gcc aag gcg tcg ctc gac ccg      2800
Tyr Pro Tyr Leu Asn Ser Thr Asp Pro Ala Lys Ala Ser Leu Asp Pro
710                 715                 720                 725 cac tac ggc aag acg gcg gcc gag ttt ctg ccg ccg cac gcg ctg gac      2848
His Tyr Gly Lys Thr Ala Ala Glu Phe Leu Pro Pro His Ala Leu Asp
                730                 735                 740 agc aac ccg cag ccg ctg ctg cgg tcg tcg ggc aag aac gag ccc ggc      2896
Ser Asn Pro Gln Pro Leu Leu Arg Ser Ser Gly Lys Asn Glu Pro Gly
            745                 750                 755 ggc aac cgc cag ctg tac gac atc ctg tac acg gtg acg gcg gac atc      2944
Gly Asn Arg Gln Leu Tyr Asp Ile Leu Tyr Thr Val Thr Ala Asp Ile
```

```
Gly Asn Arg Gln Leu Tyr Asp Ile Leu Tyr Thr Val Thr Ala Asp Ile
            760                 765                 770 acc aac acg ggc agc atc gtg ggt gcg gag gtg ccg cag ctg tac gtg      2992
Thr Asn Thr Gly Ser Ile Val Gly Ala Glu Val Pro Gln Leu Tyr Val
775                 780                 785 tcg ctg ggc ggg ccc gac gac ccc aaa gtg gtc ctg cgc ggg ttc gac      3040
Ser Leu Gly Gly Pro Asp Asp Pro Lys Val Val Leu Arg Gly Phe Asp
790                 795                 800                 805 cgc atc cgc atc gac ccg ggc aag acg gcg cag ttc cgc gtc acc ctg      3088
Arg Ile Arg Ile Asp Pro Gly Lys Thr Ala Gln Phe Arg Val Thr Leu
                810                 815                 820 acc cgc cgg gat ctc agc aac tgg gac ccg gcg atc cag gac tgg gtc      3136
Thr Arg Arg Asp Leu Ser Asn Trp Asp Pro Ala Ile Gln Asp Trp Val
                825                 830                 835 atc agc aag tac ccc aag aag gtg tac atc ggc cgg agc agc agg aag      3184
Ile Ser Lys Tyr Pro Lys Lys Val Tyr Ile Gly Arg Ser Ser Arg Lys
                840                 845                 850 ctg gaa ctc tcc gcc gac ctc gcg tgatccggcg acggccaagt acgtatgtgg     3238
Leu Glu Leu Ser Ala Asp Leu Ala
855                 860 actgccatcc gaacacctat acttttggc taggtagggg gagcagcaag gcctgagcat     3298
atactctctc cattgcacat ttctaatgta aatatatata tcattaattg ggagacccaa    3358
actcgaattt atgcatgcgt acaaagtgtg ttgaacaagt ttcggtccag cagatagtaa    3418
ccgtcttagt tcgtccatcc ctctctcgaa tgcgctgtat acacatgcgt atatagacgt    3478
tgtataggtg ccattgctag caatgcaagc tt                                  3510

<210> SEQ ID NO 24
<211> LENGTH: 861
<212> TYPE: PRT
<213> ORGANISM: Acremonium thermophilum

<400> SEQUENCE: 24

Met Arg Gln Ala Leu Val Ser Leu Ala Leu Leu Ala Ser Ser Pro Val
1               5                   10                  15

Ser Ala Ala Arg Glu Leu Ala Thr Ser Asp Pro Phe Tyr Pro Ser Pro
                20                  25                  30

Trp Met Asn Pro Glu Ala Asn Gly Trp Glu Asp Ala Tyr Ala Lys Ala
            35                  40                  45

Lys Ala Phe Val Ser Gln Leu Thr Leu Leu Glu Lys Val Asn Leu Thr
        50                  55                  60

Thr Gly Ile Gly Trp Gln Gly Gly Gln Cys Gly Asn Val Gly Ser
65                  70                  75                  80

Val Pro Arg Leu Gly Leu Arg Ser Leu Cys Met Gln Asp Ser Pro Val
                85                  90                  95

Gly Ile Arg Phe Gly Asp Tyr Val Ser Val Phe Pro Ser Gly Gln Thr
            100                 105                 110

Thr Ala Ala Thr Phe Asp Lys Gly Leu Met Asn Arg Arg Gly Asn Ala
        115                 120                 125

Met Gly Gln Glu His Lys Gly Lys Gly Val Asn Val Leu Leu Gly Pro
    130                 135                 140

Val Ala Gly Pro Ile Gly Arg Thr Pro Glu Gly Gly Arg Asn Trp Glu
145                 150                 155                 160

Gly Phe Ser Pro Asp Pro Val Leu Thr Gly Ile Ala Leu Ala Glu Thr
                165                 170                 175

Ile Lys Gly Ile Gln Asp Ala Gly Val Ile Ala Cys Ala Lys His Phe
            180                 185                 190
```

-continued

Ile Ala Asn Glu Gln Glu His Phe Arg Gln Ser Gly Glu Ala Gln Gly
              195                 200                 205

Tyr Gly Phe Asp Ile Ser Glu Ser Leu Ser Ser Asn Ile Asp Asp Lys
          210                 215                 220

Thr Met His Glu Leu Tyr Leu Trp Pro Phe Ala Asp Gly Val Arg Ala
225                 230                 235                 240

Gly Val Gly Ala Ile Met Cys Ser Tyr Asn Gln Ile Asn Asn Ser Tyr
                  245                 250                 255

Gly Cys Gln Asn Ser Lys Thr Leu Asn Asn Leu Leu Lys Asn Glu Leu
              260                 265                 270

Gly Phe Gln Gly Phe Val Met Ser Asp Trp Gln Ala Gln His Thr Gly
          275                 280                 285

Ala Ala Ser Ala Val Ala Gly Leu Asp Met Thr Met Pro Gly Asp Thr
      290                 295                 300

Ser Phe Asn Thr Gly Leu Ser Tyr Trp Gly Thr Asn Leu Thr Leu Ala
305                 310                 315                 320

Val Leu Asn Gly Thr Val Pro Glu Tyr Arg Ile Asp Asp Met Val Met
                  325                 330                 335

Arg Ile Met Ala Ala Phe Phe Lys Thr Gly Gln Thr Leu Asp Leu Pro
              340                 345                 350

Pro Ile Asn Phe Asp Ser Trp Thr Thr Asp Thr Phe Gly Pro Leu His
          355                 360                 365

Phe Ala Val Asn Glu Asp Arg Gln Gln Ile Asn Trp His Val Asn Val
      370                 375                 380

Gln Asp Asn His Gly Ser Leu Ile Arg Glu Ile Ala Ala Lys Gly Thr
385                 390                 395                 400

Val Leu Leu Lys Asn Thr Gly Ser Leu Pro Leu Asn Lys Pro Lys Phe
                  405                 410                 415

Leu Val Val Val Gly Asp Asp Ala Gly Pro Asn Pro Ala Gly Pro Asn
              420                 425                 430

Ala Cys Pro Asp Arg Gly Cys Asp Val Gly Thr Leu Gly Met Ala Trp
          435                 440                 445

Gly Ser Gly Ser Ala Asn Phe Pro Tyr Leu Ile Thr Pro Asp Ala Ala
      450                 455                 460

Leu Gln Ala Gln Ala Ile Lys Asp Gly Thr Arg Tyr Glu Ser Val Leu
465                 470                 475                 480

Ser Asn Tyr Gln Leu Asp Gln Thr Lys Ala Leu Val Thr Gln Ala Asn
                  485                 490                 495

Ala Thr Ala Ile Val Phe Val Asn Ala Asp Ser Gly Glu Gly Tyr Ile
              500                 505                 510

Asn Val Asp Gly Asn Glu Gly Asp Arg Lys Asn Leu Thr Leu Trp His
          515                 520                 525

Asp Gly Asp Ala Leu Ile Lys Ser Val Ala Gly Trp Asn Pro Asn Thr
      530                 535                 540

Ile Val Val Ile His Ser Thr Gly Pro Val Leu Val Thr Asp Trp Tyr
545                 550                 555                 560

Asp His Pro Asn Ile Thr Ala Ile Leu Trp Ala Gly Val Pro Gly Gln
                  565                 570                 575

Glu Ser Gly Asn Ala Ile Thr Asp Val Leu Tyr Gly Lys Val Asn Pro
              580                 585                 590

Ser Gly Arg Ser Pro Phe Thr Trp Gly Pro Thr Arg Glu Ser Tyr Gly
          595                 600                 605

Thr Asp Val Leu Tyr Thr Pro Asn Asn Gly Lys Gly Ala Pro Gln Gln

-continued

```
            610                 615                 620
Ala Phe Ser Glu Gly Val Phe Ile Asp Tyr Arg His Phe Asp Arg Thr
625                 630                 635                 640

Asn Ala Ser Val Ile Tyr Glu Phe Gly His Gly Leu Ser Tyr Thr Thr
                    645                 650                 655

Phe Gln Tyr Ser Asn Ile Gln Val Val Lys Ser Asn Ala Gly Ala Tyr
                660                 665                 670

Lys Pro Thr Thr Gly Thr Thr Ile Pro Ala Pro Thr Phe Gly Ser Phe
                675                 680                 685

Ser Lys Asp Leu Lys Asp Tyr Leu Phe Pro Ser Asp Gln Phe Arg Tyr
690                 695                 700

Ile Thr Gln Tyr Ile Tyr Pro Tyr Leu Asn Ser Thr Asp Pro Ala Lys
705                 710                 715                 720

Ala Ser Leu Asp Pro His Tyr Gly Lys Thr Ala Ala Glu Phe Leu Pro
                    725                 730                 735

Pro His Ala Leu Asp Ser Asn Pro Gln Pro Leu Leu Arg Ser Ser Gly
                740                 745                 750

Lys Asn Glu Pro Gly Gly Asn Arg Gln Leu Tyr Asp Ile Leu Tyr Thr
                755                 760                 765

Val Thr Ala Asp Ile Thr Asn Thr Gly Ser Ile Val Gly Ala Glu Val
770                 775                 780

Pro Gln Leu Tyr Val Ser Leu Gly Gly Pro Asp Asp Pro Lys Val Val
785                 790                 795                 800

Leu Arg Gly Phe Asp Arg Ile Arg Ile Asp Pro Gly Lys Thr Ala Gln
                805                 810                 815

Phe Arg Val Thr Leu Thr Arg Arg Asp Leu Ser Asn Trp Asp Pro Ala
                820                 825                 830

Ile Gln Asp Trp Val Ile Ser Lys Tyr Pro Lys Lys Val Tyr Ile Gly
                835                 840                 845

Arg Ser Ser Arg Lys Leu Glu Leu Ser Ala Asp Leu Ala
                850                 855                 860

<210> SEQ ID NO 25
<211> LENGTH: 3392
<212> TYPE: DNA
<213> ORGANISM: Chaetomium thermophilum
<220> FEATURE:
<221> NAME/KEY: CDS
<222> LOCATION: (608)..(2405)
<220> FEATURE:
<221> NAME/KEY: Intron
<222> LOCATION: (2406)..(2457)
<220> FEATURE:
<221> NAME/KEY: CDS
<222> LOCATION: (2458)..(2861)

<400> SEQUENCE: 25
tgcggggttg ctgcgactta attaataact ggcaaaacgg cccggagctc agctctgacc      60
tccgccacat ccgctcggca ccatgccagc gcgttgcaac ggcatgaagc gctcaggttt     120
ttcttccgcc tgctccccac tgccgatggc catctgcacc ccagctcgtc acatttatct     180
cgcgcacagc gtcttcccac cagttgcctt gctcatgacg ctgttaaaga tggccctacc     240
tagccgctga gtcccacaac gccgagatgt ctttggccct ttacaaggca cgccatggcc     300
gtccaaggtc tgttcatgag tgtgtttgtg gggccgaagg acacctcagt ggccacgaaa     360
tgccgccgag cgggccagca catgtcgaga gagacatgga catttatccc cgagatgctg     420
tattagggaa ccggtccttt tctcggagcc gtgatccgag agcgttcggg agtcgttgag     480
```

```
                                                    -continued taaaagatgt cgagttgccg ttatatatcg cgggcctgta gctatgtgcc ctctattctc        540
acaggttcaa tcatcagtcc tcgccgtgag acgtagcgcg ctgaactagc gctcgatatc        600 ttccgtc atg gct ctt cat gcc ttc ttg ttg ctg gca tca gca ttg ctg          649
        Met Ala Leu His Ala Phe Leu Leu Leu Ala Ser Ala Leu Leu
        1               5                   10 gcc cgg ggt gcc ctg agc caa cct gac aac gtc cgt cgc gct gct ccg          697
Ala Arg Gly Ala Leu Ser Gln Pro Asp Asn Val Arg Arg Ala Ala Pro
15                  20                  25                  30 acc ggg acg gcc gcc tgg gat gcc gcc cac tcg cag gct gcc gct gcc          745
Thr Gly Thr Ala Ala Trp Asp Ala Ala His Ser Gln Ala Ala Ala Ala
                35                  40                  45 gtg tcg aga tta tca cag caa gac aag atc aac att gtc acc ggc gtt          793
Val Ser Arg Leu Ser Gln Gln Asp Lys Ile Asn Ile Val Thr Gly Val
            50                  55                  60 ggc tgg ggt aag ggt cct tgc gtc ggc aat acg aac cct gtc tac agc          841
Gly Trp Gly Lys Gly Pro Cys Val Gly Asn Thr Asn Pro Val Tyr Ser
65                  70                  75 atc aac tac cca cag ctc tgc ctg cag gat ggc cca ctg ggt atc cgc          889
Ile Asn Tyr Pro Gln Leu Cys Leu Gln Asp Gly Pro Leu Gly Ile Arg
        80                  85                  90 tcc gcc acc agc gtc acg gcc ttc acg ccg ggc att caa gcc gcg tcg          937
Ser Ala Thr Ser Val Thr Ala Phe Thr Pro Gly Ile Gln Ala Ala Ser
95                  100                 105                 110 acc tgg gat gtg gag ttg atc cgg cag cgt ggt gtc tac cta gga cag          985
Thr Trp Asp Val Glu Leu Ile Arg Gln Arg Gly Val Tyr Leu Gly Gln
                115                 120                 125 gag gcc cgg gga act ggc gtg cat gtc ctg ctc ggc ccc gtg gcc ggt         1033
Glu Ala Arg Gly Thr Gly Val His Val Leu Leu Gly Pro Val Ala Gly
            130                 135                 140 gct ctt ggc aag atc ccg cac gga ggc cgt aac tgg gaa gcc ttc ggc         1081
Ala Leu Gly Lys Ile Pro His Gly Gly Arg Asn Trp Glu Ala Phe Gly
        145                 150                 155 tcc gac ccc tac ttg gcc ggt atc gct atg tcc gag acc atc gag ggc         1129
Ser Asp Pro Tyr Leu Ala Gly Ile Ala Met Ser Glu Thr Ile Glu Gly
160                 165                 170 att cag tcg gag ggt gtg cag gct tgc gcg aag cac tac atc gcc aat         1177
Ile Gln Ser Glu Gly Val Gln Ala Cys Ala Lys His Tyr Ile Ala Asn
175                 180                 185                 190 gag cag gaa ctc aac cgc gag aca atg agc agc aac gtc gac gac cgc         1225
Glu Gln Glu Leu Asn Arg Glu Thr Met Ser Ser Asn Val Asp Asp Arg
                195                 200                 205 act atg cac gag cta tac ctc tgg ccg ttc gcc gac gcc gtg cat tcc         1273
Thr Met His Glu Leu Tyr Leu Trp Pro Phe Ala Asp Ala Val His Ser
            210                 215                 220 aac gtg gcc agc gtc atg tgc agc tac aac aag ctc aac ggc acc tgg         1321
Asn Val Ala Ser Val Met Cys Ser Tyr Asn Lys Leu Asn Gly Thr Trp
        225                 230                 235 ctc tgc gag aac gat agg gcc caa aac cag ctg ctt aag agg gag ctc         1369
Leu Cys Glu Asn Asp Arg Ala Gln Asn Gln Leu Leu Lys Arg Glu Leu
240                 245                 250 ggc ttc cgc ggc tac atc gtg agc gac tgg aac gcg cag cac acc acc         1417
Gly Phe Arg Gly Tyr Ile Val Ser Asp Trp Asn Ala Gln His Thr Thr
255                 260                 265                 270 gtg ggc tcg gcc aac agt ggc atg gac atg acc atg cct ggc agc gac         1465
Val Gly Ser Ala Asn Ser Gly Met Asp Met Thr Met Pro Gly Ser Asp
                275                 280                 285 ttc aac ggc tgg aac gtc ctc tgg ggt ccg cag ctc aac aac gcc gtc         1513
Phe Asn Gly Trp Asn Val Leu Trp Gly Pro Gln Leu Asn Asn Ala Val
            290                 295                 300
```

-continued

```
aac agc ggc cag gtc tcg cag tcc cgc ctc aac gac atg gtc cag cgc    1561
Asn Ser Gly Gln Val Ser Gln Ser Arg Leu Asn Asp Met Val Gln Arg
        305                 310                 315 att ctt gct gcg tgg tac ctc ctc ggc cag aac tcc gga tac ccg tcc    1609
Ile Leu Ala Ala Trp Tyr Leu Leu Gly Gln Asn Ser Gly Tyr Pro Ser
320                 325                 330 atc aac ctg cgt gcc aac gtc caa gcc aac cac aag gag aat gtg cgt    1657
Ile Asn Leu Arg Ala Asn Val Gln Ala Asn His Lys Glu Asn Val Arg
335                 340                 345                 350 gcc gta gcc cgc gat ggc atc gtc ctc ctc aag aac gac ggc att ctg    1705
Ala Val Ala Arg Asp Gly Ile Val Leu Leu Lys Asn Asp Gly Ile Leu
                355                 360                 365 cct ctt cag cgt ccc aat aag att gct ctt gtc ggc tcc gcc gca gtc    1753
Pro Leu Gln Arg Pro Asn Lys Ile Ala Leu Val Gly Ser Ala Ala Val
        370                 375                 380 gtc aac ccc cgt ggt atg aac gcc tgc gtg gac cgt ggc tgc aac gag    1801
Val Asn Pro Arg Gly Met Asn Ala Cys Val Asp Arg Gly Cys Asn Glu
385                 390                 395 ggt gcc ctt ggc atg ggc tgg ggc tca ggc acg gtc gag tat ccc tac    1849
Gly Ala Leu Gly Met Gly Trp Gly Ser Gly Thr Val Glu Tyr Pro Tyr
400                 405                 410 ttt gtt gcg ccg tat gat gct ctg cgt gag cgg gca cag cgc gat ggc    1897
Phe Val Ala Pro Tyr Asp Ala Leu Arg Glu Arg Ala Gln Arg Asp Gly
415                 420                 425                 430 acg cag atc agt ctg cat gca tcg gac aat aca aac ggg gtt aac aac    1945
Thr Gln Ile Ser Leu His Ala Ser Asp Asn Thr Asn Gly Val Asn Asn
                435                 440                 445 gcc gtg cag ggc gct gac gcg gcg ttt gtg ttc atc act gct gac tcc    1993
Ala Val Gln Gly Ala Asp Ala Ala Phe Val Phe Ile Thr Ala Asp Ser
        450                 455                 460 ggc gaa ggg tac att acc gtt gag ggc cat gct ggc gac cgg aat cat    2041
Gly Glu Gly Tyr Ile Thr Val Glu Gly His Ala Gly Asp Arg Asn His
465                 470                 475 ctg gat cct tgg cat aat ggt aac cag ctt gtg cag gct gtt gcg cag    2089
Leu Asp Pro Trp His Asn Gly Asn Gln Leu Val Gln Ala Val Ala Gln
480                 485                 490 gca aat aag aac gtc att gtg gtt gtg cac agc gtt ggg ccg gtt att    2137
Ala Asn Lys Asn Val Ile Val Val Val His Ser Val Gly Pro Val Ile
495                 500                 505                 510 ctg gag acg atc ctc aat acg ccc ggt gtg agg gct gtt gtt tgg gct    2185
Leu Glu Thr Ile Leu Asn Thr Pro Gly Val Arg Ala Val Val Trp Ala
                515                 520                 525 ggc ttg ccg agc cag gag agc ggt aac gcg ctg gtt gat gtg ctg tac    2233
Gly Leu Pro Ser Gln Glu Ser Gly Asn Ala Leu Val Asp Val Leu Tyr
        530                 535                 540 ggc ctt gtt tcg ccg tcg ggc aag ctt gtc tac acc att gcg aag agc    2281
Gly Leu Val Ser Pro Ser Gly Lys Leu Val Tyr Thr Ile Ala Lys Ser
545                 550                 555 ccg agc gac tac ccg act agc att gtc cgt ggc gat gat aac ttc cgc    2329
Pro Ser Asp Tyr Pro Thr Ser Ile Val Arg Gly Asp Asp Asn Phe Arg
560                 565                 570 gag ggt ctg ttc atc gac tac agg cac ttc gat aac gcc cgg atc gag    2377
Glu Gly Leu Phe Ile Asp Tyr Arg His Phe Asp Asn Ala Arg Ile Glu
575                 580                 585                 590 ccc cgt ttc gag ttt ggc ttc ggt ctc t gtaagtctct taccactccg        2425
Pro Arg Phe Glu Phe Gly Phe Gly Leu
                595 ttttgtaaca acccgattct aacatccccc ag ca  tac acc aac ttc agc tat    2477
                                      Ser Tyr Thr Asn Phe Ser Tyr
                                      600                 605
```

```
tcc aac ctg ggc atc tcc tcg tcc gca acc gcc ggc cca gcc acg ggc    2525
Ser Asn Leu Gly Ile Ser Ser Ser Ala Thr Ala Gly Pro Ala Thr Gly
            610                 615                 620 ccc acc gtc ccc ggc ccg gcc gac ctc tgg aac tat gtc gcg acc        2573
Pro Thr Val Pro Gly Gly Pro Ala Asp Leu Trp Asn Tyr Val Ala Thr
            625                 630                 635 gtc acg gcg acc gtt acc aac acc ggc ggc gtg gaa ggt gcc gag gtc    2621
Val Thr Ala Thr Val Thr Asn Thr Gly Gly Val Glu Gly Ala Glu Val
    640                 645                 650 gct cag ctg tac atc tct ttg cca tct tcg gct cct gca tcg cca ccg    2669
Ala Gln Leu Tyr Ile Ser Leu Pro Ser Ser Ala Pro Ala Ser Pro Pro
655                 660                 665                 670 aag cag ctt cgt ggc ttt gtc aag ctt aag ttg gcg cct ggt caa agc    2717
Lys Gln Leu Arg Gly Phe Val Lys Leu Lys Leu Ala Pro Gly Gln Ser
                675                 680                 685 ggg acg gca acg ttt aga cta agg aag agg gat ttg gct tat tgg gat    2765
Gly Thr Ala Thr Phe Arg Leu Arg Lys Arg Asp Leu Ala Tyr Trp Asp
            690                 695                 700 gtg ggg agg cag aat tgg gtt gtt cct tcg ggg agg ttt ggc gtg ctt    2813
Val Gly Arg Gln Asn Trp Val Val Pro Ser Gly Arg Phe Gly Val Leu
            705                 710                 715 gtg ggg gct agt tcg agg gat att agg ttg cag ggg gag att gtt gtt    2861
Val Gly Ala Ser Ser Arg Asp Ile Arg Leu Gln Gly Glu Ile Val Val
        720                 725                 730 tagggggtta tgttcagcac ctagttgggg aattgatgtg taagttggag tagggg tttt    2921 cgtgtacata cataccattt ggtcaatgtt acgacattta gtttatgaag tttcctggtg    2981
gctaccgctg atgagccctc gtatgatacc cacaatctat atgttttact cttctctttc    3041
cttttttctc ttcctttttcc tttattactt cattccttgt gtactttctg tgaacctcca    3101
gtcgaccatc cgacccaatt cgaaagtctt tcctgacctg gttcaggttg gcatattctc    3161
gaaaggatgt cgaccttcct gaccctactg ggctaccggg aaagccctag gatggctgat    3221
ggacagatct ggtgatcaac tatgggaaca ctccggagat ggtgactaat atgcgatggt    3281
catttaaaga gcaccgcttc cagcgatctc cccagttgct cctcaacgat tgacacggcc    3341
aatttatcca gattccggga ttctctgagt gagctgtccc ttttttctag a             3392

<210> SEQ ID NO 26
<211> LENGTH: 734
<212> TYPE: PRT
<213> ORGANISM: Chaetomium thermophilum

<400> SEQUENCE: 26

Met Ala Leu His Ala Phe Leu Leu Leu Ala Ser Ala Leu Leu Ala Arg
1               5                   10                  15

Gly Ala Leu Ser Gln Pro Asp Asn Val Arg Arg Ala Ala Pro Thr Gly
            20                  25                  30

Thr Ala Ala Trp Asp Ala Ala His Ser Gln Ala Ala Ala Val Ser
        35                  40                  45

Arg Leu Ser Gln Gln Asp Lys Ile Asn Ile Val Thr Gly Val Gly Trp
    50                  55                  60

Gly Lys Gly Pro Cys Val Gly Asn Thr Asn Pro Val Tyr Ser Ile Asn
65                  70                  75                  80

Tyr Pro Gln Leu Cys Leu Gln Asp Gly Pro Leu Gly Ile Arg Ser Ala
                85                  90                  95

Thr Ser Val Thr Ala Phe Thr Pro Gly Ile Gln Ala Ala Ser Thr Trp
            100                 105                 110

Asp Val Glu Leu Ile Arg Gln Arg Gly Val Tyr Leu Gly Gln Glu Ala
```

```
            115                 120                 125
Arg Gly Thr Gly Val His Val Leu Leu Gly Pro Val Ala Gly Ala Leu
130                 135                 140

Gly Lys Ile Pro His Gly Gly Arg Asn Trp Glu Ala Phe Gly Ser Asp
145                 150                 155                 160

Pro Tyr Leu Ala Gly Ile Ala Met Ser Glu Thr Ile Glu Gly Ile Gln
                165                 170                 175

Ser Glu Gly Val Gln Ala Cys Ala Lys His Tyr Ile Ala Asn Glu Gln
            180                 185                 190

Glu Leu Asn Arg Glu Thr Met Ser Ser Asn Val Asp Asp Arg Thr Met
        195                 200                 205

His Glu Leu Tyr Leu Trp Pro Phe Ala Asp Ala Val His Ser Asn Val
    210                 215                 220

Ala Ser Val Met Cys Ser Tyr Asn Lys Leu Asn Gly Thr Trp Leu Cys
225                 230                 235                 240

Glu Asn Asp Arg Ala Gln Asn Gln Leu Leu Lys Arg Glu Leu Gly Phe
                245                 250                 255

Arg Gly Tyr Ile Val Ser Asp Trp Asn Ala Gln His Thr Thr Val Gly
            260                 265                 270

Ser Ala Asn Ser Gly Met Asp Met Thr Met Pro Gly Ser Asp Phe Asn
        275                 280                 285

Gly Trp Asn Val Leu Trp Gly Pro Gln Leu Asn Asn Ala Val Asn Ser
    290                 295                 300

Gly Gln Val Ser Gln Ser Arg Leu Asn Asp Met Val Gln Arg Ile Leu
305                 310                 315                 320

Ala Ala Trp Tyr Leu Leu Gly Gln Asn Ser Gly Tyr Pro Ser Ile Asn
                325                 330                 335

Leu Arg Ala Asn Val Gln Ala Asn His Lys Glu Asn Val Arg Ala Val
            340                 345                 350

Ala Arg Asp Gly Ile Val Leu Leu Lys Asn Asp Gly Ile Leu Pro Leu
        355                 360                 365

Gln Arg Pro Asn Lys Ile Ala Leu Val Gly Ser Ala Ala Val Val Asn
    370                 375                 380

Pro Arg Gly Met Asn Ala Cys Val Asp Arg Gly Cys Asn Glu Gly Ala
385                 390                 395                 400

Leu Gly Met Gly Trp Gly Ser Gly Thr Val Glu Tyr Pro Tyr Phe Val
                405                 410                 415

Ala Pro Tyr Asp Ala Leu Arg Glu Arg Ala Gln Arg Asp Gly Thr Gln
            420                 425                 430

Ile Ser Leu His Ala Ser Asp Asn Thr Asn Gly Val Asn Asn Ala Val
        435                 440                 445

Gln Gly Ala Asp Ala Ala Phe Val Phe Ile Thr Ala Asp Ser Gly Glu
    450                 455                 460

Gly Tyr Ile Thr Val Glu Gly His Ala Gly Asp Arg Asn His Leu Asp
465                 470                 475                 480

Pro Trp His Asn Gly Asn Gln Leu Val Gln Ala Val Ala Gln Ala Asn
                485                 490                 495

Lys Asn Val Ile Val Val Val His Ser Val Gly Pro Val Ile Leu Glu
            500                 505                 510

Thr Ile Leu Asn Thr Pro Gly Val Arg Ala Val Val Trp Ala Gly Leu
        515                 520                 525

Pro Ser Gln Glu Ser Gly Asn Ala Leu Val Asp Val Leu Tyr Gly Leu
    530                 535                 540
```

-continued

```
Val Ser Pro Ser Gly Lys Leu Val Tyr Thr Ile Ala Lys Ser Pro Ser
545                 550                 555                 560

Asp Tyr Pro Thr Ser Ile Val Arg Gly Asp Asn Phe Arg Glu Gly
                565                 570                 575

Leu Phe Ile Asp Tyr Arg His Phe Asp Asn Ala Arg Ile Glu Pro Arg
                580                 585                 590

Phe Glu Phe Gly Phe Gly Leu Ser Tyr Thr Asn Phe Ser Tyr Ser Asn
            595                 600                 605

Leu Gly Ile Ser Ser Ser Ala Thr Ala Gly Pro Ala Thr Gly Pro Thr
            610                 615                 620

Val Pro Gly Gly Pro Ala Asp Leu Trp Asn Tyr Val Ala Thr Val Thr
625                 630                 635                 640

Ala Thr Val Thr Asn Thr Gly Gly Val Glu Gly Ala Glu Val Ala Gln
                645                 650                 655

Leu Tyr Ile Ser Leu Pro Ser Ser Ala Pro Ala Ser Pro Pro Lys Gln
                660                 665                 670

Leu Arg Gly Phe Val Lys Leu Lys Leu Ala Pro Gly Gln Ser Gly Thr
            675                 680                 685

Ala Thr Phe Arg Leu Arg Lys Arg Asp Leu Ala Tyr Trp Asp Val Gly
            690                 695                 700

Arg Gln Asn Trp Val Val Pro Ser Gly Arg Phe Gly Val Leu Val Gly
705                 710                 715                 720

Ala Ser Ser Arg Asp Ile Arg Leu Gln Gly Glu Ile Val Val
                725                 730
```

```
<210> SEQ ID NO 27
<211> LENGTH: 1631
<212> TYPE: DNA
<213> ORGANISM: Thermoascus aurantiacus
<220> FEATURE:
<221> NAME/KEY: Intron
<222> LOCATION: (610)..(674)
<220> FEATURE:
<221> NAME/KEY: CDS
<222> LOCATION: (675)..(1628)
<220> FEATURE:
<221> NAME/KEY: CDS
<222> LOCATION: (1)..(609)

<400> SEQUENCE: 27
```

```
atg tat cag cgc gct ctt ctc ttc tct ttc ttc ctc gcc gcc gcc cgc      48
Met Tyr Gln Arg Ala Leu Leu Phe Ser Phe Phe Leu Ala Ala Ala Arg
1               5                   10                  15 gcg cag cag gcc ggt acc gta acc gca gag aat cac cct tcc ctg acc      96
Ala Gln Gln Ala Gly Thr Val Thr Ala Glu Asn His Pro Ser Leu Thr
            20                  25                  30 tgg cag caa tgc tcc agc ggc ggt agt tgt acc acg cag aat gga aaa     144
Trp Gln Gln Cys Ser Ser Gly Gly Ser Cys Thr Thr Gln Asn Gly Lys
        35                  40                  45 gtc gtt atc gat gcg aac tgg cgt tgg gtc cat acc acc tct gga tac     192
Val Val Ile Asp Ala Asn Trp Arg Trp Val His Thr Thr Ser Gly Tyr
    50                  55                  60 acc aac tgc tac acg ggc aat acg tgg gac acc agt atc tgt ccc gac     240
Thr Asn Cys Tyr Thr Gly Asn Thr Trp Asp Thr Ser Ile Cys Pro Asp
65                  70                  75                  80 gac gtg acc tgc gct cag aat tgt gcc ttg gat gga gcg gat tac agt     288
Asp Val Thr Cys Ala Gln Asn Cys Ala Leu Asp Gly Ala Asp Tyr Ser
                85                  90                  95 ggc acc tat ggt gtt acg acc agt ggc aac gcc ctg aga ctg aac ttt     336
Gly Thr Tyr Gly Val Thr Thr Ser Gly Asn Ala Leu Arg Leu Asn Phe
            100                 105                 110
```

| | | |
|---|---|---|
| gtc acc caa agc tca ggg aag aac att ggc tcg cgc ctg tac ctg ctg<br>Val Thr Gln Ser Ser Gly Lys Asn Ile Gly Ser Arg Leu Tyr Leu Leu<br>115                      120                    125 | 384 |

```
gtc acc caa agc tca ggg aag aac att ggc tcg cgc ctg tac ctg ctg      384
Val Thr Gln Ser Ser Gly Lys Asn Ile Gly Ser Arg Leu Tyr Leu Leu
            115                 120                 125 cag gac gac acc act tat cag atc ttc aag ctg ctg ggt cag gag ttt      432
Gln Asp Asp Thr Thr Tyr Gln Ile Phe Lys Leu Leu Gly Gln Glu Phe
    130                 135                 140 acc ttc gat gtc gac gtc tcc aat ctc cct tgc ggg ctg aac ggc gcc      480
Thr Phe Asp Val Asp Val Ser Asn Leu Pro Cys Gly Leu Asn Gly Ala
145                 150                 155                 160 ctc tac ttt gtg gcc atg gac gcc gac ggc gga ttg tcc aaa tac cct      528
Leu Tyr Phe Val Ala Met Asp Ala Asp Gly Gly Leu Ser Lys Tyr Pro
                165                 170                 175 ggc aac aag gca ggc gct aag tat ggc act ggt tac tgc gac tct cag      576
Gly Asn Lys Ala Gly Ala Lys Tyr Gly Thr Gly Tyr Cys Asp Ser Gln
            180                 185                 190 tgc cct cgg gat ctc aag ttc atc aac ggt cag gtacgtcaga agtgataact   629
Cys Pro Arg Asp Leu Lys Phe Ile Asn Gly Gln
    195                 200 agccagcaga gcccatgaat cattaactaa cgctgtcaaa tacag gcc aat gtt gaa    686
                                                 Ala Asn Val Glu
                                                         205 ggc tgg cag ccg tct gcc aac gac cca aat gcc ggc gtt ggt aac cac      734
Gly Trp Gln Pro Ser Ala Asn Asp Pro Asn Ala Gly Val Gly Asn His
        210                 215                 220 ggt tcc tgc tgc gct gag atg gat gtc tgg gaa gcc aac agc atc tct      782
Gly Ser Cys Cys Ala Glu Met Asp Val Trp Glu Ala Asn Ser Ile Ser
225                 230                 235 act gcg gtg acg cct cac cca tgc gac acc ccc ggc cag acc atg tgc      830
Thr Ala Val Thr Pro His Pro Cys Asp Thr Pro Gly Gln Thr Met Cys
240                 245                 250                 255 cag gga gac gac tgt ggt gga acc tac tcc tcc act cga tat gct ggt      878
Gln Gly Asp Asp Cys Gly Gly Thr Tyr Ser Ser Thr Arg Tyr Ala Gly
                260                 265                 270 acc tgc gac cct gat ggc tgc gac ttc aat cct tac cgc cag ggc aac      926
Thr Cys Asp Pro Asp Gly Cys Asp Phe Asn Pro Tyr Arg Gln Gly Asn
            275                 280                 285 cac tcg ttc tac ggc ccc ggg cag atc gtc gac acc agc tcc aaa ttc      974
His Ser Phe Tyr Gly Pro Gly Gln Ile Val Asp Thr Ser Ser Lys Phe
        290                 295                 300 acc gtc gtc acc cag ttc atc acc gac gac ggg acc ccc tcc ggc acc     1022
Thr Val Val Thr Gln Phe Ile Thr Asp Asp Gly Thr Pro Ser Gly Thr
305                 310                 315 ctg acg gag atc aaa cgc ttc tac gtc cag aac ggc aag gta atc ccc     1070
Leu Thr Glu Ile Lys Arg Phe Tyr Val Gln Asn Gly Lys Val Ile Pro
320                 325                 330                 335 cag tcg gag tcg acg atc agc ggc gtc acc ggc aac tca atc acc acc     1118
Gln Ser Glu Ser Thr Ile Ser Gly Val Thr Gly Asn Ser Ile Thr Thr
                340                 345                 350 gag tat tgc acg gcc cag aag gcc gcc ttc ggc gac aac acc ggc ttc     1166
Glu Tyr Cys Thr Ala Gln Lys Ala Ala Phe Gly Asp Asn Thr Gly Phe
            355                 360                 365 ttc acg cac ggc ggg ctt cag aag atc agt cag gct ctg gct cag ggc     1214
Phe Thr His Gly Gly Leu Gln Lys Ile Ser Gln Ala Leu Ala Gln Gly
        370                 375                 380 atg gtc ctc gtc atg agc ctg tgg gac gat cac gcc gcc aac atg ctc     1262
Met Val Leu Val Met Ser Leu Trp Asp Asp His Ala Ala Asn Met Leu
385                 390                 395 tgg ctg gac agc acc tac ccg act gat gcg gac ccg gac acc cct ggc     1310
Trp Leu Asp Ser Thr Tyr Pro Thr Asp Ala Asp Pro Asp Thr Pro Gly
400                 405                 410                 415
```

```
gtc gcg cgc ggt acc tgc ccc acg acc tcc ggc gtc ccg gcc gac gtt        1358
Val Ala Arg Gly Thr Cys Pro Thr Thr Ser Gly Val Pro Ala Asp Val
                420                 425                 430 gag tcg cag tac ccc aat tca tat gtt atc tac tcc aac atc aag gtc        1406
Glu Ser Gln Tyr Pro Asn Ser Tyr Val Ile Tyr Ser Asn Ile Lys Val
            435                 440                 445 gga ccc att ggc agc acc ggc aac cct agc ggc ggc aac cct ccc ggc        1454
Gly Pro Ile Gly Ser Thr Gly Asn Pro Ser Gly Gly Asn Pro Pro Gly
        450                 455                 460 gga aac ccg cct ggc acc acc acc cgc cgc cca gcc act acc act            1502
Gly Asn Pro Pro Gly Thr Thr Thr Thr Arg Arg Pro Ala Thr Thr Thr
    465                 470                 475 gga agc tct ccc gga cct acc cag tct cac tac ggc cag tgc ggc ggt        1550
Gly Ser Ser Pro Gly Pro Thr Gln Ser His Tyr Gly Gln Cys Gly Gly
480                 485                 490                 495 att ggc tac agc ggc ccc acg gtc tgc gcc agc ggc aca act tgc cag        1598
Ile Gly Tyr Ser Gly Pro Thr Val Cys Ala Ser Gly Thr Thr Cys Gln
                500                 505                 510 gtc ctg aac cct tac tac tct cag tgc ctg taa                            1631
Val Leu Asn Pro Tyr Tyr Ser Gln Cys Leu
            515                 520

<210> SEQ ID NO 28
<211> LENGTH: 521
<212> TYPE: PRT
<213> ORGANISM: Thermoascus aurantiacus

<400> SEQUENCE: 28

Met Tyr Gln Arg Ala Leu Leu Phe Ser Phe Phe Leu Ala Ala Ala Arg
1               5                   10                  15

Ala Gln Gln Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Cys Cys Ala Glu Met Asp Val Trp Glu Ala Asn Ser Ile Ser Thr
```

```
            225                 230                 235                 240
Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
            275                 280                 285

Ser Phe Tyr Gly Pro Gly Gln Ile Val Asp Thr Ser Lys Phe Thr
        290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
        355                 360                 365

Thr His Gly Gly Leu Gln Lys Ile Ser Gln Ala Leu Ala Gln Gly Met
    370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
            420                 425                 430

Ser Gln Tyr Pro Asn Ser Tyr Val Ile Tyr Ser Asn Ile Lys Val Gly
        435                 440                 445

Pro Ile Gly Ser Thr Gly Asn Pro Ser Gly Gly Asn Pro Pro Gly Gly
    450                 455                 460

Asn Pro Pro Gly Thr Thr Thr Thr Arg Arg Pro Ala Thr Thr Thr Gly
465                 470                 475                 480

Ser Ser Pro Gly Pro Thr Gln Ser His Tyr Gly Gln Cys Gly Gly Ile
                485                 490                 495

Gly Tyr Ser Gly Pro Thr Val Cys Ala Ser Gly Thr Thr Cys Gln Val
            500                 505                 510

Leu Asn Pro Tyr Tyr Ser Gln Cys Leu
        515                 520

<210> SEQ ID NO 29
<211> LENGTH: 1734
<212> TYPE: DNA
<213> ORGANISM: Thermoascus aurantiacus
<220> FEATURE:
<221> NAME/KEY: Intron
<222> LOCATION: (610)..(674)
<220> FEATURE:
<221> NAME/KEY: CDS
<222> LOCATION: (1726)..(1731)
<220> FEATURE:
<221> NAME/KEY: CDS
<222> LOCATION: (675)..(1661)
<220> FEATURE:
<221> NAME/KEY: CDS
<222> LOCATION: (1)..(609)
<220> FEATURE:
<221> NAME/KEY: Intron
<222> LOCATION: (1662)..(1725)

<400> SEQUENCE: 29 atg tat cag cgc gct ctt ctc ttc tct ttc ttc ctc gcc gcc gcc cgc        48
```

```
Met Tyr Gln Arg Ala Leu Leu Phe Ser Phe Leu Ala Ala Ala Arg
1               5                   10                  15 gcg cag cag gcc ggt acc gta acc gca gag aat cac cct tcc ctg acc        96
Ala Gln Gln Ala Gly Thr Val Thr Ala Glu Asn His Pro Ser Leu Thr
                20                  25                  30 tgg cag caa tgc tcc agc ggc ggt agt tgt acc acg cag aat gga aaa       144
Trp Gln Gln Cys Ser Ser Gly Gly Ser Cys Thr Thr Gln Asn Gly Lys
            35                  40                  45 gtc gtt atc gat gcg aac tgg cgt tgg gtc cat acc acc tct gga tac       192
Val Val Ile Asp Ala Asn Trp Arg Trp Val His Thr Thr Ser Gly Tyr
        50                  55                  60 acc aac tgc tac acg ggc aat acg tgg gac acc agt atc tgt ccc gac       240
Thr Asn Cys Tyr Thr Gly Asn Thr Trp Asp Thr Ser Ile Cys Pro Asp
65                  70                  75                  80 gac gtg acc tgc gct cag aat tgt gcc ttg gat gga gcg gat tac agt       288
Asp Val Thr Cys Ala Gln Asn Cys Ala Leu Asp Gly Ala Asp Tyr Ser
                85                  90                  95 ggc acc tat ggt gtt acg acc agt ggc aac gcc ctg aga ctg aac ttt       336
Gly Thr Tyr Gly Val Thr Thr Ser Gly Asn Ala Leu Arg Leu Asn Phe
            100                 105                 110 gtc acc caa agc tca ggg aag aac att ggc tcg cgc ctg tac ctg ctg       384
Val Thr Gln Ser Ser Gly Lys Asn Ile Gly Ser Arg Leu Tyr Leu Leu
        115                 120                 125 cag gac gac acc act tat cag atc ttc aag ctg ctg ggt cag gag ttt       432
Gln Asp Asp Thr Thr Tyr Gln Ile Phe Lys Leu Leu Gly Gln Glu Phe
    130                 135                 140 acc ttc gat gtc gac gtc tcc aat ctc cct tgc ggg ctg aac ggc gcc       480
Thr Phe Asp Val Asp Val Ser Asn Leu Pro Cys Gly Leu Asn Gly Ala
145                 150                 155                 160 ctc tac ttt gtg gcc atg gac gcc gac ggc gga ttg tcc aaa tac cct       528
Leu Tyr Phe Val Ala Met Asp Ala Asp Gly Gly Leu Ser Lys Tyr Pro
                165                 170                 175 ggc aac aag gca ggc gct aag tat ggc act ggt tac tgc gac tct cag       576
Gly Asn Lys Ala Gly Ala Lys Tyr Gly Thr Gly Tyr Cys Asp Ser Gln
            180                 185                 190 tgc cct cgg gat ctc aag ttc atc aac ggt cag gtacgtcaga agtgataact    629
Cys Pro Arg Asp Leu Lys Phe Ile Asn Gly Gln
        195                 200 agccagcaga gcccatgaat cattaactaa cgctgtcaaa tacag gcc aat gtt gaa    686
                                                  Ala Asn Val Glu
                                                          205 ggc tgg cag ccg tct gcc aac gac cca aat gcc ggc gtt ggt aac cac       734
Gly Trp Gln Pro Ser Ala Asn Asp Pro Asn Ala Gly Val Gly Asn His
        210                 215                 220 ggt tcc tgc tgc gct gag atg gat gtc tgg gaa gcc aac agc atc tct       782
Gly Ser Cys Cys Ala Glu Met Asp Val Trp Glu Ala Asn Ser Ile Ser
225                 230                 235 act gcg gtg acg cct cac cca tgc gac acc ccc ggc cag acc atg tgc       830
Thr Ala Val Thr Pro His Pro Cys Asp Thr Pro Gly Gln Thr Met Cys
240                 245                 250                 255 cag gga gac gac tgt ggt gga acc tac tcc tcc act cga tat gct ggt       878
Gln Gly Asp Asp Cys Gly Gly Thr Tyr Ser Ser Thr Arg Tyr Ala Gly
                260                 265                 270 acc tgc gac cct gat ggc tgc gac ttc aat cct tac cgc cag ggc aac       926
Thr Cys Asp Pro Asp Gly Cys Asp Phe Asn Pro Tyr Arg Gln Gly Asn
            275                 280                 285 cac tcg ttc tac ggc ccc ggg cag atc gtc gac acc agc tcc aaa ttc       974
His Ser Phe Tyr Gly Pro Gly Gln Ile Val Asp Thr Ser Ser Lys Phe
        290                 295                 300 acc gtc gtc acc cag ttc atc acc gac gac ggg acc ccc tcc ggc acc      1022
Thr Val Val Thr Gln Phe Ile Thr Asp Asp Gly Thr Pro Ser Gly Thr
```

```
ctg acg gag atc aaa cgc ttc tac gtc cag aac ggc aag gta atc ccc    1070
Leu Thr Glu Ile Lys Arg Phe Tyr Val Gln Asn Gly Lys Val Ile Pro
320             325                 330                 335 cag tcg gag tcg acg atc agc ggc gtc acc ggc aac tca atc acc acc    1118
Gln Ser Glu Ser Thr Ile Ser Gly Val Thr Gly Asn Ser Ile Thr Thr
        340                 345                 350 gag tat tgc acg gcc cag aag gcc gcc ttc ggc gac aac acc ggc ttc    1166
Glu Tyr Cys Thr Ala Gln Lys Ala Ala Phe Gly Asp Asn Thr Gly Phe
355                 360                 365 ttc acg cac ggc ggg ctt cag aag atc agt cag gct ctg gct cag ggc    1214
Phe Thr His Gly Gly Leu Gln Lys Ile Ser Gln Ala Leu Ala Gln Gly
        370                 375                 380 atg gtc ctc gtc atg agc ctg tgg gac gat cac gcc gcc aac atg ctc    1262
Met Val Leu Val Met Ser Leu Trp Asp Asp His Ala Ala Asn Met Leu
385                 390                 395 tgg ctg gac agc acc tac ccg act gat gcg gac ccg gac acc cct ggc    1310
Trp Leu Asp Ser Thr Tyr Pro Thr Asp Ala Asp Pro Asp Thr Pro Gly
400                 405                 410                 415 gtc gcg cgc ggt acc tgc ccc acg acc tcc ggc gtc ccg gcc gac gtt    1358
Val Ala Arg Gly Thr Cys Pro Thr Thr Ser Gly Val Pro Ala Asp Val
        420                 425                 430 gag tcg cag tac ccc aat tca tat gtt atc tac tcc aac atc aag gtc    1406
Glu Ser Gln Tyr Pro Asn Ser Tyr Val Ile Tyr Ser Asn Ile Lys Val
435                 440                 445 gga ccc atc ggc tcg acc gtc cct ggc ctt gac ggc agc aac ccc ggc    1454
Gly Pro Ile Gly Ser Thr Val Pro Gly Leu Asp Gly Ser Asn Pro Gly
        450                 455                 460 aac ccg acc acc acc gtc gtt cct ccc gct tct acc tcc acc tcc cgt    1502
Asn Pro Thr Thr Thr Val Val Pro Pro Ala Ser Thr Ser Thr Ser Arg
465                 470                 475 ccg acc agc agc act agc tct ccc gtt tcg acc ccg act ggc cag ccc    1550
Pro Thr Ser Ser Thr Ser Ser Pro Val Ser Thr Pro Thr Gly Gln Pro
480                 485                 490                 495 ggc ggc tgc acc acc cag aag tgg ggc cag tgc ggc ggt atc ggc tac    1598
Gly Gly Cys Thr Thr Gln Lys Trp Gly Gln Cys Gly Gly Ile Gly Tyr
        500                 505                 510 acc ggc tgc act aac tgc gtt gct ggc acc acc tgc act cag ctc aac    1646
Thr Gly Cys Thr Asn Cys Val Ala Gly Thr Thr Cys Thr Gln Leu Asn
515                 520                 525 ccc tgg tac agc cag gtatgtttct cttcccccctt ctagactcgc ttggatttga    1701
Pro Trp Tyr Ser Gln
        530 cagttgctaa catctgctca acag tgc ctg taa                             1734
                          Cys Leu
```

<210> SEQ ID NO 30
<211> LENGTH: 534
<212> TYPE: PRT
<213> ORGANISM: Thermoascus aurantiacus

<400> SEQUENCE: 30

```
Met Tyr Gln Arg Ala Leu Leu Phe Ser Phe Phe Leu Ala Ala Ala Arg
1               5                   10                  15

Ala Gln Gln Ala Gly Thr Val Thr Ala Glu Asn His Pro Ser Leu Thr
                20                  25                  30

Trp Gln Gln Cys Ser Ser Gly Gly Ser Cys Thr Thr Gln Asn Gly Lys
            35                  40                  45

Val Val Ile Asp Ala Asn Trp Arg Trp Val His Thr Thr Ser Gly Tyr
```

-continued

```
            50                  55                  60
Thr Asn Cys Tyr Thr Gly Asn Thr Trp Asp Thr Ser Ile Cys Pro Asp
 65                  70                  75                  80

Asp Val Thr Cys Ala Gln Asn Cys Ala Leu Asp Gly Ala Asp Tyr Ser
                 85                  90                  95

Gly Thr Tyr Gly Val Thr Thr Ser Gly Asn Ala Leu Arg Leu Asn Phe
                100                 105                 110

Val Thr Gln Ser Ser Gly Lys Asn Ile Gly Ser Arg Leu Tyr Leu Leu
                115                 120                 125

Gln Asp Asp Thr Thr Tyr Gln Ile Phe Lys Leu Leu Gly Gln Glu Phe
130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
                195                 200                 205

Trp Gln Pro Ser Ala Asn Asp Pro Asn Ala Gly Val Gly Asn His Gly
210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
                260                 265                 270

Cys Asp Pro Asp Gly Cys Asp Phe Asn Pro Tyr Arg Gln Gly Asn His
                275                 280                 285

Ser Phe Tyr Gly Pro Gly Gln Ile Val Asp Thr Ser Ser Lys Phe Thr
                290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
                340                 345                 350

Tyr Cys Thr Ala Gln Lys Ala Ala Phe Gly Asp Asn Thr Gly Phe Phe
                355                 360                 365

Thr His Gly Gly Leu Gln Lys Ile Ser Gln Ala Leu Ala Gln Gly Met
370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
                420                 425                 430

Ser Gln Tyr Pro Asn Ser Tyr Val Ile Tyr Ser Asn Ile Lys Val Gly
                435                 440                 445

Pro Ile Gly Ser Thr Val Pro Gly Leu Asp Gly Ser Asn Pro Gly Asn
                450                 455                 460

Pro Thr Thr Thr Val Val Pro Pro Ala Ser Thr Ser Thr Ser Arg Pro
465                 470                 475                 480
```

-continued

```
Thr Ser Ser Thr Ser Ser Pro Val Ser Thr Pro Thr Gly Gln Pro Gly
            485             490             495

Gly Cys Thr Thr Gln Lys Trp Gly Gln Cys Gly Gly Ile Gly Tyr Thr
            500             505             510

Gly Cys Thr Asn Cys Val Ala Gly Thr Thr Cys Thr Gln Leu Asn Pro
            515             520             525

Trp Tyr Ser Gln Cys Leu
            530
```